(12) United States Patent
Wisniewski et al.

(10) Patent No.: US 7,335,756 B2
(45) Date of Patent: Feb. 26, 2008

(54) RETINOIC ACID METABOLIZING CYTOCHROME P450

(75) Inventors: Jan Wisniewski, Harrowsmith (CA); Martin P. Petkovich, Kingston (CA); Heather Ramshaw, Napanee (CA)

(73) Assignee: Cytochroma Inc., Ontario (CA)

( * ) Notice: Subject to any disclaimer, the term of this patent is extended or adjusted under 35 U.S.C. 154(b) by 357 days.

(21) Appl. No.: 10/477,526

(22) PCT Filed: May 23, 2002

(86) PCT No.: PCT/CA02/00758

§ 371 (c)(1), (2), (4) Date: Aug. 16, 2004

(87) PCT Pub. No.: WO02/095034

PCT Pub. Date: Nov. 28, 2002

(65) Prior Publication Data

US 2005/0009021 A1    Jan. 13, 2005

Related U.S. Application Data

(60) Provisional application No. 60/292,531, filed on May 23, 2001.

(51) Int. Cl.
| | |
|---|---|
| C07H 21/04 | (2006.01) |
| C12N 1/21 | (2006.01) |
| C12N 5/08 | (2006.01) |
| C12N 15/63 | (2006.01) |
| C12N 15/53 | (2006.01) |

(52) U.S. Cl. .................. 536/23.2; 435/189; 435/252.3; 435/320.1; 435/325

(58) Field of Classification Search .................. None
See application file for complete search history.

(56) References Cited

U.S. PATENT DOCUMENTS 6,063,606 A  *  5/2000  Petkovich et al. .......... 435/189

FOREIGN PATENT DOCUMENTS

| WO | WO 97 49815 | 12/1997 |
|---|---|---|
| WO | WO 01 44443 | 6/2001 |

OTHER PUBLICATIONS

Ramsay H: "Human DNA sequence from clone RP11-348J12" Database EMBL 'Online!, Jun. 7, 2000, Database accession No. AL358613.

Smith T P L et al.: "Sequence evaluation of four pooled-tissue normalized bovine cDNA libraries and construction of a gene index for cattle", Database EMBL 'Online!, Sep. 20, 2000, Database accession No. BE749195, Genome Research, vol. 11, No. 4, 2001, pp. 626-630.

White Jay A. et al.: "Identification of the human cytochrome P450, P450RAI-2, which is predominantly expressed in the adutl cerebellum and is responsible for all-trans-retinoic acid metabolism", Proceedings of the National Academy of Sciences of USA, vol. 97, No. 12, Jun. 6, 2000, pp. 6403-6408.

\* cited by examiner

*Primary Examiner*—Elizabeth Slobodyansky
(74) *Attorney, Agent, or Firm*—Marshall, Gerstein & Borun LLP

(57) ABSTRACT

The present invention provides a novel retinoic acid metabolizing cytochrome P450, P450RAI-3, that is predominantly expressed in the adrenal gland. Methods for and uses of the new polynucleotide, polypeptide, fragments thereof and modulators thereof, include the treatment of cancer.

10 Claims, 55 Drawing Sheets

FIGURE 1

FIGURE 1 (CON'T)

FIGURE 1 (CON'T)

FIGURE 1 (CON'T)

FIGURE 1 (CON'T)

FIGURE 1 (CON'T)

FIGURE 1 (CON'T)

FIGURE 1 (CON'T)

FIGURE 1 (CON'T)

FIGURE 1 (CON'T)

FIGURE 1 (CON'T)

FIGURE 1 (CON'T)

```
ATGTTCCCTTGGGGGCTGAGCTGCCTGTCAGTGCTGGGGGCGGCGGGCAC      50
TGCTCTCCTGTGCGCGGGCCTGCTGCTCAGCCTGGCCCAGCACCTCTGGA     100
CCCTCCGCTGGATGCTGAGCCGGGACCGGGCCTCCACCCTGCCTCTGCCC     150
AAGGGCTCCATGGGGTGGCCCTTCTTCGGCGAAACGCTGCACTGGTTAGT     200
TCAGGGCTCGCGCTTCCACAGTTCTCGCCGAGAGCGCTATGGGACAGTGT     250
TCAAGACGCACCTGCTGGGCAGGCCAGTGATCCGCGTGAGCGGCGCGGAG     300
AACGTGCGCACCATCCTGCTGGGCGAGCACCGCCTGGTGCGCAGCCAGTG     350
GCCGCAGAGTGCGCACATCCTGCTGGGCTCGCACACACTGCTAGGTGCGG     400
TCGGCGAGCCGCACCGGCGGCGGCGCAAGGTGCTGGCGCGCGTGTTCAGC     450
CGCGCCGCGCTGGAGCGCTACGTGCCGCGCCTGCAGGGGGCGCTGCGGCA     500
TGAGGTGCGCTCCTGGTGCGCGGCGGGCGGGCCGGTCTCAGTCTACGACG     550
CCTCCAAAGCGCTCACCTTCCGCATGGCCGCGCGCATCCTGCTGGGGTTG     600
CGGCTGGACGAGGCGCAGTGCGCCACGCTGGCCCGGACCTTCGAGCAGCT     650
CGTGGAGAACCTCTTCTCACTGCCTCTGGACGTTCCCTTCAGTGGCCTAC     700
GCAAGGGCATCCGGGCAAGGGACCAGCTGCATCGGCACCTGGAGGGGGCC     750
ATTTCTGAGAAGCTTCACGAGGACAAGGCTGCAGAGCCGGGTGATGCCCT     800
CGACCTAATCATTCACAGTGCAAGGGAGCTGGGCCATGAGCCCTCCATGC     850
AGGAGCTGAAGGAGTCGGCTGTGGAGCTCCTCTTCGCCGCCTTCTTCACC     900
ACGGCCAGTGCCAGCACCTCGCTCGTCCTGCTGCTACTGCAGCATCCGGC     950
GGCCATCGCCAAGATTCGGGAGGAGCTGGTGGCGCAGGGGCTGGGGCGCG    1000
CGTGCGGCTGCGCGCCCGGGCCGCTGGGGGCAGCGAGGGCCCCCGCCC      1050
GACTGCGGCTGCGAGCCCGACCTCAGCCTCGCGGCGCTGGGCCGTCTGCG    1100
CTACGTCGACTGCGTGGTCAAGGAGGTGCTGCGCCTCCTGCCGCCAGTGT    1150
CCGGGGGCTACCGCACCGCCCTGCGCACCTTCGAGCTCGACGGCTACCAG    1200
ATCCCCAAGGGCTGGAGCGTGATGTATAGCATCCGGGACACGCACGAGAC    1250
GGCTGCGGTGTACCGCAGCCCTCCCGAAGGCTTCGATCCAGAGCGCTTCG    1300
GCGCAGCGCGCGAAGATTCCCGGGGCGCCTCCAGCCGCTTGCATTACATC    1350
CCGTTCGGCGGCGGTGCGCGCAGCTGCCTCGGCCAGGAGCTGGCGCAAGC    1400
CGTGCTCCAGCTGCTAGCTGTGGAGCTAGTGCGCACCGCGCGCTGGGAAC    1450
TGGCCACACCCGCCTTCCCCGCCATGCAGACGGTGCCCATCGTGCACCCA    1500
GTGGACGGGCTGCGGCTCTTTTTCCACCCCCTCACGCCTTCGGTTGCGGG    1550
GAATGGGCTATGCCTCTGA                                   1600
```

FIGURE 2

```
MFPWGLSCLSVLGAAGTALLCAGLLLSLAQHLWTLRWMLSRDRASTLPLP      50
KGSMGWPFFGETLHWLVQGSRFHSSRRERYGTVFKTHLLGRPVIRVSGAE     100
NVRTILLGEHRLVRSQWPQSAHILLGSHTLLGAVGEPHRRRRKVLARVFS     150
RAALERYVPRLQGALRHEVRSWCAAGGPVSVYDASKALTFRMAARILLGL     200
RLDEAQCATLARTFEQLVENLFSLPLDVPFSGLRKGIRARDQLHRHLEGA     250
ISEKLHEDKAAEPGDALDLIIHSARELGHEPSMQELKESAVELLFAAFFT     300
TASASTSLVLLLQHPAAIAKIREELVAQGLGRACGCAPGAAGGSEGPPP      350
DCGCEPDLSLAALGRLRYVDCVVKEVLRLLPPVSGGYRTALRTFELDGYQ     400
IPKGWSVMYSIRDTHETAAVYRSPPEGFDPERFGAAREDSRGASSRLHYI     450
PFGGGARSCLGQELAQAVLQLLAVELVRTARWELATPAFPAMQTVPIVHP     500
VDGLRLFFHPLTPSVAGNGLCL                                 550
```

FIGURE 3

```
  M  F  P  W  G  L  S  C  L  S  V  L  G  A  A  G  T  A  L  L
ATGTTCCCTTGGGGGCTGAGCTGTCAGTGCTGGGGGCGGGGCACTGCTCTCCTG          60

C  A  G  L  L  S  L  A  Q  H  L  W  T  L  R  W  M  L  S
TGCGCGGGGCCTGCTGCTTCAGCCTGGCCCAGCACCTCTGGACCCTCCGCTGGATGCTGAGC 120

R  D  R  A  S  T  L  P  L  P  K  G  S  M  G  W  P  E  F  G
CGGGACCGGGCCTCCACCCTGCCCTGCCCAAGGGCTCCATGGGCTGGCCCTTCTTCGGC    180

E  T  L  H  W  L  V  Q  G  S  R  F  H  S  S  R  R  E  R  Y
GAAACGCTGCACTGGTTAGTTCAGGGCTCGCGCTTCCACAGTTCTCGCCGAGAGCGCTAT   240

G  T  V  E  K  T  H  L  L  G  R  P  V  I  R  V  S  G  A  E
GGGACAGTGTTCAAGACGCACCTGCTGGGCAGGCCAGTGATCCGCGTGAGCGGCGCGGAG   300

N  V  R  T  I  L  L  G  E  H  R  L  V  R  S  Q  W  P  Q  S
AACGTGCGCACCATCCTGCTGGGCGAGCACCGCCTGGTGCGCAGTCAGTGGCCGCAGAGT   360

A  H  I  L  L  G  S  H  T  L  L  G  A  V  G  E  P  H  R  R
GCGCACATCCTGCTGGGCTCGCACACACTGCTAGGTGCGGTTCGGCGAGCCGCACCGGCGG 420

R  R  K  V  L  A  R  V  F  S  R  A  A  L  E  R  Y  V  P  R
CGGCGCAAGGTGCTGGCGCGCGTGTTCAGCCGCGCTGGAGCGCTACGTGCCGCGC       480

L  Q  G  A  L  R  H  E  V  R  S  W  C  A  G  G  P  V  S
CTGCAGGGGGCCCTGCGCCATGAGGTGCGCTCCTGGTGCGCGGGCGGGCCGGTCTCA     540

V  Y  D  A  S  K  A  L  T  F  R  M  A  A  R  I  L  L  G  L
GTCTACGACGCCTCCAAAGCGCTCACCTTCCGCATGGCCGCCAGGATCCTGCTGGGGTTG  600

R  L  D  E  A  Q  C  A  T  L  A  R  T  F  E  Q  L  V  E  N
CGGCTGGACGAGGCGCAGTGCGCCACGCTGGCCCGGACCTTCGAGCAGCTCGTGGAGAAC  660

L  F  S  L  P  L  D  V  P  F  S  G  L  R  K  G  I  R  A  R
CTCTTCTCACTGCCTCTGGACGTTCCCTTCAGTGGCCTACGCAAGGGCATCCGGGCAAGG  720

D  Q  L  H  R  H  L  E  G  A  I  S  E  K  L  H  E  D  K  A
GACCAGCTGCATCGGCACCTGGAGGGCGCCATTTCTGAGAAGCTTCACGAGGACAAGGCT  780

A  E  P  G  D  A  L  D  L  I  H  S  A  R  E  L  G  H  E
GCAGAGCCGGGTGATGCCCTCGACCTAATCATTCACAGTGCCAAGGAGCTGGGCCATGAG  840
```

FIGURE 4 (CON'T)

```
P  S  M  Q  E  L  K  E  S  A  V  E  L  L  F  A  A  F  F  T
CCCTCCATGCAGGAGCTGAAGGAGTCGGCTGTGGAGCTCCTCTTCGCCGCCTTCTTCACC     900

T  A  S  A  S  T  S  L  V  L  L  L  Q  H  P  A  A  I  A
ACGGCCAGTGCCAGCACCTCGCTCGTCCTGCTCCTGCAGCATCCGGCGGCCATCGCC        960

K  I  R  E  E  L  V  A  Q  G  L  G  R  A  C  G  C  A  P  G
AAGATTCGGGAGGAGCTGGTGGCGCAGGGGCTGGGGCGCGCGTGCGGGTGCGCGCCCGGG     1020

A  A  G  G  S  E  G  P  P  D  C  G  C  E  P  D  L  S  L
GCCGCTGGGGGCAGCGAGGGGCCCCCGGACTGCGGCTGCGAGCCCGACCTCAGCCTC        1080

A  A  L  G  R  L  R  Y  V  D  C  V  V  K  E  V  L  R  L  L
GCGGGCGCTGGGGCCGTCTGCGCTACGTCGACTGCGTGGTCAAGGAGGTGCTGCGCCTCCTG  1140

P  P  V  S  G  G  Y  R  T  A  L  R  T  F  E  E  L  D  G  Y  Q
CCGCCAGTGTCCGGGGGCTACCGCACCGCCCTGCGCACCTTCGAGGAGCTCGACGGCTACCAG 1200

I  P  K  G  W  S  V  M  Y  S  I  R  D  T  H  E  T  A  A  V
ATCCCCAAGGGCTGGAGCGTGATGTATAGCATCCGGGACACGCACGAGACGGCTGCGGTG    1260

Y  R  S  P  P  E  G  F  D  P  E  R  F  G  A  A  R  E  D  S
TACCGCAGCCCTCCCGAAGGCTTCGATCCCGAGCGCTTCGGCGCAGCGCGCGAAGATTCC    1320

R  G  A  S  R  L  H  Y  I  P  F  G  G  G  A  R  S  C  L
CGGGGCGCCTCCAGCCGCCTTGCATTACATCCCGTTCGGCGGCGGTGCGCGCAGCTGCCTC   1380

G  Q  E  L  A  Q  A  V  L  Q  L  L  V  E  L  V  R  T  A
GGCCAGGAGCTGGCGCAAGCCGTGCTCCAGCTGCTGGTGGAGCTGGTGCGCACCGCG       1440

R  W  E  L  A  T  P  A  F  P  A  M  Q  T  V  P  I  V  H  P
CGCTGGGAACTGGCCACACCCGCCTTCCCCGCCATGCAGACGGTGCCCATCGTGCACCCA    1500

V  D  G  L  R  L  F  F  H  P  L  T  P  S  V  A  G  N  L
GTGGACGGGCTGCGCCTCTTTTTCCACCCCCTCACGCCCTTCGGTTGCGGGAATGGGCTA    1560

C  L
TGCCTCTGA                                                        1569
```

FIGURE 6A

```
                                                                                               25
P450RAI-1  - - - M G L P A L L S A L C T E V L P V L T P L L F L A A I
                                                                                               30
P450RAI-2  M L F E G M L F D L V S A L T L A A C L L V S V T L L A V S Q
                                                                                               30
P450RAI-3  M F P W G L H L C L S V L G A A G T A L L C A G L L S L A Q

55
P450RAI-1  K L W D L Y C V S G R D S C A L P L P P K G P G T M G F P E F G
                                                                                               60
P450RAI-2  Q L W Q L R W A A T R D K S C K P H P K G S M G F P L A S G
                                                                                               60
P450RAI-3  H L W T L R W M L S R D R A S T L P L P K G S M G W P E F G

85
P450RAI-1  E T L Q M V L Q R R K F L Q M K R R E K Y G F I Y K T H L F G
                                                                                               90
P450RAI-2  E T L H G L L Q G S R R E S F Q R R K Y G N V F K T H L L G
                                                                                               90
P450RAI-3  E T L H L V Q G S R E H S R R E R Y G T V F K T H L L G

115
P450RAI-1  R P T V R V M G A D N V R R I L L G D D R L V S V H W P A S
                                                                                               120
P450RAI-2  R P L I R V T G A E N V R K I L M G E H R L V S T E W P R S
                                                                                               120
P450RAI-3  R P V I R V S G A E N V R T H L L G E H R L V R S Q W P Q
```

FIGURE 6A (CON'T)

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| P450RAI-1 | V | R | T | I | L | G | S | G | C | L | S | N | L | H | D | S | S | H | K | Q | R | K | K | V | I | M | R | A | E | F | S | 145 |
| P450RAI-2 | T | R | M | L | L | G | P | N | T | V | S | N | S | I | G | D | I | H | R | N | K | R | R | K | V | F | S | K | I | F | S | 150 |
| P450RAI-3 | A | H | I | L | L | G | S | H | T | L | L | G | A | V | G | E | P | H | R | R | R | K | V | L | A | R | V | F | S | 150 |

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| P450RAI-1 | R | E | A | L | E | C | Y | Y | P | V | H | I | T | E | E | V | G | S | S | L | E | Q | W | L | S | C | G | G | E | R | G | L | 175 |
| P450RAI-2 | H | E | A | L | E | S | Y | L | P | K | I | Q | L | V | H | I | Q | D | T | L | R | A | W | S | S | H | P | – | E | A | H | 179 |
| P450RAI-3 | R | A | A | L | E | R | Y | V | P | R | L | Q | G | A | L | R | H | E | V | R | S | W | C | A | A | G | – | G | P | V | 179 |

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| P450RAI-1 | L | V | Y | P | E | E | V | K | R | L | M | E | R | I | A | M | R | I | L | L | G | C | E | P | Q | L | A | G | D | G | D | 205 |
| P450RAI-2 | N | V | Y | Q | E | A | Q | K | L | T | E | R | M | A | A | R | I | L | L | G | F | S | H | I | P | E | E | D | L | G | – | 208 |
| P450RAI-3 | S | V | Y | D | A | S | K | A | L | T | F | R | M | A | A | R | I | L | L | G | L | R | L | D | E | A | Q | C | A | – | 208 |

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| P450RAI-1 | S | E | Q | Q | L | V | E | A | F | E | E | M | T | R | N | L | F | S | L | P | I | D | V | P | F | S | G | L | Y | R | | 235 |
| P450RAI-2 | – | – | H | L | F | E | T | Y | Q | Q | F | V | D | N | V | F | S | L | P | V | D | L | P | F | S | G | Y | R | R | | | 235 |
| P450RAI-3 | – | – | T | L | A | R | T | F | E | Q | V | E | N | L | F | S | L | P | L | D | V | P | F | S | G | L | R | K | | | | 235 |

| P450RAI-1 | G | M | K | A | R | N | L | I | H | A | R | I | E | Q | N | I | R | A | K | I | H | A | R | I | C | G | L | R | A | S | E | A | G | Q | 265 |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| P450RAI-2 | G | I | Q | A | R | Q | I | L | H | Q | K | A | L | E | K | A | I | R | E | K | L | Q | C | T | Q | – | – | – | – | – | – | – | G | K | 261 |
| P450RAI-3 | G | I | R | A | R | D | Q | L | H | L | L | G | A | I | S | E | K | L | H | E | D | K | – | – | – | – | – | – | – | – | – | – | A | A | 261 |

| P450RAI-1 | G | C | K | D | A | L | Q | L | L | H | A | R | E | H | S | W | E | R | G | E | R | L | D | M | Q | A | L | K | Q | S | T | 295 |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| P450RAI-2 | D | Y | L | D | A | L | D | L | L | K | A | K | E | H | S | S | K | E | M | T | M | Q | E | L | K | D | G | T | L | 291 |
| P450RAI-3 | E | P | G | D | A | L | D | L | I | H | A | R | H | S | S | K | E | L | G | H | P | S | M | Q | E | L | K | E | S | A | V | 291 |

| P450RAI-1 | E | L | F | G | G | H | E | T | T | A | S | S | L | I | H | Y | L | G | L | Y | P | H | V | L | Q | K | 325 |
| --- | --- | --- | --- | --- | --- | --- | --- | --- | --- | --- | --- | --- | --- | --- | --- | --- | --- | --- | --- | --- | --- | --- | --- | --- | --- | --- |
| P450RAI-2 | E | L | I | F | A | A | Y | A | T | T | A | S | S | L | I | M | Q | L | L | K | H | P | T | V | L | E | K | 321 |
| P450RAI-3 | E | L | F | A | A | F | F | T | T | A | S | S | L | V | L | L | Q | H | P | A | A | I | A | K | 321 |

| P450RAI-1 | V | R | E | E | L | K | S | K | G | L | L | C | K | S | N | Q | – | – | – | – | – | – | – | – | – | 341 |
| --- | --- | --- | --- | --- | --- | --- | --- | --- | --- | --- | --- | --- | --- | --- | --- | --- | --- | --- | --- | --- | --- | --- | --- | --- | --- |
| P450RAI-2 | L | R | D | E | L | R | A | H | G | I | L | H | S | G | G | C | P | – | – | – | – | – | – | – | – | 338 |
| P450RAI-3 | I | R | E | E | L | V | A | Q | L | G | R | A | C | G | C | A | P | G | A | A | G | G | S | E | G | P | P | P | D | 351 |

FIGURE 6A (CON'T)

FIGURE 6A (CON'T)

```
P450RAI-1  - - D N K L D M E H L E Q L K Y I G C V I K E T L R L N P              368
P450RAI-2  - - C E G T L R L D T L S G L R Y L D C V I K E V M R L E T            366
P450RAI-3  C G C E P D L S A A L G R L R Y V D C V V K E V L R L L P              381

P450RAI-1  P V P G G F R V A L K T F E L N G Y Q I H P K G W N V I L Y S I        398
P450RAI-2  P I S G G Y R T V L Q T F E L D G F Q I H P K G W S V M R L Y S I      396
P450RAI-3  P V S G G Y R T A L R T F E L D G Y Q I H P K G W S V M R L Y S I      411

P450RAI-1  C D T H D V A E I F T N K E - F N P D R F M L P H - - P E              425
P450RAI-2  R D T H D T A P V E K D N V - F D P D R F S Q A R - - S E              423
P450RAI-3  R D T H E T A A V Y R S P P E G F D P E R F G A A R E D S R            441

P450RAI-1  D A S - R E F S H I P F G G G L R S C V G K E F A K I L L K I          454
P450RAI-2  D K D G R E H Y L P F G G G V R T C L G K H L A K L F L K V            453
P450RAI-3  G A S R L H Y I P F G G G A R S C L G Q E L A Q A V L Q L              471
```

```
P450RAI-1  E T V E L A R H C D W Q L L N - G P P T M K T S P T V Y P V  483
P450RAI-2  L A V E L A S T S R F E L A T R T F P P R I T L V P V L H P V  483
P450RAI-3  L A V E L V R T A R W E L A T P A F P A M Q T V P I V H P V  501

P450RAI-1  D N L P A R F T H F H G - - - E I                              497
P450RAI-2  D G L S V K F F G L D S N Q N E I L P E T E A M L S A T V     512
P450RAI-3  D G L R L F F H P L T P - - - S V A G N G L C L               522
```

FIGURE 6A (CON'T)

CLUSTAL W(1.60) Multiple Sequence Alignments

Sequence type explicitly set to Protein

Sequence format is Pearson
Sequence 1: 0          497 aa
Sequence 2: 629        512 aa
Sequence 3: 1260       522 aa Start of Pairwise alignments
Aligning...
Sequences (1:2) Aligned. Score: 41
Sequences (1:3) Aligned. Score: 43
Sequences (2:3) Aligned. Score: 51

Start of Multiple Alignment
There are 2 groups
Aligning...
Group 1: Sequences:  2    Score:6215
Group 2: Sequences:  3    Score:6505

Alignment Score 4734

Consensus length = 539

NBRF/PIR-Alignment file created c:\progra~1\omiga\temp\clustal215.aln]

Key to sequence names:

Sequence 1:   P450RAI-1
Sequence 2:   P450RAI-2
Sequence 3:   Proposed_RAI-3_protein

FIGURE 6B

CLUSTAL W(1.60) Multiple Sequence Alignments

Sequence type explicitly set to DNA

Sequence format is Pearson
Sequence 1: 0          1743 bp
Sequence 2: 1955       4445 bp
Sequence 3: 6955       1569 bp Start of Pairwise alignments
Aligning...
Sequences (1:2) Aligned. Score: 49
Sequences (1:3) Aligned. Score: 52
Sequences (2:3) Aligned. Score: 61

Start of Multiple Alignment
There are 2 groups
Aligning...
Group 1: Sequences:   2     Score:9880
Group 2: Sequences:   3     Score:9376

Alignment Score 18899

Consensus length = 4553

NBRF/PIR-Alignment file created [c:\progra~1\omiga\temp\clustal261.aln]

Key to sequence names:

Sequence 1:     P450RAI-1
Sequence 2:     P450RAI-2
Sequence 3:     Proposed_RAI-3

FIGURE 6C

FIGURE 7 (CON'T)

| | | | | | | | | | | | |
|---|---|---|---|---|---|---|---|---|---|---|---|
| Whole Brain | Cerebellum Left | Substantia nigra | Heart | Esophagus | Colon transverse | Kidney | Lung | Liver | leukemia HL-60 | Fetal brain | yeast total RNA |
| Cerebral Cortex | Cerebellum right | Accumbens nucleus | Aorta | Stomach | Colon decending | Skeletal muscle | Placenta | Pancreas | HeLa S3 | Fetal heart | yeast tRNA |
| Frontal Lobe | Corpus Callosum | Thalamus | Atrium Left | Duodenum | Rectum | Spleen | Bladder | Adrenal gland | leukemia K-562 | Fetal kidney | E.coli rRNA |
| Perietal Lobe | Amygdala | Pituitary gland | Atrium right | Jejunum | | Thymus | Uterus | Thyroid gland | leukemia MOLT-4 | Fetal liver | E.coli DNA |
| Occipital Lobe | Caudate nucleus | Spinal cord | Ventricle Left | Ileum | | Peripheral blood leuk | Prostate | Salivary gland | Burkitt's lym., Raji | Fetal spleen | Poly r(A) |
| Temporal Lobe | Hippocampus | | Ventricle right | Ilocecum | | lymph node | Testis | mammary gland | Burkitt's lym., Daudi | Fetal thymus | human Cot-1 DNA |
| p.g.of cerebral | Medulla oblongata | | Inter-ventric septum | Appendix | | Bone | Ovary | | Colo-rectal SW480 | Fetal lung | human DNA 100 ng |
| Pons | Putamen | | Apex of heart | Colon, ascending | | Trachea | | | lung carc. A549 | | human DNA 500 ng |

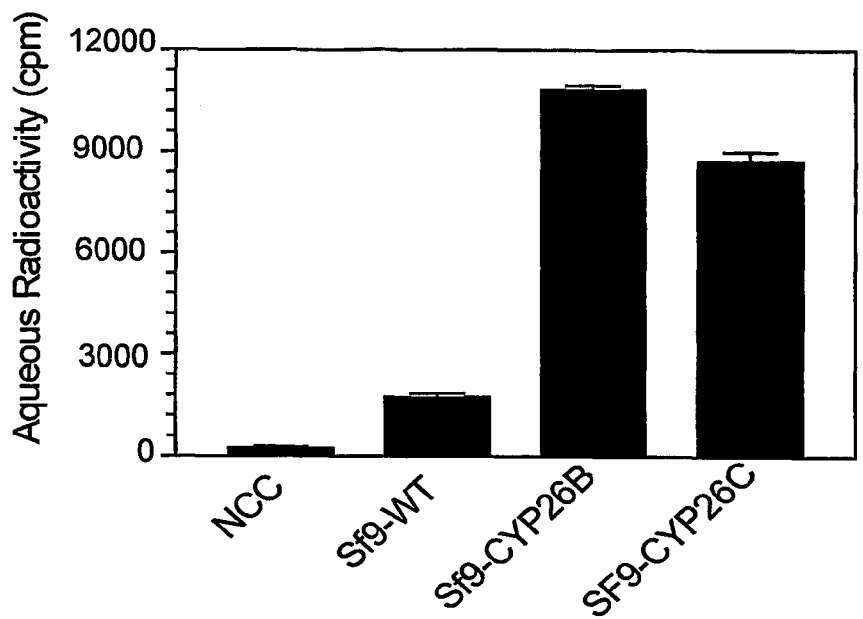
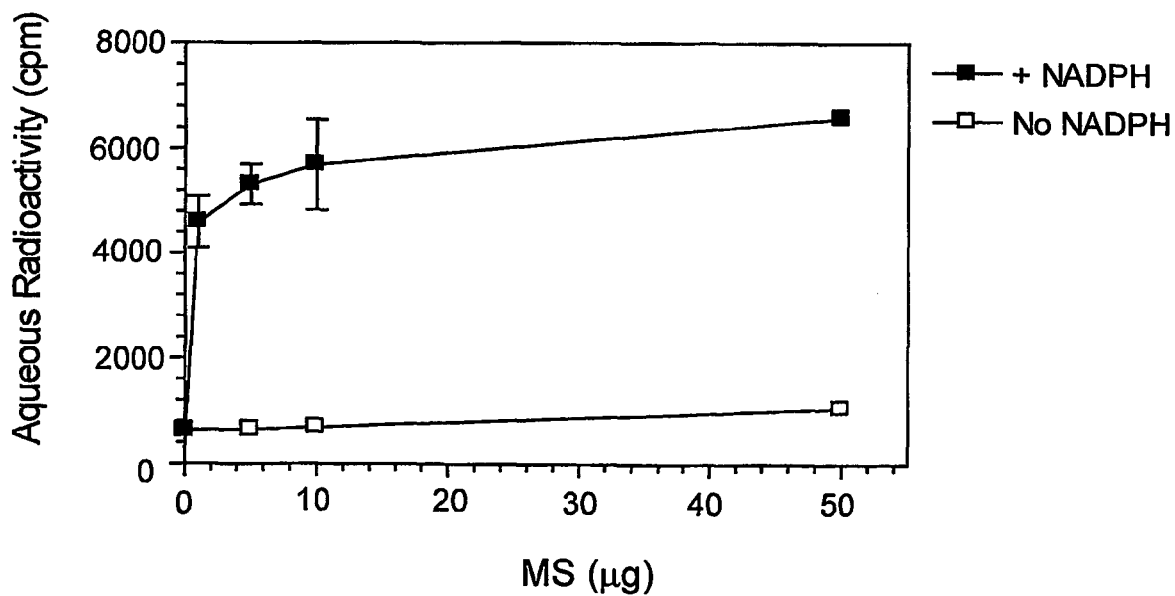
FIGURE 14

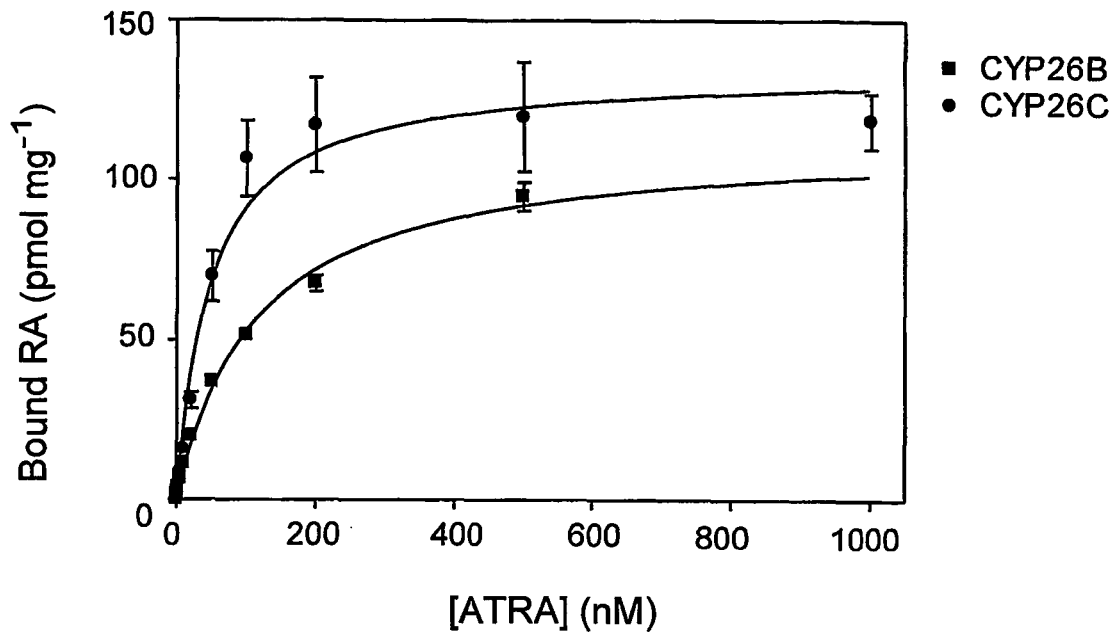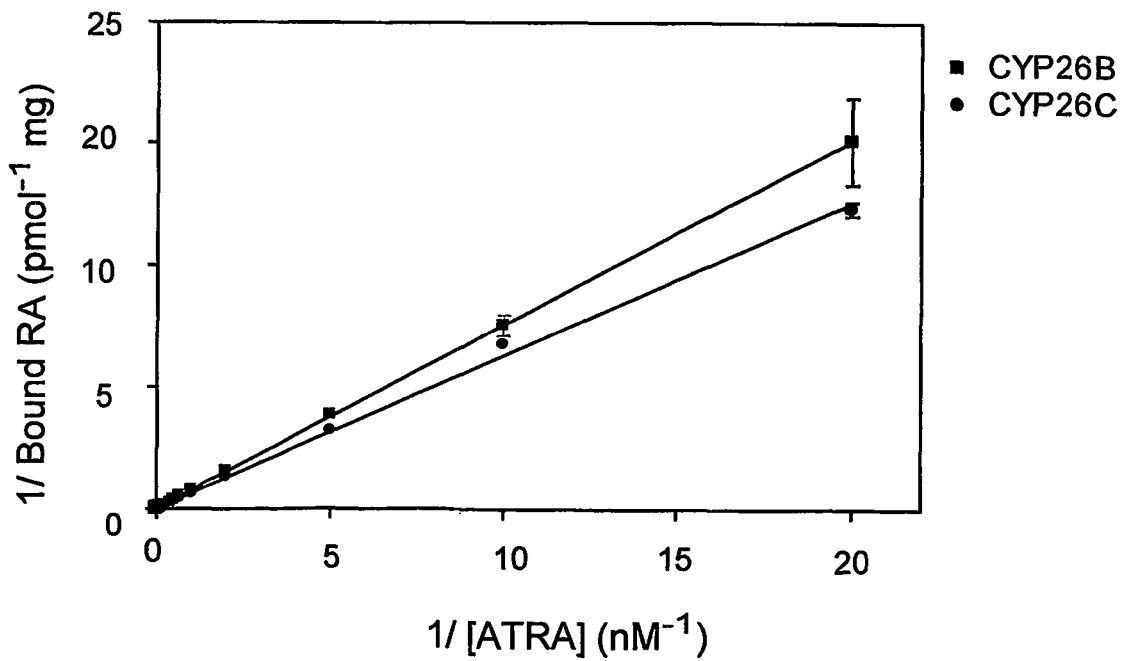
FIGURE 17

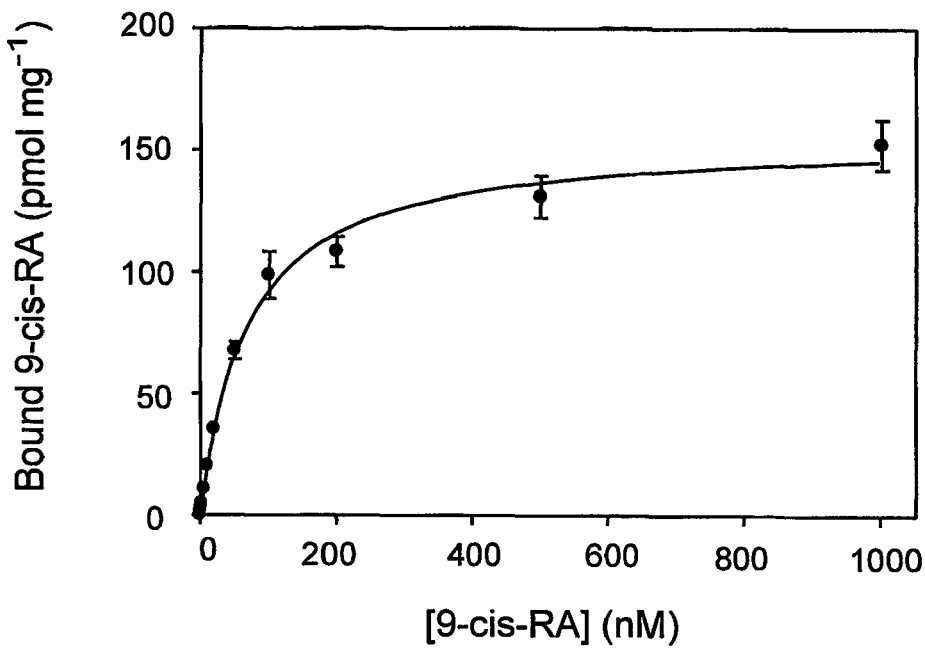
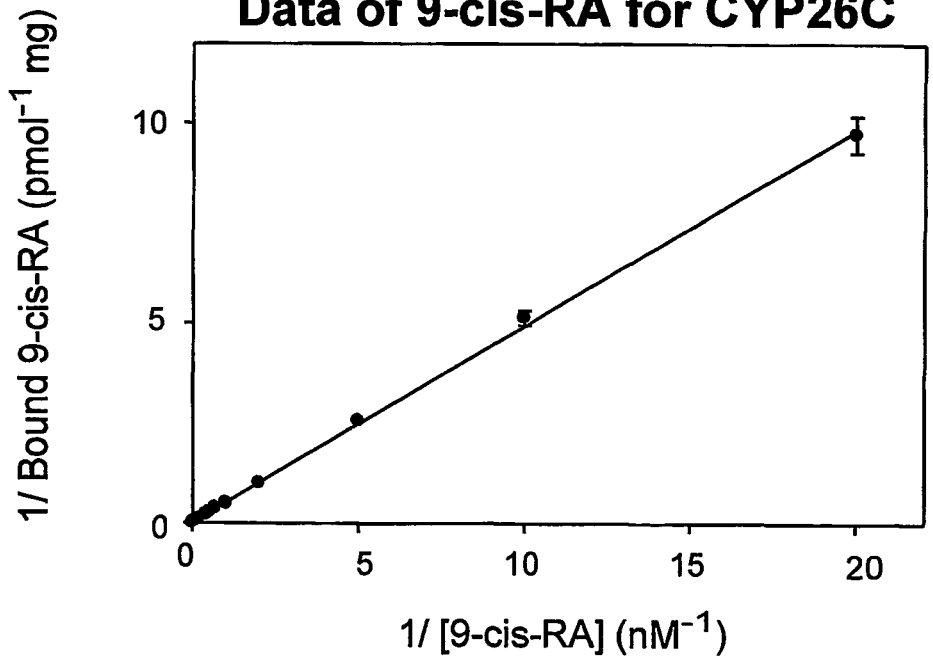
FIGURE 18

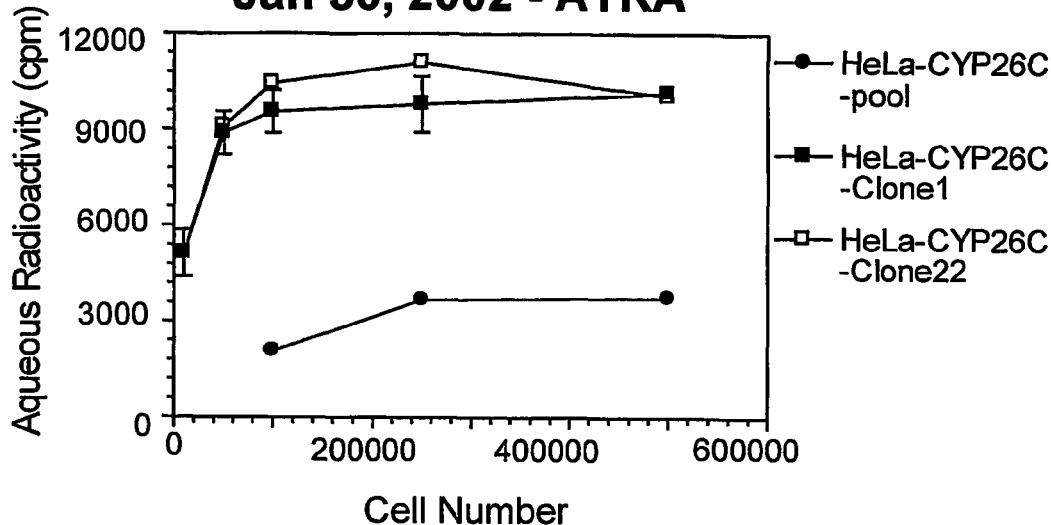
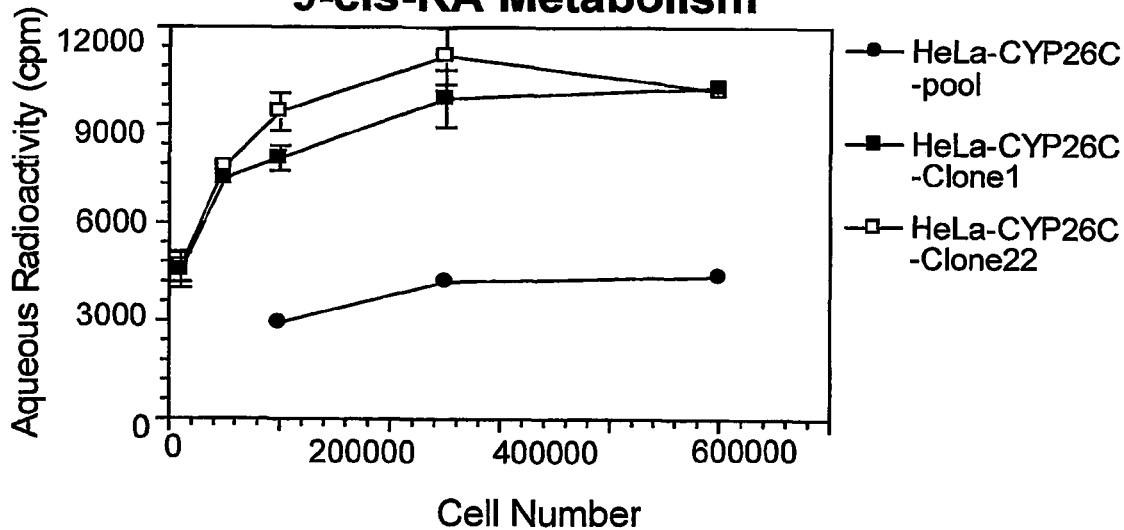
FIGURE 22

SEQUENCE LISTING

```
<160> NUMBER OF SEQ ID NOS: 29

<210> SEQ ID NO 1
<211> LENGTH: 1494
<212> TYPE: DNA
<213> ORGANISM: Homo sapiens
<220> FEATURE:
<221> NAME/KEY: CDS
<222> LOCATION: (1)..(1491)
<223> OTHER INFORMATION:

<400> SEQUENCE: 1 atg ggg ctc ccg gcg ctg ctg gcc agt gcg ctc tgc acc ttc gtg ctg      48
Met Gly Leu Pro Ala Leu Leu Ala Ser Ala Leu Cys Thr Phe Val Leu
1               5                  10                  15 ccg ctg ctg ctc ttc ctg gct gcg atc aag ctc tgg gac ctg tac tgc      96
Pro Leu Leu Leu Phe Leu Ala Ala Ile Lys Leu Trp Asp Leu Tyr Cys
            20                  25                  30 gtg agc ggc cgc gac cgc agt tgt gcc ctc cca ttg ccc ccc ggg act     144
Val Ser Gly Arg Asp Arg Ser Cys Ala Leu Pro Leu Pro Pro Gly Thr
        35                  40                  45 atg ggc ttc ccc ttc ttt ggg gaa acc ttg cag atg gta ctg cag cgg     192
Met Gly Phe Pro Phe Phe Gly Glu Thr Leu Gln Met Val Leu Gln Arg
    50                  55                  60 agg aag ttc ctg cag atg aag cgc agg aaa tac ggc ttc atc tac aag     240
Arg Lys Phe Leu Gln Met Lys Arg Arg Lys Tyr Gly Phe Ile Tyr Lys
65                  70                  75                  80 acg cat ctg ttc ggg cgg ccc acc gta cgg gtg atg ggc gcg gac aat     288
Thr His Leu Phe Gly Arg Pro Thr Val Arg Val Met Gly Ala Asp Asn
                85                  90                  95 gtg cgg cgc atc ttg ctc gga gac gac cgg ctg gtg tcg gtc cac tgg     336
Val Arg Arg Ile Leu Leu Gly Asp Asp Arg Leu Val Ser Val His Trp
```

```
                100                      105                      110
cca gcg tcg gtg cgc acc att ctg gga tct ggc tgc ctc tct aac ctg       384
Pro Ala Ser Val Arg Thr Ile Leu Gly Ser Gly Cys Leu Ser Asn Leu
        115                      120                      125 cac gac tcc tcg cac aag cag cgc aag aag gtg att atg cgg gcc ttc       432
His Asp Ser Ser His Lys Gln Arg Lys Lys Val Ile Met Arg Ala Phe
130                      135                      140 agc cgc gag gca ctc gaa tgc tac gtg ccg gtg atc acc gag gaa gtg       480
Ser Arg Glu Ala Leu Glu Cys Tyr Val Pro Val Ile Thr Glu Glu Val
145                      150                      155                  160 ggc agc agc ctg gag cag tgg ctg agc tgc ggc gag cgc ggc ctc ctg       528
Gly Ser Ser Leu Glu Gln Trp Leu Ser Cys Gly Glu Arg Gly Leu Leu
                165                      170                      175 gtc tac ccc gag gtg aag cgc ctc atg ttc cga atc gcc atg cgc atc       576
Val Tyr Pro Glu Val Lys Arg Leu Met Phe Arg Ile Ala Met Arg Ile
            180                      185                      190 cta ctg ggc tgc gaa ccc caa ctg gcg ggc gac ggg gac tcc gag cag       624
Leu Leu Gly Cys Glu Pro Gln Leu Ala Gly Asp Gly Asp Ser Glu Gln
        195                      200                      205 cag ctt gtg gag gcc ttc gag gaa atg acc cgc aat ctc ttc tcg ctg       672
Gln Leu Val Glu Ala Phe Glu Glu Met Thr Arg Asn Leu Phe Ser Leu
210                      215                      220 ccc atc gac gtg ccc ttc agc ggg ctg tac cgg ggc atg aag gcg cgg       720
Pro Ile Asp Val Pro Phe Ser Gly Leu Tyr Arg Gly Met Lys Ala Arg
225                      230                      235                  240 aac ctc att cac gcg cgc atc gag cag aac att cgc gcc aag atc tgc       768
Asn Leu Ile His Ala Arg Ile Glu Gln Asn Ile Arg Ala Lys Ile Cys
                245                      250                      255 ggg ctg cgg gca tcc gag gcg ggc cag ggc tgc aaa gac gcg ctg cag       816
Gly Leu Arg Ala Ser Glu Ala Gly Gln Gly Cys Lys Asp Ala Leu Gln
            260                      265                      270 ctg ttg atc gag cac tcg tgg gag agg gga gag cgg ctg gac atg cag       864
Leu Leu Ile Glu His Ser Trp Glu Arg Gly Glu Arg Leu Asp Met Gln
        275                      280                      285 gca cta aag caa tct tca acc gaa ctc ctc ttt gga gga cac gaa acc       912
Ala Leu Lys Gln Ser Ser Thr Glu Leu Leu Phe Gly Gly His Glu Thr
290                      295                      300 acg gcc agt gca gcc aca tct ctg atc act tac ctg ggg ctc tac cca       960
Thr Ala Ser Ala Ala Thr Ser Leu Ile Thr Tyr Leu Gly Leu Tyr Pro
305                      310                      315                  320 cat gtt ctc cag aaa gtg cga gaa gag ctg aag agt aag ggt tta ctt      1008
His Val Leu Gln Lys Val Arg Glu Glu Leu Lys Ser Lys Gly Leu Leu
                325                      330                      335 tgc aag agc aat caa gac aac aag ttg gac atg gaa att ttg gaa caa      1056
Cys Lys Ser Asn Gln Asp Asn Lys Leu Asp Met Glu Ile Leu Glu Gln
            340                      345                      350 ctt aaa tac atc ggg tgt gtt att aag gag acc ctt cga ctg aat ccc      1104
Leu Lys Tyr Ile Gly Cys Val Ile Lys Glu Thr Leu Arg Leu Asn Pro
        355                      360                      365 cca gtt cca gga ggg ttt cgg gtt gct ctg aag act ttt gaa tta aat      1152
Pro Val Pro Gly Gly Phe Arg Val Ala Leu Lys Thr Phe Glu Leu Asn
370                      375                      380 gga tac cag att ccc aag ggc tgg aat gtt atc tac agt atc tgt gat      1200
Gly Tyr Gln Ile Pro Lys Gly Trp Asn Val Ile Tyr Ser Ile Cys Asp
385                      390                      395                  400 act cat gat gtg gca gag atc ttc acc aac aag gaa gaa ttt aat cct      1248
Thr His Asp Val Ala Glu Ile Phe Thr Asn Lys Glu Glu Phe Asn Pro
                405                      410                      415 gac cga ttc agt gct cct cac cca gag gat gca tcc agg ttc agc ttc      1296
```

| | | | | | | | | | | | | | | |
|---|---|---|---|---|---|---|---|---|---|---|---|---|---|---|
|Asp|Arg|Phe|Ser|Ala|Pro|His|Pro|Glu|Asp|Ala|Ser|Arg|Phe|Ser|Phe|
| | | |420| | | |425| | | |430| | | |

```
att cca ttt gga gga ggc ctt agg agc tgt gta ggc aaa gaa ttt gca     1344
Ile Pro Phe Gly Gly Gly Leu Arg Ser Cys Val Gly Lys Glu Phe Ala
        435                 440                 445 aaa att ctt ctc aaa ata ttt aca gtg gag ctg gcc agg cat tgt gac     1392
Lys Ile Leu Leu Lys Ile Phe Thr Val Glu Leu Ala Arg His Cys Asp
    450                 455                 460 tgg cag ctt cta aat gga cct cct aca atg aaa acc agt ccc acc gtg     1440
Trp Gln Leu Leu Asn Gly Pro Pro Thr Met Lys Thr Ser Pro Thr Val
465                 470                 475                 480 tat cct gtg gac aat ctc cct gca aga ttc acc cat ttc cat ggg gaa     1488
Tyr Pro Val Asp Asn Leu Pro Ala Arg Phe Thr His Phe His Gly Glu
                485                 490                 495 atc tga                                                              1494
Ile

<210> SEQ ID NO 2
<211> LENGTH: 497
<212> TYPE: PRT
<213> ORGANISM: Homo sapiens

<400> SEQUENCE: 2

Met Gly Leu Pro Ala Leu Leu Ala Ser Ala Leu Cys Thr Phe Val Leu
1               5                   10                  15

Pro Leu Leu Leu Phe Leu Ala Ala Ile Lys Leu Trp Asp Leu Tyr Cys
            20                  25                  30

Val Ser Gly Arg Asp Arg Ser Cys Ala Leu Pro Leu Pro Pro Gly Thr
        35                  40                  45

Met Gly Phe Pro Phe Phe Gly Glu Thr Leu Gln Met Val Leu Gln Arg
    50                  55                  60

Arg Lys Phe Leu Gln Met Lys Arg Arg Lys Tyr Gly Phe Ile Tyr Lys
65                  70                  75                  80

Thr His Leu Phe Gly Arg Pro Thr Val Arg Val Met Gly Ala Asp Asn
                85                  90                  95

Val Arg Arg Ile Leu Leu Gly Asp Asp Arg Leu Val Ser Val His Trp
            100                 105                 110

Pro Ala Ser Val Arg Thr Ile Leu Gly Ser Gly Cys Leu Ser Asn Leu
        115                 120                 125

His Asp Ser Ser His Lys Gln Arg Lys Lys Val Ile Met Arg Ala Phe
    130                 135                 140

Ser Arg Glu Ala Leu Glu Cys Tyr Val Pro Val Ile Thr Glu Glu Val
145                 150                 155                 160

Gly Ser Ser Leu Glu Gln Trp Leu Ser Cys Gly Glu Arg Gly Leu Leu
                165                 170                 175

Val Tyr Pro Glu Val Lys Arg Leu Met Phe Arg Ile Ala Met Arg Ile
            180                 185                 190

Leu Leu Gly Cys Glu Pro Gln Leu Ala Gly Asp Gly Asp Ser Glu Gln
        195                 200                 205

Gln Leu Val Glu Ala Phe Glu Glu Met Thr Arg Asn Leu Phe Ser Leu
    210                 215                 220

Pro Ile Asp Val Pro Phe Ser Gly Leu Tyr Arg Gly Met Lys Ala Arg
225                 230                 235                 240

Asn Leu Ile His Ala Arg Ile Glu Gln Asn Ile Arg Ala Lys Ile Cys
                245                 250                 255

Gly Leu Arg Ala Ser Glu Ala Gly Gln Gly Cys Lys Asp Ala Leu Gln
```

```
                260                 265                 270
Leu Leu Ile Glu His Ser Trp Glu Arg Gly Glu Arg Leu Asp Met Gln
            275                 280                 285

Ala Leu Lys Gln Ser Ser Thr Glu Leu Leu Phe Gly Gly His Glu Thr
            290                 295                 300

Thr Ala Ser Ala Ala Thr Ser Leu Ile Thr Tyr Leu Gly Leu Tyr Pro
305                 310                 315                 320

His Val Leu Gln Lys Val Arg Glu Glu Leu Lys Ser Lys Gly Leu Leu
                325                 330                 335

Cys Lys Ser Asn Gln Asp Asn Lys Leu Asp Met Glu Ile Leu Glu Gln
            340                 345                 350

Leu Lys Tyr Ile Gly Cys Val Ile Lys Glu Thr Leu Arg Leu Asn Pro
            355                 360                 365

Pro Val Pro Gly Gly Phe Arg Val Ala Leu Lys Thr Phe Glu Leu Asn
            370                 375                 380

Gly Tyr Gln Ile Pro Lys Gly Trp Asn Val Ile Tyr Ser Ile Cys Asp
385                 390                 395                 400

Thr His Asp Val Ala Glu Ile Phe Thr Asn Lys Glu Glu Phe Asn Pro
                405                 410                 415

Asp Arg Phe Ser Ala Pro His Pro Glu Asp Ala Ser Arg Phe Ser Phe
            420                 425                 430

Ile Pro Phe Gly Gly Gly Leu Arg Ser Cys Val Gly Lys Glu Phe Ala
            435                 440                 445

Lys Ile Leu Leu Lys Ile Phe Thr Val Glu Leu Ala Arg His Cys Asp
450                 455                 460

Trp Gln Leu Leu Asn Gly Pro Pro Thr Met Lys Thr Ser Pro Thr Val
465                 470                 475                 480

Tyr Pro Val Asp Asn Leu Pro Ala Arg Phe Thr His Phe His Gly Glu
                485                 490                 495

Ile

<210> SEQ ID NO 3
<211> LENGTH: 1598
<212> TYPE: DNA
<213> ORGANISM: Homo sapiens

<400> SEQUENCE: 3
atgctctttg agggcttgga tctggtgtcg gcgctggcca ccctcgccgc gtgcctggtg      60
tccgtgacgc tgctgctggc cgtgtcgcag cagctgtggc agctgcgctg ggccgccact     120
cgcgacaaga gctgcaagct gcccatcccc aagggatcca tgggcttccc gctcatcgga     180
gagaccggcc actggctgct gcagggttct ggcttccagt cgtcgcggag ggagaagtat     240
ggcaacgtgt tcaagacgca tttgttgggg cggccgctga tacgcgtgac cggcgcggag     300
aacgtgcgca gatcctcat gggcgagcac cacctcgtga gcaccgagtg gcctcgcagc      360
acccgcatgt tgctgggccc caacacggtg tccaattcca ttggcgacat ccaccgcaac     420
aagcgcaagg tcttctccaa gatcttcagc cacgaggccc tggagagtta cctgcccaag     480
atccagctgg tgatccagga cactgcgc gcctggagca gccaccccga ggccatcaac       540
gtgtaccagg aggcgcagaa gctgaccttc gcatggcca tccgggtgct gctgggcttc     600
agcatccctg aggaggacct tgggcacctc tttgaggtct accagcagtt tgtggacaat     660
gtcttctccc tgcctgtcga cctgcccttc agtggctacc ggcggggcat tcaggctcgg     720
cagatcctgc agaaggggct ggagaaggcc atccgggaga gctgcagtg cacacagggc     780
```

```
aaggactact tggacgccct ggacctcctc attgagagca gcaaggagca cgggaaggag      840
atgaccatgc aggagctgaa ggacgggacc ctggagctga tctttgcggc ctatgccacc      900
acggccagcg ccagcacctc actcatcatg cagctgctga agcacccac tgtgctggag       960 aagctgcggg atgagctgcg ggctcatggc atcctgcaca gtggcggctg ccctgcgag      1020 ggcacactgc gcctggacac gctcagtggg ctgcgctacc tggactgcgt catcaaggag      1080
gtcatgcgcc tgttcacgcc catttccggc ggctaccgca ctgtgctgca gaccttcgag      1140
cttgatggtt tccagatccc caaaggctgg agtgtcatgt atagcatccg gacacccat       1200 gacacagcgc ccgtgttcaa agacgtgaac gtgttcgacc ccgatcgctt cagccaggcg      1260
cggagcgagg acaaggatgg ccgcttccat tacctcccgt cggtggcgg tgtccggacc       1320 tgcctgggca agcacctggc caagctgttc ctgaaggtgc tggcggtgga gctggctagc      1380
accagccgct ttgagctggc tacacggacc ttccccccgca tcaccttggt ccccgtcctg     1440
caccccgtgg atggcctcag cgtcaagttc tttggcctgg actccaacca gaacgagatc     1500
ctgccggaga cggaggccat gctgagcgcc acagtctaac ccaagaccca cccgcctcag     1560
cccagcccag gcagcggggt ggtggttgtg ggaggtag                             1598

<210> SEQ ID NO 4
<211> LENGTH: 512
<212> TYPE: PRT
<213> ORGANISM: Homo sapiens

<400> SEQUENCE: 4

Met Leu Phe Glu Gly Leu Asp Leu Val Ser Ala Leu Ala Thr Leu Ala
1               5                   10                  15

Ala Cys Leu Val Ser Val Thr Leu Leu Leu Ala Val Ser Gln Gln Leu
                20                  25                  30

Trp Gln Leu Arg Trp Ala Ala Thr Arg Asp Lys Ser Cys Lys Leu Pro
            35                  40                  45

Ile Pro Lys Gly Ser Met Gly Phe Pro Leu Ile Gly Glu Thr Gly His
        50                  55                  60

Trp Leu Leu Gln Gly Ser Gly Phe Gln Ser Ser Arg Arg Glu Lys Tyr
65                  70                  75                  80

Gly Asn Val Phe Lys Thr His Leu Leu Gly Arg Pro Leu Ile Arg Val
                85                  90                  95

Thr Gly Ala Glu Asn Val Arg Lys Ile Leu Met Gly Glu His His Leu
            100                 105                 110

Val Ser Thr Glu Trp Pro Arg Ser Thr Arg Met Leu Leu Gly Pro Asn
        115                 120                 125

Thr Val Ser Asn Ser Ile Gly Asp Ile His Arg Asn Lys Arg Lys Val
    130                 135                 140

Phe Ser Lys Ile Phe Ser His Glu Ala Leu Glu Ser Tyr Leu Pro Lys
145                 150                 155                 160

Ile Gln Leu Val Ile Gln Asp Thr Leu Arg Ala Trp Ser Ser His Pro
                165                 170                 175

Glu Ala Ile Asn Val Tyr Gln Glu Ala Gln Lys Leu Thr Phe Arg Met
            180                 185                 190

Ala Ile Arg Val Leu Leu Gly Phe Ser Ile Pro Glu Glu Asp Leu Gly
        195                 200                 205

His Leu Phe Glu Val Tyr Gln Gln Phe Val Asp Asn Val Phe Ser Leu
    210                 215                 220
```

-continued

Pro Val Asp Leu Pro Phe Ser Gly Tyr Arg Arg Gly Ile Gln Ala Arg
225                 230                 235                 240

Gln Ile Leu Gln Lys Gly Leu Glu Lys Ala Ile Arg Glu Lys Leu Gln
            245                 250                 255

Cys Thr Gln Gly Lys Asp Tyr Leu Asp Ala Leu Asp Leu Leu Ile Glu
        260                 265                 270

Ser Ser Lys Glu His Gly Lys Glu Met Thr Met Gln Glu Leu Lys Asp
    275                 280                 285

Gly Thr Leu Glu Leu Ile Phe Ala Ala Tyr Ala Thr Ala Ser Ala
290                 295                 300

Ser Thr Ser Leu Ile Met Gln Leu Leu Lys His Pro Thr Val Leu Glu
305                 310                 315                 320

Lys Leu Arg Asp Glu Leu Arg Ala His Gly Ile Leu His Ser Gly Gly
            325                 330                 335

Cys Pro Cys Glu Gly Thr Leu Arg Leu Asp Thr Leu Ser Gly Leu Arg
        340                 345                 350

Tyr Leu Asp Cys Val Ile Lys Glu Val Met Arg Leu Phe Thr Pro Ile
    355                 360                 365

Ser Gly Gly Tyr Arg Thr Val Leu Gln Thr Phe Glu Leu Asp Gly Phe
370                 375                 380

Gln Ile Pro Lys Gly Trp Ser Val Met Tyr Ser Ile Arg Asp Thr His
385                 390                 395                 400

Asp Thr Ala Pro Val Phe Lys Asp Val Asn Val Phe Asp Pro Asp Arg
            405                 410                 415

Phe Ser Gln Ala Arg Ser Glu Asp Lys Asp Gly Arg Phe His Tyr Leu
        420                 425                 430

Pro Phe Gly Gly Gly Val Arg Thr Cys Leu Gly Lys His Leu Ala Lys
    435                 440                 445

Leu Phe Leu Lys Val Leu Ala Val Glu Leu Ala Ser Thr Ser Arg Phe
450                 455                 460

Glu Leu Ala Thr Arg Thr Phe Pro Arg Ile Thr Leu Val Pro Val Leu
465                 470                 475                 480

His Pro Val Asp Gly Leu Ser Val Lys Phe Phe Gly Leu Asp Ser Asn
            485                 490                 495

Gln Asn Glu Ile Leu Pro Glu Thr Glu Ala Met Leu Ser Ala Thr Val
        500                 505                 510

<210> SEQ ID NO 5
<211> LENGTH: 0
<212> TYPE: PRT
<213> ORGANISM: Homo sapiens

<400> SEQUENCE: 5

000

<210> SEQ ID NO 6
<211> LENGTH: 32147
<212> TYPE: DNA
<213> ORGANISM: Homo sapiens
<220> FEATURE:
<221> NAME/KEY: misc_feature
<222> LOCATION: (8113)..(8212)
<223> OTHER INFORMATION: n is any nucleic acid

<400> SEQUENCE: 6
cgtctctaca aaaacacaa aaattagccg ggcgtggtgg tatgtgcctg tagtcccagc        60
tgcttgggag gctgaggcac aagaattgct tgaacctgag gccaggtgcg gtggctcacg       120

-continued

| | | | | | |
|---|---|---|---|---|---|
| cctgtaatcc | cagcactttg | ggaggccaag | atgggtggat | cacgaggtca | ggagtttgag | 180 |
| accagcctga | ccaacatggt | gaaaccccat | ctctaactaa | aaatacaaaa | aattagccgg | 240 |
| gcatggtggc | gtgtgcctgt | aatgccagct | actcaggagg | ctgaggcagg | agaactgctt | 300 |
| gaacctggga | ggtggaggtt | gcagtgagcc | gagatcacgc | cactgcactc | caacctgggc | 360 |
| aacaaagcga | gactccgtct | caaaaaaaaa | aaaaaaaaaa | aaaaaaaaaa | aaagaattgc | 420 |
| ttgaatccgg | gaggagaagg | ttgcagtgag | ccgagattgc | accactgcac | tccagtctgg | 480 |
| gtgacagagc | gagactctgt | ctcaaaacaa | caacaacaga | aaacacaaaa | aacaaataaa | 540 |
| taaggagtta | acatggtta | cttctgagta | cggcagtgaa | ctgttggttt | catgatatgc | 600 |
| tccatttgat | tattaactat | gtatttgata | aaattaattt | taataaatta | accacataaa | 660 |
| ttcacatgta | tgtatctata | tgctatttta | gccatggtag | tgaccaaaaa | gaaaaaaatc | 720 |
| aaaataaagc | aaatatggat | gtgtgtaaat | ccaattatgt | aaattttact | gtattcctct | 780 |
| tttttttttt | tcaaattcca | aactcaccta | gaggttatct | aggactacta | cattagctta | 840 |
| gcataaaaaa | atactttaag | aacattctac | atttgcatgt | acagttcacc | tgagtgaagt | 900 |
| tacttgaaga | gactaattcc | tttaagcagc | ttctgcagca | tgaagtgctc | agaactcact | 960 |
| cctagtcctc | acagaggtgg | gagtgaaagg | attggctgag | agcaagtcta | gcagatggga | 1020 |
| cattggaaga | gggcaggctt | gggtgaaggt | gcatcagatc | cagaaggtag | catgaaggca | 1080 |
| gttaacacct | gaaggcaaaa | aagtgaggtg | gctggaggca | caatactgtt | ttgcttttt | 1140 |
| gtattgtagt | tattgcctat | gctccttctg | actgctactt | aaaattctgt | gctacatgtg | 1200 |
| gagttttcca | aatgtggtgt | ttttagatgg | ctggaaagga | aggaaaatcc | aggtgcttta | 1260 |
| aaaatcatat | ggagctcatc | atttgacctc | acaatatatt | ttgtaaaagg | acttgtagtt | 1320 |
| ttttccaatg | tagctaattt | agtaagaccc | atttttcttg | aattcccagt | ggcaaattac | 1380 |
| tcaggatttg | ttagaaggac | aagtatttct | tccttgaagc | agtactaggg | tttaggactt | 1440 |
| ttgttgttta | aatctctgga | gcactctagg | aaccctggtc | tcagctttgc | ttttggagg | 1500 |
| caaaggaaaa | atgatctcct | ggtttacttt | tggaatctgc | aaagcaactc | tgaggtccca | 1560 |
| ggtggattta | gtgtttggaa | aagggaactt | ggggactga | ggttgaccct | gagccccag | 1620 |
| gtcactgttc | acgttacaa | aagcaaacct | ggtatcccca | gttgcttttc | tcttgaggtt | 1680 |
| ggcttaactt | tatttatctt | ctgtcctggg | tcactgcccc | tgaggtgctt | caaaagcaaa | 1740 |
| acccaaaaga | cccaaaacaa | agaaagctaa | atcagattca | aggaaaaaat | gacctggcac | 1800 |
| tgtgggttca | cttttaaaaa | ggcaaaaagt | cacttcaaga | gtttcataga | atagttttaa | 1860 |
| gtctgcctag | attcattgtg | tcatttgtac | aaagtgatct | caacaggtct | gaaaccccaa | 1920 |
| gttccttggg | catggatcga | gaatgagtct | gtaggatggg | aaactgtcag | caagctaaat | 1980 |
| gggttgacac | aaatgaattc | ctcagtgatt | ctgaagtgat | tcaactattt | tgagcatata | 2040 |
| aatgggacca | cccatgtaac | acttctttcc | ttaagctgat | ctttgtgttt | gctggacaca | 2100 |
| cacagggaat | gctgaggaag | tgaaatgtac | aactcactta | caaatgttgg | catacaccca | 2160 |
| ctttatgtta | tcagattagt | tatgaagggt | atttttgaat | ccttggtgaa | aaaaaacttg | 2220 |
| gaatactaat | ttcagataat | cttacaaatc | atgatgaggt | agaactcaag | cacatgattt | 2280 |
| tgccttttca | tttttatatc | atctgtactt | tgcttacttc | ccaaaaggat | ttaaggtgga | 2340 |
| attactttac | ttgactattg | gaagaaaccc | atttataaag | cttaatacca | attttcatta | 2400 |
| tcatatgcct | gactttatcc | tttaataagt | aattgtaaaa | ttgcttttgg | gtaatctggg | 2460 |

```
gagattttg ttttttgttca tgtttgatct acatctttga acttcaggtg tatgtgttaa    2520
ccaataaata cacctgttga gaccatgtcc tactgtttat ttacaagact gaaagagatt    2580
ttgtgtgatt aataacaaac atattatttg tgcattgcca tctgaaggaa gcaaaactta    2640
agtagagaag tgagattttt cataatgtag atcttaatat taagaacata gtgcatcctg    2700
tgaagcctaa ccaattgtga gaggcagtcc gcaaggcagt gactgttggg gtagagtgaa    2760
ggcaagtatt agtgtttgta cctggcaaca ccccagtttc ccctttttcta cccatcacac    2820 tctgactcca aagcaatcat gttctttttaa agtcatccca atcaaagacc agggtcatct    2880
tggtcggaac aggcatggat agctgcctgt ggaaatgggt tcagtccata aaatctggcc    2940
tggcataatg ttaggtggga cccaggaata aagtcctggt tttttgtttt atccttcact    3000
tcaatagaac tgaattataa aaagtgaaaa atgaccttat aattgttatg cgtgaaggag    3060
actgatagac aattcagaaa tattaacgct actttctcca ggaagatcat ttgacttact    3120
taacgttaga cccaatgctg tatcatgatg gagtctctcc tctttatcaa taccccagtg    3180
aaaagctggg agagatacag ggatgtcact tcactatatt cacttgccat agtttgcctg    3240
caagccaaca ttggccttttt tcagagagct atcagcataa gctaaagtag cctgtactta    3300
taaagcctaa gaaaaaagct cccaaggaaa cttggaataa tggtctggca tcatcattta    3360
atcagttatt tcctgaatat ctactgagtg gttagactgt gctagacaca ctttatgagc    3420
ttgcctgccc agttttgaag tttgtttcta tttacttgtt ccagcagtac aatgcatttg    3480
aaaaatcctt acacacatga aaatgataaa tgagaatatg agatcaacat gcttgctggc    3540
tccatctttg ctctctgccc atgtccatgt gtagtctttg ggacacaaac actgaaatgt    3600
ctcagccatt ggatcttcag tcattggatt catagactga gcggaatgag caggcagtca    3660
ccagcttcta tataagttaa tggtttctat tttattctat attaaagtga tagtagcttc    3720
ctcatgtgtt actgtagttt aaattactag gattctgtgt gaatagcttt tctttataat    3780
ttcttccatg ttaacatcaa aagattactg ctttattcct atcttacaat gtaagctcct    3840
tgaggaaaga gattttgtct tgttccaatg ctgtatctct ggtacctagc acagtatcta    3900
gcacgtgata ggtggggagt caatatatgt tgaataaata aatgaatctt atgtagatca    3960 ttggctttt tgtctgcttt ggcaattaat tccttaacca ttaatttgca aattcgtgca    4020
gatttctaca gatacctgta aattaactgt gtacaatatg tatttctata aatatttata    4080
caaagattaa tgtcaatatg aaagcatata gatttgtcta catatgggca ggtaggttta    4140
attttgtggt tcctgtaatt tctgcggatt tgcacataag agatttgcat atgagtatct    4200
gaccatatgt gaacattgta agcatagtgt ttctttatcc aggacagtct ggtcttgtgc    4260
tgtaaaagaa tcaattctgt attcacagtt ggagttggtg cgggttttttc attcattaag    4320 tcggctcctc ctttcccact tgggggtaaa tcagcctaga gaaaagagc cttaagaggt    4380 tgctttctgc tgacactgtg cattgcacat gcacagttgc gcaaatacac acatatacct    4440
gaaagaagaa tccttgaaaa tgaggcttct gttgacaact ctgtgagggg tgttcattat    4500
tgaaatttat tttaatatat aaatatataa accttattta taactatagt attaacacat    4560
atccattgta gagtattaca aaaataaaga aaataacagt taaccttaat cccaccacat    4620
aaatgacaat cattcttttt taaaaattac tattttagag gtgaagtctc attatgttgc    4680
ccagggtgga ctcttaactc ctgggctcaa gtgatcctcc cgcctcagtc tccagagtag    4740
ctgggactac aggaacacac caccatgccc agcttataac cggcatcctt aacgttttg    4800 caaatttttct tccagtcttt ttggatgggt ttttatgtaa cttaagtagc aacatttatc    4860
```

-continued

```
ataaacatta tcccaagtta tttaaaattc tttgtaaaca ttaattttaa taaccacatg    4920
atagtcatca tacagataga cctcactact taaccagtct cttaatattg agatttaggc    4980
tattttcagt ttttgataac acaaataaca ttttttgagat taatatcttt gtgcataaat   5040
ttttttctgt ttctcgaagt tgcattccaa gaagtaggat tgctgaatca aagggaatgg    5100
ccactttat aaggttctta aacacattgc agaatcacat tccggagacg ttatactaat     5160
ttacactctt accatctgag tgtatgaaag taacttttcc tctttgtgaa aggagggaaa    5220
aatgtggcca acaacagtt aaaaattaca cagaacttta aataagttcc cttttctttt     5280
tcagacagta tattctttaa cattgtctca gtatagtttc tatcctagtg tttcaactgt    5340
tggtatggcc cagaatggta tcttgtccga aagaaaatag agtggctttc catagttaat    5400
attttcatta tagaattttc tgcctgttgc aagaaaatct ctattaatac ctgtaaattg    5460
gatgggaaa tagtcaagca agttctttac cttcatcaag aaaagctagt ttctggtgac     5520
cttctttat gaggttttaa tcaccccaga gttttatccc tctcagagtc agtggtcggc     5580
tcttgtatcc catgagtaaa tgcaaatgtt cctccatt gaaagcaaaa ccagtaagac      5640
cccttactta taaagtgagt taaaacaaaa agaaagaata taaaaactaa aggaaggtag    5700
taagtaaagc atttagcttt ctgaaacaat tcaaatgggg ataggaagtt ggttttaaat    5760
ggcttaaagg ggattagggt tttaaagttg gataaagagt ttggtgctta ggtttaggca    5820
tggcattgct tttaaaagat tacttccata tttgacaatg attctaactg gagattataa    5880
agtaaatagt caatttaag acaccacggg aaacaagagg gtttcttttt tgttgttgtt     5940
tgtttataca aaatggtagc ctagagttaa caggctgaat cctgaagccc tcatttcata    6000
atactacaga ggatctatca ccagagagaa tctagcagag gttgtttaat gcacttaatt    6060
gagattatct gagcttttgg tttaaattac tttggaaaaa gtcttaggtg caaacagcgt    6120
ccttgaaagg taaacatact tacctctaag aaaaaaggt tcaatttaag ttcttaaaa      6180
ttcttcatac aggttagtag caccaacctt tattaattaa atctgggtac tgactaatgc    6240
ataaagataa aatttctata catcagtaca agggttaata tatattatat taacattgtt   6300
ttcattattt tacaattatt tgaaaacatg aagtatttta ctagaaaaca acccctggca    6360
ttttttagtaa tttcaaagta aaagatcta ttttgattgt aaagtacagt taatgaagtt    6420
ttaaaaatga atttccgtat tctgttccat ctaagaagca agccatatta aaatggacca    6480
aggatagcat ataattttaag tattaactgg gtaaataatc aaaagttgat ttaacatttc   6540
ccccatcttt cgcagctcct tgacctgttt atggtttggg attggtctac ttacctagct    6600
gattatgggc agccagcttc taagtacctt cgggtgaatc caaacacagc ccttactctt    6660
ttggagaagt gagtatattc tgaaactttt ttgtataaca ttttagcacc ttttgattca    6720
gtgataaact gaagaactag agatttctgt caaaaagaa aagtctagat ggagcttaaa     6780
agctcactct agtttaatga ccaaaaaata agcttttctt tcttgccctt cagagttggt    6840
gtagtttcat aagcaactgc tgtttatatt gatgtgaaca aaacatcttt cctttttgtat   6900
cctgaattgc aagcttaatt gaccttagaa atatgtttac tggggatgtg acaattggag    6960
ctttctttaa aaaaaaagt ctataactca ggaagaagg tattttgtca aatgtgacca      7020
ggaattggaa tgtttgccac cagtgttacc taaatcttag cattatggac ttggattctt    7080
tgcaggtaga gaaatatgtg atttgaaaaa aaaatacag taaaaactga ggtaatagga    7140
tttactgatg catcttgtcc aactaaacat aaatttaggt gttaactttt ccctctcatt    7200
```

```
atgtgacaga cttttctt actcaatcat atttcattta aaatgtcact attgggagac      7260
tctctgaatc tgctgtgatt ctgggggctg ctggataaga aaataaaaa agtatcacta      7320 ttaaaatttt caatttaaa ttaaaattgt tattattttc ctatatttca aaatatttgt      7380
ggtgtatttg atttgaaagg acaagaggaa gtgtttaaaa taaatgtaaa tttattttac      7440
aatgccatga aatgcaactg aggcaaaaac atcgctattt tacattttct aatgttattt      7500
tcctttcacc ttatcttgct atgaatatga ttagcagagt ctatacaggg tatgtatttt      7560
agcatacttt gtggaataat attagaaaat agtatgatag tagtaaacct agcatatttt      7620
agatgtacat actaatgcaa aaataccact taacatagaa tgtaaaataa agcttctaat      7680
tttttgcatg gttactatat ctgtatgttt atttagtatc tactttcttt gaactatatt      7740
tttcaagcat aggattagtg tgggataatt cagagcatgc caagatattt tacttgtgac      7800
agcttagctt ttaattttct tttaccaagc ttcttcattc acatatgttt ctaggatgaa      7860
ggatactagc aaaagaaca atatatttgc tcagttcagg aagaatgatc gagacaaaca      7920
gaagttgata gagacagtcg tgaaacagct gagaagtttg gtgaatggta tgtcccagca      7980
catgtagacc tcacatggct tgcactcagt gacaccaaat ccatgattca atgttgatct      8040
tgagcaagta ttggtcatga tacagtaatt tgtttacaga atccaaaaat acaatagaga      8100
agatacatga gggcttaaac aagaaatagt aataaatatc atttgtatgg attttttaaat     8160 aatcgaatac tattttatat atggaaaaaa atgaccatt ttcacttt aggggaaaat         8220 gcaaaagtgt aatacataaa ttgtcacaaa ttatacatga aattgattac aaatacattt      8280
gaaaaacata tgcctctact cataagtatt ttttctatt tagacttgaa tgataatctg       8340
ttttttgatc agtatatggc tttggaattc aatcatgtct gatatggtag tatttcacta      8400
ccattttctg acttttagct tttattttca cctcaatgtg atttaagcag accaaaattt      8460
ctaattctgc taattctgaa ggggaaatag acaaatctta aaagctgcct gaaatcaaac      8520
ttgatttaac tcagtaagaa tgtgaattat tgttctact tgggtggttt aatttaatcg       8580
ttctgaatat gaacaaaagg ttttggattt tctaaagatg cagtgttgtt tctgttcatc      8640
agggttaata tttctaacta tattgcttgt aggtgacccc attctggatt tgtttggttt      8700
ggtttggttc cagttaaaag agaggacagg aactaaatgg ggctaaccac ttcaggtgca     8760
gcttgtgcga gggtagatgg ttcctgcaca cagaagttac cacagggtc aggttacttt       8820 cttcaaatag cagatttcag tactttatcc tcattgtgga aacaagccaa accaaatgaa      8880
ctctggaaaa cctaaaacaa atgtacattt tccttgtgt atgtttccgt ggtccaaatg        8940
gcaatataaa tccagtcttt attctcctt tgttgtattt atgctgaatc ttccttttgc        9000
cttttcagga tttaggcctg taagaaacta tgcctgattc tgtaaaataa gtgtaaagaa     9060
ttatatgtac atctctggat tttgtgatga atattaaaa atattgagca agttgttgaa       9120
aatgcattac tattttgtct attcagagct tactgattta aaacaagtgc ttcctggaga     9180
aaaggcatat tatttcctag ttactggaat gggagtggca ccaaaacagt atatatacat     9240
acacacacac acacacacac atatatatac atatgcgcac ttgttctctc gatcatctct      9300
taatccaaag tatttaatgt ttttaaaaat attacatgaa aagcatggta gttcttcagg     9360
cacggtgaaa tctggaggag aggagcggtg aacagctagc tctctttgaa gactggaatg     9420
gggctgccct tcgcgcctta cccagccttc cagcgtactt gggtgtctt ccctgctttg       9480 gctgagacgt cccgggattc agagagatac tgcctttgca ctgcctggag gagaccactg     9540
tgggacctct ttactcttac caataatata aacaccctgc acccctccac acacaccca      9600
```

```
ggttgcactg tagggacaag aacgagtgag tcctgaggca tttggaaccc ttgaatggga    9660
cgcacaaagc ccaaaacgca acaatgtaga ttgacaagag tcgtcgggca aactcggggg    9720
agggagggaa ggatgtgcag ggaaggatga attcggtcct tgagaccgga aaggtgctcg    9780
tgggtatccg cttctggagg cttaggacgt ctttatgaag cctagggcag tagtggaact    9840
gccatctttg gaaggatacc tgacgtggta gatcagagag ccgggagagg tggggagctg    9900
tcggagaatc tcggctgcgc tatccctcct gggcttttgc gatgccaacg caggcgtcga    9960
cgactgcagt ttccctgaaa tagtcggagc aaaggagaga aaagcccagt tctttcacct   10020
tggagtggcg agagaaaggc acctagaagc tcgagggcgg ggacggcaga gggagccagc   10080
ggccgggggt gggccaggag cactgcgggg cgcaagcccg ggtcagttct gcgcgttggg   10140
ttcgcccact ttctgagcgc ctgcgaagag cggggaagct ctggcgcgaa cccgcaggcc   10200
ccgcccgagg acgctcgcgg ggcgagcccc cagcccagct cgagccgccc cggcgcctgc   10260
cactccctac tcagagcccc tccgtgagcg cgccgctgcc caccgcctcc aatcaccact   10320
ctgcgtggag cgctttaaat atgcaaagac acgtcacgtt gtgtgaaccg ggatcggtcc   10380 gtagggggggg agccaatatc tatataaacg tgtccagcgt gggccaagaa gggttaaacg   10440
actggaggag ggacaggtgg ggcgggggtc tgcagaccag gttggcaaca ctggtgagtt   10500
gctcttcttt cgcccctcctt cccttcttct atccaaaggg tgctgagccc gggaggaggt   10560
gggaggtgcc ccgcggagcc gggagtgagc gttcccgagg cagcaggcac cttcgagagg   10620
gactggcatt tgggcccagg agccaggaaa aagtcctgag cgtgccggcc tcaggaaggg   10680
cacgttccct aagggcgcac ggtcactgca gtctttcacc gtccgtctgt ttttagaaca   10740
gagttctggc ctgagcttat aaatctcggg cttttgccccc aaaccccagg ccttttgcgg   10800
acggaacagg tgagcactgc gcactgctcg cgccccggtt cttgcgtccc ctgctctccc   10860
tgcgctctga gcggcctggc ccccgcgggc tcatcatgtt cccttggggg ctgagctgcc   10920
tgtcagtgct gggggcggcg ggcactgctc tcctgtgcgc gggcctgctg ctcagcctgg   10980
cccagcacct ctgaccctc cgctggatgc tgagccggga ccgggcctcc accctgcctc   11040
tgcccaaggg ctccatgggg tggcccttct tcggcgaaac gctgcactgg ttagttcagg   11100
tgagcagtcc ttcgaccccg agcgctaata cggtcccttc ttccccggc tcccactgga   11160 ccctcctcag tctcaatgcc catgggattt gtagccagtc cctgcccatc gcccacgacc   11220
ccgggaagcc cgcacaactc tcgcctttac ctagatactc cgttccctcg aagggacctc   11280
aagtcactgg aattcccccc agagcaactc ccagacacaa cgcaggggt aaacataagg    11340 ggttttagga aggggtctga ggagcacgtc ctgcaagggt agaaaaggag cctgagctt    11400 ggcccagctg tgagcccttg ggccctcact tcttcactct gagtctgttt cctcatctca   11460
ccaataggaa caggagcatg tacattcccg tagagtagat accaggccca ctggggatct   11520
tgttttgtaa acgcgccagc cagggacagg aagttgtgat caaaaggcag ctggaaggtc   11580
tgggtcagat cccagcccag gcccagaagt tccagctctc caccctccgc ctcgcccgca   11640
gggctcgcgc ttccacagtt ctcgccgaga gcgctatggg acagtgttca agacgcacct   11700
gctgggcagg ccagtgatcc gcgtgagcgg gcgcggagaac gtgcgcacca tcctgctggg   11760
cgagcaccgc ctggtgcgca gccagtggcc gcagagtgcg cacatcctgc tgggctcgca   11820
cacactgcta ggtgcggtcg gcgagccgca ccggcggcgg cgcaaggtga gtggaaacgg   11880
gaatggaccg tagatacgtc ggatccgcgg tccccggcat ctgccatggg ccaggccggg   11940
```

```
gccccggtgt tggatacact gtgaacccga ccaaggtccc tggtaactag cgggtggcct    12000
tgggcgggtc cgttaccttc agcttcggtt tataaagtta ggactgcgct aaaagattct    12060
ttcatctccc atcttccgtg gctgtgatag cagaagcgct ggagactcag acctagaaag    12120
gggccaggga agacttctta gaggagatgg cagctggagc ctggatggtt gggagggact    12180
gtgtgcatca gagcagaact gggggaaatg gcgaaagcaa aagccaggaa gtttaggtct    12240
gggccgcttg gaagagggag aaaggaccgg aactggcctt ctggctactc cggaatcgcc    12300
aagcagatga ggccagaccg ccgccagcgc tgatcacgcg cgctcccaca ggtcctggcg    12360
cgcgtgttca gccgcgccgc gctggagcgc tacgtgccgc gcctgcaggg ggcgctgcgg    12420
catgaggtgc gctcctggtg cgcggcgggc gggccggtct cagtctacga cgcctccaaa    12480
gcgctcacct tccgcatggc cgcgcgcatc ctgctggggt tgcggctgga cgaggcgcag    12540
tgcgccacgc tggcccggac cttcgagcag ctcgtggaga acctcttctc actgcctctg    12600
gacgttccct tcagtggcct acgcaaggta cggccgcccc ggctccagac cttcctccga    12660
ggctccgcgg cgcgggcggg cctcccagac ccagacggga cgccctcggc gcaccccgcg    12720
cgtccgtcac ctctgctggg aacggcggca gggcccgggg gtgggaggcg ttgtggcggt    12780
ggcgtggcgg tgggctctgg gcctggcctc tgtgctggtt cgctggtgtg acctggggct    12840
ggccacacga cctccgtggg acgcgcctgc cgcgacgcgc tccagcctga gcaagcgcgg    12900
gccgccagag tttggggtct cggtggcagg cgtcctgcca gtcggtcgga ctccttccca    12960
cagcggcgcc cctggggccg gcctccatca cctcttcgga agcccagatg gctgcggaac    13020
cgaggagagc gtgagggctg cagatgagcc ccggtccagc ccagcgccag ccccggaccc    13080
aggggtgtgg gcgtcagctc caccagccct ggaccgcta ggtttcggga tcagagaact    13140
gctgcttctc cagacttcag aacaatgggc aggacccgga gagcagctag gatgcccat    13200 cccgcctttt ggtccccta ttctgggact tcccactgtt tgattccctg gttttcagtc    13260
acctgcataa aaataatatg tgtaaaggat catgctatag gctgatcacc gtggatacgt    13320
tttctgatct aatcctcgca gcctgcaaag tgttatgatt ctcatttat tggccaaact    13380 tattttattg acttacccaa gatcacaccg ttagtagggg cacgaacagg actttaacct    13440
catctcctcc gactatggaa ctcaagtgct gaattacagt gctttccccg ggggaatgct    13500
tttgctgcgg ctattccctg aactctggag aggcatcccc tattgcccac gctcttacag    13560
aggctaatgc ttacaaatcc aatagtgtcc tctaagtcag agctttgctg ggtgcatcaa    13620 ggtacccag cctgagccta gtacaggaa agggcaatgg gctgaccccta gccgcactgg    13680 gctctgtgcc aggcatggac atggacagct gtgtgactct gggcaattgc ttgacctctc    13740
tgaacttcag catcctctcc tcaggatgac agtaactctg ctgtggctca gaggggatt    13800 gtgataatca agacagaatg atgtttgtgg acagtggaca tatccccgac catttactga    13860
gcccagccat atgccaggcc aggagctaag ctggaagct gttaacacaa ggatgttggc    13920
agagccagtg ctgagaaggt tttctgggta agtggccggg cttggccccc ttagccttcc    13980
tgccccatct ttcttctctc cctgaacatc agggcatccg gcaagggac cagctgcatc    14040 ggcacctgga gggggccatt tctgagaagc ttcacgagga caaggctgca gagccgggtg    14100
atgccctcga cctaatcatt cacagtgcaa gggagctggg ccatgagccc tccatgcagg    14160
agctgaaggt aggtgctgac aggccgctcc ttctcccctc ttttgcattc ccagcaggtc    14220
cctacaccaa tgctgcatcc ccagagccac atcttgtgtg gccccacttt gaggcacagg    14280
cagtcctcaa gatgagggggc aagaggagac ctgggttcca gtaatgactc agccacactc    14340
```

```
actacctctg cagccttcag cctccagcca gccttgtcag taggagaact gaaggcaaga    14400
atcctaggcc catctttgca ggtttctggc cacaaatggc tctctctcct ttccttcccc    14460
cactgccctt ctctgccact ccatgccttt gcctctgctg tcccctgcc tacaaagccc     14520
tcattattca ttttttctag aaactctaag gggctcagga tcaaactcca catcctcaaa    14580
gctcccttct tccttccaaa atcacctctc tccttctatg agctaccttg cacctggta     14640
cctctatccg tctgtcttgt tgctgtggat ctcctggaga attaggaccc ctcccccttgt   14700
acacacatcg cacatacagt ggagggagg tggtaagctt tggaatggcc ccaggacttg    14760
cttgagcacc caaaaaggag tggagaagtt aggggagg gaagttagaa atagggagac     14820
ctcaatcttc cataagcaac tcttacgcat cctttctctg gcctcagtt tcccactttc     14880
taccagagac atccctgaag ggtaggcctc agctttagct tcttttctga gattggaact    14940
aataagagca tgagcaatgg gctcttcttg cgcagagcag accaagaaga catttagtga    15000
ctccctggga ccattccgat agggagagga tgaagccatg atgccggcat tggtacgagg    15060
ctggcactgc tgctgcaggt gcctttgttg cactgcagcc attgtcaggc tgttccactg    15120
gggttggcgg ccgcaccacc aggtggtgaa gagcactgga ctcctgccgg gagtgctagc    15180
tgtagggacc ttgagcacta ctctggagtc tccgttttca actccataaa acaagagcag    15240
caattgtgcc tcacagaggg gaggtgagaa ccgaatgagt gaatatgctt aaagcaccaa    15300
gaagagtgct tagagtaagt tcccgcattc tctctgggaa ccatcgcaag gcggtggat    15360
agatcctaat gttgcctgtt gctacagctg actttcccaa atggtggact tgagatttaa    15420
tcgacttcaa aaccgtacac acagtcgcgg cggtaatagc acttccctgc cccctggctt    15480
ttcgcaatag taaatttggg tgcttttcat ctccacgggg ccgtcgggtc agcgccccgg   15540
gcgactccac cgcccgagac tcagtgcagc ccggggctgt cttgcaggag tcggctgtgg   15600
agctcctctt cgccgccttc ttcaccacgg ccagtgccag cacctcgctc gtcctgctgc   15660
tactgcagca tccggcggcc atcgccaaga ttcgggagga gctggtggcg caggggctgg   15720
ggcgcgcgtg cggctgcgcg cccggggccg ctggggcag cgaggggccc ccgcccgact    15780
gcggctgcga gcccgacctc agcctcgcgg cgctgggccg tctgcgctac gtcgactgcg   15840
tggtcaagga ggtgctgcgc ctcctgccgc cagtgtccgg gggctaccgc accgccctgc   15900
gcaccttcga gctcgacgta agtgcgccgt gccagcccat ggccagcctc ctgcctcctg   15960
ccgcctgccg cctgccgcct gccgcctgcc gggcggcgc ccaggtggga ggagggcgga    16020
gggattcgga cggcgcggtc acctcttttg ccctcagagc ctcagccttc cgtcctataa    16080
aatgggctga gccttgttcc acctcccggg atccccgct gagggacgca aagcctggcg     16140
agactgcaag gttagggatc tcgtacccctt cagcttttgg cagcggttcg gaacggtcaa   16200
ttcaatgaga gcggagtttt agaataaaaa tactcttcta tccgtgcagc acccctccc    16260
agccagtgag tgtggatgga gaacaaagag aacccctcag tatgtcctgt gctccacccc    16320
tctggctccc tcacaagatg aaggaacccc tcattgcgac cggtccaggg ttctggctgg    16380
ggccagattc caggggaggg ggggattaaa ataccgggta gacgcttcat ctctgatcag    16440
gccggtttgg gctgagcaag gttgaggtct agaactgact ccatctccgt atgaccttgg    16500
gcagttccct cttcactctg ggcctcagtt tactctctgc aaggaagctg tcttggtcct    16560
ttccagctct gacactccat ccaggtgggt ccgggctgtg ggggtacagt ggtggcctca    16620
ggcagtggtg ctctggctgt gccaaactgt gggtgtttgc ctgaaaggct gtcgttgcag    16680
```

```
tccccctgagc accatgcttg gtggctgggt ggctccagat aaaaatgggc attccacagt    16740
gaacatttgt ggcacattgc gtgccagggt tcaggaggca tcaaagggac tgggattcta    16800
ccctggaggg gctccacttg gagaggaagg gggccgggac tgacagcctc atcccacttg    16860
tagtgtgaca gcctcatccc acttgtagtg tgaagagagt gatctctagt gctggatgac    16920
accaacacat tctgagagct ggagtttgaa ctggagcagt gaaaggtttg acgggagag     16980 cctattacag agagagcaga ctcagacaaa ggtggatgtt gagaagtgtc ttgaatgcgg    17040
aatcagtctt ggaatgcaag cttcattctg caggcgctgg agtgccctac aagaccttag    17100
ggaagcacag aaccagggtg gtgagcagag acaggaaag ggtcttagcc acctccagtt     17160
cacagatgag aacactgatg tctagagagg aaagagagct cctgggatga ttccaagatg    17220
ttctgttctc cagttagaaa ctttgagtat tcaccctgga acttgatatg agggtagcag    17280
tgtagtcagg gggttggaag acgtatcaaa aagccaaatg gttgaaaaag ctaggggtgg    17340
gcagagggaa catgaaaact gcctttcagc attttaagga tggccagttt gattctcatg    17400
tgcgccttct taaagtgtgg taccaaatct gaacattatc gtccagctga tggatgggaa    17460
ggatggcaag ttttcagttc aatgcaaaga agagctctac catggaactg acctcgagga    17520
attgtcatgt gcattttcc cactctagca gctgggaggt gtagcactag aatttaggtc      17580
tcctcatcta aggtcagaag aaaaaaagac aaaaccaaac gggaacataa ctaatagtta    17640
ccgtttactg aacactcata tgtgccaagt ccttaatttg aatcctcacc aacaaagggg    17700 ccattttttcc cctcattttt tcaaagagga aactgaagct cagagaggct gcgcatctag    17760
cccaaggtca tacatttcac cagtgaagga gttgagattg aacacagag ctttctcctg     17820 gtttccgggt taatcgcgga ttcctcctgg ttttcggaag cctgatggaa gcaccagggt    17880
ggagggtcag ttcagggccc ccccgtttcc aggtgcctcg tggtcaggct gatctcctcg    17940
cctctctgca gggctaccag atccccaagg gctggagcgt gatgtatagc atccgggaca    18000
cgcacgagac ggctgcggtg taccgcagcc ctcccgaagg cttcgatcca gagcgcttcg    18060
gcgcagcgcg cgaagattcc cggggcgcct ccagccgctt ccattacatc ccgttcggcg    18120
gcggtgcgcg cagctgcctc ggccaggagc tggcgcaagc cgtgctccag ctgctagctg    18180
tggagctagt gcgcaccgcg cgctgggaac tggccacacc cgccttcccc gccatgcaga    18240
cggtgcccat cgtgcaccca gtggacgggc tgcggctctt tttccacccc ctcacgcctt    18300
cggttgcggg gaatgggcta tgcctctgac atgcttgcgc tctaggacac ggcttggccg    18360
gtggctatgg cgcgcacgca gcgccacca tctgccgctc cccattgtag cgtcgcgcgc     18420
ccactctttc actcgttcaa caatctttca acaaatgttc gccaaacgcg gatgtgtgcc    18480
ggactcgagg aaggaggagg gcgagccacc gctgccgcgc cagagaagca tctaagccca    18540
tgggaagatg ccttctgcgc tccgcgccca gaggaaggaa aatgtcgtgg gccaagcagg    18600
aatggaggga atagatagat ccccacgagg tgctgcttgg cttccccttc ccgagccaat    18660
ccagggaggg tgcatggatg ggggaaggcg aggtaggggt ggcaggggag tgggaatatt    18720
gcaactcggg gacattgcag agacccgacg cacgcggtgg gacctgcaac ccttgtaagg    18780
aagcgggcac gccgtgggcg caaccctggc ctggctttgg gccatagaaa aaacacgcag    18840
aggatgcctg acgaaggcc ctctggcagc tggcgtctgg cttcgtgcgc cttggccact     18900
ctgccggtct cggcggaaac tagcaactgt gggcacttcc aggctcgaaa gggctcaagg    18960
tcaccggatt ctgctggcca cttcttaaaa ggaaaaattc ctaccttaag aaggcattta    19020
ctcttgtcat gtatacagag gagaataggc acaccaacac gtctccaacg ctggattatt    19080
```

```
ttcatgggag gttgagacat aattagagag gtttgagata tttgtaccaa aaataggaag    19140
gccaagaaat aaagtgtctt gggagcggtt gagtgaggag gctagggttt atctgggcag    19200
ctgctccctg gggggaaggc actggggtgc agggttgggg aggccaggga aggacccacc    19260
ccacagtaca cccagagagg agctgggagc tgggcagcct agggcctggg ctgcccagac    19320
ttctctctga gtataacccc agaagctggg ctgtgaattg tctccaggtt tcagggacct    19380
tattttattt tttatttttt tgagacaggg tcttcctctg tggcccaggc tggagtgtag    19440
tggcacaacc agctcactgc cacctctgcc tctcgtgctc aagccatcct cccatctcag    19500
cctcccaagt agctgggact acaggcacgt gccacaacgc ctagctattt tttttttctat   19560 ttttaataga cacggggggt ttcaccatgt cacccaggct ggtctcaaac tcttgggctt    19620
aagcgaacca tctgccttgg cttcccaaag tgctggggtt agaggtgtga cccaccacac    19680
cctggagtca ctcctttcca gtgactccag tctagtccct gcgccctcac ccctccctgc    19740
catttcaggg ccttctggtt ttacggcttc accatcctct ctatcacaga gaagaaattg    19800
aggagcaatc taggtgaatg actcacctga gaagcccagc aataggctcc tggactcccc    19860
agccagtgct ctcctccacc cccatccctt cactcttctg ccccaacctc tgttcctgtg    19920
gccatcaggt agggctgaac actttggcct cctttttcatg ataagcccta gctagacttg    19980
aggactctct caaccattcc ggtacagagg ttccaaccag tgtttaaatc aaagccaaaa    20040
gcctccatgt catcattccc aacagcccac ttcaatctgc cacccagctt ccaacagacc    20100
ggggcagctg gacataaggg gtgagccagg gaagtagctg cctaggcctg agctgacccc    20160
ttagtgaacc agaagaaagc cagtgccctc ctgacctcat gcttaaggtg gatcccaggg    20220
ccagaaggaa gggggacaca gcaggcactt acagggttgg tagctccaca gtacagcaag    20280
cccttccaac ctgggctgac actgccataa cccccacaca gggcaattca tcacccattg    20340
tcagccaagg gcctggtgcc aggccctgag cttgggagac accaggggca gcaaggtgg    20400 caggacgtgg gcccgcccta agagtgctct tgcaaatgca gaggacagcc tggcctgaga    20460
agcgtgggtt tgggcgagga gaaggatgca ggcttcaggg ttgattgtga tttagagaga    20520
ggagagaaga atgggggtggg gaccctcaga agcaaggcta gttgagctgg ttccaagaag    20580
acctggttga cctgcattgg ggtctggact aactataagc ctctgtaggg atggctccag    20640
ttttaatttt ccatggatac atcatgctca gtaattttga gggatatctt agctcctgtt    20700
ttagtagctg cagattctct ggggaaggag cagaggaggt tccttccctc ctgcacttga    20760
tatgctctgg agggaggcag acaagaaata aactagcaaa caaaagggta agaatatgtc    20820
cagtggtgat aatcgccgtc atggaaataa acaggcctg tgatagtgtc tgggctaaa     20880 ttaggctgga tgggtggggg gaaccttgga ggaggtgaca tttgactttg gaaggaacca    20940
gccagcggtg gcctggggga ggggtgccac atgcagaggg aacagcaggt atagaactgt    21000
gagacaggaa cgcacgttca gaaatgagac cggggggctga aaggagaaaa gcggaggtgg    21060
actcctttgc tgtgactcca gtctagtccc tgtaccctca ccccacccca ccagcaaaaa    21120
aaacaaaaaa acaaaaaaac aaaaaacccg actccccatc cccgcctctt agcaataggg    21180
aggctgtttt gtaaacatct tggaaacgag ttgtttttca gtgaacccac cccctcccc    21240 gcccaccacc acccacgaaa gcttggcgag attcctagat caaagttcct attggcctgg    21300
taatttattg accccccacc ccccgccctg ccccccctaca agatgttctt taatgatcgt    21360
tcactctcac attttaatcct ttcctgccgg acgccccccgc cggcctcgat gtacagatag    21420
```

-continued

```
attaaaacgt ttttttccct gcggcaattt ccagcgtgca ggccccgctc atcttgtgac   21480
ccggcttgag ctgaacttgg cgaggtggcc ccgcagagtt cactcggatg tcacggtccg   21540
gcctgcaggg gtcacaggcg ggtcaggccc gaggattggg aatgggcccc aggtcacgtc   21600
cccattcgtc ggctttgcac accggccgga ggcgctgtcc agaaagggc ggacccggga    21660
tttctgagaa ttacctccag cgcgattggc ctggcttcct gcagtggcca gaggttggtt   21720
cgccgtgttt acagccacca aatcgtttgc cggagactga aaccctgccc agagcctctg   21780
aaacactggg caggttatgg ggaaacgctg acccccgaa acactccctg tggcggcgac    21840
tctggcttgg agagtcgcta ggattgtgcg ggtccctccg acctctgcag atatttcctg   21900
atacctccgg gtttggggac taccgcgaga agggcaacgc atttaaactc tcaggagcag   21960
agttttccac ctccaaggga cgccttccaa ggcgtgcggc gtgcttctgc cagagacagt   22020
gttcagtttt aaacaaatgc aggtcattct gtttcatttt cggcgccgca ggtgcgttca   22080
gcgcccaaac ccaggtagcg tgtgaccctg actggtcccg agccgggaag ctccggcagg   22140
tggagagcag agagagcagg tgcgcgtccc gcagcgtctg agctccgggc attggcagct   22200
cagtagcagc tgattgtaga tgggcaaagt acagaagact tcccagtacg gatcccttca   22260
cccctcccat tagggtcgg tagagccctg agtttagggc cgagcacccc ctcacctgga    22320
tgaggacagt ggctttactc tgggtgggac ttgggagaga ggaggaggac tccagtgccc   22380
ggtgtaccgg acacccaggt aacgcagtct accgtgcctg gagctgggaa gagtagttgc   22440
aaccggagcc ccctttgggg aactcactac cctgaggctt agacaggtcg ggaatgatcg   22500
cctcccggtt aaggaggagg aaacaggcac agtgatgtgt ggtgacttgc ccaaggtcac   22560
acgcagtaca gatggagccg ggcctcgag ccaggactcc tgggctcccc ttcctcttat     22620
accgtctctt tatcctgcca gggctaagga ccccctcc tgctgtccag ctggggcgcc     22680
aagcagcagg gccctccgaa taggcgagct gtgcttggat ctcagagacg ggcaccgact   22740
gccgagcccc agacgaagtg ccccagggtc ggggatcagg cttgtgcagg gtagcacctg   22800
gggacctgag ggacctggag gccttcttgt atcctgaagt aggaccttct aagacttcat   22860
gagtcctggc cccctttgcag gggttgggga gctgggatc ccagatctgc ctattgcgcc    22920
cgatgccccg aggctctctc ttggactctg gccctgagtt cttctgcgcg atccttcgga   22980
gacgtctgga ggcctgcttt atgcatctct cttggacctc agtttcccca cacgtgggag   23040
gaggcagctg gacgattcct gaaaggactt tcccttgctt cctcatcacg tggaagagag   23100
cccacccggc acctggaaat ggaaagccag tgaaggctgc tttgggccgg ggcagcgggt   23160
gggaccgggc ggggagggatt ccaaagagac cgccggaag gctagagctt ggaattccgg    23220
ctcctcggag tcctggccct cccccaccgc cgcctcggag ctcagcacac cttggatggg   23280
ggaggcgggc agctcctagc cccgcacccc aggaggcgcg ctcggaggga agccgccacc   23340
gcgccgcctc tgcctcggcg cggaacaaac ggttaaagat tttgggcagc gcctcgcggg   23400
gggaggagcc aggggcccaa tccgcaatta aagatgaact ttgggtgaac taattgtctg   23460
accaaggtaa cgtgggcagc aacctggcc ggctataaag cggcagcgcc gtggggttg     23520
aagcgctggc ggcggcggca ggtggcgcgg gaggtcgcgg cgcgccatgg ggctcccggc   23580
gctgctggca agtgcgctct gcaccttcgt gctgccgctg ctgctcttcc tggctgcgat   23640
caagctctgg gacctgtact gcgtgagcgg ccgcgaccgc agttgtgccc tcccattgcc   23700
ccccgggact atgggcttcc ccttctttgg ggaaaccttg cagatggtac tgcaggtaag   23760
ggagggtggg gcgggacagg ctgcttcccc ggagcccggc gcggctctgg gcttctgctg   23820
```

```
aagtcgggt aggcgccccc gggaggcatg ctattgcggc taggagcagg gctggcggga    23880
gcgcggcgct ccccggcgcc ccctcatgcc cacttctctc ctccgccttc ctcccacagc    23940
ggaggaagtt cctgcagatg aagcgcagga aatacggctt catctacaag acgcatctgt    24000 tcggcggcc caccgtacgg gtgatgggcg cggacaatgt gcggcgcatc ttgctcggag     24060
agcaccggct ggtgtcggtc cactggccag cgtcggtgcg caccattctg ggatctggct    24120
gcctctctaa cctgcacgac tcctcgcaca agcagcgcaa gaaggtgggg gcaggaggcg    24180
acggctggac agggaggggg accccattta tgagcggaat tccggctgat ggatgctagg    24240
cgcgggctag cagcttgagg tgggctagga ccctctgcca gctccaggtt agctttccca    24300
gctcggagag tgccatgtgt ctggcaggac tgggggtgtc tggaagggga cggcggtaga    24360 cgagagggc ggatggaggc ttttaacgct gtcccctcct cgggactcag gtgattatgc     24420
gggccttcag ccgcgaggca ctcgaatgct acgtgccggt gatcaccgag gaagtgggca    24480
gcagcctgga gcagtggctg agctgcggcg agcgcggcct cctggtctac cccgaggtga    24540
agcgcctcat gttccgaatc gccatgcgca tcctactggg ctgcgaaccc caactggcgg    24600
gcgacgggga ctccgagcag cagcttgtgg aggccttcga ggaaatgacc cgcaatctct    24660
tctcgctgcc catcgacgtg cccttcagcg ggctgtaccg ggtaagggcg gcaaacgggc    24720
tgcggactag gggcgcggga cctgggcgtc tgctcaccgc cgcgcgctct ctgcgctcag    24780
ggcatgaagg cgcggaacct cattcacgcg cgcatcgagc agaacattcg cgccaagatc    24840
tgcgggctgc gggcatccga ggcgggccag ggctgcaaag acgcgctgca gctgttgatc    24900
gagcactcgt gggagagggg agagcggctg gacatgcagg tgagtagcag cttcagacca    24960
ggcactgcgg agtttggtcc cctggctttc caagcgctgt tcctggggcc cccaaagcgc    25020
gcgcctgggg cccagctttc tggagtgggc ggccggctca gactacagct atggaatccc    25080
gaaggaaggc tgagacaccc ggtcaggaga gctgcggaag gggctgcggc ggaactggga    25140 gcatcccta gccttccag gtttcaaagg gaaagttgga atttgcaaaa atgttaataa      25200
agaaccttgc gattttaata aaactaagac tttaactcag gagtttccgg tagagcgggg    25260
tcgtactcgc cttactgctc cagctgaact aaagggacgt tgcatttgt ttaaagatat     25320 tgctttcctt gactttctgt cagcaaaaca tttagccctt ctagtcttcc ctccagaact    25380
ctcagttcga ttctgagtaa tccttctgtc aaaccgcagg cagacttgtg agaatgtggg    25440
tctcactcta ttcttaggca ctaaagcaat cttcaaccga actcctcttt ggaggacacg    25500
aaaccacggc cagtgcagcc acatctctga tcacttacct ggggctctac ccacatgttc    25560
tccagaaagt gcgagaagag ctgaagagta aggtagggag actgggtctg ggggtgtcct    25620
tattagctta ggaaattcag ctgctcccta gccaacttcc gaataagtca gtgtgctgcc    25680
ttcatggagt attttgaaag tgcagggccc agggctgcgt gggccagtgg gcagaattag    25740
ctttgtgaat aaacaggatg gagtcttgag ctgtgagccc acttgggcag ggtttgacct    25800
tgtattccta cccctcctcc accttttgct gaaccgtgga gattctcaga taggttccac    25860
tttcttgaat tggtgtgtcc aagggcatac atagtgtgaa tagctgatta gtgtgggtgg    25920
tggtggtgag tgtggggtgg gggggcgtgg ggagaaactt ggtccttcta actggtgagc    25980
agcattctcc tgggattgta aatagatagt ggatttgggc aggcaaatgg ccattagctg    26040
ctgtttcccc ctcccagtct ctcccatcat ggggcccttt gggtttagtc tccacttaag    26100
ccctgtttac gtctgctggg ctgatttat tggagcacaa aataactgtt cacctctgta    26160
```

```
tgactgtttt gatagggttt actttgcaag agcaatcaag acaacaagtt ggacatggaa    26220
attttggaac aacttaaata catcgggtgt gttattaagg agacccttcg actgaatccc    26280
ccagttccag gagggtttcg ggttgctctg aagactttg aattaaatgt aagttaaaat     26340
tctcttcttt ctcccttttg ttgtggttta aaaactcctc tttcttccct atgctgtggc    26400
tgcaattctt atgcttttga taattgttct gccctatatg gagatatgtt tcagcaacct    26460
ggatccacct ctctcttct acctctccct tgcttttagc tcataatttc ccccaaagat     26520
atcagtgact gcttttgtt gttgaaagtt aaattccagt ttgtcagccc ttggggtttc     26580
ataatctttt gcagggatac cagattccca agggctggaa tgttatctac agtatctgtg    26640
atactcatga tgtggcagag atcttcacca acaaggaaga atttaatcct gaccgattca    26700
tgctgcctca cccagaggat gcatccaggt tcagcttcat tccatttgga ggaggcctta    26760
ggagctgtgt aggcaaagaa tttgcaaaaa ttcttctcaa atatttaca gtggagctgg     26820 ccaggcattg tgactggcag cttctaaatg gacctcctac aatgaaaacc agtcccaccg    26880
tgtatcctgt ggacaatctc cctgcaagat tcacccattt ccatggggaa atctgatgag    26940
cttgaatgtt caaacctgag acttattgga agtgtacata tgagtttta aggagtgttg     27000 tgttgacttt atatttaatt tctaaatgta tattataata tttatgtgtt ttgactatac    27060
taccacaatc tttaaatatt aaaataatga atttgtatca tttccaaata aagtaaaatt    27120
tgaaggtact tttctggtat tttaagattc ctgttgggta aaactcacca gtttagtatt    27180
ttcttagtgt atttaaccag attttacaat gcctacctgg acttatttgt catctttgca    27240
tctgttttct gtgagaagaa atcttagctg tttttttatgt taacagttat tagaaaatat    27300
atgtctgtgt gtgttattcc agacgtatct ctgtaaattc ttctacagtc acttagattc    27360
cctatttgga aaattgatcc aagttaattt aattttttt tggtttgctg tactttaggg     27420
aaagatgaac ctgaaaaggt aacactgaga actgtcactc taacctctcc agcttatcta    27480
acatgtcata aacataataa atctgtgttg tccaatagtg ccagaactgt tctctgaagt    27540
tacggtttta gataagacaa agccagtcac tccagttatg gacagctctt gactaaaatg    27600
agaccagaaa tcattggcgt gtcacccttta cttagaagtt gcatatggaa acagtattag    27660
gaaaggcgca tctctggtta agataagctg agcccaggtt ttctttattc aaaatgaggc    27720
aggaggagca gatttagcag actgacagat aaagttttta tctatcccag gcaatagggt    27780
gtgagcctga catgactgat aaaatggccc agtcatgacc ctgtgaacct tggctaacct    27840
ccgtgaaagc gcagttttgt cacatttctg accctggcat agccacagtc tgaactgaag    27900
gccagactct caatccagaa aggttagccc cagtgacttg cttatgcaag cacattttg     27960 gttttggaat ggcacaatct gctcactgaa cctctgatga cttgtaggtt tcaaacttta    28020 cattttcat tacaattta gaatttggca atactgcaga aaccaggtgg tctaaatagg      28080
tgtttgaaaa gtgttctgtc tacagttaca tattctacct gactatagtt ttttaggtag    28140
aacttgggtt gttcttattg ttggactgct ctgaatttta aaggatgttt atgtaataac    28200
tcataatgcc gttaaaaaat gagacatttc aggctatgta gtttcagcca aagctttagt    28260
gtactatagt gtgcagagat gactcttcta cccctaacat ttttcctgga catttccagc    28320
taggagcatg ctagactgag ggcataatta tttcagataa tttctacaaa ggcattttta    28380
aattttattt tatttatttt ttgagacaga gtctcactgt gtcacccagg ctggagtgta    28440
gtggcacaat cttggctcac tgcaacctcc gcctcctggg ttcaagcgat tcacctgcct    28500
cagcctcccg agtagctggg attatatatg cacaccacca tgcccggcta attttttat    28560
```

```
ttttggtaga gatagggggtt ccaccatgtt ggccagggtg gtcttgaacc cctgacctca   28620
ggtgatccac ccaccttggc ctcccagagt gctgggatta caggcgtgag ccactgcacc   28680
cggcacaaag ccattttaaa acagctttt tttttttttt gaaacagcct tgccctgtag   28740
cccaggctgg agtgtagtgg tacaatctca gctcactgca acctccacct tccgggttca   28800
agtgattctt gtgcctcagc cacttgagta gctgacacta caggcgcatg caccatgcc   28860 tggctaattt ttgtattttg gtagagatg gggttctacc acattggcca ggctggtctc   28920
gaactcctga cctcaagtga ttcatccgcc ttggcctccc aaagtgctgg gattacaggc   28980
atgagccact gtgccccatc taaaagagtt ttaatacttt tcattcttct ggaggacagc   29040
tggcctttaa aacactatct tcgctgactt agtggctctg tttctctgcg aatgtagtgc   29100
agtcggaaat ctgagccatc ttaacatatc attcattttt taatctgggg agcttcgagg   29160
aaagtgcttc tggtttgcat ttcccagggc tagatttagc ccaattatcc tgatcagtta   29220
cagagtagca aagaattcat cttgaaaata cgttaaaaac acaatctttg atcatgtgct   29280
ttgtgcagag gaaaggcagt ctggaagcat gtgagcaagg ctgctgtctt ggacaatggg   29340
cctgggtcac atctctctgg gtcaagtatg ttttatggca cagtcacctc tgggctggtg   29400
tccacgtgat ggagaaatga tgtagatttg gccaaaactg tggaaggagg ggacatgacc   29460
cctcttggac tcactctgga aaatgaccct tcgggctcct agcagcatgg tgtagcgata   29520
ggggtgctgt gctgtccagg gctgctgcgg gtgggcgacc aagctggtgc cctctgcttc   29580
cccttgcgca atgcccttgg ccttgctgc ctcccatgtt ctcttcaatc aggactgtgt   29640
tgccaccaac cacagaccac tgtcaggact gagatgtgaa agcctgaggc ttcagcattc   29700
agagggattg gagcctttac ctagcaaggt ccttggaggc ccagagacag actgtagttt   29760
tcctggggcc acacagggag tggcagaacc aggaaagacc tccagatgcc attttttttc   29820
tttctttttt taaacagcta ataacacttg cccgatttct aactcgctgt tgccagacat   29880
aatccagggg tctcaacttc ctagcttcct tttatgtccc ctgctaccac tcccgtgcca   29940
gcacagatca attctcttgc aggtccccag aggtggttgg tgaaatggga gcgctgagag   30000
gaggtggctg ctccccgaga ctccctgtct ccggttgggg tttcagtgct ttttgcaccc   30060
tgttactctc cagagatcca caaggggggcg ggcttctccc ttctatgcca ggctcagagg   30120
ccagtggttt tccccaccag tgtccacgaa ttccagtgta caagactctg gcccagggct   30180
tgcttttacc ccggacagtg agaagctaca ggccacccag ggcttagcaa gtacttagca   30240
ccaggtctgg tcaaggctgc ctggcccctc tggaaggggt catcccaggc tgggctgacc   30300
tgcgcgtctt tcagttcctg aagcagccgc caacccttgg tggtctatgg ggtcagcggc   30360
ccaggtttcc agcattgccc ccacactgcc cacgtgtggc ttatgttgct ttcactctac   30420
ctggaaaatc gctgtcagtt ttgagggagc agggagcaca gtttccaaag aacgcgggca   30480
aactaatcag ccttcggatg accgcaacca ggtgcgggag ccaccgcaca aaagcaccta   30540
gggaggaacg agggacgtat agggaggttg cggtggctcc tttagacagt caaagggctg   30600
ctgtagtaaa cacaggttca gacccgttct gagggacaga gcatgctctt aggagggtaa   30660
agtaggagag agatgctggc gccatgtaag gaaaacattc tgagacaact ccagcccttt   30720
ggtgatgaaa caggctacct tgtgagaggg agagagtgag ctctctgtca acagaggcag   30780
ccaaatacaa agctggatac ctaagccgcc acagagatca agacatggag ggtgagcttg   30840
ggttagatga cccccccatcc cccttccaaa attaaacagt tgtgaatctc cgaaatgtga   30900
```

-continued

```
ttctgtatta attcagttcc tcagatacccc actttgaaat gcctggggct gtggagatgg    30960
gacatcccca cgtcctattc cagaggcatt cagcagtctt tggtgatcat tctcccaaac    31020
ctcagaggca gatgtggaag tgggagccca gatatgtgac ctcagaaagg caccaagtgc    31080
cctgtgttga ctgcccaggg acctctcccc tgccctgtga cttggtgttt cctgctccag    31140
gtcctgtgtc tgctccaacc acccctagtt cccccaacct gcccatgctg accattcgct    31200
tgacctggcc tctggggtca catcctgctt ccttccccag tcctcccgg gtccccataa    31260 tcccatgcac tgacattgtc ctctacccat cccagctgtc ctttgtctcc acctcctgaa    31320
atgtgctggg aggcaggaac tgtgtctcat tgttctaatc ttatacattt agtccatttt    31380
cacataccct ccagcctcc cctggaatgt acatgtagta ggtgttctct ggaagaaata    31440
cttcttgggg ccaattgaca ccatttacct tatgtttctc cagcttacat ggtgccatgt    31500
ttttctttga aaagtgaaac tttcatcctt gaaaaatctc agcggccgca agcatacacg    31560
gctgtggttt aacagcatgt cacattcctg aaaccgacgc tccacgggta tttgaccaaa    31620
caagctttcc ttcctttgaa gtagagtcaa ctcgagttag aaccctgaga cagggatgaa    31680
gattcagcct gggactgcat ggtgggtttt ctgggtgaga catatcatgt tgcaatattc    31740
ataaccacgc accctcagca cagaagctgc cccacactgt aagatttctc actgctgctg    31800
agccctccct ggtacgttga ggagttagaa acctgttcac gcctttagga tggtagatgc    31860
ttcaggattt ttgtttgttt gttttgtttt gttttttttg agatggagtc tcactctgtc    31920
gccaggctgg agtgcagtgg cacgatctca gctcacagca acctccacct cccaggttca    31980
agcgattctc ctgcctcaac ctccccagta gctgggacta cagggacgct ccaccacgcc    32040
cagctaattt ttgtattttt agtagagatg ggatttcgcc atgttaagaa ggatggtctc    32100
aatctcttga catcgtgatc caccgcctc ggcctcccag agtgctg                   32147
```

<210> SEQ ID NO 7
<211> LENGTH: 10
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: x=any residue
<220> FEATURE:
<221> NAME/KEY: MISC_FEATURE
<222> LOCATION: (9)..(9)
<223> OTHER INFORMATION: x=any residue
<220> FEATURE:
<221> NAME/KEY: MISC_FEATURE
<222> LOCATION: (5)..(7)
<223> OTHER INFORMATION: x=any residue

<400> SEQUENCE: 7

Phe Xaa Xaa Gly Xaa Xaa Xaa Cys Xaa Gly
1               5                   10

<210> SEQ ID NO 8
<211> LENGTH: 10
<212> TYPE: PRT
<213> ORGANISM: Homo sapiens

<400> SEQUENCE: 8

Phe Gly Gly Gly Ala Arg Ser Cys Leu Gly
1               5                   10

<210> SEQ ID NO 9
<211> LENGTH: 22179

<212> TYPE: DNA
<213> ORGANISM: Homo sapiens

<400> SEQUENCE: 9

```
tgagtagctg ggactacagg tgcctgccac catgcccggc taatttttta tatatttttt      60
tagtagagac agggtttcac tgtattagcc aggatggtct cgatctcatg tcatcatgat     120
ccaccctcct tggcctccca aagtgctggg attacaggcg tgagccacgg tgcccggccc     180
agcagcatta ttttaatag ccaaaaaaga taaatgtcca tcaactgatg attggataaa     240
caaggtgtgg tacatccata caatatatta ttatttgtca ataaaaagga atgaagtaat     300
aatgcatgct acaacgtgat gaaccttgaa atatattgc ttaagtgaaa gaagccagtt      360
acaaaagacc aggtaggtct ttttgttttg tttgttttgt tttgtgttgt tttgttttaa     420
atagaggcag ggtcttgctc tgctgcccat cctggagtac agttcattgc tcactgcagc     480
ctccaccttc tggactcaag ctagcctccc acctcagcct cccaagtagc tagcactaca     540
ggtgtgcacc accacagcca gctaattttt aattgtatgt cgaaacaggg tctcaccgtg     600
ttgcccaggc tggtctcaaa ctcctagtct caagccttgg cctctcaaag tgctaggatt     660
acagggtga gccaccatgg taggccagaa gaccacatgt tatttgattc ccatttgggg      720
agtgattgct aatggctacg gggtttcttt caggggctct aaaattgatt gagatggttg     780
cacaattctg tgaatagagt caaaaccatt gatttgtgcc ctttaaatga gttaactgta     840
tggtacatct caaagctgtt taaaaaaaaa ttttaaagt tataaacaa gaaatagagg       900
tttaattata ttaaagttat aaaaacaaaa atagacaaaa atggtaggat agctacccaa     960
gaagagagct ggtataaagt aaggtaaatt ctcatatgtg atagctgtaa aataataaac    1020
tcaaaattag aaaaataagc ctattaggga tagtgagata atcactagaa ctaaaagagg    1080
agttaaaggc cagacgcagt ggctcacacc tgtaatccca gcattttggg aggccgaggt    1140
gggtggatca cttgaggcca ggagtttgag accagcctgg gcaacatggt gaaacccgt    1200
ctctacaaaa aacacaaaaa ttagccgggc gtggtggtat gtgcctgtag tcccagctgc    1260
ttgggaggct gaggcacaag aattgcttga acctgaggcc aggtgcggtg gctcacgcct    1320
gtaatcccag cactttggga ggccaagatg ggtggatcac gaggtcagga gtttgagacc    1380
agcctgacca acatggtgaa accccatctc taactaaaaa tacaaaaaat tagccgggca    1440
tggtggcgtg tgcctgtaat gccagctact caggaggctg aggcaggaga actgcttgaa    1500
cctgggaggt ggaggttgca gtgagccgag atcacgccac tgcactccaa cctgggcaac    1560
aaagcgagac tccgtctcaa aaaaaaaaa aaaaaaaaa gaattgcttg aatccgggag    1620
gagaaggttg cagtgagccg agattgcacc actgcactcc agtctgggtg acagagcgag    1680
actctgtctc aaaacaacaa caacagaaaa cacaaaaaac aaataaataa ggagttaaac    1740
atggttactt ctgagtacgg cagtgaactg ttggtttcat gatatgctcc atttgattat    1800
taactatgta tttgataaaa ttaattttaa taaattaacc acataaattc acatgtatgt    1860
atctatatgc tattttagcc atggtagtga ccaaaaagaa aaaatcaaa ataaagcaaa     1920
tatggatgtg tgtaaatcca attatgtaaa ttttactgta ttcctctttt ttttttttca    1980
aattccaaac tcacctagag gttatctagg actactacat tagcttagca taaaaaaata    2040
ctttaagaac attctacatt tgcatgtaca gttcacctga gtgaagttac ttgaagagac    2100
taattccttt aagcagcttc tgcagcatga agtgctcaga actcactcct agtcctcaca    2160
gaggtgggag tgaaaggatt ggctgagagc aagtctagca gatgggacat tggaagaggg    2220
```

```
caggcttggg tgaaggtgca tcagatccag aaggtagcat gaaggcagtt aacacctgaa    2280
ggcaaaaaag tgaggtggct ggaggcacaa tactgttttg ctttttttgta ttgtagttat    2340 tgcctatgct ccttctgact gctacttaaa attctgtgct acatgtggag ttttccaaat    2400
gtggtgtttt tagatggctg gaaaggaagg aaaatccagg tgcttaaaaa atcatatgga    2460
gctcatcatt tgacctcaca atatattttg taaaaggact tgtagttttt tccaatgtag    2520
ctaatttagt aagacccatt tttcttgaat tcccagtggc aaattactca ggatttgtta    2580
gaaggacaag tatttcttcc ttgaagcagt actagggttt aggacttttg ttgtttaaat    2640
ctctggagca ctctaggaac cctggtctca gctttgcttt ttggaggcaa aggaaaaatg    2700
atctcctggt ttacttttgg aatctgcaaa gcaactctga ggtcccaggt ggatttagtg    2760
tttgaaaaag ggaacttggg ggactgaggt tgacctgag cccccaggtc actgttcacg    2820
tttacaaaag caaacctggt atccccagtt gcttttctct tgaggttggc ttaactttat    2880
ttatcttctg tcctgggtca ctgccctga ggtgcttcaa aagcaaaacc caaagaccc     2940 aaaacaaaga aagctaaatc agattcaagg aaaaaatgac ctggcactgt gggttcactt    3000
ttaaaaaggc aaaaagtcac ttcaagagtt tcatagaata gttttaagtc tgcctagatt    3060
cattgtgtca tttgtacaaa gtgatctcaa caggtctgaa accccaagtt ccttgggcat    3120
ggatcgagaa tgagtctgta ggatgggaaa ctgtcagcaa gctaaatggg ttgacacaaa    3180
tgaattcctc agtgattctg aagtgattca actattttga gcatataaat gggaccaccc    3240
atgtaacact tcttcctta agctgatctt tgtgtttgct ggacacacac agggaatgct    3300
gaggaagtga aatgtacaac tcacttacaa atgttggcat acacccactt tatgttatca    3360
gattagttat gaagggtatt tttgaatcct tggtgaaaaa aaacttggaa tactaatttc    3420
agataatctt acaaatcatg atgaggtaga actcaagcac atgattttgc cttttcattt    3480
ttatatcatc tgtactttgc ttacttccca aaaggattta aggtggaatt actttacttg    3540
actattggaa gaaacccatt tataaagctt aataccaatt ttcattatca tatgcctgac    3600
tttatccttt aataagtaat tgtaaaattg cttttgggta atctggggag attttttgttt    3660 ttgttcatgt ttgatctaca tctttgaact tcaggtgtat gtgttaacca ataaatacac    3720
ctgttgagac catgtcctac tgtttatta caagactgaa agagattttg tgtgattaat    3780
aacaaacata ttatttgtgc attgccatct gaaggaagca aaacttaagt agagaagtga    3840
gatttttcat aatgtagatc ttaatattaa gaacatagtg catcctgtga agcctaacca    3900
attgtgagag gcagtccgca aggcagtgac tgttggggta gagtgaaggc aagtattagt    3960
gtttgtacct ggcaacaccc cagtttcccc ttttctaccc atcacactct gactccaaag    4020
caatcatgtt cttttaaagt catcccaatc aaagaccagg gtcatcttgg tcggaacagg    4080
catggatagc tgcctgtgga aatgggttca gtccataaaa tctggcctgg cataatgtta    4140
ggtgggaccc aggaataaag tcctggtttt ttgttttatc cttcacttca atagaactga    4200
attataaaaa gtgaaaaatg accttataat tgttatgcgt gaaggagact gatagacaat    4260
tcagaaatat taacgctact ttctccagga agatcatttg acttacttaa cgttagaccc    4320
aatgctgtat catgatggag tctctcctct ttatcaatac cccagtgaaa agctggggaga    4380 gatacaggga tgtcacttca ctatattcac ttgccatagt ttgcctgcaa gccaacattg    4440
gcctttttca gagagctatc agcataagct aaagtagcct gtacttataa agcctaagaa    4500
aaaagctccc aaggaaactt ggaataatgg tctggcatca tcatttaatc agttatttcc    4560
tgaatatcta ctgagtggtt agactgtgct agacacactt tatgagcttg cctgcccagt    4620
```

```
tttgaagttt gtttctattt acttgttcca gcagtacaat gcatttgaaa aatccttaca    4680
cacatgaaaa tgataaatga gaatatgaga tcaacatgct tgctggctcc atctttgctc    4740
tctgcccatg tccatgtgta gtctttggga cacaaacact gaaatgtctc agccattgga    4800
tcttcagtca ttggattcat agactgagcg gaatgagcag gcagtcacca gcttctatat    4860
aagttaatgg tttctatttt attctatatt aaagtgatag tagcttcctc atgtgttact    4920
gtagtttaaa ttactaggat tctgtgtgaa tagcttttct ttataatttc ttccatgtta    4980
acatcaaaag attactgctt tattcctatc ttacaatgta agctccttga ggaaagagat    5040
tttgtcttgt tccaatgctg tatctctggt acctagcaca gtatctagca cgtgataggt    5100
ggggagtcaa tatatgttga ataaataaat gaatcttatg tagatcattg gcttttttgt    5160
ctgctttggc aattaattcc ttaaccatta atttgcaaat tcgtgcagat ttctacagat    5220
acctgtaaat taactgtgta caatatgtat ttctataaat atttatacaa agattaatgt    5280
caatatgaaa gcatatagat ttgtctacat atgggcaggt aggtttaatt ttgtggttcc    5340
tgtaatttct gcggatttgc acataagaga tttgcatatg agtatctgac catatgtgaa    5400
cattgtaagc atagtgtttc tttatccagg acagtctggt cttgtgctgt aaaagaatca    5460
attctgtatt cacagttgga gttggtgcgg gtttttcatt cattaagtcg gctcctcctt    5520
tcccacttgg gggtaaatca gcctagagaa aaagagcctt aagaggttgc tttctgctga    5580
cactgtgcat tgcacatgca cagttgtgca aatacacaca tatacctgaa agaagaatcc    5640
ttgaaaatga ggcttctgtt gacaactctg tgagggtgt tcattattga aatttatttt    5700
aatatataaa tatataaacc ttatttataa ctatagtatt aacacatatc cattgtagag    5760
tattacaaaa ataagaaaa taacagttaa ccttaatccc accacataaa tgacaatcat    5820
tcttttttaa aaattactat tttagaggtg aagtctcatt atgttgccca gggtggactc    5880
ttaactcctg ggctcaagtg atcctcccgc ctcagtctcc agagtagctg ggactacagg    5940
aacacaccac catgcccagc ttataaccgg catccttaac gttttttgcaa atttttcttcc    6000 agtcttttttg gatgggtttt tatgtaactt aagtagcaac atttatcata aacattatcc    6060
caagttattt aaaattcttt gtaaacatta attttaataa ccacatgata gtcatcatac    6120
agatagacct cactacttaa ccagtctctt aatattgaga tttaggctat ttcagtttt    6180 tgataacaca ataacatttt ttgagattaa tatctttgtg cataaatttt tttctgtttc    6240
tcgaagttgc attccaagaa gtaggattgc tgaatcaaag ggaatggcca cttttataag    6300
gttcttaaac acattgcaga atcacattcc ggagacgtta tactaattta cactcttacc    6360
atctgagtgt atgaaagtaa cttttcctct ttgtgaaagg agggaaaaat gtggccaaac    6420
aacagttaaa aattacacag aactttaaat aagttccctt ttcttttttca gacagtatat    6480 tctttaacat tgtctcagta tagtttctat cctagtgttt caactgttgg tatggcccag    6540
aatggtatct tgtccgaaag aaaatagagt ggctttccat agttaatatt ttcattatag    6600
aattttctgc ctgttgcaag aaaatctcta ttaatacctg taaattggat ggggaaatag    6660
tcaagcaagt tctttacctt catcaagaaa agctagtttc tggtgacctt tctttatgag    6720
gttttaatca ccccagagtt ttatccctct cagagtcagt ggtcggctct tgtatcccat    6780
gagtaaatgc aaatgtttcc tccatttgaa agcaaaacca gtaagacccc ttacttataa    6840
agtgagttaa aacaaaaaga aagaatataa aaactaaagg aaggtagtaa gtaaagcatt    6900
tagctttctg aaacaattca aatggggata ggaagttggt tttaaatggc ttaaggggga    6960
```

```
ttagggttttt aaagttggat aaagagtttg gtgcttaggt ttaggcatgg cattgctttt      7020
aaaagattac ttccatattt gacaatgatt ctaactggag attataaagt aaatagtcaa      7080
ttttaagaca ccacgggaaa caagagggtt tcttttttgt tgttgtttgt ttatacaaaa      7140
tggtagccta gagttaacag gctgaatcct gaagccctca tttcataata ctacagagga      7200
tctatcacca gagagaatct agcagaggtt gtttaatgca cttaattgag attatctgag      7260
cttttggttt aaattacttt ggaaaaagtc ttaggtgcaa acagcgtcct tgaaaggtaa      7320
acatacttac ctctaagaaa aaaggttca atttaagttc tttaaaattc ttcatacagg       7380
ttagtagcac caacctttat taattaaatc tgggtactga ctaatgcata aagataaaat      7440
ttctatacat cagtacaagg gttaatatat attatattaa cattgttttc attattttac      7500
aattatttga aaacatgaag tattttacta gaaacaacc cctggcattt ttagtaattt       7560
caaagtaaaa agatctattt tgattgtaaa gtacagttaa tgaagtttta aaaatgaatt      7620
tccgtattct gttccatcta agaagcaagc catattaaaa tggaccaagg atagcatata      7680
atttaagtat taactgggta aataatcaaa agttgattta acatttcccc catctttcgc     7740
agctccttga cctgttttatg gtttgggatt ggtctactta cctagctgat tatgggcagc    7800
cagcttctaa gtaccttcgg gtgaatccaa acacagccct tactcttttg gagaagtgag     7860
tatattctga aacttttttg tataacattt tagcaccttt tgattcagtg ataaactgaa     7920
gaactagaga tttctgtcaa aaaagaaaag tctagatgga gcttaaaagc tcactctagt     7980
ttaatgacca aaaaataagc ttttctttct tgcccttcag agttggtgta gtttcataag     8040
caactgctgt ttatattgat gtgaacaaaa catctttcct tttgtatcct gaattgcaag     8100
cttaattgac cttagaaata tgtttactgg ggatgtgaca attggagctt tctttaaaaa    8160
aaaaagtcta taactcagga aagaaggtat tttgtcaaat gtgaccagga attggaatgt     8220
ttgccaccag tgttacctaa atcttagcat tatggacttg gattctttgc aggtagagaa     8280
atatgtgatt tgaaaaaaaa aatacagtaa aaactgaggt aataggattt actgatgcat     8340
cttgtccaac taaacataaa tttaggtgtt aacttttccc tctcattatg tgacagactt     8400
tttctttact caatcatatt tcatttaaaa tgtcactatt gggagactct ctgaatctgc     8460
tgtgattctg ggggctgctg gataagaaaa ataaaaaagt atcactatta aaattttcaa     8520
ttttaaatta aaattgttat tattttccta tatttcaaaa tatttgtggt gtatttgatt     8580
tgaaaggaca agaggaagtg tttaaaataa atgtaaattt attttacaat gccatgaaat     8640
gcaactgagg caaaaacatc gctattttac attttctaat gttattttcc tttcaccta     8700 tcttgctatg aatatgatta gcagagtcta tacagggtat gtattttagc atactttgtg     8760
gaataatatt agaaaatagt atgatagtag taaacctagc atattttaga tgtacatact     8820
aatgcaaaaa taccacttaa catagaatgt aaaataaagc ttctaatttt ttgcatggtt     8880
actatatctg tatgttattt tagtatctac tttctttgaa ctatattttt caagcatagg    8940
attagtgtgg gataattcag agcatgccaa gatatttac ttgtgacagc ttagcttta      9000 attttctttt accaagcttc ttcattcaca tatgttcta ggatgaagga tactagcaaa     9060
aagaacaata tatttgctca gttcaggaag aatgatcgag acaaacagaa gttgatagag     9120
acagtcgtga aacagctgag aagtttggtg aatggtatgt cccagcacat gtagacctca     9180
catggcttgc actcagtgac accaaatcca tgattcaatg ttgatcttga gcaagtattg    9240
gtcatgatac agtaatttgt ttacagaatc caaaaataca atagagaaga tacatgaggg    9300
cttaaacaag aaatagtaat aaatatcatt tgtatggatt tttaaataat cgaatactat     9360
```

```
tttatatatg gaaaaaaatg accatttttt cactttttagg ggaaaatgca aaagtgtaat    9420
acataaattg tcacaaatta tacatgaaat tgattacaaa tacatttgaa aaacatatgc    9480
ctctactcat aagtattttt ttctatttag acttgaatga taatctgttt tttgatcagt    9540
atatggcttt ggaattcaat catgtctgat atggtagtat ttcactacca ttttctgact    9600
tttagctttt attttcacct caatgtgatt taagcagacc aaaatttcta attctgctaa    9660
ttctgaaggg gaaatagaca aatcttaaaa gctgcctgaa atcaaacttg atttaactca    9720
gtaagaatgt gaattatttg ttctacttgg gtggtttaat ttaatcgttc tgaatatgaa    9780
caaaaggttt tggattttct aaagatgcag tgttgtttct gttcatcagg gttaatattt    9840
ctaactatat tgcttgtagg tgaccccatt ctggatttgt ttggtttggt ttggttccag    9900
ttaaaagaga ggacaggaac taaatggggc taaccacttc aggtgcagct tgtgcgaggg    9960
tagatggttc ctgcacacag aagttaccac aggggtcagg ttactttctt caaatagcag   10020
atttcagtac tttatcctca ttgtggaaac aagccaaacc aaatgaactc tggaaaacct   10080
aaaacaaatg tacattttcc tttgtgtatg tttccgtggt ccaaatggca atataaatcc   10140
agtctttatt ctccctttgt tgtatttatg ctgaatcttc cctttgcctt ttcaggattt   10200
aggcctgtaa gaaactatgc ctgattctgt aaaataagtg taaagaatta tatgtacatc   10260
tctggatttt gtgatgaaat attaaaaata ttgagcaagt tgttgaaaat gcattactat   10320
tttgtctatt cagagcttac tgatttaaaa caagtgcttc ctggagaaaa ggcatattat   10380
ttcctagtta ctggaatggg agtggcacca aaacagtata tatacataca cacacacaca   10440
cacacacata tatatacata tgcgcacttg ttctctcgat catctcttaa tccaaagtat   10500
ttaatgtttt taaaaatatt acatgaaaag catggtagtt cttcaggcac ggtgaaatct   10560
ggaggagagg agcggtgaac agctagctct ctttgaagac tggaatgggg ctgcccttcg   10620
cgccttaccc agccttccag cgtacttggg gtgtcttccc tgctttggct gagacgtccc   10680
gggattcaga gagatactgc ctttgcactg cctggaggag accactgtgg gacctcttta   10740
ctcttaccaa taatataaac accctgcacc cctccacaca caccccaggt tgcactgtag   10800
ggacaagaac gagtgagtcc tgaggcattt ggaacccttg aatgggacgc acaaagccca   10860
aaacgcaaca atgtagattg acaagagtcg tcgggcaaac tcgggggagg gagggaagga   10920
tgtgcaggga aggatgaatt cggtccttga daccggaaag gtgctcgtgg gtatccgctt   10980
ctggaggctt aggacgtctt tatgaagcct agggcagtag tggaactgcc atctttggaa   11040
ggatacctga cgtggtagat cagagagccg ggagaggtgg ggagctgtcg gagaatctcg   11100
gctgcgctat ccctcctggg cttttgcgat gccaacgcag cgtcgacga ctgcagtttc   11160
cctgaaatag tcggagcaaa ggagagaaaa gcccagttct ttcaccttgg agtggcgaga   11220
gaaaggcacc tagaagctcg agggcgggga cggcagaggg agccagcggc cggggtgggg   11280
ccaggagcac tgcggggcgc aagcccgggt cagttctgcg cgttgggttc gcccactttc   11340
tgagcgcctg cgaagagcgg ggaagctctg gcgcgaaccc gcaggccccg cccgaggacg   11400
ctcgcggggc gagcccccag cccagctcga gccgccccgg cgcctgccac tccctactca   11460
gagcccctcc gtgagcgcgc cgctgcccac cgcctccaat caccactctg cgtggagcgc   11520
tttaaatatg caaagacacg tcacgttgtg tgaacccggga tcggtccgta ggggggggagc   11580
caatatctat ataaacgtgt ccagcgtggg ccaagaaggg ttaaacgact ggaggaggga   11640
caggtggggc gggggtctgc agaccaggtt ggcaacactg tgagttgct cttctttcgc   11700
```

```
cctccttccc ttcttctatc caaagggtgc tgagcccggg aggaggtggg aggtgccccg   11760
cggagccggg agtgagcgtt cccgaggcag caggcacctt cgagagggac tggcatttgg   11820
gcccaggagc caggaaaaag tcctgagcgt gccggcctcg aggaaggcac gttccctaag   11880
ggcgcacggt cactgcagtc tttcaccgtc cgtctgtttt tagaacagag ttctggcctg   11940
agcttataaa tctcgggctt tgcccccaaa ccccaggcct tttgcggacg gaacaggtga   12000
gcactgcgca ctgctcgcgc cccggttctt gcgtcccctg ctctccctgc gctctgagcg   12060
gcctggcccc cgcgggctca tcatgttccc ttggggctg agctgcctgt cagtgctggg   12120
ggcggcgggc actgctctcc tgtgcgcggg cctgctgctc agcctggccc agcacctctg   12180
gaccctccgc tggatgctga gccgggaccg ggcctccacc ctgcctctgc ccaagggctc   12240 catgggtgg cccttcttcg gcgaaacgct gcactggtta gttcaggtga gcagtccttc   12300
gaccccgagc gctaatacgg tcccttcttc ccccggctcc cactggaccc tcctcagtct   12360
caatgcccat gggatttgta gccagtccct gcccatcgcc cacgaccccg ggaagcgcgc   12420
acaactctcg cctttaccta gatactccgt tccctcgaag ggacctcaag tcactggaat   12480 tcccccccaga gcaactccca gacacaacgc agggggtaaa cataaggggt tttaggaagg   12540
ggtctgagga gcacgtcctg caagggtaga aaaggagcct ggagcttggc ccagctgtga   12600
gcccttgggc cctcacttct tcactctgag tctgtttcct catctcacca ataggaacag   12660
gagcatgtac attcccgtag agtagatacc aggcccactg gggatcttgt tttgtaaacg   12720
cgccagccag ggacaggaag ttgtgatcaa aaggcagctg gaaggtctgg gtcagatccc   12780
agcccaggcc cagaagttcc agctctccac cctccgcctc gcccgcaggg ctcgcgcttc   12840
cacagttctc gccgagagcg ctatgggaca gtgttcaaga cgcacctgct gggcaggcca   12900
gtgatccgcg tgagcggcgc ggagaacgtg cgcaccatcc tgctgggcga gcaccgcctg   12960
gtgcgcagcc agtggccgca gagtgcgcac atcctgctgg gctcgcacac actgctaggt   13020
gcggtcggcg agccgcaccg gcggcggcgc aaggtgagtg gaaacgggaa tggaccgtag   13080
atacgtcgga tccgcggtcc ccggcatctg ccatgggcca ggccgggcc ccggtgttgg   13140 atacactgtg aacccgacca aggtccctgg taactagcgg gtggccttgg gcgggtccgt   13200
taccttcagc ttcggtttat aaagttagga ctgcgctaaa agattctttc atctcccatc   13260
ttccgtggct gtgatagcag aagcgctgga gactcagacc tagaaagggg ccagggaaga   13320
cttcttagag gagatggcag ctggagcctg gatggttggg agggactgtg tgcatcagag   13380
cagaactggg ggaaatggcg aaagcaaaag ccaggaagtt taggtctggg ccgcttggaa   13440
gagggagaaa ggaccggaac tggccttctg gctactccgg aatcgccaag cagatgaggc   13500
cagaccgccg ccagcgctga tcacgcgcgc tcccacaggt cctggcgcgc gtgttcagcc   13560
gcgccgcgct ggagcgctac gtgccgcgcc tgcagggggc gctgcggcat gaggtgcgct   13620
cctggtgcgc ggcgggcggg ccggtctcag tctacgacgc ctccaaagcg ctcaccttcc   13680
gcatggccgc gcgcatcctg ctggggttgc ggctggacga ggcgcagtgc gccacgctgg   13740
cccgaccctt cgagcagctc gtggagaacc tcttctcact gcctctggac gttcccttca   13800
gtggcctacg caaggtacgg ccgccccggc tccagacctt cctccgaggc tccgcggcgc   13860
gggcgggcct cccagaccca gacgggacgc cctcggcgca cccgcgcgt ccgtcacctc   13920 tgctgggaac ggcggcaggg cccggggtg ggaggcgttg tggcggtggc gtggcggtgg   13980
gctctgggcc tggcctctgt gctggttcgc tggtgtgacc tggggctggc cacacgacct   14040
ccgtgggacg cgcctgccgc gacgcgctcc agcctgagca agcgcgggcc gccagagttt   14100
```

```
ggggtctcgg tggcaggcgt cctgccagtc ggtcggactc cttcccacag cggcgcccct   14160
ggggccggcc tccatcacct cttcggaagc ccagatggct gcggaaccga ggagagcgtg   14220
agggctgcag atgagcccg gtccagccca gcgccagccc cggacccagg ggtgtgggcg    14280
tcagctccac cagccctgga cccgctaggt ttcgggatca gagaactgct gcttctccag   14340
acttcagaac aatgggcagg acccggagag cagctaggat gccccatccc gccttttggt   14400 cccctattc tgggacttcc cactgtttga ttccctggtt ttcagtcacc tgcataaaaa    14460
taatatgtgt aaaggatcat gctataggct gatcaccgtg gatacgtttt ctgatctaat   14520
cctcgcagcc tgcaaagtgt tatgattctc attttattgg ccaaacttat tttattgact   14580
tacccaagat cacaccgtta gtaggggcac gaacaggact ttaacctcat ctcctccgac   14640
tatggaactc aagtgctgaa ttacagtgct ttccccgggg gaatgctttt gctgcggcta   14700
ttccctgaac tctggagagg catccctat  tgcccacgct cttacagagg ctaatgctta   14760
caaatccaat agtgtcctct aagtcagagc tttgctgggt gcatcaaggt accccagcct   14820
gagcctagta cagggaaagg gcaatgggct gaccctagcc gcactgggct ctgtgccagg   14880
catggacatg gacagctgtg tgactctggg caattgcttg acctctctga acttcagcat   14940
cctctcctca ggatgacagt aactctgctg tggctcagag ggggattgtg ataatcaaga   15000
cagaatgatg tttgtggaca gtggacatat ccccgaccat ttactgagcc cagccatatg   15060
ccaggccagg agctaagctg ggaagctgtt aacacaagga tgttggcaga gccagtgctg   15120
agaaggtttt ctgggtaagt ggccgggctt ggccccctta gccttcctgc ccatctttc    15180 ttctctccct gaacatcagg gcatccgggc aagggaccag ctgcatcggc acctggaggg   15240
ggccatttct gagaagcttc acgaggacaa ggctgcagag ccgggtgatg ccctcgacct   15300
aatcattcac agtgcaaggg agctgggcca tgagccctcc atgcaggagc tgaaggtagg   15360
tgctgacagg ccgctccttc tccctctttt tgcattccca gcaggtccct acaccaatgc   15420
tgcatcccca gagccacatc ttgtgtggcc ccactttgag gcacaggcag tcctcaagat   15480
gaggggcaag aggagacctg ggttccagta atgactcagc cacactcact acctctgcag   15540
ccttcagcct ccagccagcc ttgtcagtag gagaactgaa ggcaagaatc ctaggcccat   15600 cttttgcaggt ttctggccac aaatggctct ctctcctttc cttcccccac tgcccttctc   15660
tgccactcca tgcctttgcc tctgctgtcc ccctgcctac aaagccctca ttattcattt   15720
tttctagaaa ctctaagggg ctcaggatca aactccacat cctcaaagct cccttcttcc   15780
ttccaaaatc acctctctcc ttctatgagc taccttggca cctggtacct ctatccgtct   15840
gtcttgttgc tgtggatctc ctggagaatt aggaccctc  cccttgtaca cacatcgcac   15900
atacagtgga ggggaggtgg taagctttgg aatggcccca ggacttgctt gagcacccaa   15960
aaaggagtgg agaagttagg gggaggggaa gttagaaata gggagacctc aatcttccat   16020
aagcaactct tacgcatcct ttctctgggc ctcagtttcc cactttctac cagagacatc   16080
cctgaagggt aggcctcagc tttagcttct tttctgagat tggaactaat aagagcatga   16140
gcaatgggct cttcttgcgc agagcagacc aagaagacat ttagtgactc cctgggacca   16200
ttccgatagg gagaggatga agccatgatg ccggcattgg tacgaggctg gcactgctgc   16260
tgcaggtgcc tttgttgcac tgcagccatt gtcaggctgt tccactgggg ttggcggccg   16320
caccaccagg tggtgaagag cactggactc ctgccgggag tgctagctgt agggaccttg   16380
agcactactc tggagtctcc gttttcaact ccataaaaca agagcagcaa ttgtgcctca   16440
```

```
cagaggggag gtgagaaccg aatgagtgaa tatgcttaaa gcaccaagaa gagtgcttag   16500
agtaagttcc cgcattctct ctgggaacca tcgcaaggcg ggtggataga tcctaatgtt   16560
gcctgttgct acagctgact ttcccaaatg gtggacttga gatttaatcg acttcaaaac   16620
cgtacacaca gtcgcggcgg taatagcact tccctgcccc ctggcttttc gcaatagtaa   16680
atttgggtgc ttttcatctc cacggggccg tcgggtcagc gccccgggcg actccaccgc   16740
ccgagactca gtgcagcccg gggctgtctt gcaggagtcg gctgtggagc tcctcttcgc   16800
cgccttcttc accacggcca gtgccagcac ctcgctcgtc ctgctgctac tgcagcatcc   16860
ggcggccatc gccaagattc gggaggagct ggtggcgcag gggctgggc gcgcgtgcgg    16920 ctgcgcgccc ggggccgctg ggggcagcga ggggcccccg cccgactgcg gctgcgagcc   16980
cgacctcagc ctcgcggcgc tgggccgtct gcgctacgtc gactgcgtgg tcaaggaggt   17040
gctgcgcctc ctgccgccag tgtccggggg ctaccgcacc gccctgcgca ccttcgagct   17100
cgacgtaagt gcgccgtgcc agcccatggc cagcctcctg cctcctgccg cctgccgcct   17160
gccgcctgcc gcctgccgcg gcggcgccca ggtgggagga gggcggaggg attcggacgg   17220
cgcggtcacc tcttttgccc tcagagcctc agccttccgt cctataaaat gggctgagcc   17280
ttgttccacc tccccggatc ccccgctgag ggacgcaaag cctggcgaga ctgcaaggtt   17340
agggatctcg tacccttcag cttttggcag cggttcggaa cggtcaattc aatgagagcg   17400
gagttttaga ataaaaatac tcttctatcc gtgcagcacc ccctcccagc cagtgagtgt   17460
ggatggagaa caaagagaac ccctcagtat gtcctgtgct ccaccctct ggctccctca    17520 caagatgaag gaaccctca ttgcgaccgg tccagggttc tggctggggc cagattccag     17580 gggaggggg gattaaaata ccgggtagac gcttcatctc tgatcaggcc ggtttgggct     17640
gagcaaggtt gaggtctaga actgactcca tctccgtatg accttgggca gttccctctt   17700
cactctgggc ctcagtttac tctctgcaag gaagctgtct tggtcctttc cagctctgac   17760
actccatcca ggtgggtccg ggctgtgggg gtacagtggt ggcctcaggc agtggtgctc   17820
tggctgtgcc aaactgtggg tgtttgcctg aaaggctgtc gttgcagtcc cctgagcacc   17880
atgcttggtg gctgggtggc tccagataaa aatgggcatt ccacagtgaa catttgtggc   17940
acattgcgtg ccagggttca ggaggcatca aagggactgg gattctaccc tggaggggct   18000
ccacttggag aggaaggggg ccgggactga caacatcatc ccacttgtag tgtgacagcc   18060
tcatcccact tgtagtgtga agagagtgat ctctagtgct ggatgacacc aacacattct   18120
gagagctgga gtttgaactg gagcagtgaa aggtttggac gggagagcct attacagaga   18180
gagcagactc agacaaaggt ggatgttgag aagtgtcttg aatgcggaat cagtcttgga   18240
atgcaagctt cattctgcag gcgctggagt gccctacaag accttaggga agcacagaac   18300
cagggtggtg agcagaggac aggaaagggt cttagccacc tccagttcac agatgagaac   18360
actgatgtct agagaggaaa gagagctcct gggatgattc caagatgttc tgttctccag   18420
ttagaaactt tgagtattca ccctggaact tgatatgagg gtagcagtgt agtcagggg    18480 ttggaagacg tatcaaaaag ccaaatggtt gaaaaagcta ggggtgggca gagggaacat   18540
gaaaactgcc tttcagcatt ttaaggatgg ccagtttgat tctcatgtgc gccttcttaa   18600
agtgtggtac caaatctgaa cattatcgtc cagctgatgg atgggaagga tggcaagttt   18660
tcagttcaat gcaaagaaga gctctaccat ggaactgacc tcgaggaatt gtcatgtgca   18720
tttttcccac tctagcagct gggaggtgta gcactagaat ttaggtctcc tcatctaagg   18780
tcagaagaaa aaaagacaaa accaaacggg aacataacta atagttaccg tttactgaac   18840
```

```
actcatatgt gccaagtcct taatttgaat cctcaccaac aaagggggcca tttttcccct    18900 cattttttca aagaggaaac tgaagctcag agaggctgcg catctagccc aaggtcatac    18960
atttcaccag tgaaggagtt gagattggaa cacagagctt tctcctggtt tccgggttaa    19020
tcgcggattc ctcctggttt tcggaagcct gatggaagca ccagggtgga gggtcagttc    19080 agggccccc cgtttccagg tgcctcgtgg tcaggctgat ctcctcgcct ctctgcaggg     19140
ctaccagatc cccaagggct ggagcgtgat gtatagcatc cgggacacgc acgagacggc    19200
tgcggtgtac cgcagccctc ccgaaggctt cgatccagag cgcttcggcg cagcgcgcga    19260
agattcccgg ggcgcctcca gccgcttgca ttacatcccg ttcggcggcg gtgcgcgcag    19320
ctgcctcggc caggagctgg cgcaagccgt gctccagctg ctagctgtgg agctagtgcg    19380
caccgcgcgc tgggaactgg ccacacccgc cttccccgcc atgcagacgg tgcccatcgt    19440
gcacccagtg gacgggctgc ggctcttttt ccaccccctc acgccttcgg ttgcggggaa    19500
tgggctatgc ctctgacatg cttgcgctct aggacacggc ttggccggtg gctatggcgc    19560
gcacgcagcg ccacccatct gccgctcccc attgtagcgt cgcgcgccca ctctttcact    19620
cgttcaacaa tctttcaaca aatgttcgcc aaacgcggat gtgtgccgga ctcgaggaag    19680
gaggagggcg agccaccgct gccgcgccag agaagcatct aagcccatgg gaagatgcct    19740
tctgcgctcc gcgcccagag gaaggaaaat gtcgtgggcc aagcaggaat ggagggaata    19800
gatagatccc cacgaggtgc tgcttggctt cccttcccg agccaatcca gggagggtgc     19860
atggatgggg gaaggcgagg taggggtggc aggggagtgg gaatattgca actcggggac    19920
attgcagaga cccgacgcac gcggtgggac ctgcaaccct tgtaaggaag cgggcacgcc    19980
gtgggcgcaa ccctggcctg gctttgggcc atagaaaaaa cacgcagagg atgcctgacg    20040
gaaggccctc tggcagctgg cgtctggctt cgtgcgcctt ggccactctg ccggtctcgg    20100
cggaaactag caactgtggg cacttccagg ctcgaaaggg ctcaaggtca ccggattctg    20160
ctggccactt cttaaaagga aaaattccta ccttaagaag gcatttactc ttgtcatgta    20220
tacagaggag aataggcaca ccaacacgtc tccaacgctg gattattttc atgggaggtt    20280
gagacataat tagagaggtt tgagatattt gtaccaaaaa taggaaggcc aagaaataaa    20340
gtgtcttggg agcggttgag tgaggaggct agggtttatc tgggcagctg ctccctgggg    20400
ggaaggcact ggggtgcagg gttggggagg ccagggaagg acccaccccca cagtacaccc   20460 agagaggagc tgggagctgg gcagcctagg gcctgggctg cccagacttc tctctgagta    20520
taaccccaga agctgggctg tgaattgtct ccaggtttca gggaccttat ttttattttt    20580
atttttttga gacagggtct tcctctgtgg cccaggctgg agtgtagtgg cacaaccagc    20640
tcactgccac ctctgcctct cgtgctcaag ccatcctccc atctcagcct cccaagtagc    20700
tgggactaca ggcacgtgcc acaacgccta gctattttt tttctatttt taatagagac    20760
ggggggtttc accatgtcac ccaggctggt ctcaaactct tgggcttaag cgaaccatct    20820
gccttggctt cccaaagtgc tggggttaga ggtgtgaccc accacaccct ggagtcactc    20880 cttttccagtg actccagtct agtccctgcg ccctcacccc tccctgccat ttcagggcct   20940
tctggtttta cggcttcacc atcctctcta tcacagagaa gaaattgagg agcaatctag    21000
gtgaatgact cacctgagaa gcccagcaat aggctcctgg actccccagc cagtgctctc    21060
ctccaccccc atcccttcac tcttctgccc caacctctgt tcctgtggcc atcaggtagg    21120
gctgaacact ttggcctcct tttcatgata agccctagct agacttgagg actctctcaa    21180
```

```
ccattccggt acagaggttc caaccagtgt ttaaatcaaa gccaaaagcc tccatgtcat    21240
cattcccaac agcccacttc aatctgccac ccagcttcca acagaccggg gcagctggac    21300
ataaggggtg agccagggaa gtagctgcct aggcctgagc tgacccctta gtgaaccaga    21360
agaaagccag tgccctcctg acctcatgct taaggtggat cccagggcca gaaggaaggg    21420
ggacacagca ggcacttaca gggttggtag ctccacagta cagcaagccc ttccaacctg    21480
ggctgacact gccataaccc ccacacaggg caattcatca cccattgtca gccaagggcc    21540
tggtgccagg ccctgagctt gggagacacc aggggcagca aggtggcag gacgtgggcc     21600 cgccctaaga gtgctcttgc aaatgcagag gacagcctgg cctgagaagc gtgggtttgg    21660
gcgaggagaa ggatgcaggc ttcagggttg attgtgattt agagagagga gagaagaatg    21720
gggtggggac cctcagaagc aaggctagtt gagctggttc caagaagacc tggttgacct    21780
gcattggggt ctggactaac tataagcctc tgtagggatg gctccagttt taattttcca    21840
tggatacatc atgctcagta attttgaggg atatcttagc cctgttttta gtagctgcag    21900
attctctggg gaaggagcag aggaggttcc ttccctcctg cacttgatat gctctggagg    21960
gaggcagaca agaaataaac tagcaaacaa aagggtaaga atatgtccag tgaaaataaa    22020
aaccgtcatg gaaataaaac aggcctgtga tagtgtctgg ggctaaatta ggctggatgg    22080 gtgggggaa ccttgaggag ggtgacattt gactttggaa ggaaccagcc agcggtggct     22140
ggaggtagtt ttgccacagc agagggacac gcaggtata                           22179

<210> SEQ ID NO 10
<211> LENGTH: 1569
<212> TYPE: DNA
<213> ORGANISM: Homo sapiens

<400> SEQUENCE: 10
atgttccctt gggggctgag ctgcctgtca gtgctggggg cggcgggcac tgctctcctg      60
tgcgcgggcc tgctgctcag cctggcccag cacctctgga ccctccgctg gatgctgagc     120
cgggaccggg cctccaccct gcctctgccc aagggctcca tggggtggcc cttcttcggc     180
gaaacgctgc actggttagt tcagggctcg cgcttccaca gttctcgccg agagcgctat     240
gggacagtgt tcaagacgca cctgctgggc aggccagtga tccgcgtgag cggcgcggag     300
aacgtgcgca ccatcctgct gggcgagcac cgcctggtgc gcagccagtg gccgcagagt     360
gcgcacatcc tgctgggctc gcacacactg ctaggtgcgg tcggcgagcc gcaccggcgg     420
cggcgcaagg tcctggcgcg cgtgttcagc cgcgccgcgc tggagcgcta cgtgccgcgc     480
ctgcaggggg cgctgcggca tgaggtgcgc tcctggtgcg cggcgggcgg gccggtctca     540
gtctacgacg cctccaaagc gctccacttc cgcatggccg cgcgcatcct gctgggggttg    600 cggctggacg aggcgcagtg cgccacgctg gcccggacct tcgagcagct cgtggagaac    660
ctcttctcac tgcctctgga cgttcccttc agtggcctac gcaagggcat ccgggcaagg    720
gaccagctgc atcggcacct ggaggggggcc atttctgaga agcttcacga ggacaaggct    780
gcagagccgg tgatgccct cgacctaatc attcacagtg caagggagct gggccatgag    840
ccctccatgc aggagctgaa ggagtcggct gtggagctcc tcttcgccgc cttcttcacc    900
acggccagtg ccagcacctc gctcgtcctg ctgctactgc agcatccggc ggccatcgcc    960
aagattcggg aggagctggt ggcgcagggg ctggggcgcg cgtgcggctg cgcgcccggg   1020
gccgctgggg gcagcgaggg gccccgcgcc gactgcggct gcgagccga cctcagcctc   1080 gcggcgctgg gccgtctgcg ctacgtcgac tgcgtggtca aggaggtgct gcgcctcctg   1140
```

-continued

```
ccgccagtgt ccgggggcta ccgcaccgcc ctgcgcacct tcgagctcga cggctaccag     1200
atccccaagg gctggagcgt gatgtatagc atccgggaca cgcacgagac ggctgcggtg     1260
taccgcagcc ctcccgaagg cttcgatcca gagcgcttcg gcgcagcgcg cgaagattcc     1320
cggggcgcct ccagccgctt gcattacatc ccgttcggcg gcggtgcgcg cagctgcctc     1380
ggccaggagc tggcgcaagc cgtgctccag ctgctagctg tggagctagt gcgcaccgcg     1440
cgctgggaac tggccacacc cgccttcccc gccatgcaga cggtgcccat cgtgcaccca     1500
gtggacgggc tgcggctctt tttccacccc ctcacgcctt cggttgcggg gaatgggcta     1560
tgcctctga                                                              1569
```

<210> SEQ ID NO 11
<211> LENGTH: 522
<212> TYPE: PRT
<213> ORGANISM: Homo sapiens

<400> SEQUENCE: 11

```
Met Phe Pro Trp Gly Leu Ser Cys Leu Ser Val Leu Gly Ala Ala Gly
1               5                   10                  15

Thr Ala Leu Leu Cys Ala Gly Leu Leu Ser Leu Ala Gln His Leu
            20                  25                  30

Trp Thr Leu Arg Trp Met Leu Ser Arg Asp Arg Ala Ser Thr Leu Pro
        35                  40                  45

Leu Pro Lys Gly Ser Met Gly Trp Pro Phe Phe Gly Glu Thr Leu His
    50                  55                  60

Trp Leu Val Gln Gly Ser Arg Phe His Ser Ser Arg Arg Glu Arg Tyr
65                  70                  75                  80

Gly Thr Val Phe Lys Thr His Leu Leu Gly Arg Pro Val Ile Arg Val
                85                  90                  95

Ser Gly Ala Glu Asn Val Arg Thr Ile Leu Leu Gly Glu His Arg Leu
            100                 105                 110

Val Arg Ser Gln Trp Pro Gln Ser Ala His Ile Leu Leu Gly Ser His
        115                 120                 125

Thr Leu Leu Gly Ala Val Gly Glu Pro His Arg Arg Arg Lys Val
    130                 135                 140

Leu Ala Arg Val Phe Ser Arg Ala Ala Leu Glu Arg Tyr Val Pro Arg
145                 150                 155                 160

Leu Gln Gly Ala Leu Arg His Glu Val Arg Ser Trp Cys Ala Ala Gly
                165                 170                 175

Gly Pro Val Ser Val Tyr Asp Ala Ser Lys Ala Leu Thr Phe Arg Met
            180                 185                 190

Ala Ala Arg Ile Leu Leu Gly Leu Arg Leu Asp Glu Ala Gln Cys Ala
        195                 200                 205

Thr Leu Ala Arg Thr Phe Glu Gln Leu Val Glu Asn Leu Phe Ser Leu
    210                 215                 220

Pro Leu Asp Val Pro Phe Ser Gly Leu Arg Lys Gly Ile Arg Ala Arg
225                 230                 235                 240

Asp Gln Leu His Arg His Leu Glu Gly Ala Ile Ser Glu Lys Leu His
                245                 250                 255

Glu Asp Lys Ala Ala Glu Pro Gly Asp Ala Leu Asp Leu Ile Ile His
            260                 265                 270

Ser Ala Arg Glu Leu Gly His Glu Pro Ser Met Gln Glu Leu Lys Glu
        275                 280                 285
```

```
Ser Ala Val Glu Leu Leu Phe Ala Phe Phe Thr Thr Ala Ser Ala
    290                 295                 300

Ser Thr Ser Leu Val Leu Leu Leu Gln His Pro Ala Ala Ile Ala
305                 310                 315                 320

Lys Ile Arg Glu Glu Leu Val Ala Gln Gly Leu Gly Arg Ala Cys Gly
                325                 330                 335

Cys Ala Pro Gly Ala Ala Gly Gly Ser Glu Gly Pro Pro Asp Cys
                340                 345                 350

Gly Cys Glu Pro Asp Leu Ser Leu Ala Ala Leu Gly Arg Leu Arg Tyr
                355                 360                 365

Val Asp Cys Val Val Lys Glu Val Leu Arg Leu Leu Pro Pro Val Ser
    370                 375                 380

Gly Gly Tyr Arg Thr Ala Leu Arg Thr Phe Glu Leu Asp Gly Tyr Gln
385                 390                 395                 400

Ile Pro Lys Gly Trp Ser Val Met Tyr Ser Ile Arg Asp Thr His Glu
                405                 410                 415

Thr Ala Ala Val Tyr Arg Ser Pro Pro Glu Gly Phe Asp Pro Glu Arg
                420                 425                 430

Phe Gly Ala Ala Arg Glu Asp Ser Arg Gly Ala Ser Ser Arg Leu His
                435                 440                 445

Tyr Ile Pro Phe Gly Gly Gly Ala Arg Ser Cys Leu Gly Gln Glu Leu
    450                 455                 460

Ala Gln Ala Val Leu Gln Leu Leu Ala Val Glu Leu Val Arg Thr Ala
465                 470                 475                 480

Arg Trp Glu Leu Ala Thr Pro Ala Phe Pro Ala Met Gln Thr Val Pro
                485                 490                 495

Ile Val His Pro Val Asp Gly Leu Arg Leu Phe Phe His Pro Leu Thr
                500                 505                 510

Pro Ser Val Ala Gly Asn Gly Leu Cys Leu
                515                 520

<210> SEQ ID NO 12
<211> LENGTH: 204
<212> TYPE: DNA
<213> ORGANISM: Homo sapiens

<400> SEQUENCE: 12
atgttccctt gggggctgag ctgcctgtca gtgctggggg cggcgggcac tgctctcctg      60
tgcgcgggcc tgctgctcag cctggcccag cacctctgga ccctccgctg gatgctgagc     120
cgggaccggg cctccaccct gcctctgccc aagggctcca tggggtggcc cttcttcggc     180
gaaacgctgc actggttagt tcag                                            204

<210> SEQ ID NO 13
<211> LENGTH: 68
<212> TYPE: PRT
<213> ORGANISM: Homo sapiens

<400> SEQUENCE: 13

Met Phe Pro Trp Gly Leu Ser Cys Leu Ser Val Leu Gly Ala Ala Gly
1               5                   10                  15

Thr Ala Leu Leu Cys Ala Gly Leu Leu Leu Ser Leu Ala Gln His Leu
                20                  25                  30

Trp Thr Leu Arg Trp Met Leu Ser Arg Asp Arg Ala Ser Thr Leu Pro
            35                  40                  45

Leu Pro Lys Gly Ser Met Gly Trp Pro Phe Phe Gly Glu Thr Leu His
```

```
            50                  55                  60
Trp Leu Val Gln
65

<210> SEQ ID NO 14
<211> LENGTH: 225
<212> TYPE: DNA
<213> ORGANISM: Homo sapiens

<400> SEQUENCE: 14
ggctcgcgct tccacagttc tcgccgagag cgctatggga cagtgttcaa gacgcacctg      60
ctgggcaggc cagtgatccg cgtgagcggg gcggagaacg tgcgcaccat cctgctgggc     120
gagcaccgcc tggtgcgcag ccagtggccg cagagtgcgc acatcctgct gggctcgcac     180
acactgctag gtgcggtcgg cgagccgcac cggcggcggc gcaag                     225

<210> SEQ ID NO 15
<211> LENGTH: 75
<212> TYPE: PRT
<213> ORGANISM: Homo sapiens

<400> SEQUENCE: 15

Gly Ser Arg Phe His Ser Ser Arg Arg Glu Arg Tyr Gly Thr Val Phe
1               5                   10                  15

Lys Thr His Leu Leu Gly Arg Pro Val Ile Arg Val Ser Gly Ala Glu
            20                  25                  30

Asn Val Arg Thr Ile Leu Leu Gly Glu His Arg Leu Val Arg Ser Gln
        35                  40                  45

Trp Pro Gln Ser Ala His Ile Leu Leu Gly Ser His Thr Leu Leu Gly
    50                  55                  60

Ala Val Gly Glu Pro His Arg Arg Arg Lys
65                  70                  75

<210> SEQ ID NO 16
<211> LENGTH: 276
<212> TYPE: DNA
<213> ORGANISM: Homo sapiens

<400> SEQUENCE: 16
gtcctggcgc gcgtgttcag ccgcgccgcg ctggagcgct acgtgccgcg cctgcagggg      60
gcgctgcggc atgaggtgcg ctcctggtgc gcggcgggcg ggccggtctc agtctacgac     120
gcctccaaag cgctcacctt ccgcatggcc gcgcgcatcc tgctggggtt gcggctggac     180
gaggcgcagt gcgccacgct ggcccggacc ttcgagcagc tcgtggagaa cctcttctca     240
ctgcctctgg acgttccctt cagtggccta cgcaag                               276

<210> SEQ ID NO 17
<211> LENGTH: 92
<212> TYPE: PRT
<213> ORGANISM: Homo sapiens

<400> SEQUENCE: 17

Val Leu Ala Arg Val Phe Ser Arg Ala Ala Leu Glu Arg Tyr Val Pro
1               5                   10                  15

Arg Leu Gln Gly Ala Leu Arg His Glu Val Arg Ser Trp Cys Ala Ala
            20                  25                  30

Gly Gly Pro Val Ser Val Tyr Asp Ala Ser Lys Ala Leu Thr Phe Arg
        35                  40                  45
```

```
Met Ala Ala Arg Ile Leu Leu Gly Leu Arg Leu Asp Glu Ala Gln Cys
 50                  55                  60

Ala Thr Leu Ala Arg Thr Phe Glu Gln Leu Val Glu Asn Leu Phe Ser
 65                  70                  75                  80

Leu Pro Leu Asp Val Pro Phe Ser Gly Leu Arg Lys
                 85                  90

<210> SEQ ID NO 18
<211> LENGTH: 156
<212> TYPE: DNA
<213> ORGANISM: Homo sapiens

<400> SEQUENCE: 18
ggcatccggg caagggacca gctgcatcgg cacctggagg gggccatttc tgagaagctt      60
cacgaggaca aggctgcaga gccgggtgat gccctcgacc taatcattca cagtgcaagg     120
gagctgggcc atgagccctc catgcaggag ctgaag                               156

<210> SEQ ID NO 19
<211> LENGTH: 52
<212> TYPE: PRT
<213> ORGANISM: Homo sapiens

<400> SEQUENCE: 19

Gly Ile Arg Ala Arg Asp Gln Leu His Arg His Leu Glu Gly Ala Ile
 1               5                  10                  15

Ser Glu Lys Leu His Glu Asp Lys Ala Ala Glu Pro Gly Asp Ala Leu
             20                  25                  30

Asp Leu Ile Ile His Ser Ala Arg Glu Leu Gly His Glu Pro Ser Met
         35                  40                  45

Gln Glu Leu Lys
 50

<210> SEQ ID NO 20
<211> LENGTH: 330
<212> TYPE: DNA
<213> ORGANISM: Homo sapiens

<400> SEQUENCE: 20
gagtcggctg tggagctcct cttcgccgcc ttcttcacca cggccagtgc cagcacctcg      60
ctcgtcctgc tgctactgca gcatccggcg gccatcgcca agattcggga ggagctggtg     120
gcgcaggggc tggggcgcgc gtgcggctgc gcgcccgggg ccgctggggg cagcgagggg     180
cccccgcccg actgcggctg cgagcccgac ctcagcctcg cggcgctggg ccgtctgcgc     240
tacgtcgact gcgtggtcaa ggaggtgctg cgcctcctgc cgccagtgtc cgggggctac     300
cgcaccgccc tgcgcacctt cgagctcgac                                      330

<210> SEQ ID NO 21
<211> LENGTH: 110
<212> TYPE: PRT
<213> ORGANISM: Homo sapiens

<400> SEQUENCE: 21

Glu Ser Ala Val Glu Leu Leu Phe Ala Ala Phe Phe Thr Thr Ala Ser
 1               5                  10                  15

Ala Ser Thr Ser Leu Val Leu Leu Leu Gln His Pro Ala Ala Ile
             20                  25                  30

Ala Lys Ile Arg Glu Glu Leu Val Ala Gln Gly Leu Gly Arg Ala Cys
         35                  40                  45
```

```
Gly Cys Ala Pro Gly Ala Ala Gly Gly Ser Glu Gly Pro Pro Asp
     50                  55                  60
Cys Gly Cys Glu Pro Asp Leu Ser Leu Ala Ala Leu Gly Arg Leu Arg
 65                  70                  75                  80
Tyr Val Asp Cys Val Val Lys Glu Val Leu Arg Leu Pro Pro Val
                 85                  90                  95
Ser Gly Gly Tyr Arg Thr Ala Leu Arg Thr Phe Glu Leu Asp
            100                 105                 110
```

<210> SEQ ID NO 22
<211> LENGTH: 378
<212> TYPE: DNA
<213> ORGANISM: Homo sapiens

<400> SEQUENCE: 22

```
ggctaccaga tccccaaggg ctggagcgtg atgtatagca tccgggacac gcacgagacg      60
gctgcggtgt accgcagccc tcccgaaggc ttcgatccag agcgcttcgg cgcagcgcgc     120
gaagattccc ggggcgcctc cagccgcttg cattacatcc cgttcggcgg cggtgcgcgc     180
agctgcctcg gccaggagct ggcgcaagcc gtgctccagc tgctagctgt ggagctagtg     240
cgcaccgcgc gctgggaact ggccacaccc gccttccccg ccatgcagac ggtgcccatc     300
gtgcacccag tggacgggct gcggctcttt ttccaccccc tcacgccttc ggttgcgggg     360
aatgggctat gcctctga                                                   378
```

<210> SEQ ID NO 23
<211> LENGTH: 125
<212> TYPE: PRT
<213> ORGANISM: Homo sapiens

<400> SEQUENCE: 23

```
Gly Tyr Gln Ile Pro Lys Gly Trp Ser Val Met Tyr Ser Ile Arg Asp
 1               5                  10                  15
Thr His Glu Thr Ala Ala Val Tyr Arg Ser Pro Pro Glu Gly Phe Asp
                 20                  25                  30
Pro Glu Arg Phe Gly Ala Ala Arg Glu Asp Ser Arg Gly Ala Ser Ser
             35                  40                  45
Arg Leu His Tyr Ile Pro Phe Gly Gly Gly Ala Arg Ser Cys Leu Gly
         50                  55                  60
Gln Glu Leu Ala Gln Ala Val Leu Gln Leu Leu Ala Val Glu Leu Val
 65                  70                  75                  80
Arg Thr Ala Arg Trp Glu Leu Ala Thr Pro Ala Phe Pro Ala Met Gln
                 85                  90                  95
Thr Val Pro Ile Val His Pro Val Asp Gly Leu Arg Leu Phe Phe His
            100                 105                 110
Pro Leu Thr Pro Ser Val Ala Gly Asn Gly Leu Cys Leu
            115                 120                 125
```

<210> SEQ ID NO 24
<211> LENGTH: 213
<212> TYPE: DNA
<213> ORGANISM: Homo sapiens

<400> SEQUENCE: 24

```
ctcatcatgt tcccttgggg gctgagctgc ctgtcagtgc tgggggcggc gggcactgct      60
ctcctgtgcg cgggcctgct gctcagcctg gcccagcacc tctggaccct ccgctggatg     120
```

```
ctgagccggg accgggcctc caccctgcct ctgcccaagg gctccatggg gtggcccttc    180
ttcggcgaaa cgctgcactg gttagttcag cag                                 213

<210> SEQ ID NO 25
<211> LENGTH: 25
<212> TYPE: DNA
<213> ORGANISM: Homo sapiens

<400> SEQUENCE: 25
ctcatcatgt tcccttgggg gctga                                           25

<210> SEQ ID NO 26
<211> LENGTH: 27
<212> TYPE: DNA
<213> ORGANISM: Homo sapiens

<400> SEQUENCE: 26
ctgctgaact aaccagtgca gcgtttc                                         27

<210> SEQ ID NO 27
<211> LENGTH: 27
<212> TYPE: DNA
<213> ORGANISM: Homo sapiens

<400> SEQUENCE: 27
gcaagggacc agctgcatcg gcacctg                                         27

<210> SEQ ID NO 28
<211> LENGTH: 25
<212> TYPE: DNA
<213> ORGANISM: Homo sapiens

<400> SEQUENCE: 28
ctcgtgcgtg tcccggatgc tatac                                           25

<210> SEQ ID NO 29
<211> LENGTH: 26
<212> TYPE: DNA
<213> ORGANISM: Homo sapiens

<400> SEQUENCE: 29
cccttgcact gtgaatgatt aggtcg                                          26
```

RETINOIC ACID METABOLIZING CYTOCHROME P450

RELATED APPLICATIONS

This application claim the benefit and priority from U.S. Provisional Patent Application No. 60/292,531 filed May 23, 2001.

FIELD OF THE INVENTION

This invention relates to a novel retinoic acid metabolizing cytochrome P450 and to fragments and variants thereof. It further relates to the nucleic acid encoding said peptides. Products derived or identified using said peptides and nucleic acid molecules of the invention. Methods and uses of said peptides, nucleic acid molecules and products are also encompassed within the scope of said invention.

BACKGROUND OF THE INVENTION

Cytochrome P450s

The cytochromes P450 comprise a large gene superfamily that encodes over 500 distinct heme-thiolate proteins that catalyze the oxidation of drugs and numerous other compounds in the body [Nelson et al., (1996); Guengerich (1991)]. Since there are at least 500 different cytochrome P450 enzymes, it is of considerable interest in the pharmaceutical and other fields to identify which of these enzymes are most important in the metabolism of individual compounds. There are now numerous examples of adverse drug-drug interactions and side effects that can now be understood in terms of the cytochrome P450 enzymes.

P450 proteins are ubiquitous in living organisms, and have been identified in bacteria, yeast, plants and animals [Nelson et al (1996); and Nelson, (1999a)]. The P450 enzymes catalyze the metabolism of a wide variety of drugs, xenobiotics, carcinogens, mutagens, and pesticides, and are responsible for the bioactivation of numerous endogenous compounds including steroids, prostaglandins, bile acids and fatty acids body [Nelson et al., (1996); Guengerich (1991); Nebert et al., (1989)].

Cytochrome P450 metabolism of xenobiotics can result in detoxification of toxic compounds by their conjugation into excretable forms or can result in activation of compounds into metabolites that are toxic, mutagenic, or carcinogenic. Many steroids are deactivated by cytochrome P450-catalyzed oxidation.

Microsomal cytochromes occur on the membrane of the ER and require NADPH cytochrome P450 reductase and a flavoprotein for activity, whereas mitochondrial cytochromes occur on the inner mitochondrial membrane and require ferredoxin and NADPH ferredoxin reductase for activity (Beckman, M., and DeLuca, H. (1997) *Methods in Enzymol.* 282, 200-223; Armbrecht, H. J., Okuda, K., Wongsurawat, N., Nemani, R., Chen, M., and Boltz, M. (1992) *J. Steroid Biochem. Molec. Biol.* 43, 1073-1081.)

Vitamin A and Retinoic Acid

Vitamin A metabolism gives rise to several active forms of retinoic acid (RA), which are involved in regulating gene expression during development, regeneration, and in the growth and differentiation of epithelial tissues. [Maden, 1992; Chambon, 1995; Mangelsdorf, 1995; Gudas, 1994; Lotan, 1995; Morriss-Kay, 1996] RA has been linked to apoptosis, or programmed cell death in a number of cell types; and to have anticarcinogenic and antitumoral properties [Lotan, 1996].

Early studies of retinol deficiency indicated a correlation between vitamin A depletion and a higher incidence of cancer and increased susceptibility to chemical carcinogenesis [Chytil, 1984]. Several animal models have been used to demonstrate the effectiveness of retinoids in suppressing carcinogenesis in a variety of tissues including skin, mammary epithelia, oral cavity, aerodigestive tract, liver, bladder and prostate [Moon, 1994]. These studies have led to the preventative use of retinoids to treat premalignant lesions including actinic keratosis and oral leukoplakia, as well as in the prevention of secondary tumors of the head and neck and the recurrence of non-small cell lung carcinomas, and basal cell carcinomas [Hong, 1994; Lippman, 1995]. RA itself has been found to be useful therapeutically, notably in the treatment of cancers, including acute promyelocytic leukemia (APL), tumors of the head and neck, and skin cancer, as well as in the treatment of skin disorders such as the premalignancy associated actinic keratoses, acne, psoriasis and ichthyosis. There is evidence that the effectiveness of RA as an anti-tumor agent is at least partially due to induction of cellular differentiation and/or inhibition of proliferation [Lotan, 1996]. Studies over the past several years indicate that a high proportion of patients with acute promyelocytic leukemia (APL) achieve complete remission after a short period of treatment with all-trans RA. Unfortunately, this high rate of remission is in most cases brief. Following relapse, patients are clinically resistant to further treatment with RA [Warrell, 1994; Warrell, et al., 1994; Chomienne, 1996; Muindi, 1992]. The nature of this resistance is unknown. Interestingly, leukemic cells taken from patients exhibiting clinical resistance to RA have been shown to be sensitive to the differentiating action of RA when grown in vitro [Muindi, 1992; Muindi, 1994]. This suggests that pharmacokinetic mechanisms may account for the acquired resistance to RA. This possibility is supported by studies showing that peak plasma concentrations of RA were much higher in patients after initial administration than in patients treated following relapse. This decrease in peak plasma RA concentration was accompanied by a 10-fold increase in urinary 4-oxo-retinoic acid concentration. In addition, ketoconazole, a broad spectrum inhibitor of cytochrome P450 function was shown to modulate RA pharmacokinetics in vivo [Muindi, 1992; Muindi, 1994]. It is therefore likely that RA increases the rate of its own metabolism, which in turn results in the inability to sustain effective therapeutic doses of RA. Therapeutic administration of RA can result in a variety of undesirable side effects and it is therefore important to establish and maintain the minimal requisite doses of RA in treatment. For example, RA treatments during pregnancy can lead to severe teratogenic effects on the fetus. Adverse reactions to RA treatment also include headache, nausea, chelitis, facial dermatitis, conjunctivitis, and dryness of nasal mucosa. Prolonged exposure to RA can cause major elevations in serum triglycerides and can lead to severe abnormalities of liver function, including hepatomegaly, cirrhosis and portal hypertension.

RA metabolism may also account for the lack of response of certain tumors to RA treatment. For example, recent studies have shown that cytochrome P450 inhibitors that block RA metabolism, resulting in increased tissue levels of RA, may be useful therapeutic agents in the treatment of prostate cancer [Wouters, 1992; De Coster, 1996]. Thus RA metabolizing cytochrome P450s may be useful targets for the treatment of a number of different types of cancer.

The classical view of vitamin A metabolism holds that all trans-RA, the most active metabolite is derived from conversion of retinol to retinaldehyde to RA through two oxidation steps and that RA is further metabolized to the polar derivatives 4-OH RA and 4-oxo RA [Blaner, 1994; Napoli, 1995; Formelli, 1996; Napoli, 1996]. It is unknown whether the 4-oxo- and 4-OH— metabolites are simply intermediates in the RA catabolic pathway or whether they can also have specific activities which differ from those of all-trans RA and 9-cis RA. Pijnappel et al. [Pijnappel, 1993] have shown that, in *Xenopus*, 4-oxo-RA can efficiently modulate positional specification in early embryos and exhibits a more potent ability to regulate Hoxb-9 and Hoxb-4 gene expression than all-trans RA. 4-oxo-RA has been found to bind to retinoic acid receptor-β (RAR-β) with affinity comparable to all-trans RA [Pijnappel, 1993] but poorly to RAR-γ [Reddy, 1992], suggesting that this metabolite exhibits some receptor selectivity. 4-oxo-RA also binds to cellular retinoic acid binding protein (CRABP) but with an affinity slightly lower than that of all-trans RA [Fiorella, 1993]. Takatsuka et al. [Takatsuka, 1996] have shown that growth inhibitory effects of RA correlate with RA metabolic activity but it is unknown whether there is a causal relationship between production of RA metabolites and growth inhibition. The asymmetric distribution of these metabolites in developing embryos suggests that they may be preferentially sequestered or generated by tissue specific isomerases [Creech Kraft, 1994]. The normal balance of these metabolites is dependent upon rate of formation from metabolic precursors, retinol and retinaldehyde [Leo, 1989], and rate of catabolism. Little is presently known about the enzymes involved in this metabolic scheme, in particular the catabolism of RA.

The catabolism of RA is thought to be initiated by hydroxylation either at the C4-, or C18-position of the β-ionone ring of RA [Napoli, 1996]. The C4-hydroxylation step is mediated by cytochrome P450 activity, as judged by the ability of broad spectrum P450 inhibitors such as ketoconazole and liarazole to block 4-hydroxylation [Williams, 1987, Van Wauwe, 1988; Van Wauwe, 1990, Van Wauwe, 1992, Wouters, 1992]. In certain tissues, including testis, skin and lung and in numerous cell lines, such as NIH3T3 fibroblasts, HL 60 myelomonocytic leukemic cells, F9 and P19 murine embryonal carcinoma cell lines and MCF7, RA metabolism can be induced by RA pretreatment [Frolik, 1979, Roberts, 1979a and b; Duell, 1992; Wouters, 1992]. Studies involving targeted disruption of RAR genes in F9 cells suggest that RAR-α and RAR-γ isoforms may play a role in regulating the enzymes responsible for this increased metabolism [Boylan, 1995].

The glucuronidation of RA is a significant metabolic step in the inactivation of RA [Blaner, 1994; Formelli, 1996]. The elimination of RA may require oxidation to 4-oxo, followed by conjugation to form the 4-oxo all-trans RA glucuronide. This is supported by studies in both primates and humans showing that the 4-oxo RA glucuronide is the only retinoid conjugate found in urine [Muindi, 1992; Muindi, 1994]. The fact that following RA therapy, 4-oxo RA is not present or barely detectable in serum, suggests that oxidation may be the rate limiting step in this process.

It has recently been shown that 4-oxoretinol (4-oxo-ROL) can have greater biological activity than retinol. The 4-oxo-ROL is inducible by RA in F9 and P19 mouse teratocarcinoma cells [Blumberg et al., 1995; Achkar et al., 1996].

It is known that zebrafish fins regenerate through an RA sensitive process, which utilizes many gene regulatory pathways involved in early vertebrate development [White, 1994; Akimenko, 1995a & b].

Cytochome P450s and Retinoic Acid Metabolism

In 1979, Roberts et al., [Roberts (1979a)] first postulated that the catabolism of retinoic acid (RA) was mediated by a cytochrome P450 enzyme. Several P450s have since been shown to metabolize RA, including P450 proteins from human, zebrafish and mouse. For example, human P450RAI, which is induced by RA, metabolizes RA to more poplar derivatives including 4-hydroxy retinoic acid (4-OHRA) and 4-oxo retinoic acid (4-oxo RA) [White et al. (1996a)]. Since RA is useful as an antitumor agent, it is desirable to maintain high tissue levels of RA. Thus, cytochrome P450 inhibitors that block RA metabolism, resulting in increased tissue levels of RA, may be useful therapeutic agents in the treatment of cancers, such as prostate cancer [Wouters et al., (1992); and De Coster et al., (1996)].

International Patent Publication No. WO 97/49815, published Dec. 31, 1997, describes a family of retinoid metabolizing proteins, CYP26A, including proteins from human, zebrafish and mouse and their coding sequences. This earlier publication is incorporated herein in its entirety. cDNAs encoding a cytochrome P450-dependent enzyme (P450RAI) which is induced by RA have been cloned and characterized from zebrafish and the protein metabolizes RA to more polar derivatives including 4-hydroxy retinoic acid (4-OH RA) and 4-oxo retinoic acid (4-oxo RA) [White et al., 1996a]. The identification of P450RAI gene is an important step in the understanding of RA signaling but its presence has been known since Roberts et al. (1979a) first postulated that the catabolism of RA was mediated by a P450 enzyme [Frolik et al., 1979; Roberts et al., 1979a]. More recently, the isolation of cDNAs which encode the full-length human and mouse P450RAI orthologs whose expression, like that of the fish cytochrome, is highly inducible by RA has been achieved [Fujii et al., 1997; Ray et al., 1997]. Human and mouse genomic P450RAI-1 sequences and the mouse cDNA sequence encoding P450RAI-1 I have been identified. The human cDNA and amino acid sequence of P450RAI-1 is identified herein as SEQ. ID. NOS. 1 and 2, respectively (also see FIG. 6A). Homologs have also been isolated from human, mouse, chick and *xenopus* all exhibiting a high degree of sequence conservation [Abu-Abed et al., 1998; Hollermann et al., 1998; White et al., 1997]. There is extensive identity between the human and fish P450RAI genes which overall is 68% at the amino acid level (over 90% between mouse and human).

MCF7 cells have been shown to have RA inducible RA metabolism [Butler and Fontana, 1992; Wouters et al., 1992]. The expression of P450RAI in these cells is dependent on the continuous presence of RA [White et al., 1997]. This suggests that P450RAI regulation by RA forms an autoregulatory feedback loop that functions to limit local concentrations of RA, such that when normal physiological levels of RA are exceeded, induction of P450RAI acts to normalize RA levels. The inducible expression of P450RAI in mouse embryos also suggests that a similar autoregulatory mechanism may limit exposure to RA sensitive tissues during development [Iulianella et al., 1999].

A second retinoic acid metabolizing cytochrome P450, P450RAI-2 has also recently been identified in human, rat, mouse and zebrafish. The human cDNA and amino acid sequence are identified herein as SEQ. ID. NOS. 3 and 4, respectively.

Retinoic Acid, Cytochrome p450 and Embryonic Development

All-trans-RA is a critical regulator of gene expression during embryonic development and in the maintenance of adult epithelial tissues [Gudas, et al. (1994).; Lotan, R. M. (1995); Lotan, R. (1996); Morriss-Kay, G. M. (1996)]. The effects of all-trans-RA are mediated by heterodimers of nuclear receptors for retinoic acid (RARs) and retinoid-X-receptors, which are regulated by the 9-cis isomer of RA. Three different subtypes exist for each of these receptors (RARα, β and γ; RXR RAR α, β and γ), which individually are expressed in a tissue specific manner but collectively can be found in essentially all cell types, both during embryonic development and in the adult [Chambon, P. (1995).]. The activity of RA in these tissues is controlled, to a large extent, by enzymes involved in its synthesis from retinaldehyde (ALDH-1 and RALDH-2) and its catabolism to 4-OH, 4-oxo and 18-OH products (P450RAI) [White J. A., et al. (1997); lulianella, A. et al. (1999); McCaffery P. et al., (1999) Niederreither, K. et al. (1999) Swindell E., et al. (1999)].

It has been shown that P450RAI-1 (CYP26A) from zebrafish, mouse, human, chick and *xenopus* is responsible for the metabolism of active all-trans-RA to inactive polar metabolites including 4-OH-RA, 4-oxo-RA and 18-OH-RA [White J., et al. (1997); Swindell E., et al. (1999); White, J. & Petkovich, M. (1996); Abu-Abed, et al. (1998); Fujii, H. et al. (1997); Ray, W. et al. (1997); Hollermann, T et al. (1998)]. P450RAI-1 expression can be induced by all-trans-RA pre-treatment in multiple tissues, and cell types, and this expression is concomitant with increased all-trans-RA catabolism. In MCF7 cells, all all-trans-RA suggesting a feedback-loop mechanism is dependent on the continued presence of all-trans-RA suggesting a feedback-loop mechanism for the regulation of all-trans-RA levels [White J., et al. (1997)]. Inducible expression of P450RAI-1 has also been observed in vivo in zebrafish, chick, *xenopus* and mouse embryos suggesting that this autoregulatory feedback-loop plays an important role in balancing all-trans-RA levels in certain developing tissues.

Studies from several groups show that tissues such as neural folds in chick embryos [Swindell E., et al. (1999)], caudal neuroepithelia [lulianella, A et al. (1999); Fujii, H. et al. (1997)] and developing retina [McCaffery P. et al. (1999)] from mouse express P450RAI-1 constitutively thus forming a barrier to all-trans-RA exposure. Comparison of the expression patterns of RALDH-2 and P450RAI-1 in these models suggests that these enzymes act together to form regions of RA synthesis and activity (where RALDH-2 is expressed). RALDH-2 expressing tissues have been shown to contain retinoid activity as measured by both retinoid responsive reporter gene activity and direct measurement of RA levels from tissue extracts; by similar analyses, P450RAI-1 expressing tissues do not [lulianella, A et al. (1999); McCaffery P. et al. (1999)]. In addition, over expression of P450RAI-1 in *xenopus* embryos has been shown to abrogate the teratogenic effects of exogenously applied RA, consistent with a catabolic role for its enzyme [Hollermann, T et al. (1998)].

The Adrenal Glands

The adrenal glands comprise an inner part (the medulla) that secretes hormones such as adrenaline (epinephrine) that affect blood pressure, heart rate, sweating, and other activities also regulated by the sympathetic nervous system. The outer part (the cortex) secretes many different hormones, including corticosteroids, androgens and minerlocorticoids, which control blood pressure and the levels of salt and potassium in the body.

The adrenal glands are part of a complex system that produces interacting hormones. The hypothalamus produces corticotropin-releasing hormone, triggering the pituitary gland to secrete corticotropin, which regulates the production of orticosteroids by the adrenal glands. Adrenal glands may stop functioning when either the pituitary or hypothalamus fails to produce sufficient amounts of the appropriate hormones. Underproduction or overproduction of any adrenal hormones can lead to serious illness. Diseases associated with the adrenal gland include Addison's disease, Cushing's syndrome, pheochromocytoma, adenoma, hyperaldosteronism, high blood pressure, weakness, paralysis, darkening of the skin, osteoporosis, and fat accumulation.

SUMMARY OF THE INVENTION

The present invention is directed to a novel cytochrome P450 that is part of the retinoic acid metabolizing family of cytochrome P450s. In another aspect, the novel cytochrome P450 is preferentially expressed in the adrenal gland. In another embodiment the novel cytochrome metabolized 13-all-trans-retnoic acid. In yet another embodiment the novel cytochrome metabolized 9-cis-retnoic acid.

The present inventors have characterized for the first time human cytochrome P450RAI-3 [hereinafter "P450RAI-3 or "CYP26C"]. In one embodiment the P450RAI-3 is a microsomal cytochrome. In one embodiment the P450RAI-3 is isolated from adrenal tissue. These findings have important implications in terms of increased understanding of cytochrome P450s and the retinoic acid pathway and the application to various disease states, such as those noted above, i.e. cancer, adenoma, high blood pressure, muscle weakness, skin discolouration, osteoporosis, fat accumulation, pheochromocytoma, Addison's disease, Cushing's syndrome.

Although, the P450RAI-3 and encoding nucleic acid sequence of the invention can be isolated and characterized from any tissue, it is preferably isolated and characterized from adrenal tissue.

Accordingly, the present invention provides an isolated polynucleotide comprising a nucleotide sequence encoding a P450RAI-3, preferably a human P450RAI-3 and to variants, homologs, analogs thereof and to fragments thereof. Complimentary (or antisense) polynucleotide sequences to the polynucleotides of the invention are also encompassed within the scope of the invention.

In a preferred embodiment, an isolated polynucleotide is provided comprising a nucleic acid sequence as shown in SEQ. ID. NOS.: 9 (FIG. 1) or 10 (FIG. 2) Most preferably, the purified and isolated polynucleotide comprises: (a) a nucleic acid sequence encoding the amino acid sequence of SEQ. ID. NO. 11 (FIG. 3), wherein T can also be U; (b) nucleic acid sequences complementary to (a): (c) nucleic acid sequences which are homologous to (a) or (b), or, (d) a fragment of (a) to (c) that will hybridize to (a) to (c) under stringent hybridization conditions. Preferably the fragment is 10 or more, preferably at least 15 bases, most preferably 20 to 30 bases. In another embodiment, the isolated polynucleoticle of the invention comprises a sequence encoding any one or more of exons 1 to 6 of P450RAI-3 as depicted in SEQ. ID. NOS.: 13, 15, 17, 19, 21, or 23 (See FIG. 5 for amino acid regions) or SEQ. ID. NOS.: 12, 14, 15, 18, 20 or 22 (See FIG. 5). In a further embodiment, the invention provides polynucleotides that consist of the isolated polynucleotides noted herein.

The present invention also includes the P450RAI-3 polypeptide. In one embodiment, the invention provides a polypeptide having an amino acid sequence as shown in SEQ. ID. NO. 11 (FIG. 3) and to variants, homologs, and analogs, insertions, deletions, substitutions and mutations thereto. The invention also comprises polypeptides comprising fragments of the amino acid sequence of SEQ. ID. NO. 11 (FIG. 3) or to their respective variants, homologs, analogs, insertions, deletions, substitutions and mutations. In another embodiment the fragments preferably comprise 14 or more amino acid residues and are most preferably antigenic or immunogenic. In another embodiment the invention provides polypeptides encoded by a polynucleotide having the sequence of SEQ. ID. NO. 10 (FIG. 2), or to variants, homologs, analogs or fragments thereof. In another embodiment the polypeptide of the invention comprises or consists of any one or more of the amino acid sequences of exons 1 to 6 of P450RAI-3 as depicted in SEQ. ID. NOS. 13, 15, 17, 19, 21 or 23 (see FIG. 5).

Accordingly, in one embodiment the invention relates to vectors, host cells comprising the polynucleotides of the invention or that can express the polypeptides of the invention. Antibodies to the polypeptides of the invention are also encompassed within the scope of this invention. The invention further provides recombinant methods for producing P450RAI-3 polypeptides and polynucleotides of the invention. In one embodiment, the invention provides a polynucleotide of the invention operationally linked to an expression control sequence in a suitable expression vector. In another embodiment, the expression vector comprising a polynucleotide of the invention is capable of being activated to express the peptide, which is encoded by the polynucleotide and is capable of being transformed or transfected into a suitable host cell. Such transformed or transfected cells are also encompassed with the scope of this invention.

The invention also provides a method of preparing a polypeptide of the invention utilizing a polynucleotide of the invention. In one embodiment, a method for preparing the polypeptide, preferably P450RAI-3 is provided comprising: transforming a host cell with a recombinant expression vector comprising a polynucleotide of the invention; (b) selecting transformed host cells from untransformed host cells; (c) culturing a selected transformed host cell under conditions which allow expression of the protein; and (d) isolating the protein.

In yet another embodiment, the invention also includes diagnostic methods for detecting and screening for disorders related to P450RAI-3 gene expression and polypeptides and to therapeutic methods for treating such disorders.

As such, the invention also includes a method for detecting a P450RAI-3 related condition in an animal. A P450RAI-3 related condition includes but is not limited to diseases associated with vitamin A or retinoic acid metabolism. The method comprises assaying for P450RAI-3 from a sample, such as a biopsy, or other cellular or tissue sample, from an animal susceptible of having such a condition. In one embodiment, the method comprises contacting the sample with an antibody of the invention, which binds P450RAI-3, and measuring the amount of antibody bound to P450RAI-3 in the sample, or unreacted antibody. In another embodiment, the method involves detecting the presence of a nucleic acid molecule having a sequence encoding a P450RAI-3, comprising contacting the sample with a nucleotide probe which hybridizes with the nucleic acid molecule, preferably mRNA or cDNA to form a hybridization product under conditions which permit the formation of the hybridization product, and assaying for the hybridization product.

The invention further includes a kit for detecting a P450RAI-3 related condition from a sample comprising an antibody of the invention, preferably a monoclonal antibody. Preferably directions for its use are also provided. The kit may also contain reagents, which are required for binding of the antibody to a P450RAI-3 protein in the sample.

The invention also provides a kit for detecting the presence of a polypeptide having a sequence encoding a polypeptide of, related to or analogous to a polypeptide of the invention, comprising a nucleotide probe which hybridizes with the nucleic acid molecule, reagents required for hybridization of the nucleotide probe with the nucleic acid molecule, and directions for its use.

The invention also includes screening methods for identifying binding partners of P450RAI-3. In addition, the invention relates to screening methods for identifying modulators, such as agonists and antagonists, of P450RAI-3 activity. In one embodiment such modulators of P450RAI-3 activity or expression can include antibodies to P450RAI-3 and antisense polynucleotides to the P450RAI-3 gene or fragment thereof.

The invention further provides a method of treating or preventing a disease associated with P450RAI-3 expression comprising administering an effective amount of an agent that activates, simulates or inhibits P450RAI-3 expression, as the situation requires, to an animal in need thereof. In a preferred embodiment, P450RAI-3, a therapeutically active fragment thereof, or an agent, which activates or simulates P450RAI-3 expression is administered to the animal in need thereof to treat a disease or condition associated with too much retinoic acid. In another embodiment the disease is associated with over expression of P450RAI-3 or retinoic acid deficiency (i.e. not enough retinoic acid or desire to maintain retinoic acid levels) and the method of treatment comprises administration of an effective amount of an agent that inhibits P450RAI-3 expression such as an antagonist of P450RAI-3, an antibody to P450RAI-3, a mutation thereof, or an antisense nucleic acid molecule to all or part of the P450RAI-3 gene.

In another embodiment the invention provides pharmaceutical compositions comprising a modulator of P450RAI-3 activity and a pharmaceutical acceptable carrier. In another embodiment, the pharmaceutical composition of the invention comprises P450RAI-3 (preferably a soluble form thereof) or a therapeutically effective fragment thereof and a pharmaceutically acceptable carrier. In another embodiment the pharmaceutical compositions of the invention comprise both a modulator of P450RAI-3 activity and P450RAI-3 (preferably a soluble form thereof) or a therapeutically effective fragment thereof. In a further embodiment the pharmaceutical compositions of the invention can further comprise a modulator of P450RAI-3 and any one or more of: (a) retinoic acid, (b) a ligand of P450RAI-3; a substrate of P450RAI-3.

The invention also includes a method of identifying a modulator of P450RAI-3 activity comprising:

[a] incubating P450RAI-3 or a cell expressing P450RAI-3 with a test compound under conditions that promote P450RAI-3 expression or activity;

[b] detecting the activity or expression, as the case may be, of P450RAI-3 in the presence of said test compound, a decrease in said activity or expression being indicative that the test compound is an inhibitor of P450RAI-3 expression or activity, while an increase in said expression or activity is indicative that the test compound is a P450RAI-3 agonist.

Another aspect of the invention relates to a method of identifying a substate of P450RAI-3 comprising:

[a] incubating P450RAI-3 with a test substrate under conditions that promote P450RAI-3/substate complex formation or interaction;

[b] determining P450RAI-3/substrate complex formation or interaction.

The incubation step optionally further comprises a known modulator of P450RAI-3. Step [b] can be determined by comparing the effect on P450RAI-3 in the absence and presence of the test substrate.

Another aspect of the invention is a method for identifying a substance which associates with a protein of the invention comprising (a) reacting the protein with at least one substance which potentially can associate with the protein, under conditions which permit the association between the substance and protein, and (b) removing or detecting protein associated with the substance, wherein detection of associated protein and substance indicates the substance associates with the protein.

Another embodiment of the invention relates to a method for evaluating a compound for its ability to modulate the biological activity of a protein of the invention comprising providing the protein with a substance which associates with the protein and a test compound under conditions which permit the formation of complexes between the substance and protein, and removing and/or detecting complexes.

The invention also relates to a method for identifying inhibitors of a P450RAI-3 Protein interaction, comprising (a) providing a reaction mixture including the P450RAI-3 Related Protein and a substance that binds to the P450RAI-3 Related Protein, or at least a portion of each which interact;

(b) contacting the reaction mixture with one or more test compounds;

(c) identifying compounds which inhibit the interaction of the P450RAI-3 Related Protein and substance.

The invention also includes a method for detecting a nucleic acid molecule encoding a protein comprising an amino acid sequence of SEQ. ID. NO. 11 in a biological sample comprising the steps of:

(a) hybridizing a nucleic acid molecule of claim 1 to nucleic acids of the biological sample, thereby forming a hybridization complex: and (b) detecting the hybridization complex wherein the presence of the hybridization complex correlates with the presence of a nucleic acid molecule encoding the protein in the biological sample.

In one embodiment of the above-noted method the nucleic acids of the biological sample are amplified by the polymerase chain reaction prior to the hybridizing step.

The invention also includes a composition comprising one or more of a nucleic acid molecule or protein of the invention, or a substance or compound identified using a method of the invention, and a pharmaceutically acceptable carrier, excipient or diluent. The invention also includes a nucleic acid molecule or protein of the invention, or a substance or compound identified using a method of the invention in the preparation of a pharmaceutical composition for treating a condition mediated by a protein of the invention, or a nucleic acid molecule of the invention.

The invention includes compounds identified with methods of the invention.

Another aspect of the invention includes a vaccine for stimulating or enhancing in a subject to whom the vaccine is administered production of antibodies directed against a protein of the invention. The invention also includes a method for stimulating or enhancing in a subject production of antibodies directed against a protein. The invention includes a method involving administering to the subject a vaccine of the invention in a dose effective for stimulating or enhancing production of the antibodies.

The invention includes the use of the isolated polypeptide of the invention, and optionally a modulator of P450RAI-3 activity for preparation of a pharmaceutical substance. The invention also includes the use of a therapeutically effective amount of the polypeptide of the invention or of the polynucleotide of the invention and/or a modulator of P450RAI-3 for preventing, treating or ameliorating a medical condition related to P450RAI-3 expression.

The invention includes the use of a therapeutically effective polypeptide of the invention and/or an agonist thereof for treating a disease or condition related to vitamin A or retinoic acid metabolism in a patient. The invention also includes the use of a P450RAI-3 inhibitor and a P450RAI-3 substrate for preventing, treating or ameliorating a medical condition related to P450RAI-3 expression or for preparation of a pharmaceutical substance.

Another embodiment of the invention relates to a method of determining the ATRA and/or 9-cis-RA metabolizing activity of a polypeptide of the invention, comprising: expressing the polypeptide in a host cell, adding ATRA and/or 9-cis-RA to the cell, and determining the amount and/or rate of ATRA and/or 9-cis-RA metabolism.

Another embodiment of the invention relates to a method of determining the substrate of a polypeptide of the invention, comprising: expressing the polypeptide in a host cell, adding a candidate substrate, and determining if the substrate is metabolized, wherein metabolization indicates that the candidate substrate is a substrate of the polypeptide.

The invention also relates to a method of determining the binding activity of a substrate to a polypeptide of the invention, comprising expressing the polypeptide in a host cell, adding a candidate substrate, and determining a Kd value.

Other objects, features and advantages of the present invention will become apparent from the following detailed description. It should be understood, however, that the detailed description and the specific examples, while indicating preferred embodiments of the invention, are given by way of illustration only. Various changes and modifications within the spirit and scope of the invention will become apparent to those skilled in the art from this detailed description.

BRIEF DESCRIPTION OF THE DRAWINGS

Figure 1:
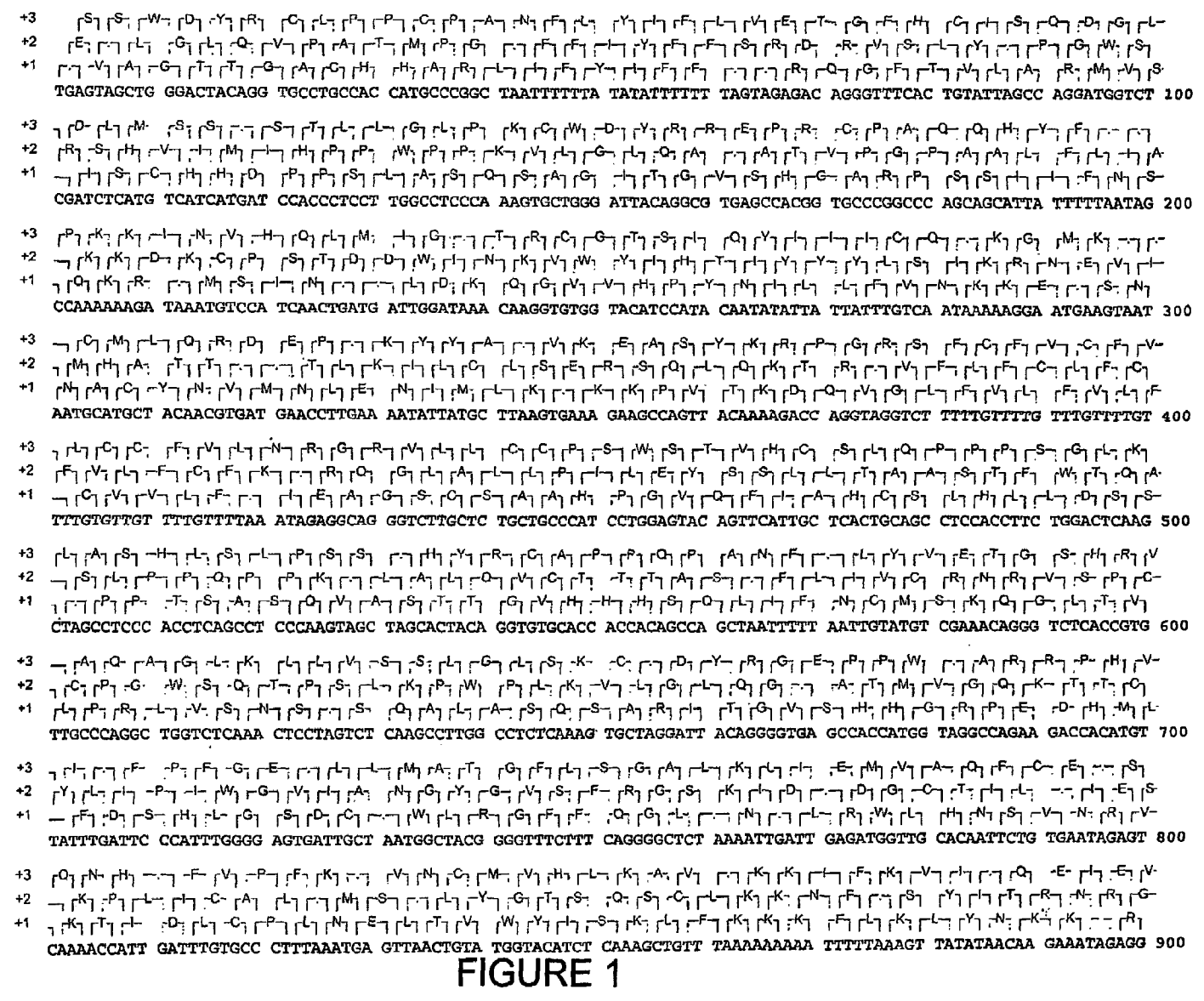
Figure 1:
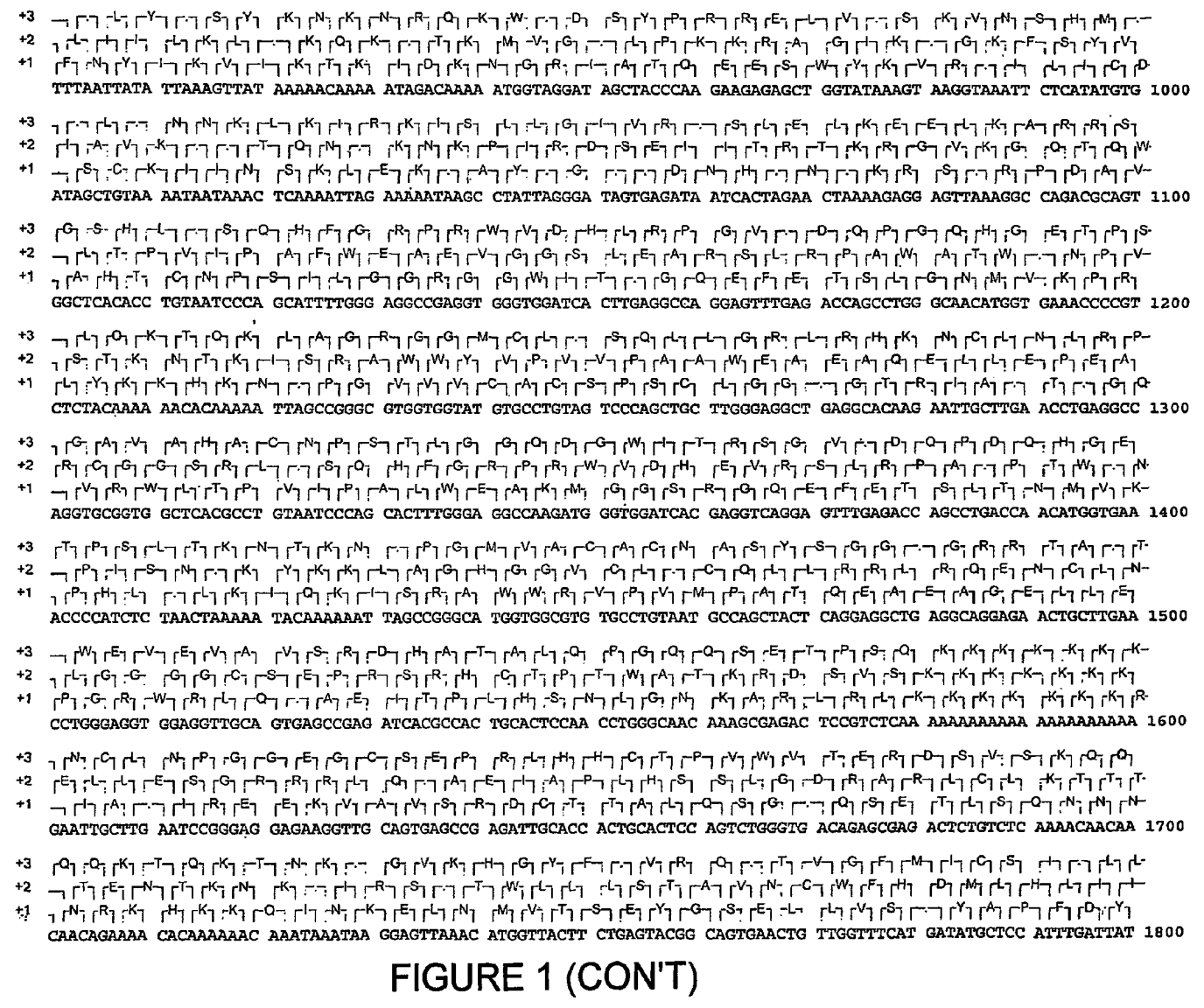
Figure 1:
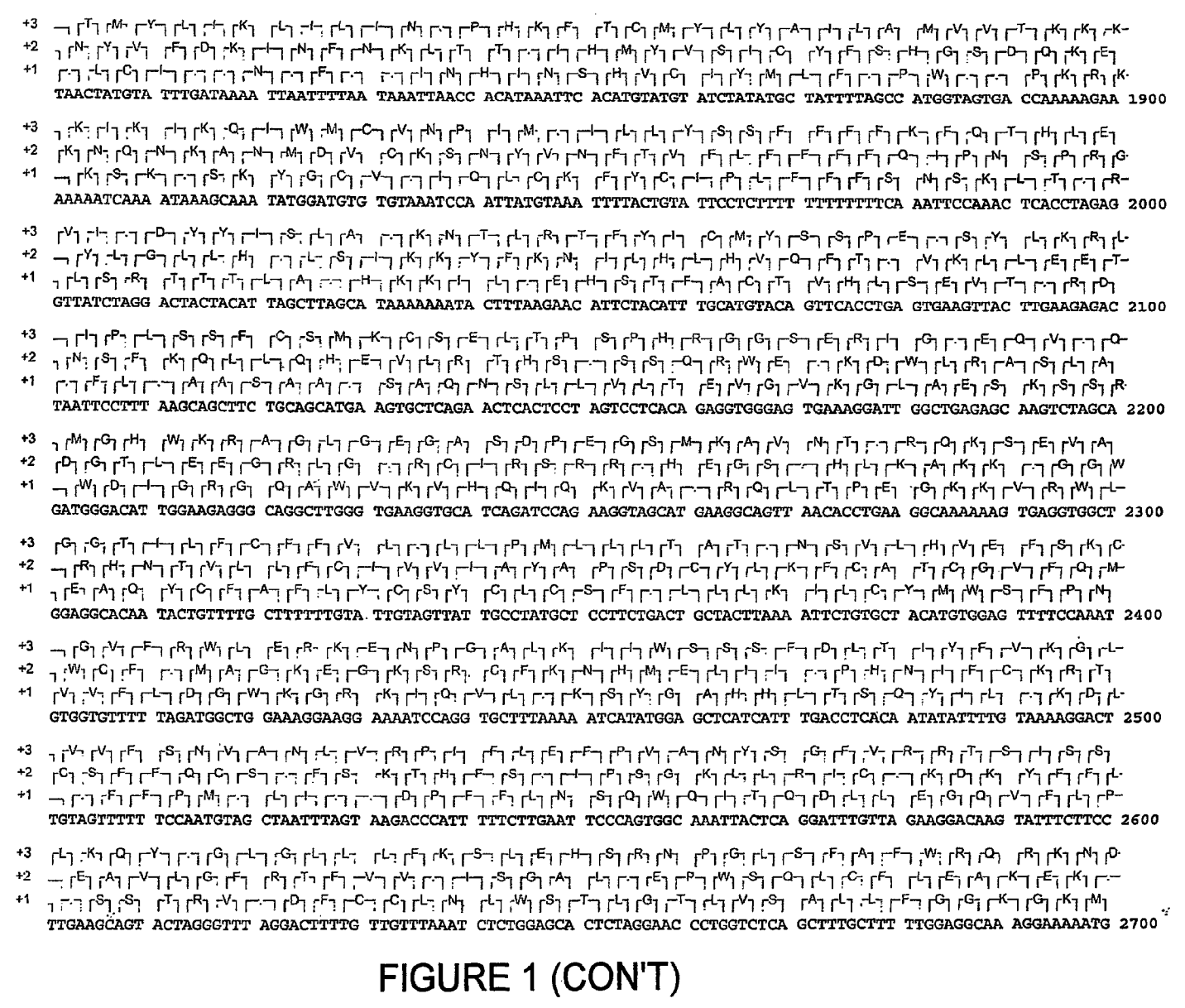
Figure 1:
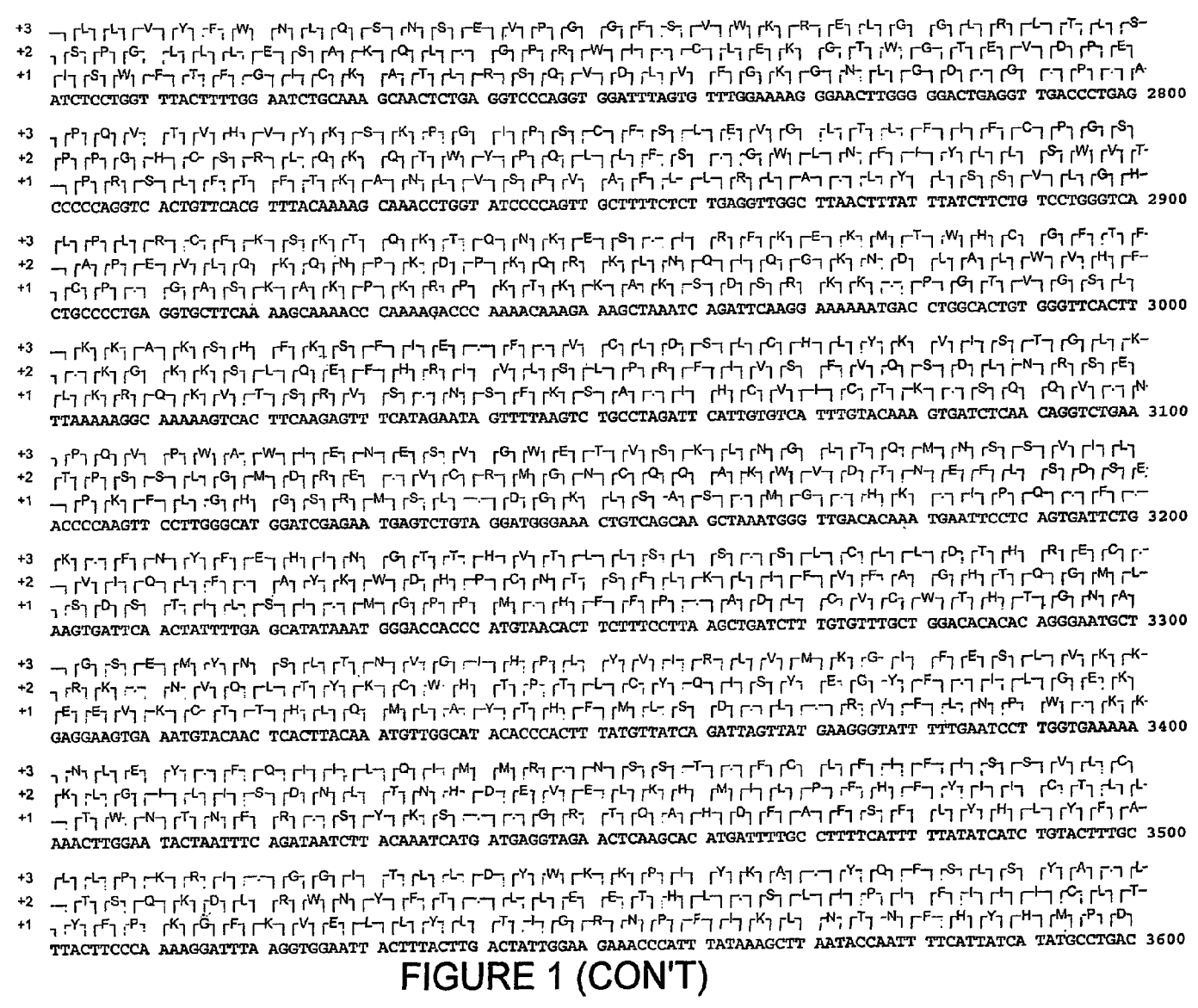
Figure 1:
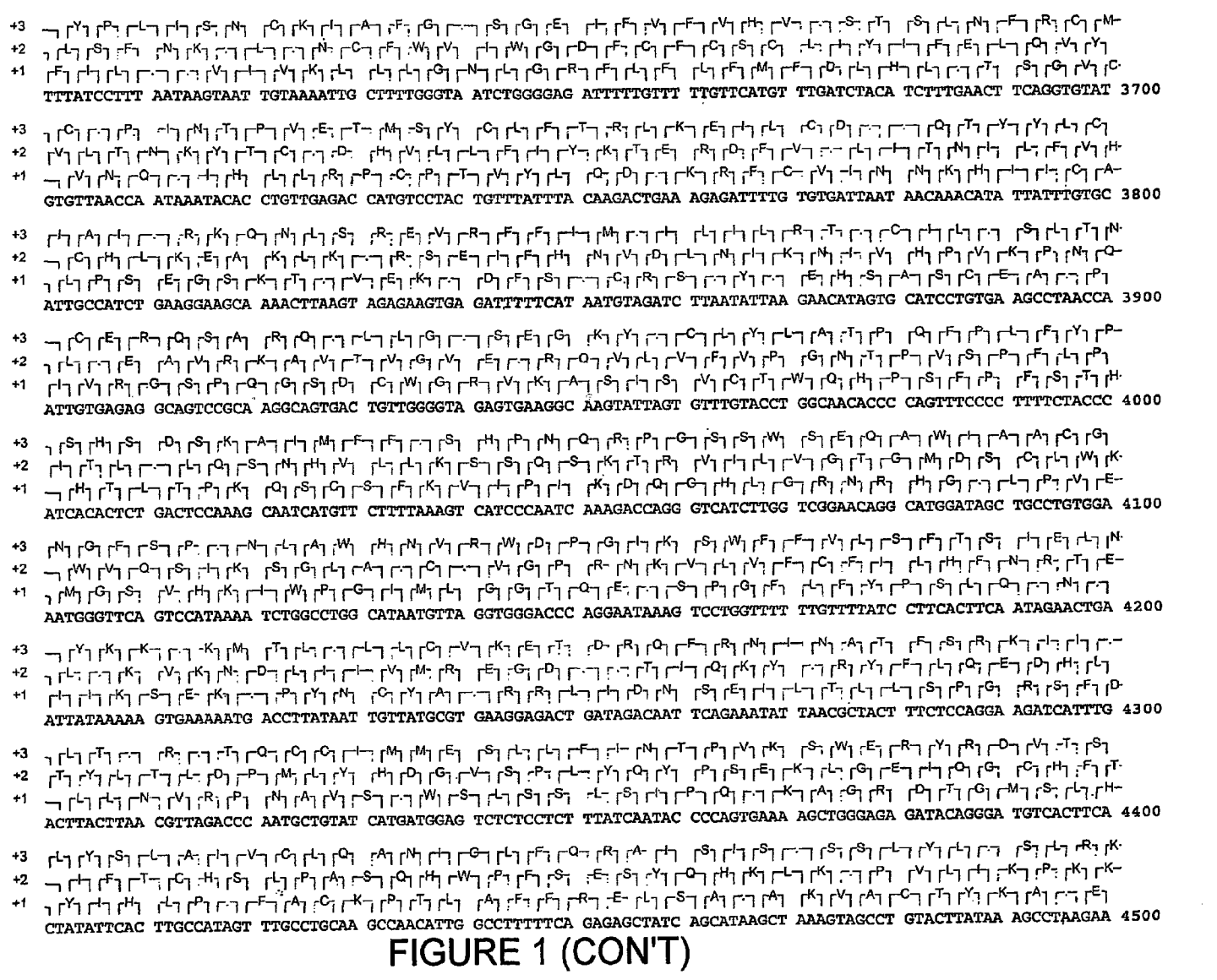
Figure 1:
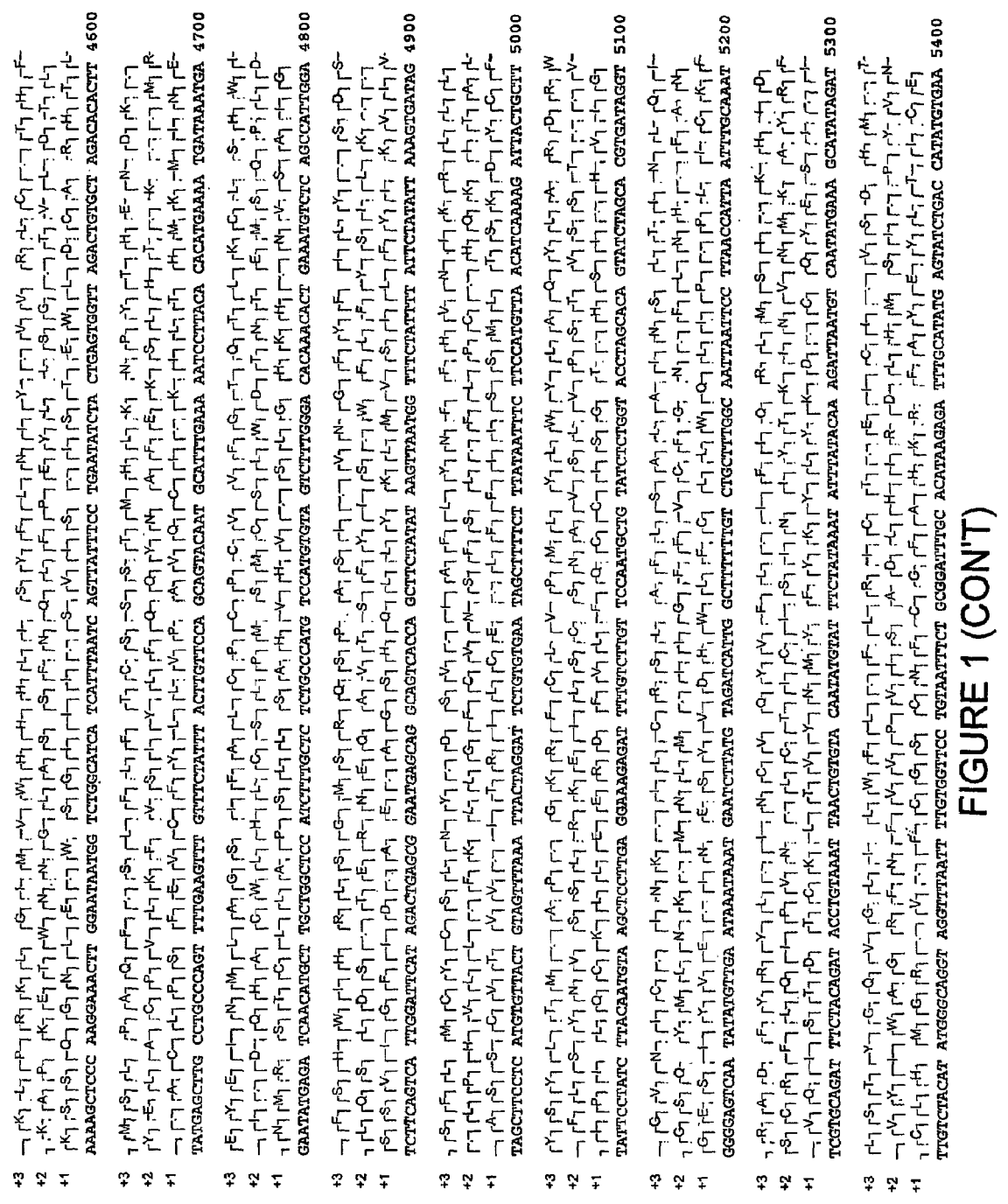
Figure 1:
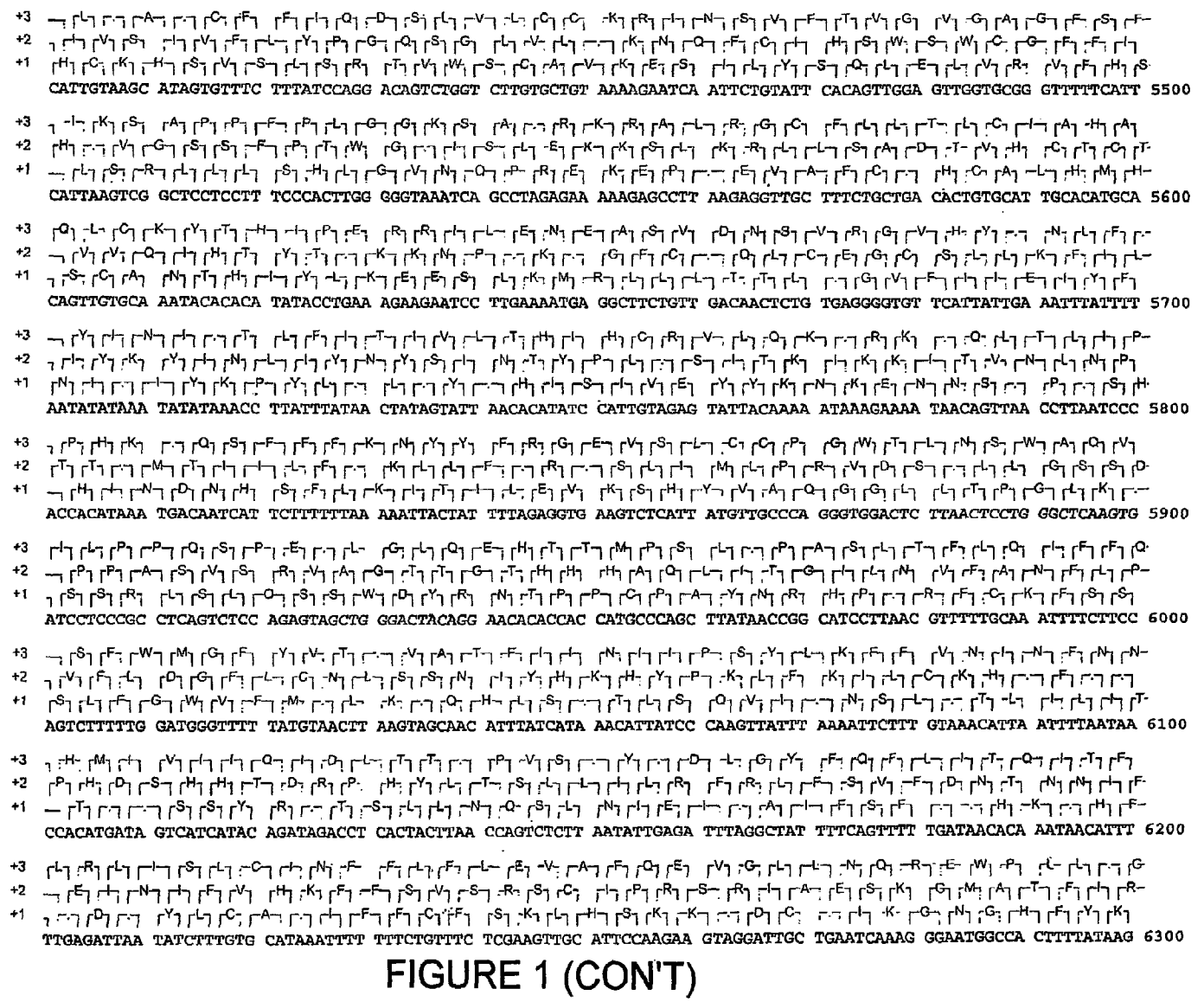
Figure 1:
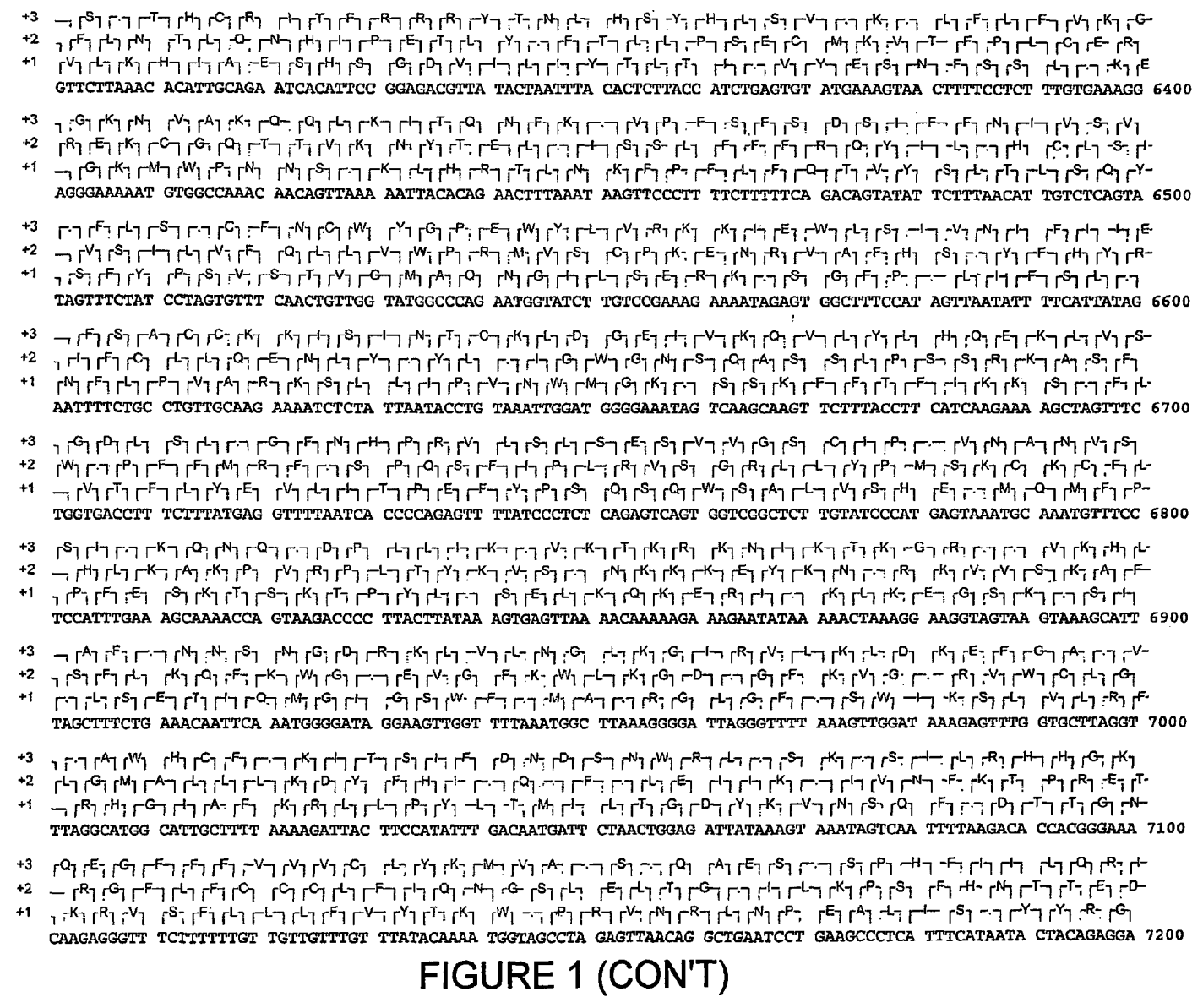
Figure 1:
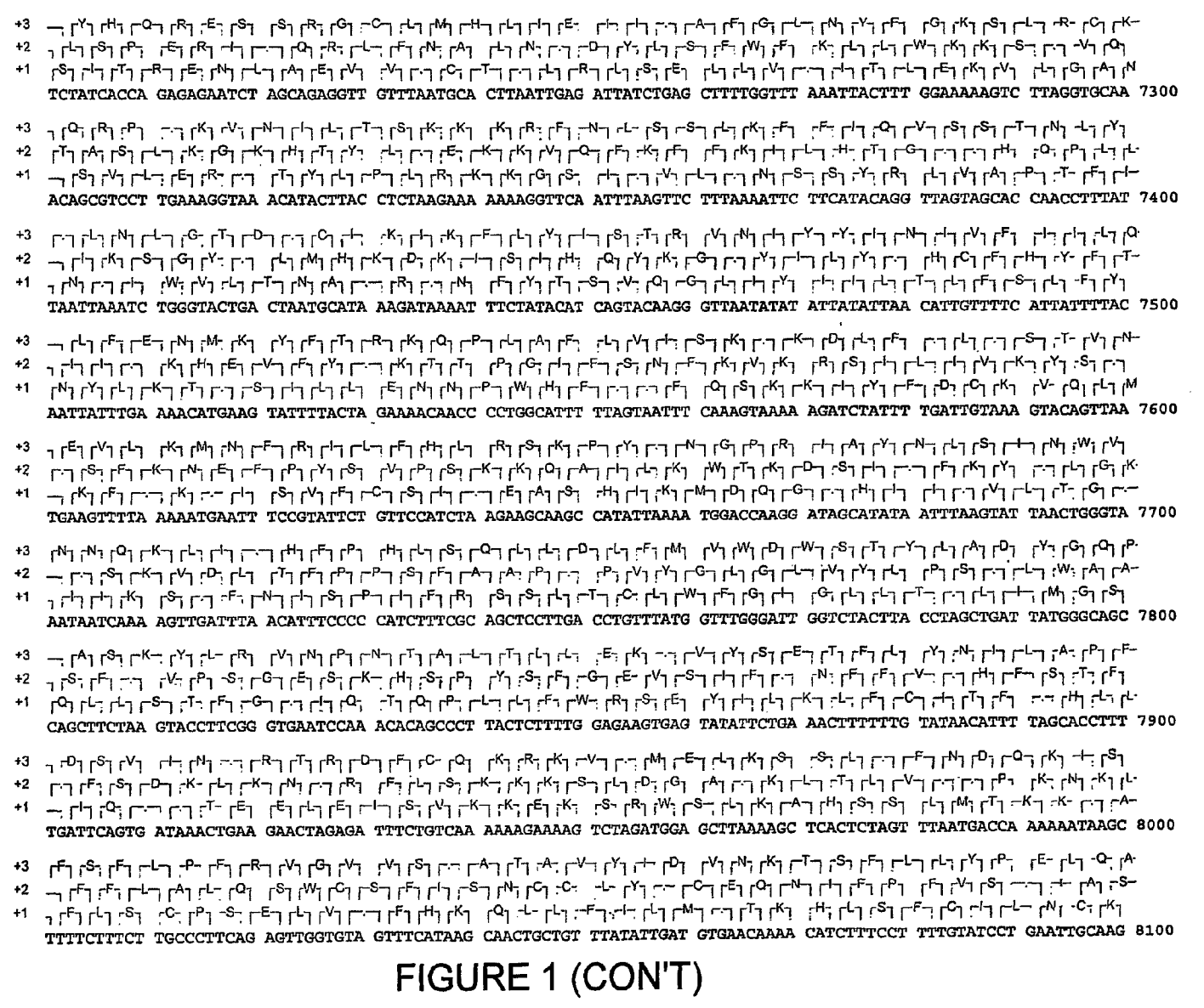
Figure 1:
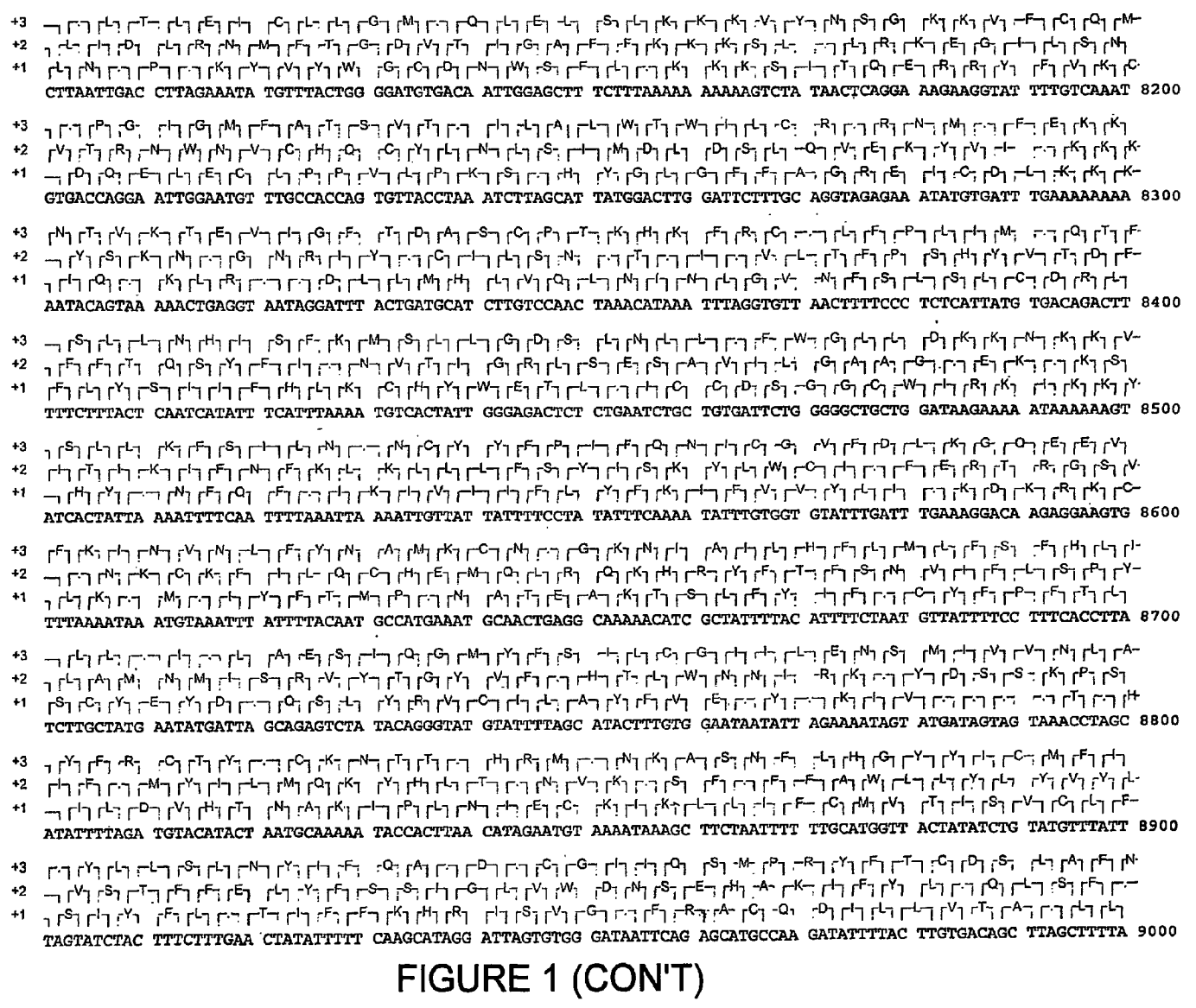
Figure 1:
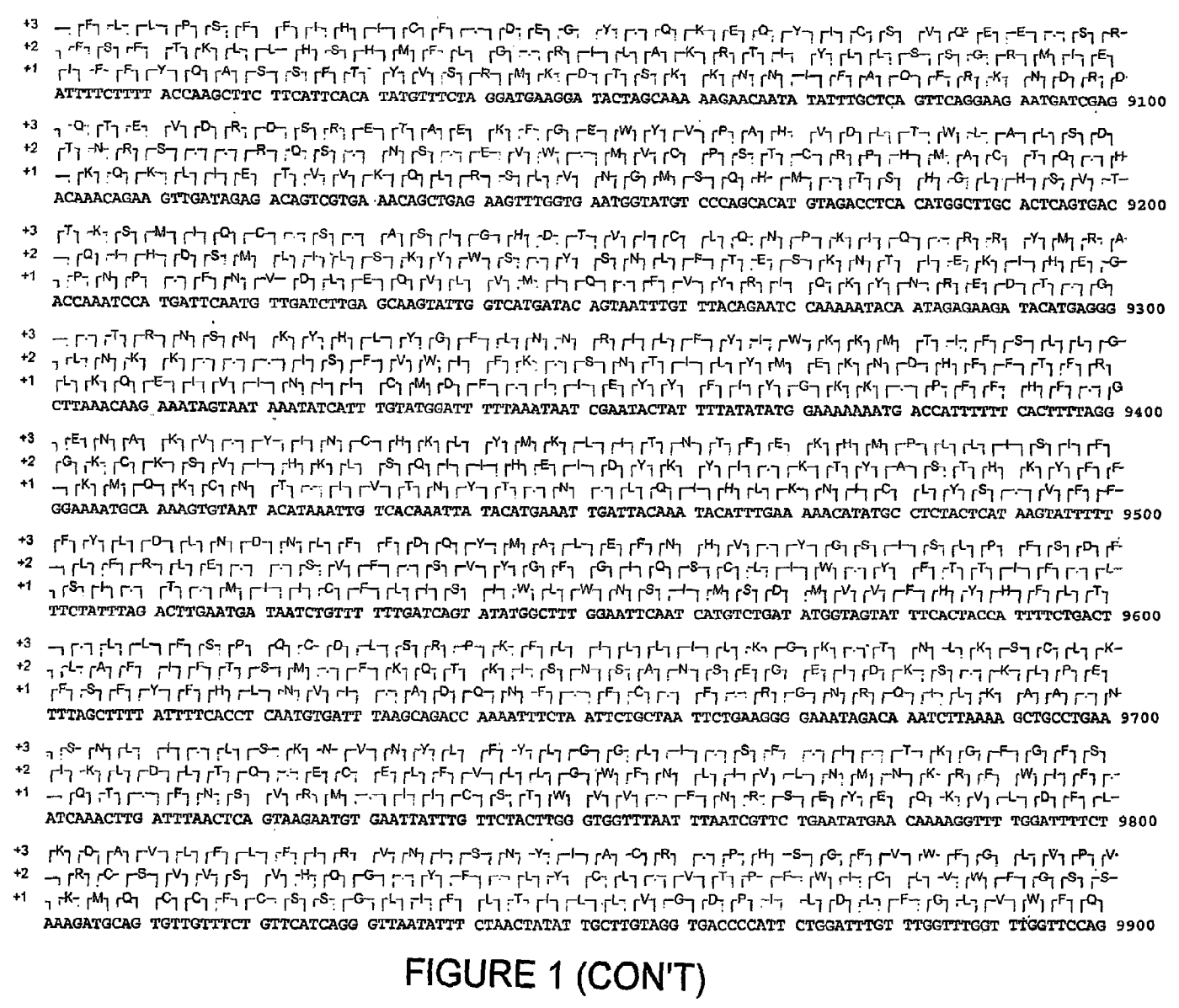
Figure 1:
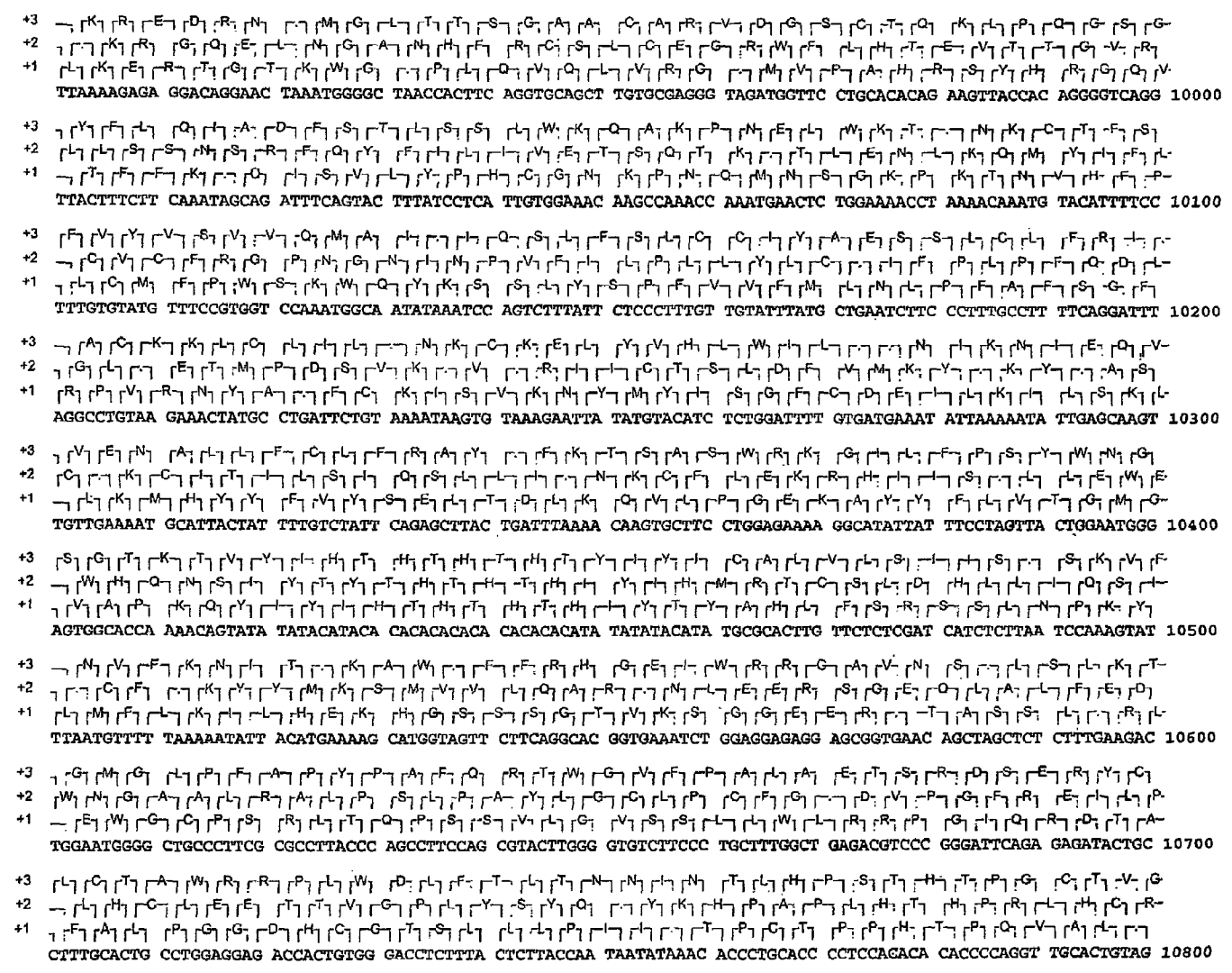
Figure 1:
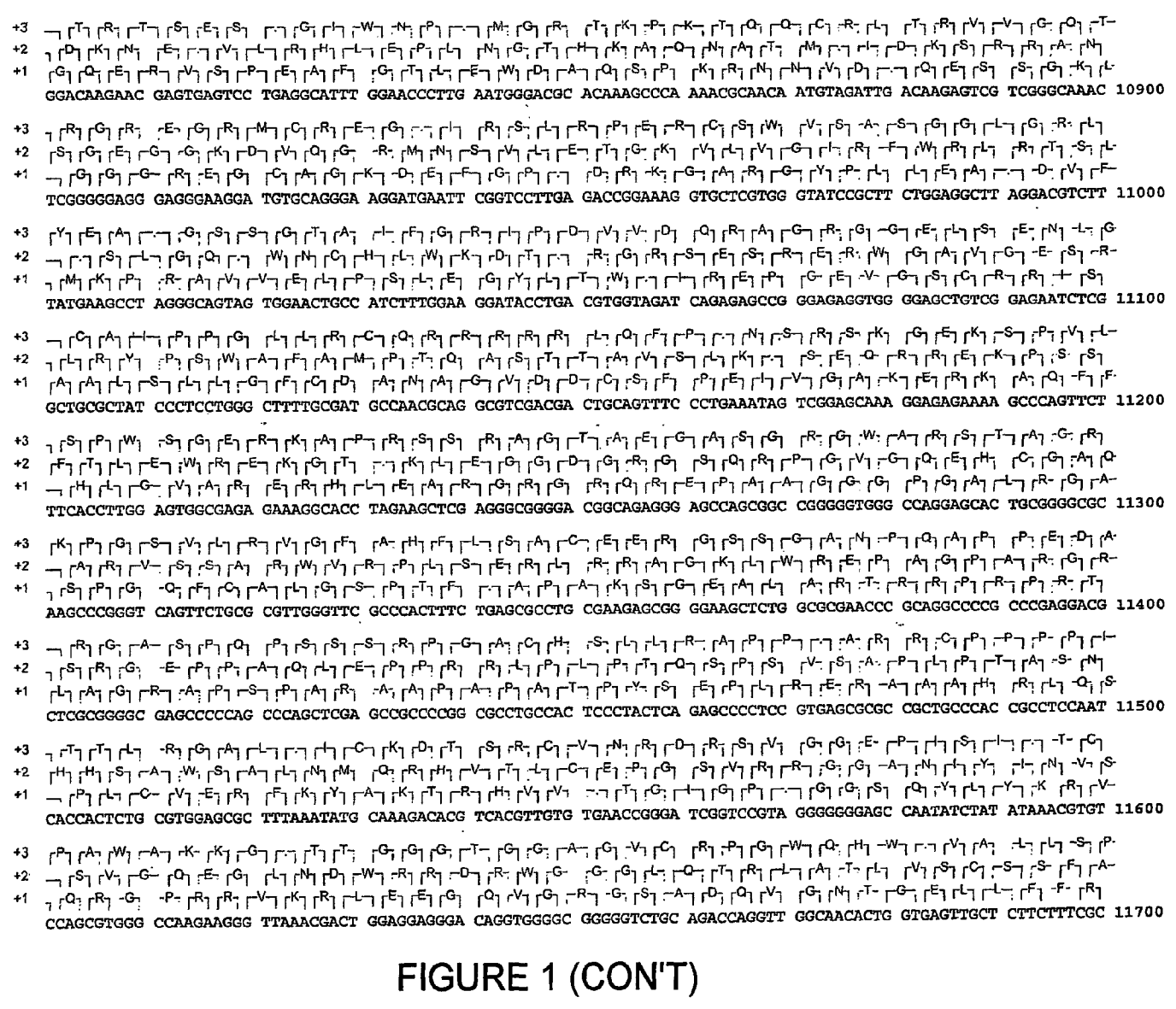
Figure 1:
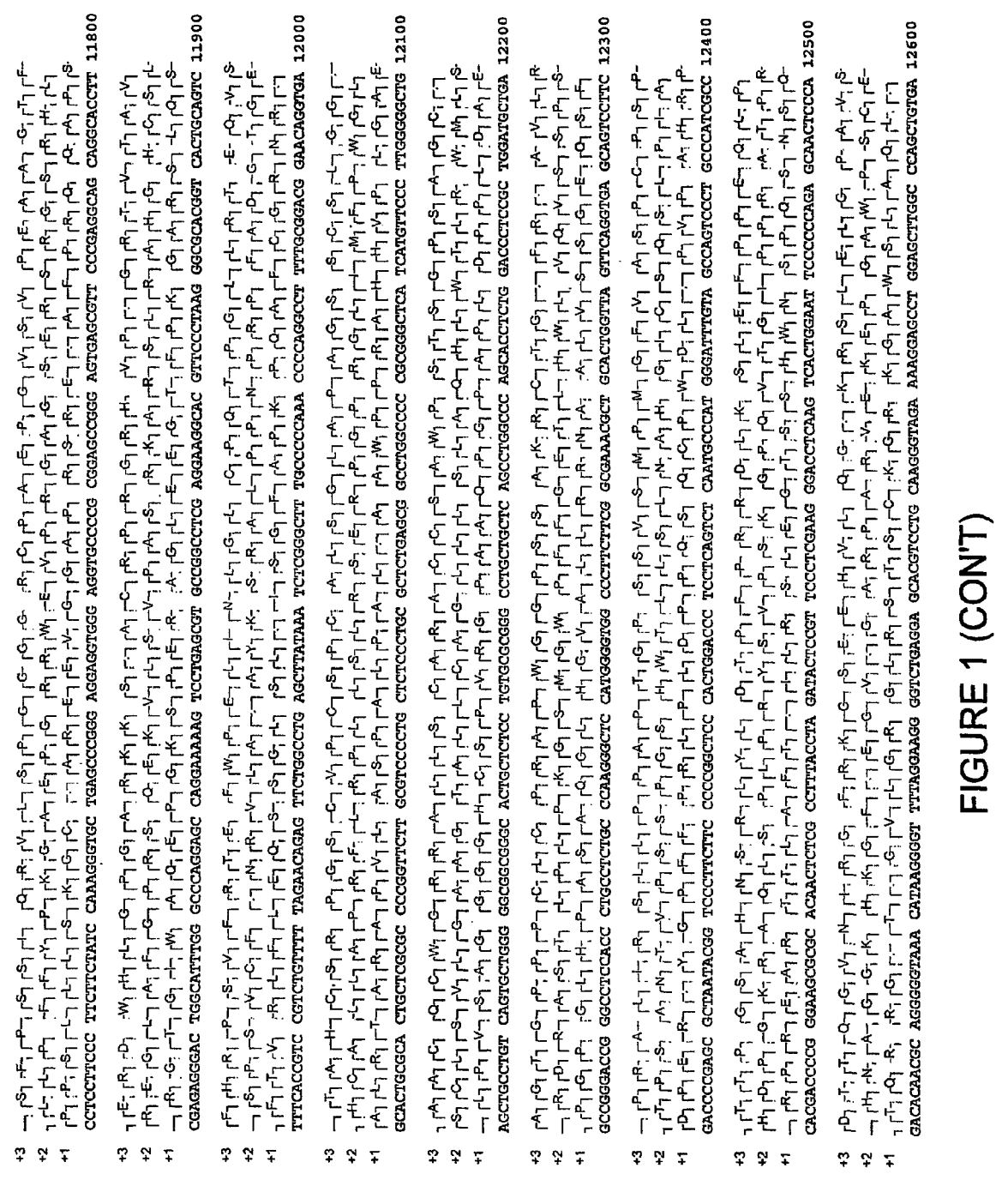
Figure 1:
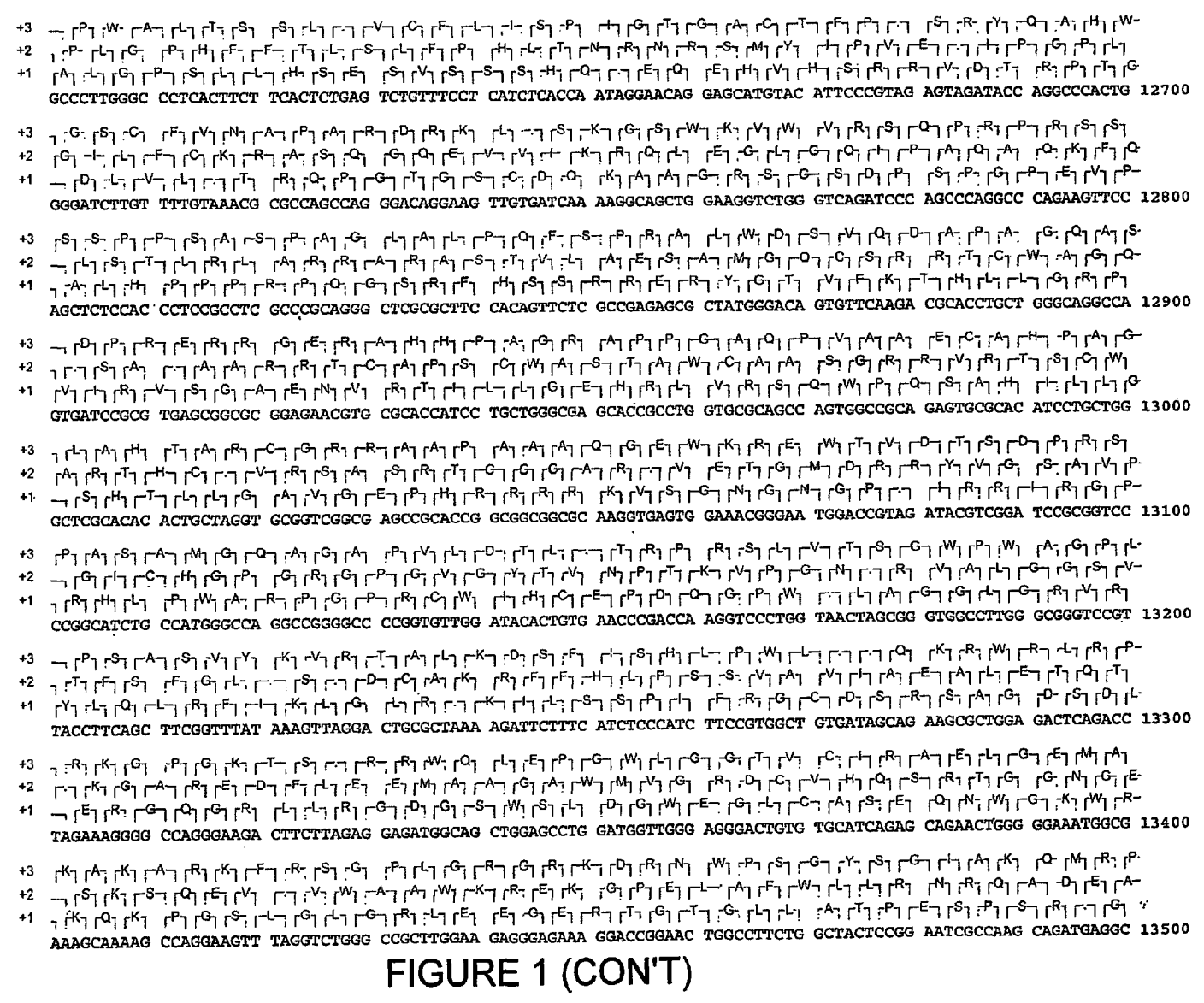
Figure 1:
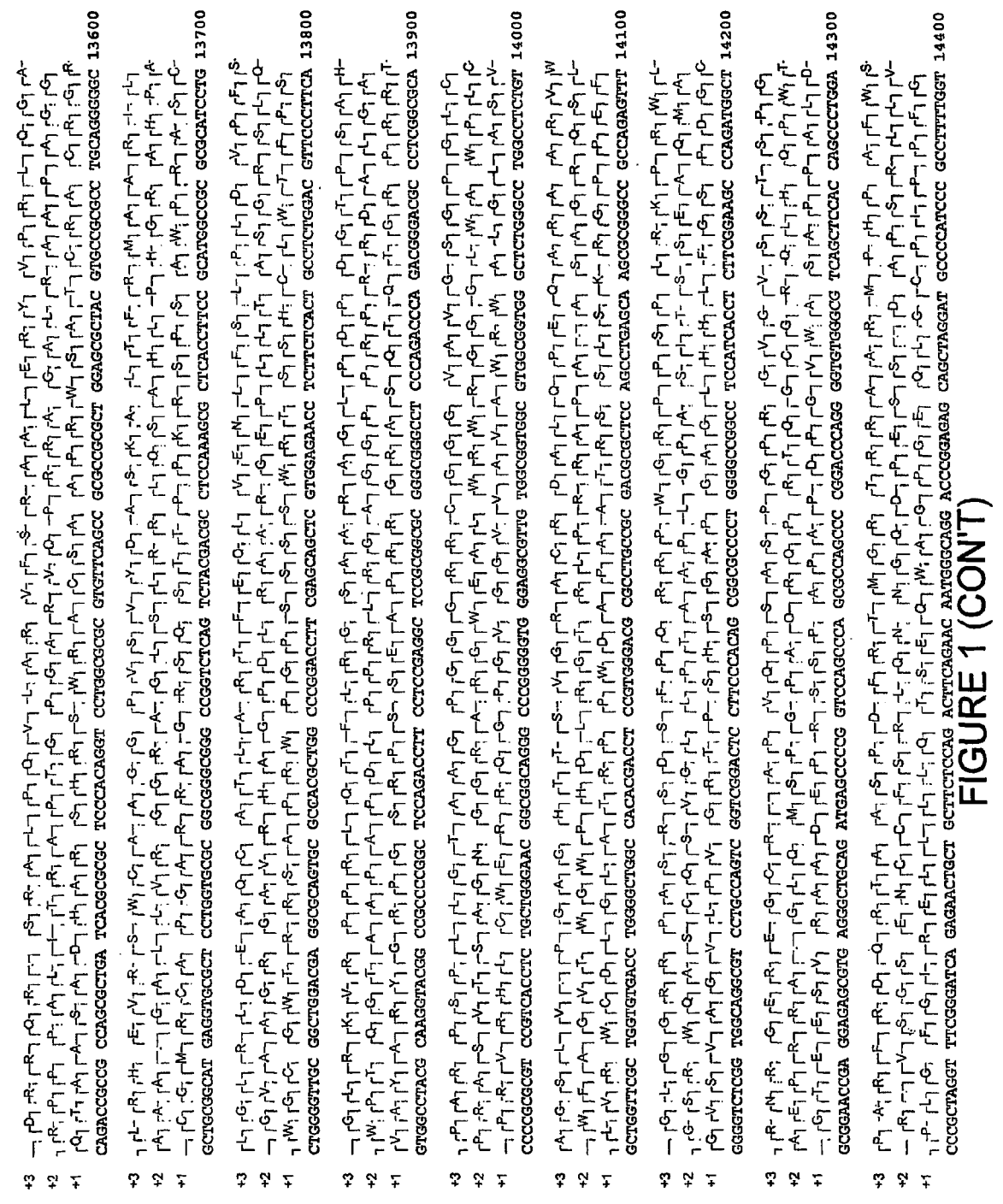
Figure 1:
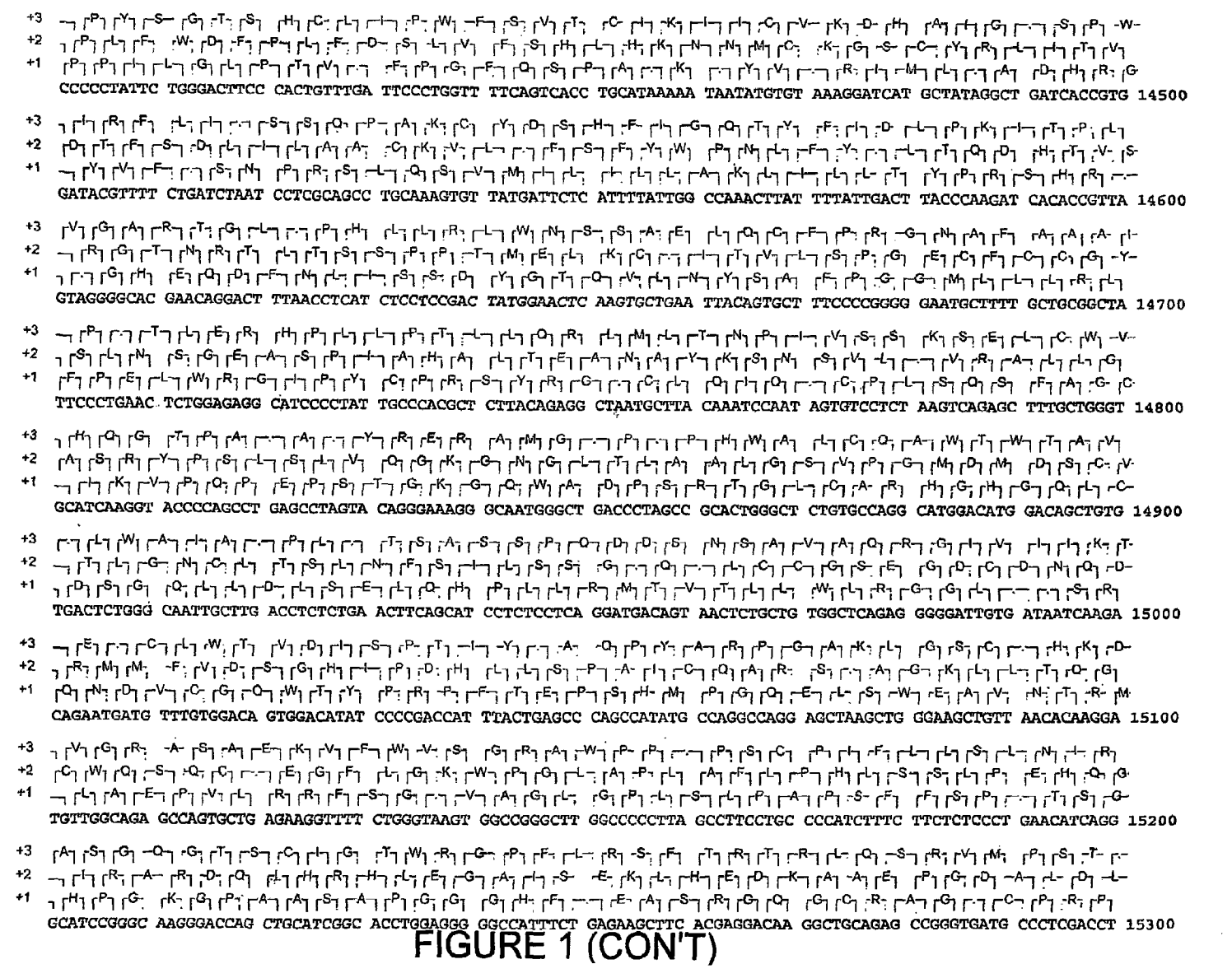
Figure 1:
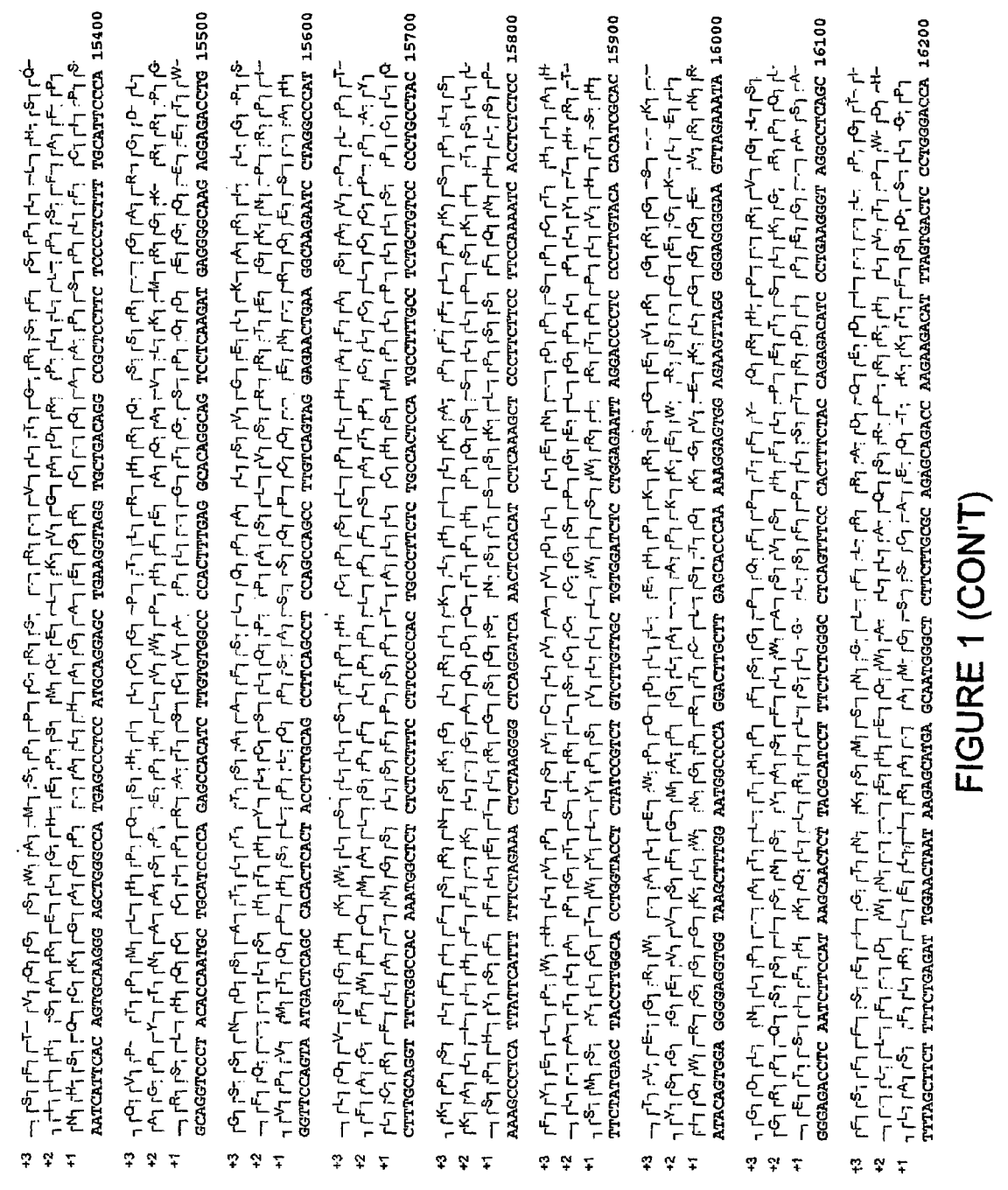
Figure 1:
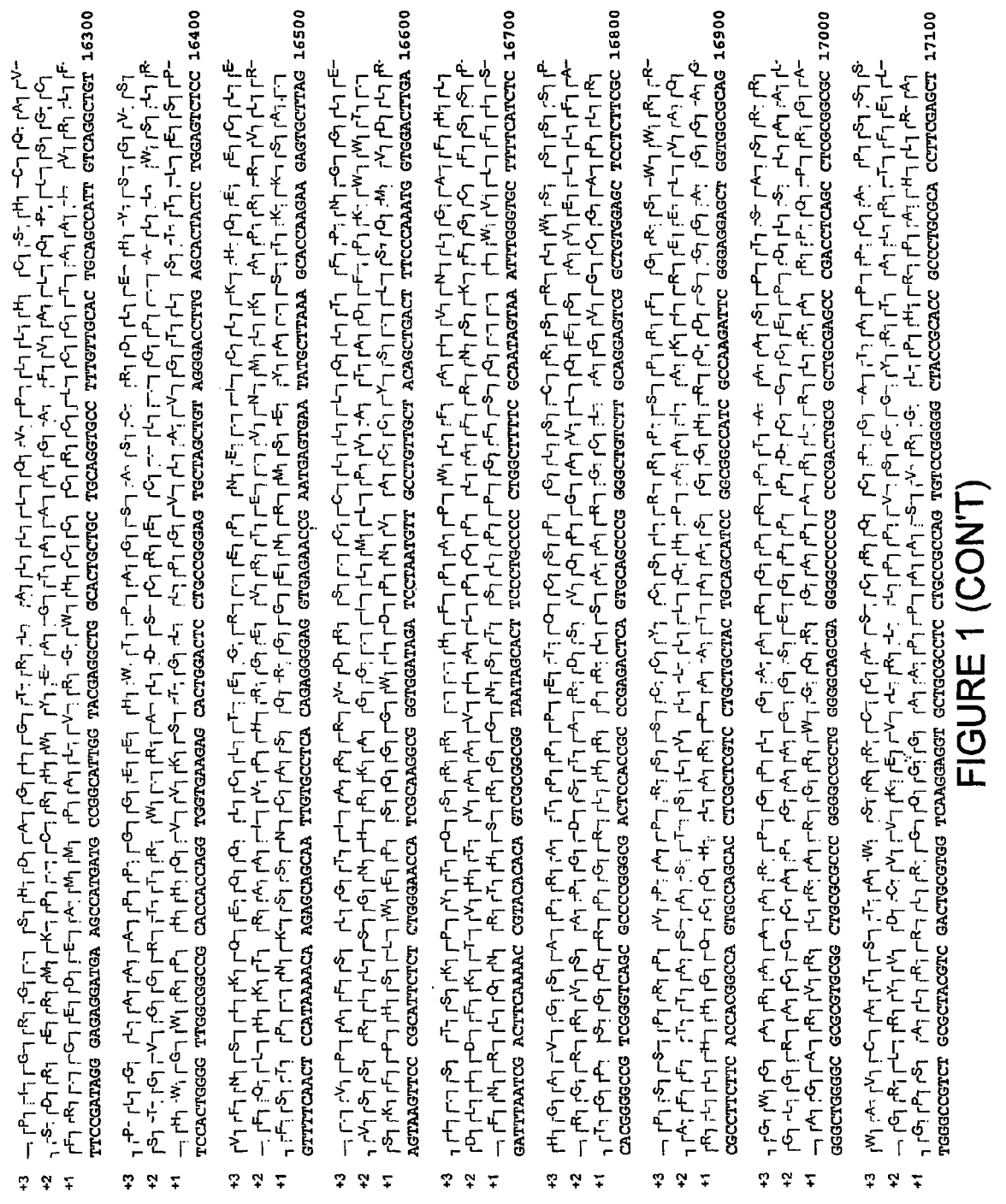
Figure 1:
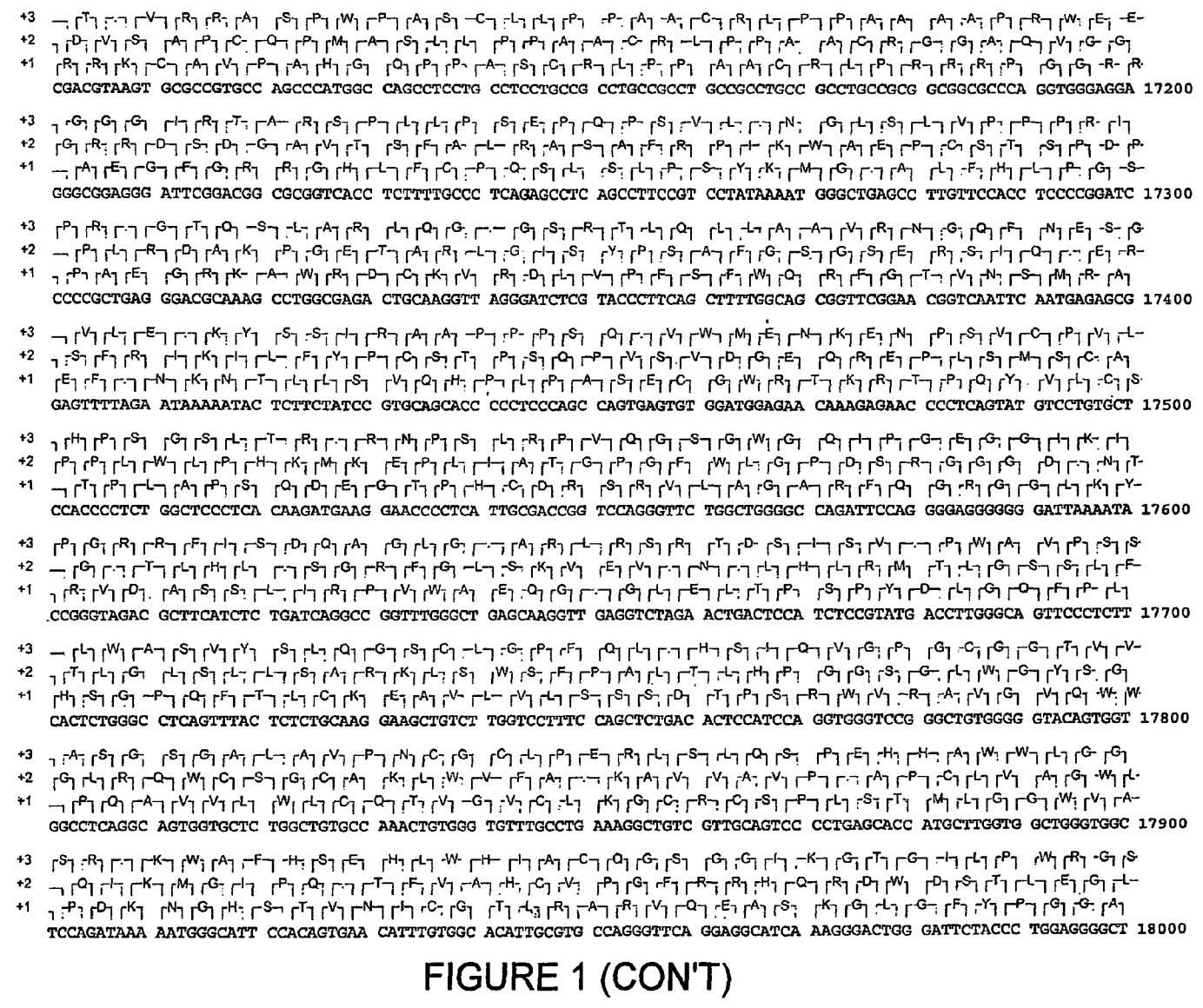
Figure 1:
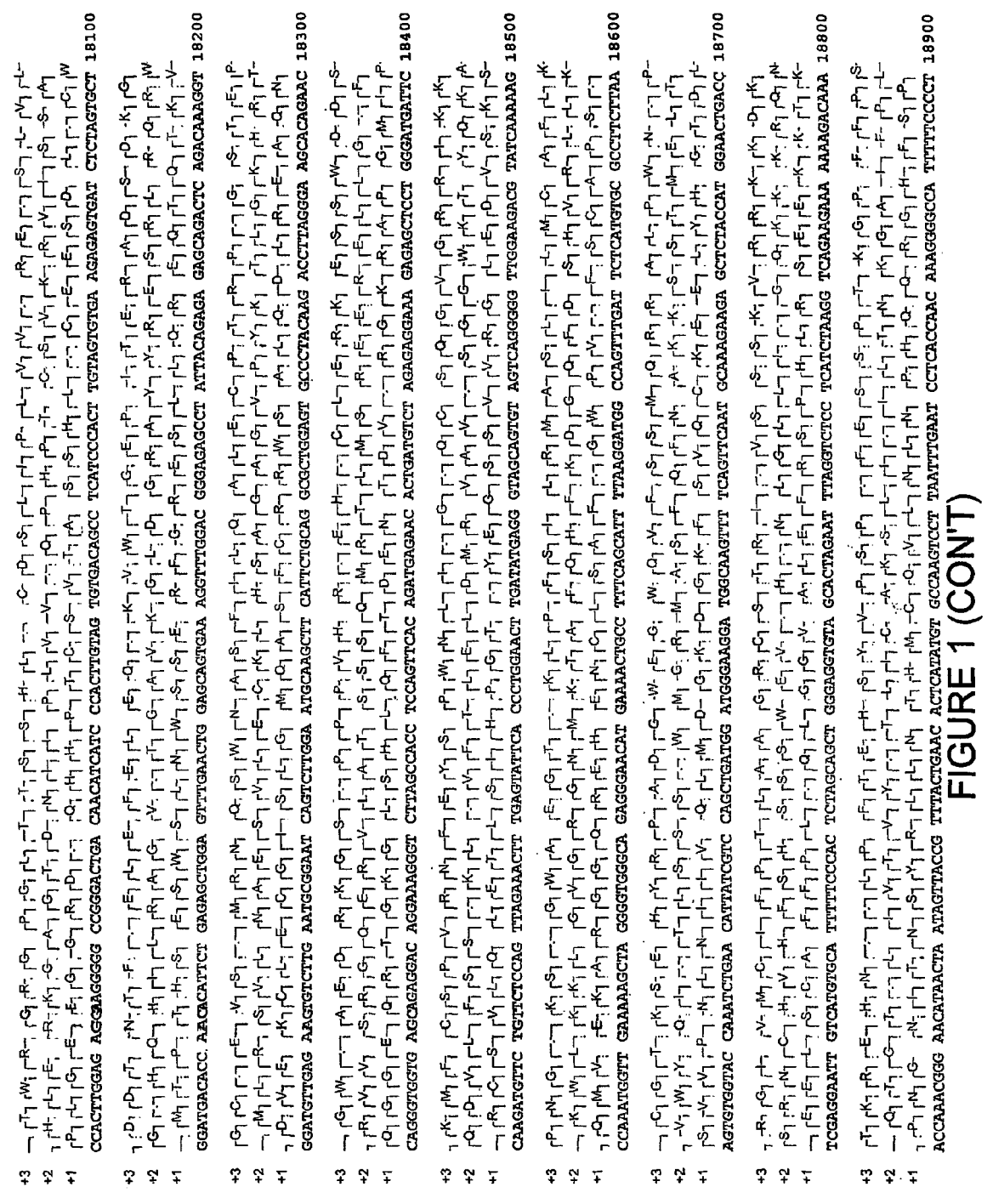
Figure 1:
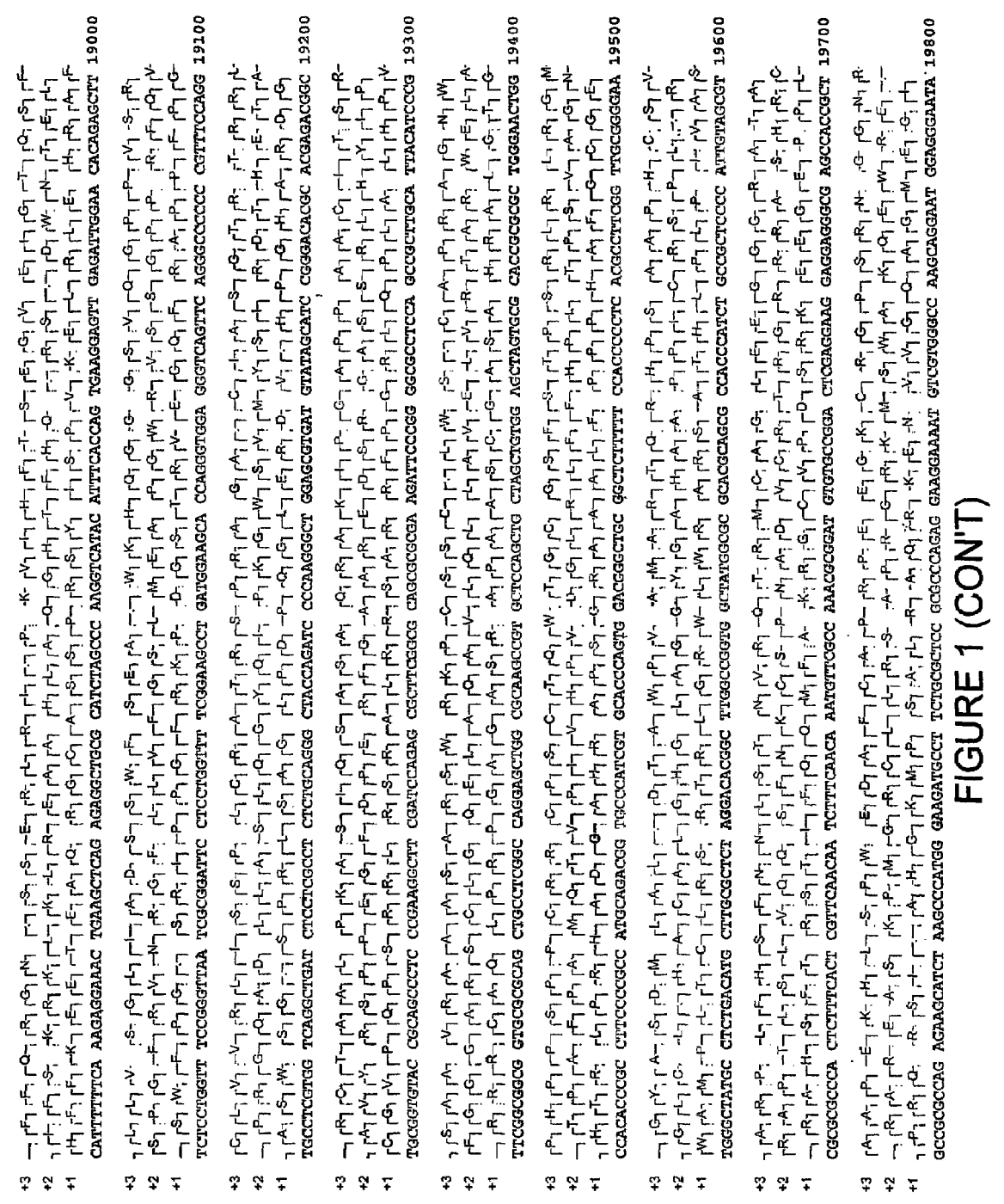
Figure 1:
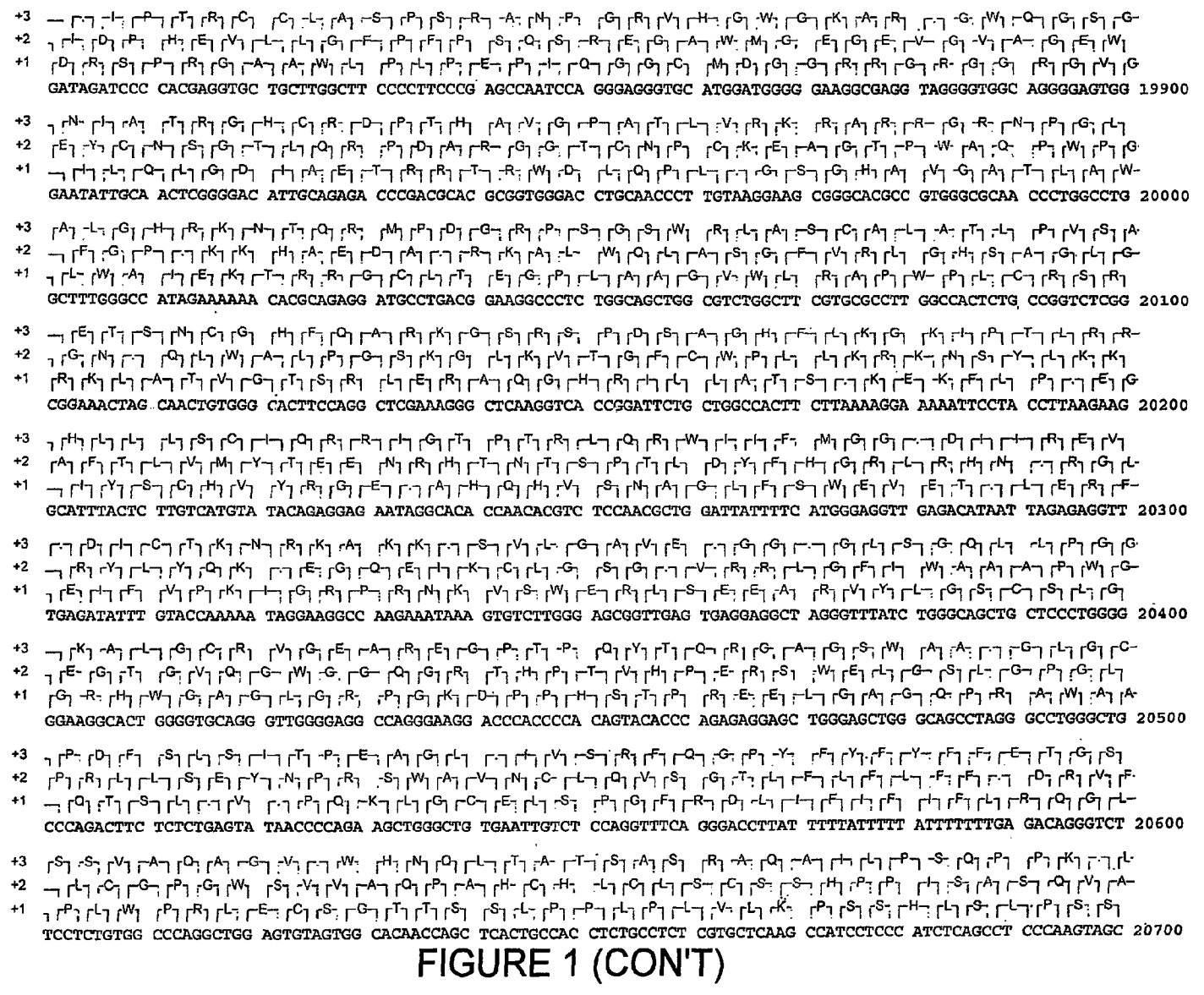
Figure 1:
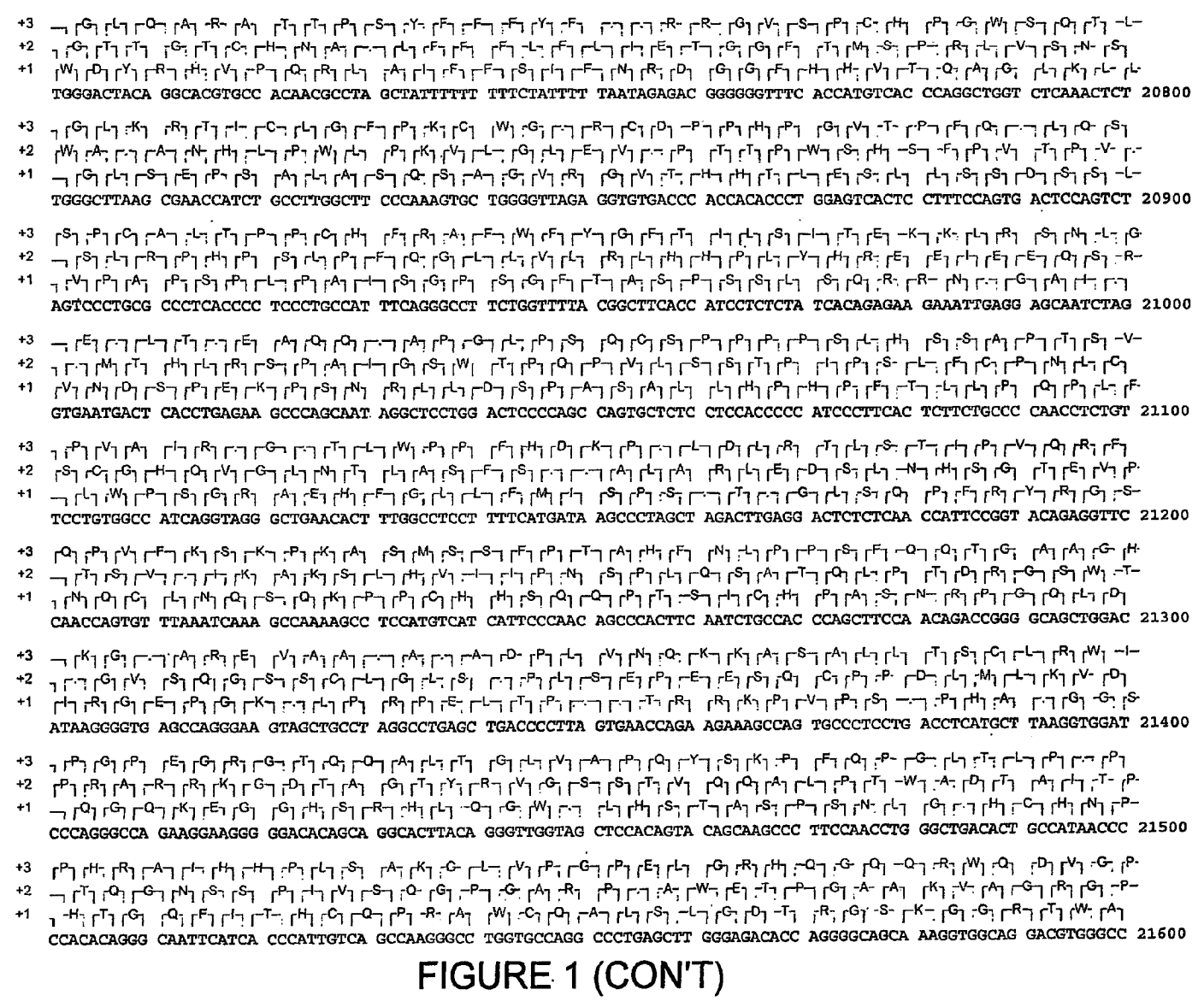
Figure 1:
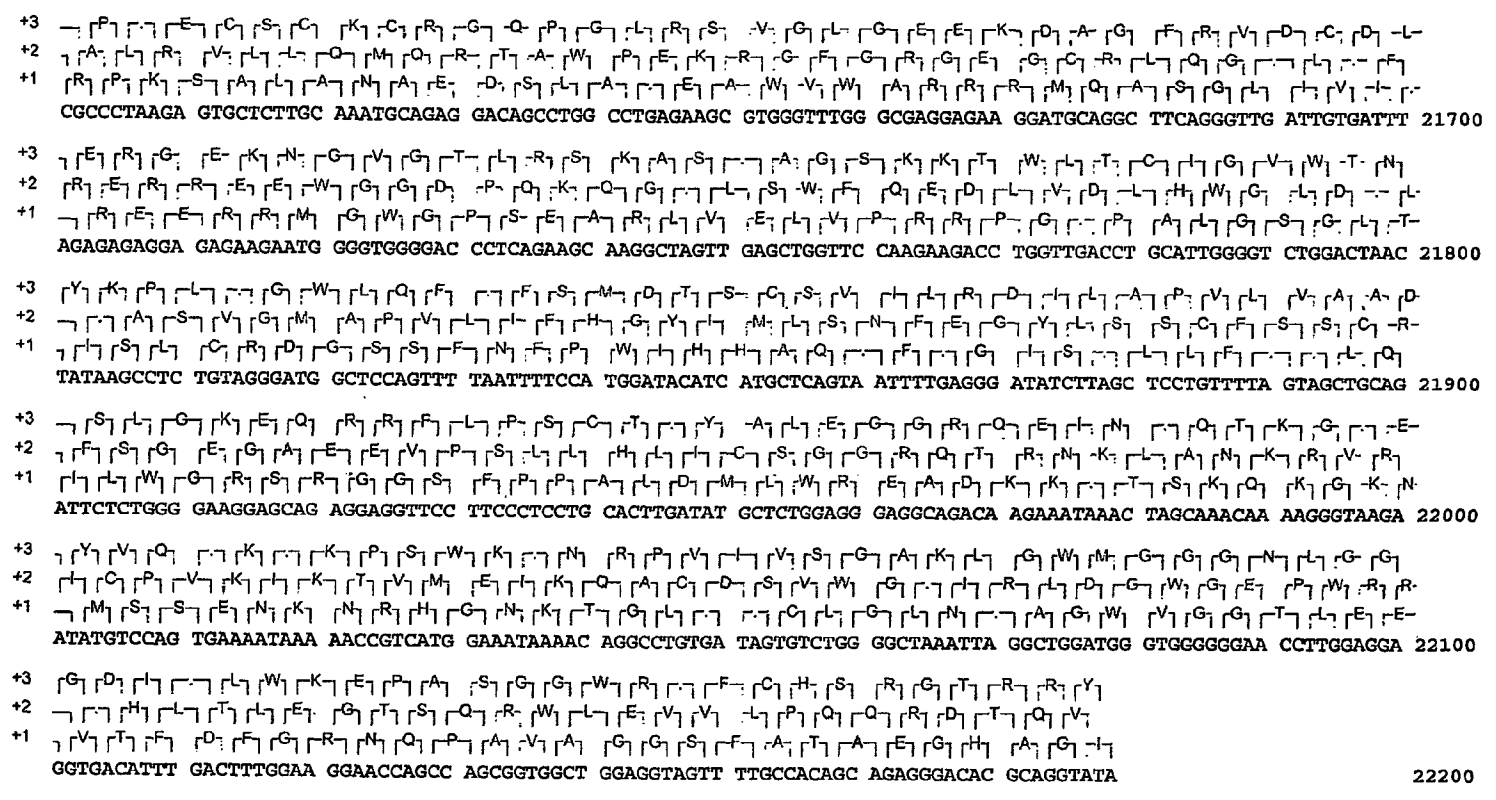

FIG. 1 is the 22,179 bp genomic DNA sequence of P450RAI-3 [SEQ. ID. NO. 9] based on contig information from AL358613 and the sequence obtained from the Centre for Applied Genomics. The corresponding amino acid sequence (from three different reading frames of the nucleotide sequence) are also shown.

FIG. 2 is the 1569 bp cDNA sequence of P450RAI-3 [SEQ. ID. NO. 10].

FIG. 3 is the 522 amino acid sequence of P450RAI-3 [SEQ. ID. NO. 11].

FIG. 4 is the nucleotide and amino acid sequence alignment of P450RAI-3.

FIG. 6A shows the amino acid sequence alignment of P450RAI-1, P450RAI-2 and P450RAI-3. FIG. 6B shows the alignment score amongst the three cytochrome P450RAIs on an amino acid level. FIG. 6C shows the alignment score amongst the three cytochrome P450RAIs at a nucleic acid level.

FIG. 14A is a bar graph illustrating an assessment of RA-metabolism in P450RAI-3 (CYP26C) and CYP26-B-infected Sf9-cells.

FIG. 14B is illustrated P450RAI-3 activity in the presence and absence of NADPH. The results are consistent with P450RAI-3 being a microsomal cytochrome P450.

FIGS. 17A (linear graph) and B (Lineweaver-Burk plot) are graphs illustrating results of ATRA/P450RAI-3 and CYP26B binding assay of Example 7 using Sf9-Bac-P450RAI-3 and Sf9-Bac-CYP26B insect microsomes.

FIGS. 18A (linear graph) and B (Lineweaver-Burk plot) are graphs illustrating results of 9-cis RA/CYP26C (P450RAI-3) binding assay of Example 7. Determination of binding of 9-cis-RA to CYP26-A, B, and C was carried out at substrate concentrations of 0.05 nM to 1000 nM but it was not possible to determine the kD values for CYP26A and CYP26B (See Example 7).

FIGS. 22A and B are graphs illustrating the assessment of ATRA (A) and 9-cis-RA (B) metabolism in Hela cell clones (pcEBVclone #1, pcDNA-clone #22).

DETAILED DESCRIPTION OF THE INVENTION

Figure 5:
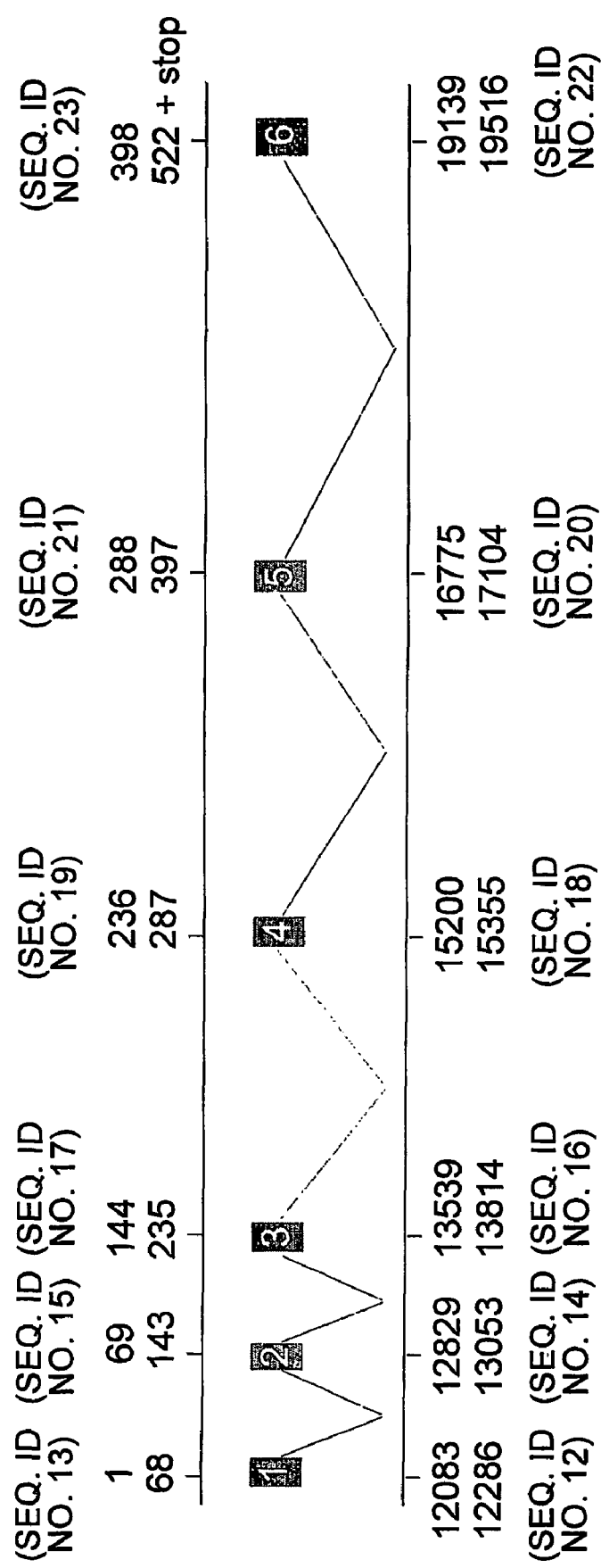
FIG. 5 is a schematic diagram illustrating the 6 exons of human cytochrome P450RAI-3 on human genomic clone (SEQ. ID. NO. 9). The numbers above the schematic diagram indicate the amino acid regions of the exons with respect to FIG. 3 [SEQ. ID. NO. 11] and the numbers below the schematic refer to the nucleotide positions on the human genomic clone sequence (SEQ. ID. NO. 9, or FIG. 1).

In accordance with the present invention there may be employed conventional molecular biology, microbiology, and recombinant DNA techniques within the skill of the art. Such techniques are explained fully in the literature. See for example, Sam brook, Fritch, & Maniatis, Molecular Cloning: A Laboratory Manual, Second Edition (1989, Cold Spring Harbor Laboratory Press, Cold Spring Harbor, N.Y.); DNA Cloning: A practical Approach, Volumes I and II (D. N. Glover ed. 1985); Oligonucleotide Synthesis (M. J. Gait ed. 1984); Nucleic Acid Hybridization B. D. Hames & S. J. Higgens eds. (1985); Transcription and Translation B. D. Hames & S. J. Higgins eds (1984); Animal Cell Culture R. I. Freshney, ed. (1986); Immobilized Cells and enzymes IRL Press (1986); and B. Perbal, A practical Guide to Molecular Cloning (1984).

The following definitions are provided to facilitate understanding of certain terms used in this application.

Abbreviations for amino acid residues are the standard 3-letter and/or 1-letter codes used in the art to refer to one of the 20 common L-amino acids. Likewise abbreviations for nucleic acids are the standard codes used in the art.

In the present invention, "isolated" refers to material removed from its original environment [e.g., the natural environment if it is naturally occurring], and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. However, isolated polynucleotides do not include chromosomes in the present invention.

In the present invention a "secreted" protein refers to a protein capable of being directed to the ER, secretory vesicles, or the extracellular space as a result of a signal sequence, as well as a protein released into the extracellular space without necessarily containing a signal sequence. If the secreted protein is released into the extracellular space, the secreted protein can undergo extracellular processing to produce a mature protein. Release into the extracellular space can occur by many mechanisms, including exocytosis and proteolytic cleavage.

The term "agonist" of a polypeptide of interest, refers to a compound that interacts with the polypeptide e.g.

P450RAI-3, either directly or indirectly and maintains or increases the activity of the polypeptide. Agonists may include proteins, peptides, nucleic acids, carbohydrates, or any other molecules. Agonists also include a molecule derived from P450RAI-3 or a substrate or ligand thereto. Peptide mimetics, synthetic molecules with physical structures designed to mimic structural features of particular peptides, may serve as agonists. The stimulation may be direct, or indirect, or by a competitive or non-competitive mechanism.

The term "antagonist", as used herein, of a polypeptide of interest, for example P450RAI-3, refers to a compound that does not maintain or inhibits the activity of the polypeptide. Antagonists may include proteins, peptides, nucleic acids, carbohydrates, or any other molecules. Antagonists also include a molecule derived from a P450RAI-3 or a substrate or ligand thereto. Peptide mimetics, synthetic molecules with physical structures designed to mimic structural features of particular peptides, may serve as antagonists. The inhibition may be direct, or indirect, or by a competitive or non-competitive mechanism.

"Peptide mimetics" or "peptidomimetics" are structures, which serve as substitutes for peptides in interactions between molecules (See Morgan et al (1989), Ann. Reports Med. Chem. 24:243-252 for a review). Peptide mimetics include synthetic structures, which may or may not contain amino acids and/or peptide bonds but retain the structural and functional features of a peptide, or agonist or antagonist (i.e. enhancer or inhibitor) of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a motif, peptide, or agonist or antagonist (i.e. enhancer or inhibitor) of the invention.

The terms "interact", "interaction", or "interacting" refer to any physical association between proteins, other molecules such as lipids, carbohydrates, nucleotides, and other cell metabolites. Examples of interactions include protein-protein interactions, protein-lipid interactions, and lipid-lipid interactions. The term preferably refers to a stable association between two molecules due to, for example, electrostatic, hydrophobic, ionic and/or hydrogen-bond interactions under physiological conditions. Certain interacting or associated molecules interact only after one or more of them has been stimulated (e.g. phosphorylated). An interaction between proteins and other cellular molecules may be either direct or indirect. Various methods known in the art can be used to measure the level of an interaction. For example, the strength of covalent bonds may be measured in terms of the energy required to break a certain number of bonds.

"P450RAI-3" or "CYP26C" as used herein both refer to the novel cytochrome P450 retinoic acid inducible polypeptide of the invention.

ii) P450RAI-3 Polynucleotides and Polypeptides

The present invention provides a novel cytochrome P450 polypeptide, P450RAI-3, and polynucleotide encoding the same. Fragments and modifications (or variants) to the polypeptide and polynucleotide of the novel cytochrome and obvious chemical equivalents thereof, are also encompassed within the scope of the present invention.

The present inventors isolated human P450RAI-3 and the encoding polynucleotide. P450RAI-3 showed expression in the adrenal gland. The genomic nucleotide sequence or P450RAI-3 is shown in FIG. 1 [SEQ. ID. NO. 9]. The cDNA coding sequence is shown in FIG. 2 [SEQ. ID. NO. 10]. It is 1569 nucleotides in length and contains an open reading frame encoding a polypeptide of 522 amino acid residues, the sequence of which is shown in FIG. 3[SEQ. ID. NO. 11]. Certain exons [exons 1, 4, 5, and 6] of P450RAI-3 were first identified on genomic clone AL358613.4, a 160,532 bp long polynucleotide sequence. The present inventors have identified the whole cDNA sequence and determined its function.

Elevated P450RAI-3 protein expression was observed in the human adrenal gland. These results suggest P450RAI-3 may have a role in retinoic acid metabolism in the adrenal gland and associated conditions.

P450RAI-3 has application to general physiological processes including various conditions such as those related to retinoic acid metabolism. P450RAI-3 metabolizes all-trans-retinoic-acid (ATRA) to polar metabolites. 9-cis-RA competes strongly for P450RAI-3 activity ($ID_{50}$ 1 µM) while ketoconazole is a weak inhibitor ($ID_{50}$ 70 µM). P450RAI-3 metabolies ATRA as well as 9-cis-RA to hydroxy and oxo-metabolites. Retinol (Vitamin A) and Retinal are not substrates for CYP26-C.

P450RAI-3 has been shown to be about 43% identical at the amino acid level with P450RAI-1 and 51% identical to P450RAI-2. At the nucleic acid level, P450RAI-3 is 52% and 61% homologous to P450RAI-1 and P450RAI-2, respectively.

The cytochrome P450s are heme-binding proteins that contain the putative family signature F(XX)G(XXX)C(X)G (X means any residue; conserved residues are in bold (SEQ. ID. NO. 1)). (Nelson, D. R., Methods in Molecular Biology, Vol. 107: Cytochrome P450 Protocols, Cytochrome P450 Nomenclature, pp. 15-24, Phillips, I. R. and Shephard, E. A., eds., Humana Press Inc., Totowa, N.J. (1998)). The heme-binding signature in P450RAI-3 can be found at amino acids 452-461 of FIG. 3 and contains the motif FGGGARSCLG. (SEQ. ID. NO. 8)

Heme-binding proteins, such as myoglobin, hemoglobin and cytochromes, play an important role in several cellular processes, such as respiration and detoxification. For example, the capacity of myoglobin or hemoglobin to bind oxygen depends on the presence of a heme group. Heme consists of an organic part and an iron atom. The iron atom in heme alternates between a ferrous (+2) and a ferric(+3) state; however, only heme containing an iron atom in the +2 oxidation state binds oxygen. (For a review, see e.g., Stryer, Biochemistry ($3^{rd}$ edition) W.H. Freeman and Co., New York, pp. 144 and 404-405 (1988).)

Cytochrome P450s play an important role in the detoxification of toxic substances (xenobiotics), such as phenobarbital, codeine and morphine, by oxidation. It is the ability of P450s to bind heme and oxygen that enables them to function as oxidative enzymes. (for a review, see e.g. Darnelle et al., Molecular Cell Biology ($2^{nd}$ edition), W.H. Freemand and Co., New York, pp 397 and 981-982 (1990)). Thus peptides of P450RAI-3 containing the heme-binding motif or the oxygen binding domain and related activities and functions are also contemplated by the invention.

The P450RAI-3 cDNA sequence (SEQ. ID. NO. 10), such as in FIG. 2, is useful for designing nucleic acid hybridization probes that will detect nucleic acid sequences contained in P450RAI-3 cDNA sequence. These probes will also hybridize to nucleic acid molecules in biological samples, thereby enabling a variety of forensic and diagnostic methods of the invention. Similarly, polypeptides identified from the P450RAI-3 amino acid sequence, such as disclosed in FIG. 3 (SEQ. ID. NO. 11), may be used to generate antibodies, which bind specifically to P450RAI-3.

Nonetheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequences. In this case, the predicted amino acid sequences diverge from the actual amino acid sequences, even though the generated DNA sequences may be greater than 99.9% identical to the actual DNA sequence. For example, one base insertion or deletion in an open reading frame of over 1000 bases.

For those applications requiring precision in the nucleotide sequence or the amino acid sequence, the present invention provides the generated nucleotide sequence of P450RAI-3 as depicted in FIG. 2 (SEQ. ID. NO. 10) and the predicted translated amino acid sequence of FIG. 3 ((SEQ. ID. NO. 11).

The present invention also relates to the P450RAI-3 gene and the gene corresponding to FIG. 1 (genomic DNA (SEQ. ID. NO. 9)) or 2 (cDNA (SEQ. ID. NO. 10)). The P450RAI-3 gene can be isolated in accordance with known methods using the sequence information disclosed herein. Such methods include preparing probes or primers from the disclosed sequence and identifying or amplifying the P450RAI-3 gene from appropriate sources of genomic materials.

Also provided in the present invention are species homologs of human P450RAI-3. Species homologs may be isolated and identified by making suitable probes or primers from the sequences provided herein and screening a suitable nucleic acid source for the desired homolog.

As used herein and encompassed within the scope of this invention, a P450RAI-3 "nucleic acid" or "nucleic acid molecule" or "polynucleotide" refers to a molecule having the nucleic acid sequence as shown in FIG. 1 (SEQ. ID. NO. 9) or the coding region thereof, such as the sequence of FIG. 2 (SEQ. ID. NO. 10). For example, P450RAI-3 polynucleotide can contain the nucleotide sequence of the full length cDNA sequence as well as fragments, epitomes, domains and variants of the nucleic acid. Furthermore, a P450RAI-3 "polypeptide" as used herein refers to a molecule having the translated amino acid sequence generated from the polynucleotide as broadly defined and preferably having the sequence of FIG. 3 (SEQ. ID. NO. 11).

A P450RAI-3 "polynucleotide" also refers to isolated polynucleotides, which encode the P450RAI-3 polypeptides and to polypeptides closely related thereto.

A P450RAI-3 "polynucleotide" also refers to isolated polynucleotides, which encode the amino acid sequence in FIG. 3 (SEQ. ID. NO. 11), or a biochemically active fragment thereof, including obvious chemical equivalents thereof.

A P450RAI-3 polynucleotide also encompasses those polynucleotides which differ from any of the polynucleotides of the invention in codon sequence due to the degeneracy of the genetic code such polynucleotides encode functionally equivalent polypeptides but differ in sequence from the above mentioned sequences due to degeneracy in the genetic code.

A P450RAI-3 "polynucleotide" also includes those polynucleotides capable of hybridizing, under stringent hybridization conditions, to polynucleotide sequences disclosed herein, such as those of FIG. 1 (SEQ. ID. NO. 9) or 2 (SEQ. ID. NO. 10) or the complement thereof. "Stringent hybridization conditions" refers to an overnight incubation at 42° C. in a solution comprising 50% formamide, 5×SSC [750 mM NaCl, 75 mm sodium citrate], 50 mM sodium phosphate [pH 7.6], 5× Denhardt's solution, 10% dextran sulfate, and 20 ug/ml denatured, sheared salmon sperm DNA, followed by washing the filters in 0.1×SSC at about 65° C.

Of course, a polynucleotide which hybridizes only to poly A+ sequences [such as any 3' terminal poly A+ tract of a cDNA] or to a complementary stretch of T [or U] residues, would not be included in the definition of "polynucleotide", since such a polynucleotide would hybridize to any nucleic acid molecule containing a poly [A] stretch or the complement thereof [e.g., practically any double-stranded cDNA clone].

The P450RAI-3 polynucleotide can be composed of any polyribonucleotide or polydeoxyribonucleotide, which may be unmodified RNA or DNA or modified RNA or DNA. As such, in the sequences referred to herein "T" can also be "U". For example, P450RAI-3 polynucleotide can be composed of single- and double-stranded DNA, DNA that is a mixture of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double stranded regions. In addition, the P450RAI-3 polynucleotide or hybrid thereof can be composed of triple-stranded regions comprising RNA or DNA or both RNA and DNA.

In addition, P450RAI-3 polynucleotide may contain one or more modified bases or DNA or RNA backbones modified for stability or for other reasons. "Modified" bases include, for example, tritiated bases and unusual bases such as inosine. A variety of modifications can be made to DNA and RNA; thus, "polynucleotide" embraces chemically, enzymatically, or metabolically modified forms. Modified forms also encompass analogs of the polynucleotide sequence of the invention, wherein the modification does not alter the utility of the sequences described herein. In one embodiment, the modified sequence or analog may have improved properties over unmodified sequence.

One example of a modification to prepare an analog within the scope of this invention is to replace one of the naturally occurring bases (i.e. adenine, guanine, cytosine or thymidine) of the sequence shown in FIG. 1 or 2 (SEQ. ID. NOS. 9 or 10) with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in FIG. 1 or 2 (SEQ. ID. NOS. 9 or 10). For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The P450RAI-3 polypeptide of the invention can be composed of amino acids joined to each other by peptide bonds or modified peptide bonds, i.e., peptide isosteres, and may contain amino acids other than the 20 gene-encoded amino acids. The P450RAI-3 polypeptides may be modified by either natural processes, such as post-translational processing or by chemical modification techniques, which are well known in the art. Such modifications are described in basic texts, research manuals and research literature. Modifications may occur anywhere in the P450RAI-3 including the peptide backbone, the amino acid side-chain and the amino or carboxyl termini. It will be appreciated that the same type of modification may be present in the same or varying degree at several sites in a given P450RAI-3 polypeptide. In addition, a given P450RAI-3 may contain many types of modification. The modifications may result from post-translational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulphide bond formation, demethylation, formation of covalent cross-links, reduction of disulphide bonds into free cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulphation, transfer-RNA mediated addition of amino acids to proteins such as arginylation and ubiquitination [See, for example, Proteins-Structure and Molecular Properties, 2nd Ed., T. E. Creighton, W.H. Freeman and Company, New York (1993); Post-Translational Covalent Modification of Proteins, B. C. Johnson, Ed., Academic Press, New York, p 1-12 (1983); Seifter et al., Methods in Enzymology 182: 626-646 (1990); Rattan et al., Ann. NY Acad. Sci. 663: 48-62 (1992).]

A P450RAI-3 exhibiting activity similar, but not necessarily identical to, an activity of a P450RAI-3 polypeptide, including mature forms, as measured by a given biological assay, with or without dose dependency are also encompassed within the scope of this invention. Where dose dependency exists, it need not be identical to the P450RAI-3 polypeptide but rather substantially similar to the dose-dependency in a given activity as compared to the P450RAI-3 polypeptide. For example, the candidate polypeptide will exhibit greater activity or not more than about 25-fold less and, preferably, not more than about tenfold less activity and most preferably, not more than about three-fold less activity relative to P450RAI-3 polypeptide.

P450RAI-3 polypeptide thereof may include various structural forms of the primary protein that retain biological activity. For example, a polypeptide of the invention may be in the form of acidic or basic salts or in neutral form. The polypeptides of the invention may be in the form of a secreted protein (i.e. could include fusion proteins or solubilized forms of the proteins of the invention), including the mature form or may be part of a larger protein such as a fusion protein. It is often advantageous to include an additional amino acid sequence which contains secretory or leader sequences, pro-sequences, sequences which aid in purification, such as multiple histidine residues, or an additional sequence for stability during recombinant production.

P450RAI-3 polypeptides are preferably provided in an isolated form, and preferably are substantially purified, A recombinantly produced version of a P450RAI-3 polypeptide (including the secreted polypeptide, if genetically modified to be a secreting protein), can be substantially purified by the one-step method described in Smith and Johnson, Gene 67: 31-40 (1988). P450RAI-3 polypeptides also can be purified from natural or recombinant sources using antibodies of the invention raised against the polypeptides of the invention in methods well known in the art.

Production of Polynucleotides and Polypeptides of the Invention

The polynucleotides and polypeptides of the invention can be prepared in any suitable manner, such means being known to persons skilled in the art. Such methods include isolating naturally occurring polypeptides and polynucleotides, recombinantly or synthetically/chemically produced polynucleotides or polypeptides or a combination of these methods.

An isolated nucleic acid molecule of the invention which comprises DNA can be isolated by preparing a labelled nucleic acid probe based on all or part of the nucleic acid sequences as shown in FIG. 1 or 2 (SEQ. ID. NOS. 9 or 10) and using this labelled nucleic acid probe to screen an appropriate DNA library (e.g. a cDNA or genomic DNA library). For example, a genomic library isolated can be used to isolate a DNA encoding a novel protein of the invention by screening the library with the labelled probe using standard techniques. Nucleic acids isolated by screening of a cDNA or genomic DNA library can be sequenced by standard techniques.

An isolated nucleic acid molecule of the invention, which is DNA, can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid sequence as shown in FIG. 1 or 2 (SEQ. ID. NOS. 9 or 10) for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294 5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention, which is RNA, can be isolated by cloning a cDNA encoding a novel protein of the invention into an appropriate vector, which allows for transcription of the cDNA to produce an RNA molecule, which encodes a protein of the invention. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis, which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. A cDNA having the activity of a novel protein of the invention so isolated can be sequenced by standard techniques, such as dideoxynucleotide chain termination or Maxam-Gilbert chemical sequencing or by automated DNA sequencing, to determine the nucleic acid sequence and the predicted amino acid sequence of the encoded protein.

The initiation codon and untranslated sequences of nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene, which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. The term "antisense" nucleic acid molecule is a nucleotide sequence that is complementary to its target. Preferably, an antisense sequence is constructed by inverting a region preceding or targeting the initiation codon or an unconserved region. In another embodiment the antisense sequence targets all or part of the mRNA or cDNA encoding P450RAI-3. In particular, the nucleic acid sequences contained in the nucleic acid molecules of the invention or a fragment thereof, preferably a nucleic acid sequence shown in FIG. 1 or 2 (SEQ. ID. NOS. 9 or 10) may be inverted relative to its normal presentation for transcription to produce antisense nucleic acid molecules. In one embodiment the antisense molecules can be used to inhibit P450RAI-3 expression and/or retinoic acid metabolism.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

The proteins of the invention (including modifications, variations, truncations, insertions, analogs, fusion proteins, etc.) may be prepared using recombinant DNA methods. These proteins may be purified and/or isolated to various degrees using techniques known in the art. Accordingly, nucleic acid molecules of the present invention having a sequence which encodes a protein of the invention may be incorporated according to procedures known in the art into an appropriate expression vector, which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner, which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown in FIG. 1 or 2 (SEQ. ID. NOS. 9 or 10) or fragments thereof. Regulatory sequences operatively linked to the antisense nucleic acid can be chosen which direct the continuous expression of the antisense RNA molecule.

The recombinant expression vectors of the invention may also contain a selectable marker gene, which facilitates the selection of host cells transformed or transfected with a recombinant molecule of the invention. Examples of selectable marker genes are genes encoding a protein which confers resistance to certain drugs, such as G418 and hygromycin. Examples of other markers which can be used are:

green fluorescent protein (GFP), b-galactosidase, chloramphenicol acetyltransferase, or firefly luciferase. Transcription of the selectable marker gene is monitored by changes in the concentration of the selectable marker protein such as b-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium chloride mediated transformation. Nucleic acid can be introduced into mammalian cells via conventional techniques such as calcium phosphate or calcium chloride co precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego Calif. (1991).

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

iii) Polynucleotide and Polypeptide Variants

"Variant" refers to a polynucleotide or polypeptide differing from the P450RAI-3 polynucleotide or polypeptide, but retaining essential properties thereof. Typically, variants are overall closely similar and, in many regions, identical to the P450RAI-3 polynucleotide or polypeptide. The invention includes homologs, analogs and isoforms of the polypeptides and as applicable polynucleoitdes of the invention. Insertions, deletions, mutations and substitutions are also intended to be encompassed within the scope of the invention.

It will be appreciated that the invention includes polynucleotides comprising nucleic acid sequences having substantial sequence homology with the sequences of FIG. 1 or 2 (SEQ. ID. NOS. 9 or 10). The term "sequences having substantial sequence homology" means those nucleic acid sequences which have slight or inconsequential sequence variations from these sequences, i.e., the sequences function in substantially the same manner to produce functionally equivalent proteins. The variations may be attributable to local mutations or structural modifications. Preferably such polucucleotides have at least 85, preferably 90 and most preferably 95% identity with the sequence of FIG. 1 or 2 (SEQ. ID. NOS. 9 or 10). However, it should be noted that the invention is not limited thereto and includes polynucletide sequence having at least 50%, 60% and 70% homology to the sequence of FIG. 1 or 2 (SEQ. ID. NOS. 9 or 10).

By a polynucleotide having a nucleotide sequence at least, for example, 90% "identical" to a reference nucleotide sequence of the present invention, it is intended that the nucleotide sequence of the polypeptide is identical to the reference sequence except that the polynucleotide sequence may include up to ten point mutations per each 100 nucleotides of the reference nucleotide sequence encoding the P450RAI-3 polypeptide. Therefore, to obtain a polynucleotide having a nucleotide sequence at least 90% identical to a reference nucleotide sequence, up to 10% of the nucleotides in the reference sequence may be deleted or substituted with another nucleotide, or a number of nucleotides up to 10% of the total nucleotides in the reference sequence may be inserted into a reference sequence. The query sequence may be an entire nucleotide sequence of P450RAI-3 or any fragment specified as described herein.

Whether a particular nucleic acid molecule or polypeptide is at least 90%, 95%, 96%, 97%, 98% or 99% homologous to a nucleotide sequence of the present invention can be determined conventionally using known computer programs. A preferred method for determining the best overall match between a query sequence [a sequence of the present invention] and a subject sequence, also referred to as a global alignment, can be determined using the FASTDB computer program based on the algorithm of Brutlag et al., Comp. App. Biosci. 6: 237-245 (1990). In a sequence alignment, the query and the subject sequence are both DNA sequences. An RNA sequence can be compared by converting U's to T's. The result of said global sequence alignment is in percent identity. Preferred parameters used in a FASTDB alignment of DNA sequences to calculate percent identity are: Matrix-Unitary, k-tuple=4, Mismatch Penalty=1, Joining Penalty=30, Randomization Group Length=09, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the result. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment.

This percentage is then subtracted from the percent identity, calculated by the above FASTDB program using the specific parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated from the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a match/alignment of the first 10 bases at 5' end. The 10 unpaired bases represent 10% of the sequence [number of bases at the 5' and 3' ends not matched/total number of bases in the query sequence] so 10% is subtracted from the percent identity score calculated by the FASTDB program. If the remaining 90 bases were perfectly matched the final percent identity would be 90%. As another example, a 90 base subject sequence may be compared with a 100 base query sequence. This time the deletion may be an internal deletion so that there are no bases on the 5' or 3' end of the subject sequence which are not matched/aligned with the query. In such a case, the percent identity calculated by FASTDB is not manually corrected. Only bases 5' and 3' of the subject sequence which are not match/aligned with the query sequence are manually corrected.

By a polypeptide having an amino acid sequence at least, for example, 90% "identical" or homologous to a query amino acid sequence of the present invention, such as P450RAI-3 (SEQ. ID. NO. 11), it is intended that the amino acid sequence of the subject polypeptide is identical to the query sequence except that the subject polypeptide sequence may include up to ten amino acid alterations per each 100 amino acids of the query amino acid sequence. Therefore, to obtain a polypeptide having an amino acid sequence at least 90% identical to a query amino acid sequence, up to 10% of the amino acid residues in the subject sequence may be inserted, deleted or substituted with another amino acid. The alterations in the reference sequences may occur at the amino or carboxy terminal position of the reference amino acid sequence or anywhere between those terminal positions, interspersed either individually among residues in the reference sequence or in one or more contiguous groups within the reference sequence.

Whether any particular polypeptide is at least 90%, 95%, 96%, 97%, 98% or 99% homologous to the amino acid sequences encoded by clone RP11-30F3 can be determined conventionally using known computer programs. A preferred method for determining the best overall match between a query sequence [a sequence of the present invention] and a subject sequence, also referred to as a global sequence alignment, can be determined using the FASTDB computer program based on the algorithm of Brutlag et al., Comp. App. Biosci. 6: 237-245 (1990). In a sequence alignment the query and subject sequences are either both nucleotide sequences or both amino acid sequences. The results of said global sequence alignment is in percent identity. Preferred parameters used in a FASTDB amino acid alignment are: Matrix=PAM 0, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is match/aligned is determined by results of FASTDB sequence alignment. This percentage is then subtracted from the percent identity, calculated by the above FASTDB program using the specific parameters, to arrive at a final percent identity score. Only residues to the N- and C-termini of the subject sequence, which are not matched/aligned with the query sequence, are considered for the purposes of manually adjusting the percent identity score.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence [number of residues at the N- and C-termini not matched/total number of residues in the query sequence] so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Only residues positions outside the N- and C-terminal ends of the subject sequence, as displayed in the FASTDB alignment, which are not matched/aligned with the query sequence are manually corrected for.

P450RAI-3 variants may contain alterations in the coding regions, non-coding regions or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted or added in any combination are also preferred. P450RAI-3 polynucleotide variants can be produced for a variety of reasons including to optimize codon expression for a particular host.

Naturally occurring P450RAI-3 variants are called "allelic variants" and refer to one of several alternate forms of a gene occupying a given locus on a chromosome of an organism. These allelic variants can vary at either the polynucleotide and/or polypeptide level. Alternatively, non-naturally occurring variants may be produced by mutagenesis techniques or by direct synthesis. It will be appreciated that variant forms of polynucleotides of the invention which arise by alternative splicing of an mRNA corresponding to a cDNA of the invention are encompassed by the invention.

Using known methods of protein engineering and recombinant DNA technology, variants may be generated to improve or alter the characteristics of P450RAI-3 polypeptide. For example, one or more amino acids may be deleted from the N-terminus or C-terminus of the protein without substantial loss of biological function [see for example Ron et al., J. Biol. Chem. 268: 2984-2988 (1993); Dobeli et al. J. Biotechnology 7; 199-216 (1988); and Gayle et al. J. Biol. Chem. 268: 22105-22111].

If deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or the C-terminus. Whether a particular polypeptide lacking N- or C-terminal residues of a protein retains such immunological activities can readily be determined by routine methods described herein and know in the art.

The invention further includes P450RAI-3 polypeptide variants which show substantial biological activity. Such variants include deletions, insertions, inversions, repeats and substitutions selected according to general rules known in the art [see for example Bowie, J. U. et al., Science 247: 1306-1310 (1990)].

One strategy exploits the tolerance of amino acid substitutions by natural selection during the process of evolution. By comparing amino acid sequences in different species, conserved amino acids can be identified. These conserved amino acids are likely important for protein function. In contrast, the amino acids positions where substitutions have been tolerated by natural selection indicates that these positions are not critical for protein function. Therefore, positions tolerating amino acid substitutions could be modified while still maintaining biological activity of the protein.

Another strategy employs genetic engineering to introduce amino acid changes at specific positions of a cloned gene to identify regions critical for protein function. For example, site directed mutagenesis or alanine-scanning mutagenesis can be used [see for example Cunningham and Wells, Science 244; 1081-1085 (1989)]. The resulting polypeptide may be tested for biological activity.

Besides conservative amino acid substitutions, this invention contemplates variants of P450RAI-3 including [1] substitutions with one or more of the non-conserved amino acid residues, where the substituted amino acid residues may or may not be one encoded by the genetic code, or [2] substitution with one or more of the amino acid residues having a substituent group, or [3] fusion of the mature polypeptide with another compound, such as a compound to increase the stability and/or solubility of the polypeptide or [4] fusion of the polypeptide with additional amino acids, such as an IgGFc fusion region peptide, or a sequence facilitating purification. Such variants are deemed to be within the scope of those skilled in the art from teachings herein.

For example, P450RAI-3 polypeptide variants containing amino acid substitutions of charged amino acids with another charged or neutral amino acids my produce polypeptides with improved characteristics [see for example. Pinckard et al., Clin. Exp. Immunol. 2: 331-340 (1967); Robbins et al., Diabetes 36: 838-845 (1987); and Clevland et al., Crit. Rev. Therapeutic Drug Carrier System 10: 307-377 9!993)].

iv) Polynucleotide and Polypeptide Fragments

In the present invention "polynucleotide fragment" refers to a short polynucleotide having part of a nucleic acid sequence of FIG. 1 or 2. The short nucleotide fragments are preferably at least about 15 nt and more preferably at least about 20 nt, still more preferably at least about 30 nucleotide (nt), and even more preferably, at least about 40 nt in length. For example, a fragment "at least 20 nt is length" is intended to include 20 or more contiguous bases from the cDNA sequences of FIG. 1 or 2 (SEQ. ID. NOS. 1 or 2) or the nucleotide sequence encoding the peptide of FIG. 3 (SEQ. ID. NO. 11). The nucleotide fragments may be useful as diagnostic probes and primers. In addition, larger fragments are also useful as diagnostic probes [for example. 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, etc . . . nucleotides.] Further any of the nucleotide sequences encoding the exons shown in FIG. 5 are also intended to be included in the invention.

In one embodiment the polynucleotide fragments of the invention preferably hybridize to nucleic acid molecules of the invention (such as FIG. 1 or 2) under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, such as at about 65° C.

Examples of representative polynucleotide fragments are 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1151-1200, 1201-1250, 1251-1300, 1301-1350, 1351-1400, 1401-1450, 1451-1500, 1501-1550, 1551-etc . . . to the end of the cDNA contained in FIG. 2 or the nucleotide sequences encoding any one or more of the exons 1 to 6 in FIG. 5. In a preferred embodiment the polynucleotide fragment comprises or consists of all or at least about a 15 nucleotide portion encoding SEQ. ID. NO. 8. In this context, "about" includes the particular ranges that may be larger or smaller by several nucleotides at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence of FIG. 3 (SEQ. ID. NO. 11) or encoded by the cDNA of FIG. 2 (SEQ. ID. NO. 10). Protein fragments may be "free-standing" or comprised within a larger polypeptide of which the fragment forms a part or region, most preferably as a single continuous region. For example, polypeptide fragments may include fragments from about amino acid number 1-20, 21-40, 41-60 etc. to the end of the coding region. The polypeptide fragments may be about 20, 30, 40, 50, 60, 70, 80, 90, etc. amino acids in length. "About" includes the ranges described herein and ranges larger or smaller by several amino acids, at either extremes or both extremes. The polypeptide fragments may also include anyone or more of exons 1 to 6 of FIG. 5 (SEQ. ID. NOS. 13, 15, 17, 19, 21 or 23).

Preferred polypeptide fragments include the nascent and mature forms of P450RAI-3. Furthermore, any combination of amino and carboxy terminus deletions are preferred. For example, the ability of shortened P450RAI-3 mutants to induce and/or bind to antibodies which recognize the complete or mature forms of the polypeptide generally will be retained when less than the majority of the residues of the complete or mature polypeptide are removed from the N-terminus. Whether a particular polypeptide lacking N-terminal residues of a complete polypeptide retains such immunologic activities can readily be determined by methods known in the art. It is not unlikely that a P450RAI-3 mutant with a large number of deleted N-terminal amino acid residues may retain some biological or immunogenic activities. In fact, peptides composed of as few as five amino acid residues may evoke an immune response.

Accordingly, the present invention further provides polypeptides having one or more residues deleted from the amino terminus of P450RAI-3. For example, the ability of the shortened P450RAI-3 mutant to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described in the art. It is not unlikely that a P450RAI-3 mutant with a large number of deleted C-terminal amino acid residues may retain some biological or immunological activities.

The invention also contemplates polypeptides having one or more amino acids deleted from both the amino and the carboxy termini of P450RAI-3 polypeptide.

Many polynucleotide sequences, such as EST sequences, are publicly available and accessible through sequence databases. Some of these sequences would be related to P450RAI-3 sequence and may have been publicly available prior to conception of the present invention. Preferably, such related polynucleotides are specifically excluded from the scope of the present invention.

Preferred fragments are those demonstrating some biological or biochemical activity. Such fragments are those exhibiting activity similar, but not necessarily identical to P450RAI-3 polypeptide or polynucleotide. The activity may include an improved desired activity or a decreased undesired activity. Such fragments would also include, but is not necessarily limited to any polypeptide or polynucleotide fragments which are beneficial in the modulation or simulation of P450RAI-3 or P450RAI-3 expression, or in the identification or production of such agents.

v) Epitopes and Antibodies

In the present invention, "epitope" refers to P450RAI-3 or fragments having antigenic or immunogenic activity in an animal. A preferred embodiment of the present invention relates to P450RAI-3 fragment comprising an epitope, as well as the polynucleotide encoding fragment. A region of a protein molecule to which an antibody can bind is defined as an "antigenic epitope". In contrast, an "immunogenic epitope" is defined as a part of a protein that elicits an antibody response [see for example, Geysen et al., Proc. Natl. Acad. Sci. USA 81: 3998-4002 (1983)].

Fragments which function as epitopes may be produced by any conventional means. [see for example, Houghten, R. A., Proc. Natl. Acad. Sci. USA 82: 5131-5135 (1985)].

In the present invention, antigenic epitopes preferably contain a sequence of seven or more, more preferably at least nine, and most preferably, between about 15 to about 30 amino acids. Antigenic epitopes are useful to raise antibodies, including monoclonal antibodies, that specify binding the epitope [see for example, Wilson et al., Cell 37: 767-778 (1984); and Sutcliffe J. G. et al., science 218: 660-666].

Similarly, immunogenic epitopes can be used to induce T cells according to methods well known in the art [see for example, Chow, M. et al. Proc. Natl. Acad. Sci. USA 82: 910-914; and Bittle, F. J. et al. J. Gen. Virol. 66: 2347-2354 (1985)]. The immunogenic epitope may be presented together with a carrier protein, such as an albumin, to an animal system (such as rabbit or mouse) or, if it is long enough (at least about 25 amino acids, without a carrier. However, immunogenic epitopes comprising as few as 8 to 10 amino acids have been shown to be sufficient to raise antibodies capable of binding to, at the very least, linear epitopes in a denatured polypeptide such as Western blotting.

As used herein, the term "antibody" [Ab] or "monoclonal antibody" [mAb] is meant to include intact molecules as well as antibody fragments [for example Fab and F(ab')2 fragments] which are capable of specifically binding proteins. Such fragments lack the Fc fragment of intact antibody and are typically produced by proteolytic cleavage using enzymes such as papin (to produce Fab fragments) or pepsin (to produce F(ab') fragments). Fab and F(ab')2 fragments clear more rapidly from the circulation and may have less non-specific tissue binding than an intact antibody [see for example Wahl et al., J. Nucl. Med. 24: 316-325 (1983)]. Thus these fragments are preferred, as are the products of a Fab or other immunoglobulin expression library. This invention includes chimeric, single chain and humanized antibodies. In addition, target protein-binding fragments can be produced through the application of recombinant DNA technology or through synthetic chemistry.

These methodologies are known in the art. For further references, see examples including Current Protocols in Immunology, John Wiley & Sons, New York; Kennett, R. et al, eds., Monoclonal Antibodies, Hybridoma: A New Dimension in Biological Analysis, Plenum Press, New York (1980) and Campbell, A., "Monoclonal Antibody Technology" in Burden, R., et al., eds., Laboratory Techniques in Biochemistry and Molecular Biology, Vol. 13, Elsevere, Amsterdam (1984).

Antibodies generated against a target epitope can be obtained by direct injection of the epitope or polypeptide into an animal or by administrating the polypeptides to an animal, preferably a nonhuman. Such an antibody will then bind the polypeptide itself. With this method, a sequence encoding only a fragment of the polypeptide can be used to generate antibodies binding the whole native polypeptide. Such antibodies can be used to isolate the polypeptide encoding the polypeptide from an expression library using the method described herein.

For the preparation of monoclonal antibodies, any technique that provides antibodies produced by continuous cell line cultures can be used. Examples include the hybridoma technique [Kohler and Milstein, Nature 256: 495-497 (1975)], the trioma technique, the human B-cell hybridoma technique [Kozbor et al., Immunol. Today 4: 72 (1983)], and the EBV-hybridoma technique to produce human monoclonal antibodies [Cole et al., in Monoclonal Antibodies and Cancer Therapy, Alan R. Liss, Inc. p 77-96 (1985)].

Techniques described for the production of a single chain antibodies [U.S. Pat. No. 4,946,778] can be adapted to produce single chain antibodies to immunogenic polypeptide products of interest.

The antibodies useful in the present invention may be prepared by any of a variety of methods known in the art. For example, cells expressing the target protein or an antigenic fragment thereof can be administered to an animal in order to induce the introduction of sera containing polyclonal antibodies. In another method, a preparation of target protein is prepared and purified to render it substantially free of natural contaminants. Such a preparation is then introduced into an animal in order to produce polyclonal antisera of greater specific activity.

In a preferred method, antibodies used in the present invention are monoclonal antibodies [or target protein-binding fragments thereof]. Such monoclonal antibodies can be prepared using hybridoma technology known in the art. In general, such procedures involve immunizing an animal [preferably a mouse] with a target protein antigen or, preferably, with a target protein-expressing cell. Suitable cells can be recognized by their capacity to bind an anti-target protein antibody. Such cells may be cultured in any suitable tissue culture medium. The splenocytes of immunized mice are extracted and fused with a suitable myeloma cell line. Any suitable myeloma cell line may be employed in accordance with the present invention. Preferably SP20 myeloma cell line is used which is available from American Type Culture Collection, Mannassas, Va. After fusion, the resulting hybridoma cells are selectively maintained in HAT medium followed by cloning out by limited dilution as described in the art [see for example, Wands et al., Gastroenterology 80: 225-232 (1981)]. The hybridoma cells obtained through such a selection are then assayed to identify clones which secrete antibodies capable of binding the target protein antigen.

Alternatively, additional antibodies capable of binding to the target protein antigen may be produced in a two-step procedure through the use of anti-idiotypic antibodies. Such a method makes use of the fact that antibodies are themselves antigens, and that, therefore, it is possible to obtain an antibody which binds to second antibody. With this method, target-protein specific antibodies are used to immunize an animal, preferably a mouse. The splenocytes of such an animal are then used to produce hybridoma cells, and the hybridoma cells are screened to identify clones which produce an antibody whose ability to bind to the target protein-specific antibody can be clocked by the target antigen. Such antibodies comprise anti-idiotypic antibodies to the target protein-specific antibody and can be used to immunize an animal to induce formation of further target protein-specific antibodies.

Suitable labels for the target protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase and acetylcholine esterase.

Examples of suitable radioactive labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$ etc. Examples of suitable non-radioactive isotopic labels include $^{157}Gd$, $^{55}Mn$, $^{162}Dy$, $^{52}Tr$ and $^{56}Fe$.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label and a fluorescamine label.

Examples of chemiluminescent labels include a luminal label, an isoluminal label, an aromatic acridinium ester label, an imidazole label, an acridinium salt label, an oxalate ester label, a luciferin label, a luciferase label and an aequorin label.

Examples of nuclear magnetic resonance contrasting agents include heavy metal nuclei such as Gd, Mn and iron.

Typical techniques for binding the above-described labels to antibodies are provided by Kennedy et al., Cin. Chem. Acta. 70;1-31 (1976) and Schurs et al., Clin. Cem. Acta 82: 1-40 (1970). Coupling techniques mentioned in the latter are gluteraldehyde method, the periodate method, the dimaleimide method, the m-maleimidobenzyl-N-hydroxy-succinimide ester method, all of which methods are incorporated by reference herein.

For in vivo use of antibodies in humans, it may be preferable to use "humanized" chimeric monoclonal antibodies. Such antibodies can be produced using genetic constructs derived from hybridoma cells producing the monoclonal antibodies described herein. Methods for producing chimeric antibodies are known in the art. (For example, Morrison, Science 229:1202 (1985); Oi et al. Bio Techniques 4:214 91986); cabilly et al., U.S. Pat. No. 4,816,567; Taniguchi et al., EP 171496; Morrison et al., EP 173494; Neuberger et al., WO 8601533; Robinson et al., WO 8702671; Boulianne et al, Nature 312:643 (1984); Neuberger et al., Nature 314:268 (1985).)

vi) Disease States Diagnosis and Prognosis

It is believed that certain conditions may cause mammals to express significantly altered levels of P450RAI-3 protein and mRNA levels encoding P450RAI-3 protein when compared to a corresponding "standard" mammal i.e., a mammal of the same species not having the condition. Cytochrome P450s have been associated with a number of pathways and have been implicated in a number of medical conditions. In addition to conditions which may be associated with cytochrome P450s in general, P450RAI-3 has elevated expression in the adrenal gland. This coupled with the degree of homology with the other retinoic acid metabolizing cytochrome P450s (P450RAI-1 and -2) suggest a role in cellular differentiation of carcinogenic, tumor and embryonic cell lines. Thus the polypeptides and polynucleotides of this invention or modulators thereof may be useful in diagnosing and treating conditions related to cellular differentiation, such as cancer or developmental disorders. It may also be useful in treating conditions such as psoriasis, high blood pressure, conditions related to sterol or hormone disorders, to name a few and other conditions of the adrenal glands noted herein.

Further, P450RAI-3 or the polypeptides, polynucleotides of this invention and/or modulators of P450RAI-3 activity may be useful in treating disorders or conditions involving the vitamin A or retinoic acid metabolic pathway, such as those noted herein.

Where a diagnosis has already been made according to conventional methods, the present invention is useful as a prognostic indicator whereby patients exhibiting altered P450RAI-3 gene expression will experience a worse or better clinical outcome relative to patients expressing the gene at a normal level.

By "assaying the expression of the gene encoding the P450RAI-3 polypeptide" is intended qualitatively and quantitatively measuring or estimating the level of P450RAI-3 protein or the level of the mRNA encoding the P450RAI-3 protein in a first biological sample either directly [e.g., by determining or estimating absolute protein level or mRNA level] or relatively [e.g. by comparing to the P450RAI-3 protein level or mRNA level in a second biological sample].

Preferably, the P450RAI-3 protein level or mRNA level in the first biological sample is measured or estimated and compared to a standard P450RAI-3 protein level or RNA level, the standard being taken from a second biological sample obtained from an individual not having the condition. As will be appreciated in the art, once a standard P450RAI-3 protein level or mRNA level is known, it can be used repeatedly as a standard for comparison.

By "biological sample" is intended any biological sample obtained from an individual, cell line, tissue culture or other source which contains CYP26C or mRNA. Methods for obtaining tissue biopsies and body fluids from mammals are well known in the art. Where the biological sample is to include mRNA, a tissue biopsy is the preferred source.

Preferred mammals include monkeys, apes, cats, dogs, cows, pigs, horses, rabbits, mice, and humans. Particularly preferred are humans.

Total cellular RNA can be isolated by methods well known in the art [see for example, Chmczynski and ZSacchi, Anal. Biochem. 162: 156-159 (1987)]. Levels of mRNA encoding the P450RAI-3 protein are then assayed using an appropriate method. These include Northern blot analysis [Harada et al., Cell 63: 303-312 (1990)], S1 nuclease mapping [Fujita et al., Cell 49: 357-367 (1987)], the polymerase chain reaction [PCR], reverse transcription in combination with the polymerase chain reaction [RT-PCR] [Mariko et al., Technique 2: 295-301 (1990)] and reverse transcription in combination with the ligase chain reaction [RT-LCR].

Assaying P450RAI-3 protein levels in a biological sample can occur using antibody-based techniques. For example, P450RAI-3 protein expression in tissue can be studied with classical immunohistological methods known in the art [for example, Jalkanen, M., et al., J. Cell Biol. 105: 3087-3096 (1987)].

Other antibody-based methods used for detecting P450RAI-3 protein gene expression including immunoassays, such as enzyme linked immunosorbent assay [ELISA] and the radioimmunoassay [RIA].

Suitable labels are known in the art and include enzyme labels, such as, glucose oxidase, and radioisotope, such as iodine [$^{125}$I, $^{121}$I], carbon [$^{14}$C], sulfer [$^{35}$S], tritium [$^{3}$H], indium [$^{112}$In] and technetium [$^{99m}$Tc] and fluorescent labels, such as fluorescein and rhodamine and biotin.

Antibody labels or markers for in vivo imaging of protein include those detectable by X-radiography, NMR or ESR. For X-radiography, suitable labels include radioisotopes such as barium or cesium, which emit detectable radiation but are not overly harmful to the subject. Suitable markers for NMR and ESR include those with a detectable characteristic spin, such as deuterium, which may be incorporated into antibody by labelling of nutrients for the relevant hybridoma.

A protein-specific antibody or antibody fragment which has been labelled an appropriate detectable imaging moiety, such as a radioisotope [for example, $^{131}$I, $^{112}$In, $^{99m}$TC], a radio-opaque substance, or a material detectable by nuclear magnetic resonance, is introduced [for example, parenterally, subcutaneously, or intraperitoneally] into mammals. It will be understood in the art that the size of the subject and the imaging system used will determine the quality of imaging moiety needed to produce diagnostic images. In vivo tumour imaging is described in S. W. Burchiel et al., "Immunopharmackinetics of Radiolabeled Antibodies and Their Fragments" [see also, Chapter 13 in Tumour Imaging: The Radiochemical Detection of Cancer, S. W. Burchiel and B. A. Rhodes, eds., Masson Publishing Inc. (1982)].

vii) Fusion Proteins

Any P450RAI-3 polypeptide (any polypeptide of the invention—hybrid, variations, fragments, etc.) may be used to generate fusion proteins. For example, the P450RAI-3 polypeptide, when fused to a second polypeptide, can be used as an antigenic tag. Antibodies raised against the P450RAI-3 polypeptide can be used to indirectly detect the second protein by binding to the P450RAI-3 polypeptide. Examples of domains that can be fused to P450RAI-3 include heterologous functional regions. The fusion does not necessarily need to be direct, but may occur through linker sequences.

In certain preferred embodiments, P450RAI-3 fusion polypeptides may be constructed which include additional N-terminal and/or C-terminal amino acid residues. In particular, any N-terminally or C-terminally deleted P450RAI-3 polypeptide disclosed herein may be altered by inclusion of additional amino acid residues at the N-terminus to produce a P450RAI-3 fusion polypeptide, In addition, P450RAI-3 fusion polypeptides are contemplated which include additional N-terminal and/or C-terminal amino acid residues fused to a P450RAI-3 polypeptides comprising any combination of N- and C-terminal deletions set forth above.

In addition, fusion proteins may be engineered to improve characteristics of the P450RAI-3 polypeptide. For instance, a region of additional amino acids, particularly charged amino acids, may be added to the N-terminus of the P450RAI-3 polypeptide to improve stability and persistence during purification from the host cell or subsequent handling and storage. Furthermore, peptide moieties may be added to the P450RAI-3 polypeptide to facilitate purification. Such regions may be removed prior to final preparation of the P450RAI-3 polypeptide. The addition of peptide moieties to facilitate handling of polypeptides are familiar and routine techniques in the art.

P450RAI-3 polypeptides, including fragments, and specifically epitopes, can be combined with parts of the constant domain of immunoglobulins [IgG], resulting in chimeric polypeptides. These proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394, 827; Traunecker et al., *Nature* 331: 84-86 (1988). Fusion proteins having disulphide-linked dimeric structures [due to the IgG] can also be more efficient in binding and neutralizing other molecules, than the monomeric secreted protein or protein fragment alone [see for example, Fountoulakis et al., J. Biochem. 270: 3958-3964 (1995)].

Similarly, EP-A-O 469 533 (Canadian counterpart 2045869) disclosed fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262). Alternatively, deleting the Fc part after the fusion protein has been expressed, detected, and purified, would be desired. For example, the Fc portion may hinder therapy and diagnosis if the fusion protein is used as an antigen for immunizations. In addition, in drug discovery, human proteins, such as hIL-5, have been fused with FC portion for the purpose of high-throughout screening assays to identify antagonists of hIL-5 [see for example, Bennet, D. et al., J. Molecular Recognition 8: 52-58 (1995); K. Johanson et al., J. Biol. Chem. 270: 9459-9471 (1995)].

Moreover, the P450RAI-3 polypeptides of the invention can be fused to other proteins, e.g. NADPH cytochrome P450 reductase, NADPH ferredoxin reductase, other flavoproteins or ferrodixins or other proteins or co-factors which may function as a cytochrome P450RAI-3 reductase or facilitate such an activity to create a multiprotein fusion complex. Such a multiprotein fusion complex may function as an enzymatically active covalently linked P450RAI-3-reductase complex. A multiprotein complex can be synthesized by the means of chemical crosslinking or assembled via novel intramolecular interactions, e.g., by the use of specific antibodies stabilizing the complex.

P450RAI-3 polypeptide can be fused to hydrophilic molecules, including but not limited to polyethylene glycol and modified oligosaccharide and polysaccharides, whereby the hydrophobic moieties are used to stabilize P450RAI-3 interactions with other proteins, natural membranes, or artificial membranes, or to create new interactions with other proteins, natural membranes or artificial membranes. Fusion of the P450RAI-3 polypeptide to hydrophilic molecules can also be used to change its solubility.

P450RAI-3 polypeptide variants which contain non-standard amino acids or additional chemical modifications which have use in purification, stabilization or identification of the resulting modified P450RAI-3 protein, or influence its other properties such as enzymatic activity or interaction with other proteins, membranes, solid supports or chromatographic resin are contemplated. This includes, but is not limited to, biotinylated derivatives or fusions of P450RAI-3 polypeptides.

Also, modification of the P450RAI-3 polynucleotide sequence include those where relevant regions of the P450RAI-3 gene or polypeptide are inserted into another gene sequence to create a chimeric protein with a desired activity (enzymatic or otherwise). Such chimeric proteins can be obtained by, for example, replacing regions of other cytochrome P450 genes or polypeptides with a relevant P450RAI-3 regions whereby such a modification confers a new functional property to the resulting chimeric protein, including but not limited to new specificity, changed enzymatic kinetics, new or changed interactions with reductase or other relevant molecules or membranes, changed solubility and changed stability.

Moreover, the P450RAI-3 polypeptide can be used to marker sequences, such as a peptide which facilitates purification of P450RAI-3. In preferred embodiments, the marker amino acid sequence is a hexa-histidine peptide [His-tag], such as the tag provided in a pQE vector [QIAGEN, In., 9259 Eton Avenue, Chatsworth, Calif., 91311], among others, many of which are commercially available. [for example see Gentz et al., Proc. Natl. Acad. Sci. USA 86: 821-824 (1989)], for instance, hexa-histidine provides for convenient purification of the fusion protein. Another peptide tag useful for purification, the "HA" tag, corresponding to an epitope derived from the influenza haemagglutonin protein [see for example, Wilson et al., Cell 37: 767 (1984)].

Any of these fusions can be engineered using the P450RAI-3 polynucleotides or the P450RAI-3 polypeptides of this invention.

viii) Vectors, Host Cells and Protein Production

The present invention also relates to vectors containing the polynucleotides of the invention, preferably the polynucleotide encoding P450RAI-3, host cells and to the production of the polypeptides of the invention, preferably the P450RAI-3 polypeptide, by recombinant techniques. For example, the vector may be a phage, plasmid, viral, or retroviral. Retroviral vectors may be replication competent or replication defective. In the latter case, viral propagation generally will occur only in complementing host cells.

Introduction of constructs into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods in Molecular Biology (1986).

P450RAI-3 can be recovered and purified from recombinant cell cultures by methods well-known in the art including ammonium sulfate or ethanol precipitation, acid extraction, anion or cation exchange chromatography, phosphocellulose chromatography, affinity chromatography, hydroxylapatite chromatography and lectin chromatography. High performance liquid chromatography ["HPLC"] may be employed for purification.

In addition to encompassing host cells containing the vector constructs discussed herein, the invention also encompasses primary, secondary and immortalized host cells of vertebrate origin, particularly mammalia, origin, that have been engineered to delete or replace endogenous genetic material and/or to include genetic material [e.g. heterologous polynucleotide sequences] that is operably associated with P450RAI-3 polynucleotide of the invention, and which activates, alters, and/or amplifies endogenous P450RAI-3 polynucleotides. For example, techniques known in the art may be used to operably associate heterologous control regions [e.g. promoter and/or enhancer] and endogenous P450RAI-3 polynucleotide sequences via homologous recombinations [see for example Koller et al., Proc. Natl. Acad. Sci. 86: 8932-8935 (1989); and Zijilstra et al., Nature 342: 435438 (1989)].

ix) Uses of P450RAI-3 Polynucleotide

The P450RAI-3 polynucleotides referred to herein can be used in numerous ways as agents. The following describes some examples using techniques know in the art.

There exists an ongoing need to identify new chromosome markers, since few chromosome marking reagents, based on actual sequence data [repeat polymorphisms], are presently available.

Briefly, sequences can be mapped to chromosomes by PCR primers [preferably 5-25 bp] from the sequence shown in FIG. 1 or 2. Primers can be selected using computer analysis so that primers do not span more than one predicted exon in the genomic DNA. These primers can then be used for PCR screening of somatic cell hybrids containing individual human chromosomes. Only those hybrids containing the human P450RAI-3 gene corresponding to the given sequence (preferably the sequence of FIG. 2) will yield an amplified fragment.

Similarly, somatic hybrids provide a rapid method of PCR mapping of the polynucleotides to particular chromosomes. Three or more clones can be assigned per day using a single thermal cycle. Moreover, sublocalization of the P450RAI-3 polynucleotide may be achieved with panels of specific chromosome fragments. Other gene mapping strategies that can be used include in situ hybridization, prescreening with labelled flow-sorted chromosomes and preselection by hybridization to construct chromosomes specific-cDNA libraries.

Precise chromosomal location of P450RAI-3 polynucleotides can also be achieved using fluorescent in situ hybridization [FISH] of a metaphase chromosomal spread. This technique uses polynucleotides as short as 500 or 600 bases; however, polynucleotides 2,000-4,000 bp are preferred [see for example. Verma et al., "Human Chromosomes: a Manual of Basic Techniques", Pergamon Press, New York (1988)].

For chromosome mapping, the P450RAI-3 polynucleotide can be used individually [to mark a single chromosome or a single site on that chromosome] or in panel [for marking multiple sites and/or multiple chromosomes]. Preferred polynucleotides corresponding to the noncoding regions of the cDNAs becomes the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Assuming 1 megabase mapping resolution and one gene per 20 kb, a cDNA precisely localized to a chromosomal region associated with the disease could be one of 50-500 potential causative genes.

Therefore, once coinheritance is established, differences in the P450RAI-3 polynucleotide and the corresponding gene between affected and unaffected individuals can be examined. First, visible structural alterations in the chromosomes, such as deletions or translocations, are examined in chromosomes spreads or by PCR. If no structural alterations exist, the presence of point mutations is ascertained. Mutations observed in some or all affected individuals, but not in normal individuals, indicates that the mutation may cause the disease. However, complete sequencing of the P450RAI-3 polynucleotide and the corresponding gene from several normal individuals is required to distinguish the mutation from a polymorphism. If a new polymorphism is identified, this polymorphic polypeptide can be used for further linkage analysis. The presence of a polymorphism can also be indicative of a disease or a predisposition to a disease. Therefore, a method of diagnosis of a P450RAI-3-related condition or predisposition to a P450RAI-3 related-condition, by identifying a polymorphism in P450RAI-3 gene, is also contemplated by this invention. In addition, a diagnostic kit for identification of polymorphisms in the P450RAI-3 gene by screening the P450RAI-3 gene from human for polymorphisms is also an embodiment of the present invention.

Furthermore, increased or decreased expression of the gene in affected individuals as compared to unaffected individuals can be assessed using P450RAI-3 polynucleotides. Any of these alterations [altered expression, chromosomal rearrangement or mutation] can be used as a diagnostic or prognostic marker.

In addition, P450RAI-3 polynucleotide can be used to control gene expression through triple helix formation or antisense DNA or RNA. Both methods rely on binding of the polypeptide to DNA or RNA. For these techniques, preferred polynucleotides are usually 20 to 40 bases in length and complementary to either the region of the gene involved in transcription or to the mRNA itself [see for example, Dervan et al., Science 251: 1360 (1991); Okano, J. Neurochem. 56; 560 (1991)]. Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotide in an effort to treat disease.

P450RAI-3 polynucleotides are also useful in gene therapy. One goal of gene therapy is to insert a normal gene into an organism having a defective gene, in an effort to correct the gene defect. P450RAI-3 offers a means of targeting such genetic defects in a highly accurate manner. Thus, for example, cells removed from a patient can be engineered with a P450RAI-3 polynucleotide [DNA or RNA] encoding a P450RAI-3 polypeptide ex vivo, with the engineered cells then being infused back into a patient to be treated with the polypeptide. Such methods are well-known in the art. For example, cells can be engineered by procedures known in the art by use of a retroviral particle containing RNA encoding P450RAI-3.

Another goal of gene therapy is to insert a new gene that was not present in the host genome, thereby producing a new trait in the host cell.

The P450RAI-3 polynucleotides are also useful for identifying individuals from minute biological samples. The United States military, for example, is considering the use of restriction fragment length polymorphism [RFLP] for identification of person. In this technique, an individual's genomic DNA is digested with one or more restriction enzymes and probed on a Southern blot to yield unique bands for identifying personnel. The P450RAI-3 polynucleotides can be used as additional DNA markers for RFLP.

The P450RAI-3 polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences.

Forensic biology also benefits from using DNA-based identification techniques as described herein. DNA sequences taken from very small biological samples such as tissues e.g., hair, or skin or body fluids such as blood or saliva can be amplified using PCR [see for example Erlich, H. PCR Technology, Freeman and Co. (1992)]. Similarly, P450RAI-3 polynucleotide can be used as polymorphic markers for forensic purposes.

The invention provides a diagnostic method of a disorder, which involves: [1] assaying P450RAI-3 gene expression level in a biological sample from the individual, such as a tissue or cell sample of an individual; [2] comparing the P450RAI-3 gene expression level with a standard P450RAI-3 gene expression level, whereby an increase or decrease in the assayed P450RAI-3 gene expression level compared to the standard expression level is indicative of the disorder.

In the very least, the P450RAI-3 polynucleotide can be used as a molecular weight marker on Southern gels, as diagnostic probes for the presence of a specific mRNA in a cell type, as a probe to "subtract-out" known sequences in the process of discovering novel polynucleotides, for selecting and making oligomers for attachment to a "gene chip" or other support, or raise anti-DNA antibodies using DNA immunization techniques and as an antigen to elicit an immune response.

x) Uses of P450RAI-3 Polypeptides

P450RAI-3 polypeptide can be used in a number of ways including the following examples.

P450RAI-3 polypeptide can be used to assay protein levels in a biological sample using antibody-based techniques. For example, protein expression in tissue can be studied with classical immunohistological techniques [see for example, Jalkanen, M. et al., J. Cell Biol. 105: 3087-3096 (1987)]. Other antibody-based methods used for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine [$^{125}$I, $^{121}$I], carbon [$^{14}$C], sulfer [$^{35}$S], tritium [$^{3}$H], indium [$^{112}$In] and technetium [$^{99m}$Tc] and fluorescent labels, such as fluorescein and rhodamine and biotin.

Moreover, the P450RAI-3 polypeptides of the invention can be used to treat disease. For example, patients can be administered P450RAI-3 polypeptides in an effort to replace absent or decreased levels of the P450RAI-3 polypeptide, to supplement absent or decreased levels of a different polypeptide or molecule, to inhibit the activity of a polypeptide to activate the activity of a polypeptide to reduce the activity of a membrane bound receptor by competing with it for free ligand, or to bring about a desired response.

Antibodies directed to P450RAI-3 polypeptide may be used to treat disease. As described in detail in the "Epitopes and Antibodies" section herein the polypeptides of the present invention can be used to raise polyclonal and monoclonal antibodies, which are useful in assays for detecting P450RAI-3 protein expression from a recombinant cell, as a way of assessing transformation of the host cell, or as antagonists capable of inhibiting P450RAI-3 protein function. Similarly, administration of an antibody can activate the polypeptide, such as by binding to a polypeptide bound to a membrane (receptor). Further, such polypeptides can be used, in the yeast two-hybrid system to "capture" P450RAI-3 protein binding proteins which are also candidate agonist and antagonist according to the present invention. The yeast two hybrid system is described in Fields and Song, Nature 340:245-246 (1989).

Small molecules that are specific substrates (such as ATRA or 9-cis RA) or metabolites of P450RAI-3 protein can also be used in the diagnosis or analysis of disease state involving P450RAI-3 or to monitor progress of therapy.

P450RAI-3 or its derivatives, P450RAI-3 fusions, complexes and chimeric proteins can also be used in the analysis of individual chemicals or complex mixtures of chemicals including, but not limited to, the screening for improved or changed small molecules. These molecules may have use in development of new therapeutic agents or new diagnostic methods for P450RAI-3-related conditions.

P450RAI-3 or its derivatives, P450RAI-3 fusions, complexes and chimeric proteins in an isolated state or as a part of complex mixtures can also be used to synthesize or modify small molecules. These molecules can in turn be used as therapeutic or diagnostic agents. Furthermore, these molecules can be used in the development of additional new molecules for therapeutic or diagnostic use.

P450RAI-3 or its derivatives, P450RAI-3 homologs, chimeras and protein fusions can be expressed in natural host cells or organisms, or in experimentally created cells or organisms for the purpose of producing, analyzing or modifying therapeutically and diagnostically important small molecules.

P450RAI-3 or its derivatives and P450RAI-3 fusions can be expressed in cells or organisms to modify the normal or diseased function and state of such hosts. In particular, this encompasses, but is not limited to, the use of P450RAI-3 polypeptides and derivatives for gene-therapy of humans or animals. P450RAI-3 polypeptides can also be used in experimental animals to reproduce physiological states, which are useful in the study and analysis of human disease, health or development.

P450RAI-3 polypeptides or derivatives and P450RAI-3 fusions can be expressed in natural host cells or organisms or in experimentally created cells or organisms and used in the extraction, conversion, localization or bioremediation of small molecules in natural or artificial environments. This use includes, but is not limited to, the removal or neutralization of environmental or industrial pollutants by cultivating transgenic or genetically modified plants or microorganisms in water or soil, or by assembling so-called bioreactors that host such organisms.

At the very least, P450RAI-3 polypeptide may be used as a molecular weight marker on SDS-PAGE gels or on molecular sieve gel filtration columns using methods well known to those of skill in the art.

xi) Heme-binding, Oxygen-binding and Detoxification

All cytochrome P450s are heme-binding proteins that contain the putative family signature, F[XX]G[XXX]C[X]G [X=any residue; conserved residues are in bold].

Heme-binding proteins, such as the cytochromes P450s, play an important role in the detoxification of toxic substances or xenobiotics. For example, toxic substances can be detoxified by oxidation. Cytochrome P450s can function as oxidative enzymes to detoxify toxic substances, such as phenobarbital, codeine and morphine. The capacity of cytochrome P450s to bind oxygen depends on the presence of a heme group and the oxygen-binding domain. Thus, the ability of P450s to bind heme and molecular oxygen enables them to detoxify toxic substances by oxidation.

Thus P450RAI-3 polypeptides are also useful as oxidative enzymes to detoxify toxic substances or xenobiotics, such as phenobarbital, codeine and morphine.

xii) Antagonist, Agonist and Antisense Methods

This invention further provides methods for screening compounds to identify agonists and antagonists to the P450RAI-3 polypeptides of the present invention.

Examples of potential P450RAI-3 agonists could include P450RAI-3 it self or biologically active fragment thereof, a variant of P450RAI-3 or biologically active fragment thereof, a nucleic acid construct encoding any of the peptide agonists, or nucleic acid, a drug or small molecule that can enhance P450RAI-3 expression or activity.

Examples of potential P450RAI-3 antagonists include antibodies, drugs, small molecules or in some cases, oligonucleotides, which bind to the polypeptides.

Antisense constructs prepared using antisense technology are also potential antagonists. Therefore, the present invention is further directed to inhibiting P450RAI-3 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the [mature] polypeptides of the present invention, is used to design an antisense RNA oligonucleotide of from about 10 to 40 base pairs in length. The antisense RNA oligonucleotide hybridizes to the mRNA in vivo and blocks translation of the mRNA molecule into the polypeptides [for example, antisense-Okano, J. Neurochem. 56: 560 (1991); Oligodeoxynucleotides as Antisense Inhibitors of Gene Expression, CPR Press, Boca Raton, Fla. (1988)]. A DNA oligonucleotide is designed to be complementary to a region of the gene involved in transcription [triple-helix, see Lee et al., Nucl. Acids Res. 6: 3073 (1979); Cooney et al., Science 241: 456 (1988); and Dervan et al., Science 251: 1360 (1991)], thereby preventing transcription and the production of the P450RAI-3 polypeptides.

Another potential P450RAI-3 antagonist is a peptide derivative of the polypeptides which are naturally or synthetically modified analogs of the polypeptides that have lost biological function yet still recognize P450RAI-3 substrate(s). Examples of peptide derivatives include, but are not limited to, small peptides or peptide-like molecules.

The antagonist may be employed to treat disorders which are either P450RAI-3-induced or enhanced or modulated, for example, vitamin A or retinoic acid metabolic disorders.

Instead of inhibiting P450RAI-3 activity at the nucleic acid level, P450RAI-3 activity can be directly inhibited by binding to an agent, such as a suitable small molecule or drug. The present invention thus includes a method of screening drugs for their effect on activity [i.e., as a modulator (e.g. agonist or antagonist), preferably an inhibitor] of P450RAI-3 polypeptide. In particular, modulators of P450RAI-3 activity, such as drugs or peptides or other chemical compounds or molecules, can be identified in a biological assay by expressing P450RAI-3 in a cell, adding a substrate (for example 9-cis RA or ATRA) and detecting activity of P450RAI-3 polypeptide on the substrate in the presence, and optionally for a control in the absence of, the potential modulator. The assay can also be done in microsomes that comprise P450RAI-3 or other environments where P450RAI-3 is present in addition to cofactors that may be necessary for its activity such as in one embodiment NADPH cytochrome P450 reductase and/or a flavoprotein and/or NADPH. Thus, the P450RAI-3 protein can be exposed to a prospective inhibitor or modulating drug and the effect on protein activity can be determined. Prospective drugs can be tested for inhibition of the activity of other P450 cytochromes, which are desired not to be inhibited. In this way, drugs that are selectively inhibit P450RAI-3 over other P450s can be identified. Uses of the P450RAI-3 modulators identified by the assays of the invention are also encompassed within the scope of the present invention.

xiii)—Other Methods of the Invention

The methods of the invention also include a method of conducting a drug discovery and pharmaceutical business comprising:
(a) providing one or more assay systems for identifying agents by their ability to modulate P450RAI-3 activity or expression or retinoic acid metabolism;
(b) conducting therapeutic profiling of agents identified in step (a), or further analogs thereof, for efficacy and toxicity in animals; and
(c) formulating a pharmaceutical preparation including one or more agents identified in step (b) as having an acceptable therapeutic profile.

The method may further include a step of establishing a distribution system for distributing the pharmaceutical preparation for sale. The method can further include establishing a sales group for marketing the pharmaceutical preparation.

The present invention also provides a method of conducting a target discovery business comprising:
(a) providing one or more assay systems for identifying agents by their ability to modulate P450RAI-3 or retinoic acid metabolism;
(b) (optionally) conducting therapeutic profiling of agents identified in step (a) for efficacy and toxicity in animals; and
(c) licensing, to a third party, the rights for further drug development and/or sales for agents identified in step (a), or analogs thereof.

xiv) Pharmaceutical Compositions

P450RAI-3 may play a role in a number of diseases or medical conditions. A "P450RAI-3 related condition" as used herein is one wherein P450RAI-3 expression or activity (whether over expression or activity, under expression or activity, or modified expression or activity) is characteristic of the disorder and/or a condition where modifying P450RAI-3 expression or activity can assist in treating the condition.

Such disorders may include but are not limited to those associated with retinoic acid expression or activity, where expression of P450RAI-3 results in oxidation of retinoic acid. As such, expression of P450RAI-3 can decrease retinoic acid levels, where such decrease may or may not be desired. P450RAI-3 may also play a role in the activity of the adrenal gland. As such, modulating P450RAI-3 expression or activity can be effective in treating conditions of the adrenal gland. Examples of such adrenal glands conditions were noted above, in the background of the invention section.

However, P450RAI-3 is not limited to being associated with such conditions only. In particular P450RAI-3 may play a more general role in cell differentiation disorders, such as cancer.

The invention comprises methods for modulating or simulating P450RAI-3 activity or P450RAI-3 expression, preferably for treating or preventing a P450RAI-3 related condition. The invention further comprises use of the modulating (any change or controlling effect on P450RAI-3 activity or expression, including administration of P450RAI-3 itself) or simulating agents disclosed herein for the preparation of a medicament for treating or preventing a condition associated with P450RAI-3 expression or activity. In another embodiment the invention provides a use of the modulating or simulating agents for the treatment or prevention of a P450RAI-3 related condition.

Accordingly, the present invention provides a method of treating or preventing a disease associated with P450RAI-3 expression or activity comprising administering an agent that modulates or simulates P450RAI-3 expression or activity to an animal in need thereof.

In one embodiment, such agents stimulate or simulate P450RAI-3 activity. Examples of agents that activate or simulate P450RAI-3 activity would include without limitations, P450RAI-3, the gene encoding for P450RAI-3 with suitable promoters, such promoters preferably being tissue specific promoters and therapeutically (or functionally) effective fragments of the nucleic acid and amino acid sequences of the invention. Further, such agent may include agonists of P450RAI-3, such as small molecules or drugs identified to have such effect.

In another embodiment, preferably the P450RAI-3, if administered is solubilized. In another embodiment, the P450RAI-3 polypeptide of the invention can be co-administered preferably with co-factors such as with the suitable NADPH cytochrome P450 reductase and preferably a flavoprotein. In another embodiment NADPH could also be administered. In another embodiment, the P450RAI-3 polypeptide of the invention can be co-administered with the substrate, retinoic acid (e.g. ATRA, 9 cis RA) e.g., where increased levels of a metabolite of retinoic acid are desired. The substrate and co-factors could both be administered with the P450RAI-3 polypeptide, or can potentially be effective alone or together.

Further, there may be diseases or conditions in which inhibition of P450RAI-3 may be required, such as in the case where retinoic acid levels or activity is to be maintained or increased. Accordingly, the invention provides a method for treating or preventing a disease or condition associated with P450RAI-3 expression or activity, (either any expression or activity or elevated expression or activity) by administering to a patient in need thereof an agent which inhibits or suppresses P450RAI-3 expression or activity.

Examples of agents that inhibit P450RAI-3 include antisense nucleic acid molecules to P450RAI-3 or fragments thereof, antibodies, antagonists, and transdominant inhibitors, as described herein.

Agents that modulate P450RAI-3 expression or activity (either alone or with another agent, such as retinoic acid, as explained above) can be formulated into pharmaceutical compositions for administration to subjects in a biologically compatible form suitable for administration in vivo. Preferably the modulator of P450RAI-3 is an inhibitor of P450RAI-3 and it is administered either alone or together with a P450RAI-3 substrate such as ATRA or 9 cis RA. Such a treatment can assist in maintaining retinoic acid levels when desired, such as in the treatment of cancer where patients may develop resistance to RA treatment, as noted above. As used herein "biologically compatible form suitable for administration in vivo" means a form of the substance to be administered in which therapeutic effects outweigh any toxic effects. The substances may be administered to animals in need thereof. Animals, as used herein refers to any animal susceptible to a P450RAI-3 related condition preferably dogs, cats, mice, horses and humans.

The pharmaceutical composition will be formulated and doses in a fashion consistent with good medical practice, taking into account the clinical condition of the individual patient (and potential side effects), the site of delivery, the method of administration, the scheduling of administration, and other factors known to a practitioner. Administration of an "effective amount" of pharmaceutical compositions of the present invention is defined as an amount of the pharmaceutical composition, at dosages and for periods of time necessary to achieve the desired result. For example, a therapeutically active amount of a substance may vary according to factors such as disease state, age, sex, and weight of the recipient, and the ability of the substance to elicit a desired response in the recipient. Dosage regime may be adjusted to provide an optimum therapeutic response. For example, several divided doses may be administered daily or the dose may be proportionally reduced as indicated by the exigencies of the therapeutic situation. Subject to therapeutic discretion, preferably dosages of administration of active compound (modulator of P450RAI-3 expression or activity, either alone or with another compound, such as a retinoic acid substrate) will be in the range of about 1 µg/kg/day to 10 mg/kg/day of patient body weight and most preferably at least 0.01 mg/kg/day, and most preferably for humans between about 0.01 and 1 mg/kg/day.

An active substance may be administered in a convenient manner such as by injection (subcutaneous, intravenous, topical, intratumoral etc.), oral administration, inhalation, transdermal application, or rectal administration. Depending on the route of administration, the active substance may be coated in a material to protect the compound from the action of enzymes, acids and other natural conditions which may inactivate the compound, prior to reaching the desired site of delivery. It can also be formulated into a sustained release composition.

The compositions described herein can be prepared by known methods for the preparation of pharmaceutically acceptable compositions which can be administered to subjects, such that an effective quantity of the active substance is combined in a mixture with a pharmaceutically acceptable carrier. Suitable carriers are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Recombinant nucleic acid molecules comprising a sense, an antisense sequence or oligonucleotide fragment thereof, may be directly introduced into cells or tissues in vivo using delivery vehicles known in the art such as retroviral vectors, adenoviral vectors and DNA virus vectors. They may also be introduced into cells in vivo using physical techniques known in the art such as microinjection and electroporation or chemical methods such as coprecipitation and incorporation of DNA into liposomes. Recombinant molecules may also be delivered in the form of an aerosol or by lavage.

The utility of the substances, antibodies, sense and anti-sense nucleic acid molecules, and compositions of the invention may be confirmed in animal experimental model systems. Suitable animal model systems which can be used to determine activity may include, but is not limited to retinoic acid or P450RAI-3 knock-out transgenic animals.

xv) Transgenic and Knock-Out Animals and Methods of Making Same

Nucleic acid molecules that encode P450RAI-3 or that encode proteins having a biological activity similar to that of a P450RAI-3, can be used to generate either transgenic animals or "knock-out" animals. These animals are useful in the development and screening of therapeutically useful reagents. A transgenic animal [e.g. a mouse] is an animal having cells that contain a transgene, which was introduced into the animal or an ancestor of the animal at prenatal, e.g. an embryonic stage. A transgene is a DNA molecule that has integrated into the genome of a cell from which a transgenic animal develops.

In one embodiment, a human P450RAI-3 cDNA, comprising the nucleotide sequence (SEQ. ID. NOS. 9 or 10), or an appropriate variant, fragment or sub-sequence thereof, can be used to generate transgenic animals that contain cells which express human P450RAI-3. Methods for generating transgenic animals, such as rats, hamsters, rabbits, sheep and pigs, and particularly mice, have become conventional in the art [see for example U.S. Pat. Nos. 4,736,866 and 4,870,009].

In a preferred embodiment, plasmids containing recombinant molecules of the present invention are microinjected into mouse embryos. In particular, the plasmids of the present invention are microinjected into the male pronuclei of fertilized one-cell mouse embryos, the injected embryos at the 2-4 cell stage are transferred to pseudo-pregnant foster females, and the embryos in the foster females are allowed to develop to term. [see Hogan et al., A Laboratory Manual, Cold Spring Harbour, N.Y. Cold Spring Harbour (1986)]

Alternatively, an embryonal stem cell line can be transfected with an expression vector comprising a polynucleotide encoding a protein having P450RAI-3 activity, and cells containing the polynucleotide can be used to form aggregation chimeras with embryos from a suitable recipient mouse stain. The chimeric embryos can be implanted into a suitable pseudopregnant female mouse of the appropriate strain and the embryo brought to term. Progeny harbouring the transfected DNA in their germ cells can be used to breed uniformly transgenic mice.

Transgenic animals that include a copy of a P450RAI-3 transgene introduced into the germ line of the animal by an embryonic stage can also be used to examine the effect of increased P450RAI-3 expression in various tissues.

Conversely, "knock-out" animals that have a defective or altered P450RAI-3 gene can be constructed [see for example Lemoine and Cooper, Gene Therapy, Human Molecular Genetics Series, BIOS Scientific Publishers, Oxford, U.K. (1996)]. Knock-out animals can be made that cannot express a functional P450RAI-3 polypeptide. For example, a portion of the of P450RAI DNA (e.g. an exon) can be deleted or replaced with another gene, such as a gene encoding a selectable marker, that can be used to monitor integration.

The altered P450RAI-3 DNA can then be transfected into an embryonal stem cell line where it will homologously recombine with the endogenous P450RAI-3 gene in certain cells. Clones containing the altered gene can be selected. Cells containing the altered gene are injected into a blastocyst of an animal, such as a mouse, to form aggregation chimeras and chimeric embryos are implanted as described above for transgenic animals. Transmission of the altered gene into the germline of a resultant animal can be confirmed using standard techniques and the animal can be used to breed animals having an altered P450RAI-3 gene in every cell. Such a knock-out animal may be used, for example, to test the effectiveness of an agent in the absence of a P450RAI-3 protein, if lack of P450RAI-3 expression does not result in lethality. The knock-out animal can also be used to monitor the development of any conditions related to altered P450RAI-3 expression or activity.

The following non-limiting examples are illustrative of the present invention:

EXAMPLES

Example 1

Determination of cDNA Sequence Encoding P450RAI-3

The Unfinished High Throughput Genomic Sequences (htgs) database at the National Center for Biotechnology Information (NCBI), available over the Internet at http://www.ncbi.nlm.nih.gov/BLAST/was searched using the amino acid sequences of human P450RAI-1 (SEQ. ID. NO. 2, or see FIG. 6A) and human P450RAI-2 (SEQ. ID. NO. 4 or see FIG. 6A). The TBLASTN algorithm of the Translated BLAST program was used to search the 6 possible reading frames of all the HTG sequences against the two protein query sequences. Parameters for all searches were the defaults of Blosum 62 which use a gap existence cost of 11, per residue cost of 1 and lambda ratio of 0.85. The nucleotide and the corresponding amino acid sequences, which showed similarity to SEQ. ID. NO. 2 or 4 (also see FIG. 6A) were retrieved from GenBank.

One of the subject sequences obtained from GenBank (AL358613), identified here as SEQ. ID. NO. 6, a 160,532 bp clone from human chromosome 10 (clone name RP11-348J12, library RPCI-11.2, sequencing ongoing at Sanger Genome Center; center project name: bA348J12, http://www.sanger.ac.uk) showed similarity to the nucleotide sequence encoding the amino acid sequences identified as SEQ. ID. NO. 2 and 4 (See FIG. 6A). As described below, the present inventor determined that this clone comprised within it the polynucleotide sequence encoding the novel cytochrome P450 of the invention, P450RAI-3.

Using the amino acid sequences of human P450RAI-1 (SEQ. ID. NO. 2, see also FIG. 6A) and human P450RAI-2 (SEQ. ID. NO. 4, See also FIG. 6A) aligned to the 6 possible reading frame translations of SEQ. ID. NO. 6 (in 43 unordered pieces), the N-terminal exon 1, as well as exons 4 and 5 and part of C-terminal exon 6 were predicted. Exon 6 contained the heme thiolate benchmark sequence characteristic of all P450s (FXXGXXXCXG, where X can be any amino acid, SEQ. ID. NO. 7), FGGGARSCLG (SEQ. ID. NO. 8).

A bacterial stab of the BAC clone (AL358613) was obtained from the Sanger Genome Center. Colonies were PCR screened using two sets of primers to identify positives containing the known fragments of P450RAI-3. One set was specific for the first predicted exon, 5'-CTCATCATGTTC-CCTTGGGGGCTGA (SEQ. ID. NO. 25) (nucleotides 1-19 bp of SEQ. ID. NO. 10) and 5'-CTGCTGAACTMCCAGT-GCAGCGTTTC (SEQ. ID. NO. 26) (complementary to nucleotides 204-181 bp of SEQ. ID. NO. 10). The other set was within predicted exon 4, 5'-GCAAGGGACCAGCTG-CATCGGCACCTG (SEQ. ID. NO. 27) (nucleotides 715-741 bp of SEQ. ID. NO. 10) and 5'-CCCTTGCACTGT-GAATGATTAGGTCG (SEQ. ID. NO. 29) (complementary to nucleotides 826-801 bp of SEQ. ID. NO. 10). BAC clone DNA was prepared and sent to the Centre for Applied Genomics at the Hospital for Sick Children in Toronto, Ontario and the sequencing was performed to complete the genomic sequence around the identified regions containing P450RAI-3.

Using the contig sequence information from AL358613 and the sequence obtained from the Centre for Applied Genomics, a 22,179 bp piece of genomic DNA (SEQ. ID. NO. 9) was predicted. The nr database (all GenBank+EMBL+DDBJ+PDB sequences) was searched using SEQ. ID. NO. 9 using the BLASTN and BLASTX algorithms and a BLASTN and TBLASTX search was conducted against the htgs database. The nucleotide (SEQ. ID. NO. 10, also see FIG. 2) and resulting translated protein sequence (SEQ. ID. NO. 11, also see FIG. 3) of P450RAI-3 was identified. The intron/exon boundaries were deduced based on the loss of amino acid similarity between P450RAI-1, P450RAI-2 and the relevant regions of the genomic sequence. The 6 exons and the intron/exon boundaries of the novel P450, P450RAI-3 are shown in FIG. 5. The amino acids encoded within the respective exons are identified above the schematic diagram and nucleotide positions in relation to the human genomic sequence (SEQ. ID. NO. 9, also see FIG. 1) are provided below the diagram. However, it would be appreciated that the positions of the exons noted in FIG. 5 are approximate and may vary from the actual boundaries.

The sequence has been termed P450RAI-3 based on sequence homology with P450RAI-1 (CYP26A1) and P450RAI-2 (CYP26B1). The amino acid sequence comparison between human P450RAI-3 and human P450RAI-1 and P450RAI-2 is shown in FIG. 6A. Overall P450RAI-1 and P450RAI-3 show 43% identity at the amino acid level and 52% at the nucleotide level over the region of the predicted open reading frame. The overall similarity of the two putative open reading frames is somewhat higher when conservatively substituted amino acids are considered. Overall P450RAI-2 and P450RAI-3 show 51% identity at the amino acid level and 61% at the nucleotide level over the region of the predicted open reading frame. Again, the overall similarity of the two putative open reading frames is somewhat higher when conservatively substituted amino acids are considered.

Example 2

P450RAI-3 Tissue Expression

Figure 7:
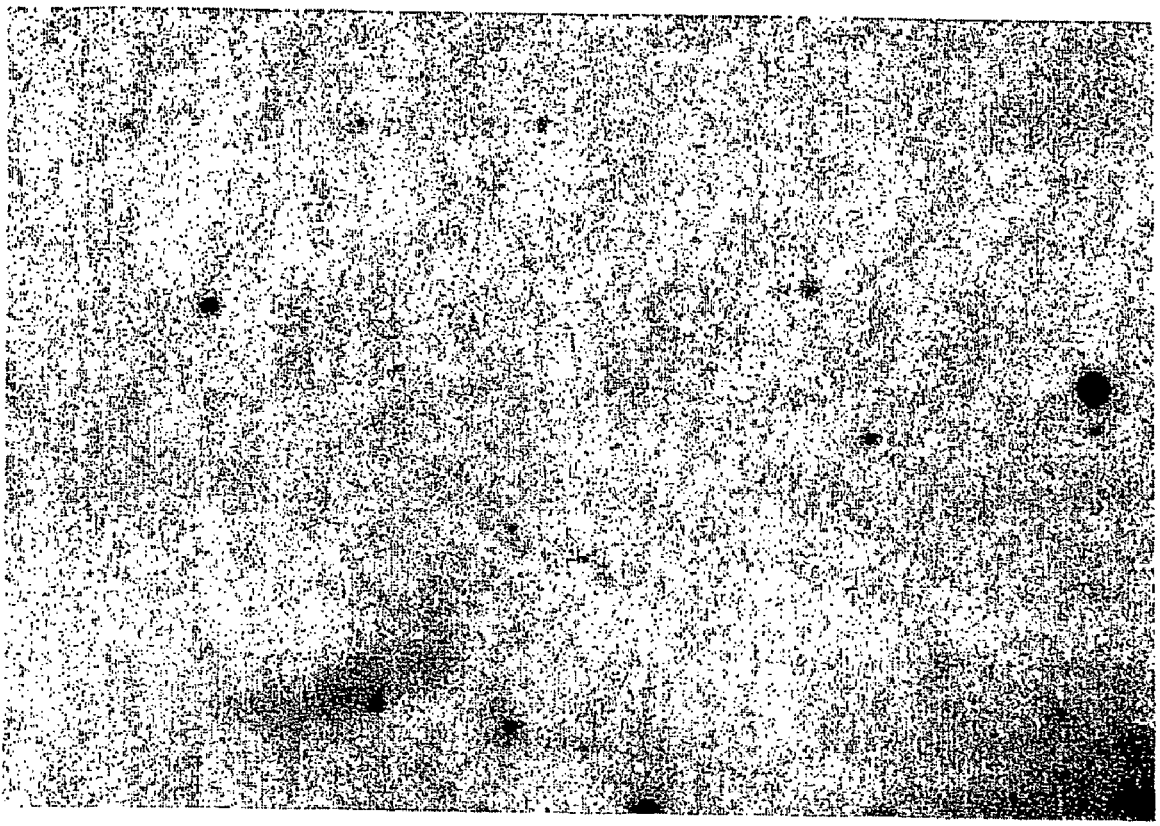
FIG. 7A is a dot-blot illustrating expression of P450RAI-3 in various human tissues.
FIG. 7B is the legend of the dot blot of FIG. 7A.

In order to find tissues in which P450RAI-3 is expressed, a multi-tissue poly A+ RNA dot blot containing 76 different human tissues (Clontech, Calif.) was probed. A 200 bp PCR fragment (SEQ. ID. NO. 24) was amplified from peripheral blood leukocyte cDNA (Origene, Md.) using the primer set for the first predicted exon, SEQ. ID. NOS. 25 and 26. The random-primed a-[$^{32}$P]dATP-labeled probe was hybridized to the blot using conditions described by the manufacturer. FIG. 7A illustrates the results. A distinct signal of P450RAI-3 was detected in the adrenal gland. FIG. 7B depicts the tissue map of the 76 tissue samples.

Figure 8:
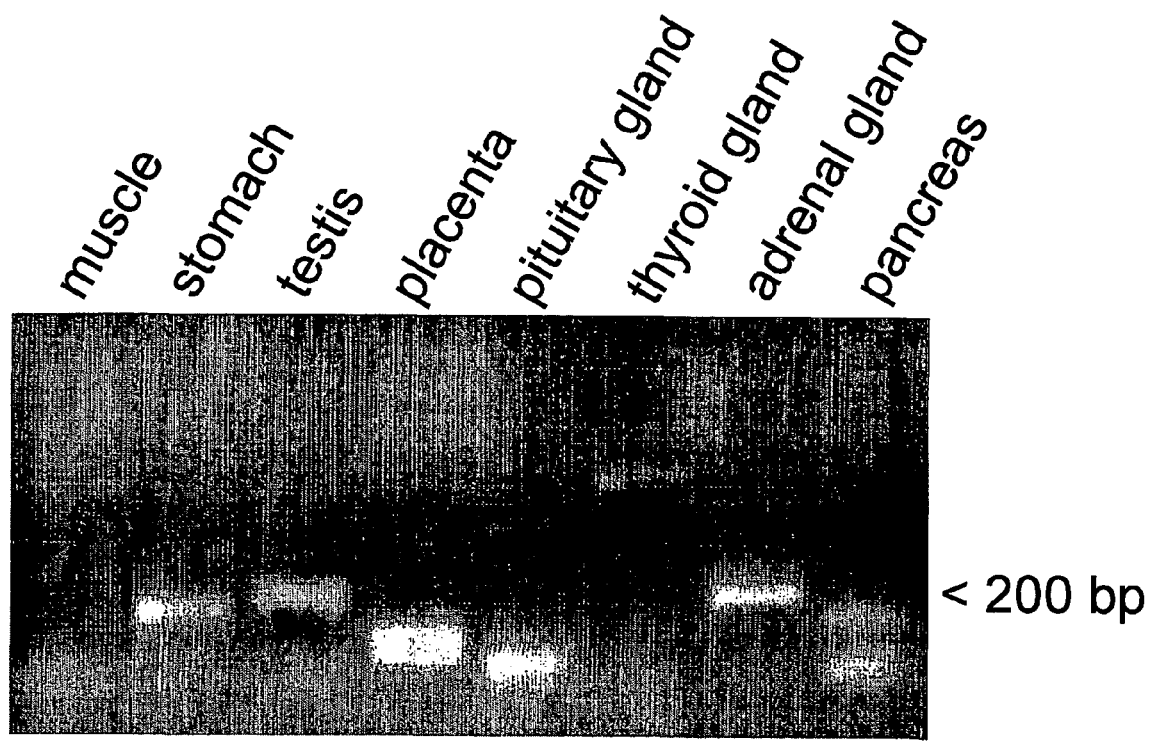
FIG. 8 is a 1% agarose gel illustrating expression of P450RAI-3 in various human tissues.

Multi-tissue RACE cDNA panels (Origene, Md.) representing different human tissues (muscle, stomach, testis, placenta, pituitary gland, thyroid gland, adrenal gland and pancreas) were PCR-amplified using a set of primers specific for the first predicted exon of the putative P450RAI-3 gene (SEQ. ID. NOS. 25 and 26). Thus, any amplified product from P450RAI-3 should be the size of exon 1, or about 200 bp. PCR products were fractionated on 1% agarose gel and analyzed under UV. The results are shown in FIG. 8. From the figure it can be seen that the 200 bp amplified fragment is expressed again primarily in the adrenal gland, and to a lesser extent, was detected in testis.

Figure 9:
FIG. 9 is a Southern blot illustrating expression of P450RAI-3 in the human adrenal gland.

P450RAI-3 expression in the adrenal gland was confirmed by the results illustrated in FIG. 9. Adrenal gland mRNA (Ambion, Tex.) was used for RT-PCR with a primer specific to the predicted exon 4 (SEQ. ID. NO. 27) and one within exon 6,5'-CTCGTGCGTGTCCCGGATGCTATAC (SEQ. ID. NO. 28) (complementary to nucleotides 1248-1224 bp of SEQ. ID. NO. 10) of P450RAI-3. Amplification was conducted in accordance to manufacturer's recommendations (Clontech, Calif.). Amplification products were fractionated on 1% agarose gel and visualized under ultraviolet light along side DNA markers (FIG. 9, panel A). The gel was then blotted on Hybond ECL nitrocellulose membrane (Amersham Pharmacia Biotech, UK) and fixed to the membrane by baking at 80° C. for 2 hours under vacuum. Prehybridization and hybridization steps were performed using ExpressHyb (Clontech, Calif.) according to the manufacturer's directions. The blot was probed with an end-labeled [g-[$^{32}$P]ATP using T4 polynucleotide kinase] internal exon 4-specific oligonucleotide, (SEQ. ID. NO. 29). The blot was washed two times for 15 minutes in 2×SSC, 0.1% SDS at room temperature then for 15 minutes at 60° C. in 0.1% SSC and 0.1% SDS and exposed at 70° C. overnight to Kodak X-OMAT AR film (Eastman Kodak Company, NY) (FIG. 9, panel B). A 0.5 kbp fragment corresponding to the predicted PCR amplified product from P450RAI-3 can be seen in FIG. 9, panel B.

Example 3

All-Trans-Retinoic-Acid (ATRA)-Metabolism Activity

Mammalian Cell Transfection: Enzymatic Activity

Figure 10:
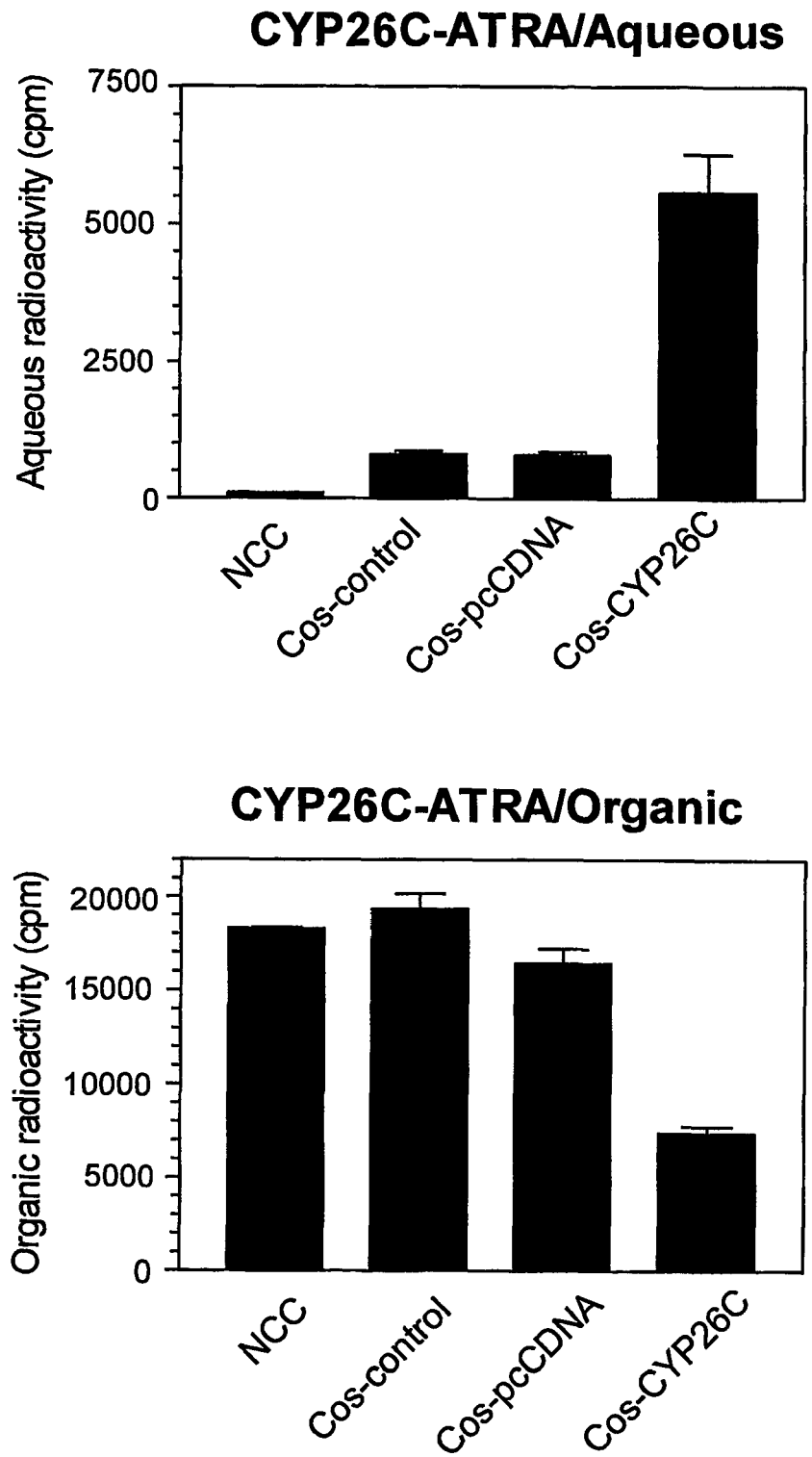
FIGS. 10A and B are bar graphs illustrating all trans retinoic acid activity (radioactivity counts) for aqueous (A) and organic (B) fraction of mammalian Cos-1 cells transfected with either pcDNA-P450RAI-3 or pcDNA-control vector. Results for Cos cells alone and NCC are also provided.

Mammalian Cos-1 cells were transfected with either pcDNA-P450RAI-3 or pcDNA-control vector using Fugene™ (Roche diagnostic) according to the manufacturers directions. After 48 hours post-tranfection, cells were washed with PBS and assessed for ATRA-metabolism activity as described Briefly, transfected cells were incubated with radio-labeled $^3$[H]-ATRA (18000 cpm, 2 nM) for 3 hours. Organic and Water-soluble metabolites were extracted using Bligh-Dyer procedure and radioactivity counted (FIG. 10).

Figure 11:
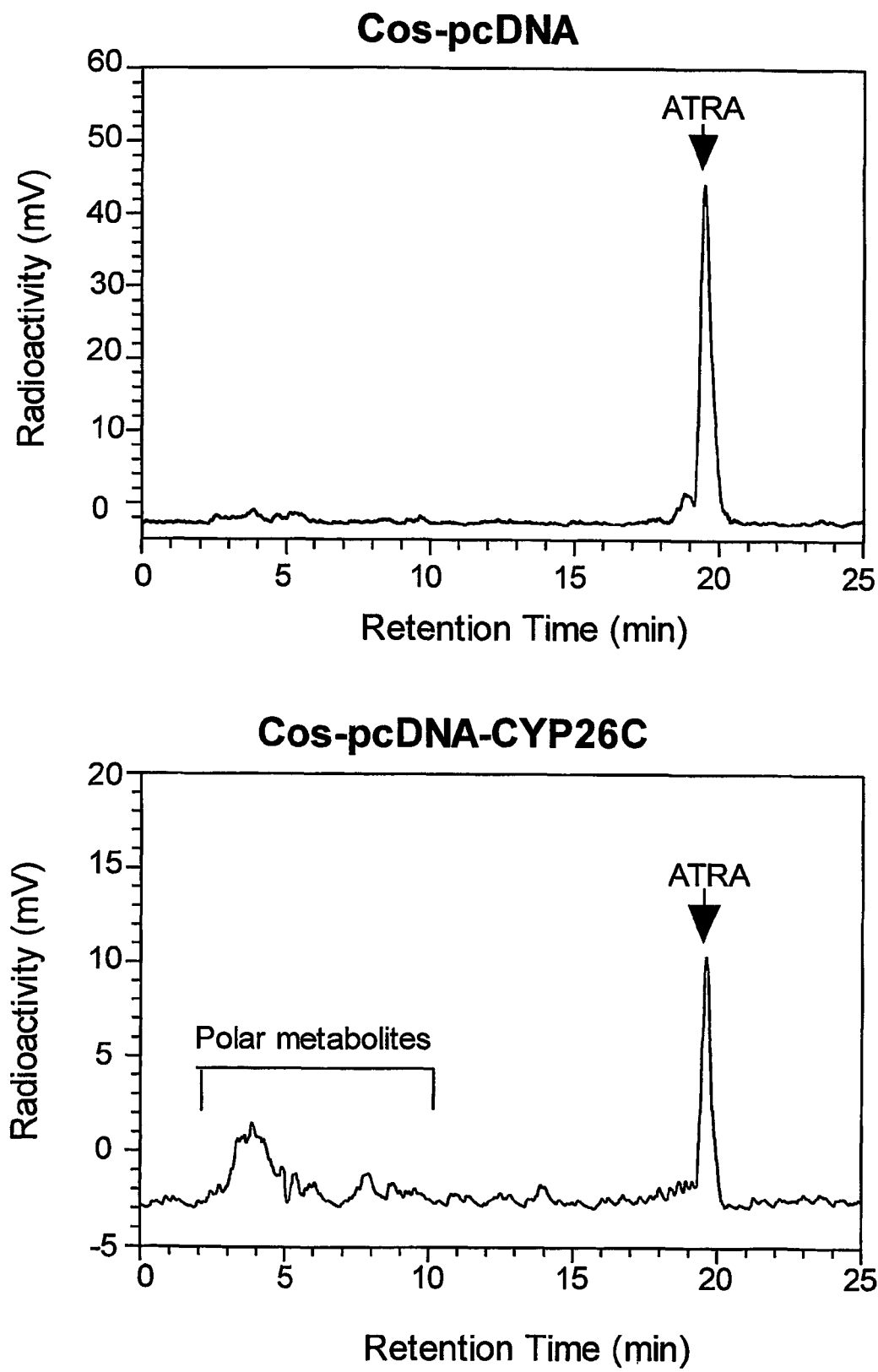
FIG. 11 illustrates the HPLC analysis of organic metabolites from ATRA metabolism assay showing that P450RAI-3 (Cos-pcDNA-CYP26C) (B) metabolizes ATRA to polar metabolites, whereas no such metabolic activity is seen in the control (Cos-pcDNA) (A).

HPLC analysis of the organic metabolites: the Bligh-Dyer organic button-layer was dried out and residues were suspended in HPLC solvent and then analyzed by HPLC as described in [White et al, PNAS, vol 97, pg 6403-6408], FIG. 11.

P450RAI-3 was found to efficiently metabolize ATRA to polar metabolites.

Example 4

Substrate Competition in Cell Assay—Competition with Retinoid Isomers and Metabolites The purpose of these experiments is to determine the specific substrates for P450RAI-3. Unlabeled ATRA, 9-cis, 13-cis-RA, 4-OH-RA, 4-Oxo-RA, 18-OH-RA Retinol, Retinal, and ketoconazole were used in [$^3$H]-RA-metabolism inhibition assay as follows: P450-RAI stable transfected Hela cells were maintained in MEM medium containing 10% FBS and 100 µg/ml Hygromycin B. Cells were cultured in cell culture dishes, exponentially growing cells (70 to 80% confluents) were harvested, washed with PBS and then plated in a 48-well plate at 5×10$^5$ cells per well in 0.150 ml MEM medium containing 10% FBS. Increasing concentration of either unlabeled ATRA, RA-precursors (Retinol, Retinal), RA-isomers (13-cis and 9-cis forms), or RA-metabolites (4OH-RA, 4-OXORA, and 18-OHRA) were dissolved in DMSO and added to the cells. The RA metabolism reaction was started by the addition of 50 ul of [$^3$H]-RA solution (20000 cpm, 2 nM final concentration). Cells were incubated for 3 hours in a humidified CO$_2$ incubator at 37 degrees Celsius. The reaction was stopped by the addition of 5 ul of 10% acetic acid. Organic and aqueous soluble radio-labelled metabolites were extracted using the Bligh-Dyer procedure.

Figure 12:
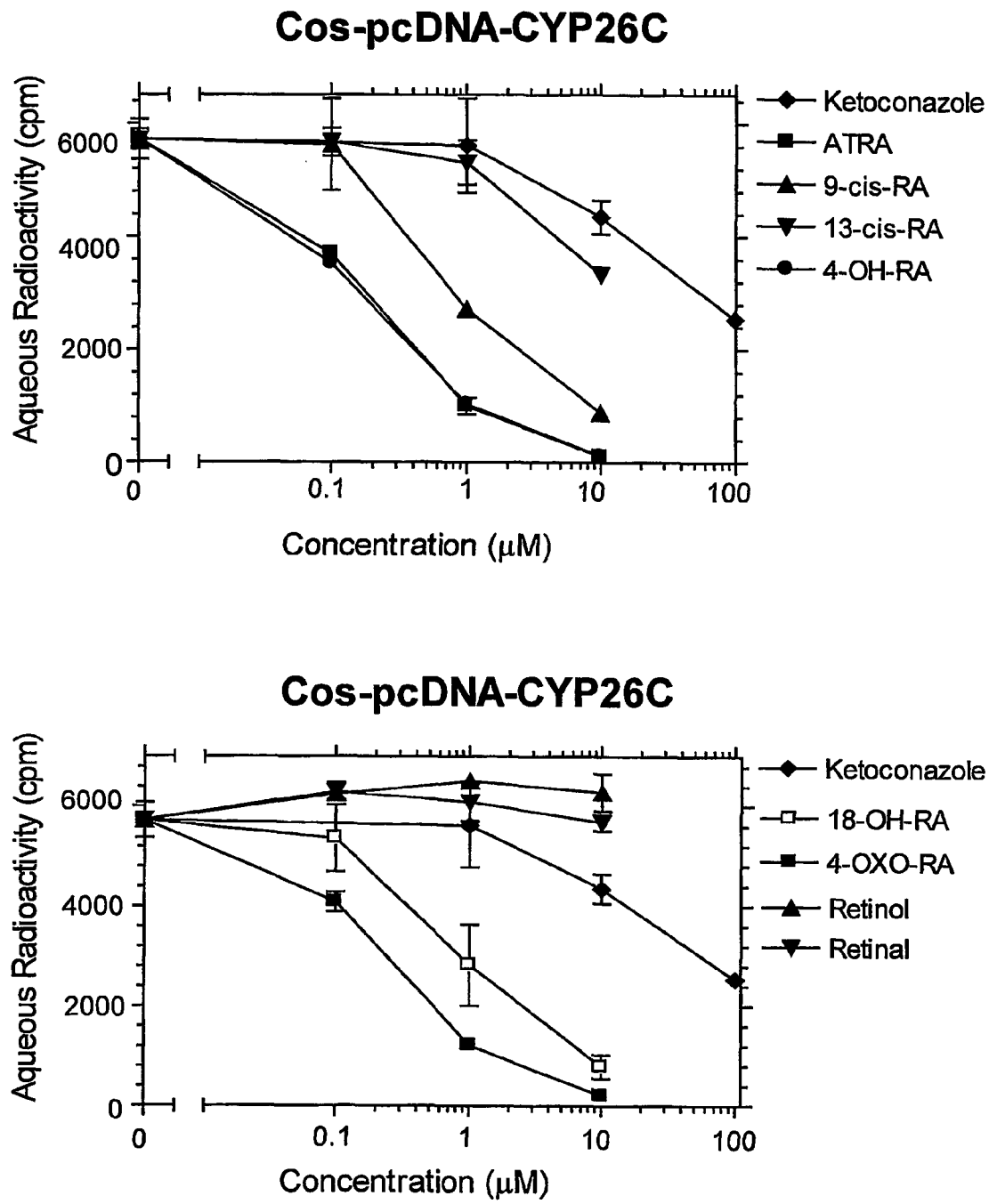
FIGS. 12A and B are linear graphs, illustrating the results of the substrate assay of Example 4. Determination of P450RAI-3 substrates among the candidate compounds ATRA, RA-precursors (Retinol, Retinal), RA-isomers (13-cis and 9-cis forms), or RA-metabolites (4OH-RA, 4-OXORA, and 18-OHRA).

Results were presented in FIG. 12.

ATRA was the best competing substrate (ID$_{50}$ 0.3 µM), then the RA-metabolites (4OH-RA, and 4-OXO-RA). Surprisingly, even at lower concentrations 9-cis-RA was found to compete for P450RAI-3 (ID$_{50}$ 1 µM) and ketoconazole was a weak inhibitor (ID$_{50}$ 70 µM). However, as was determined for CYP26-A and CYP26-B from previous data, Retinol (Vitamin A) and Retinal were not substrates for CYP26—C.

Substrate Competition: Comparison of P450RAI-3 vs. CYP26-B

Figure 13:
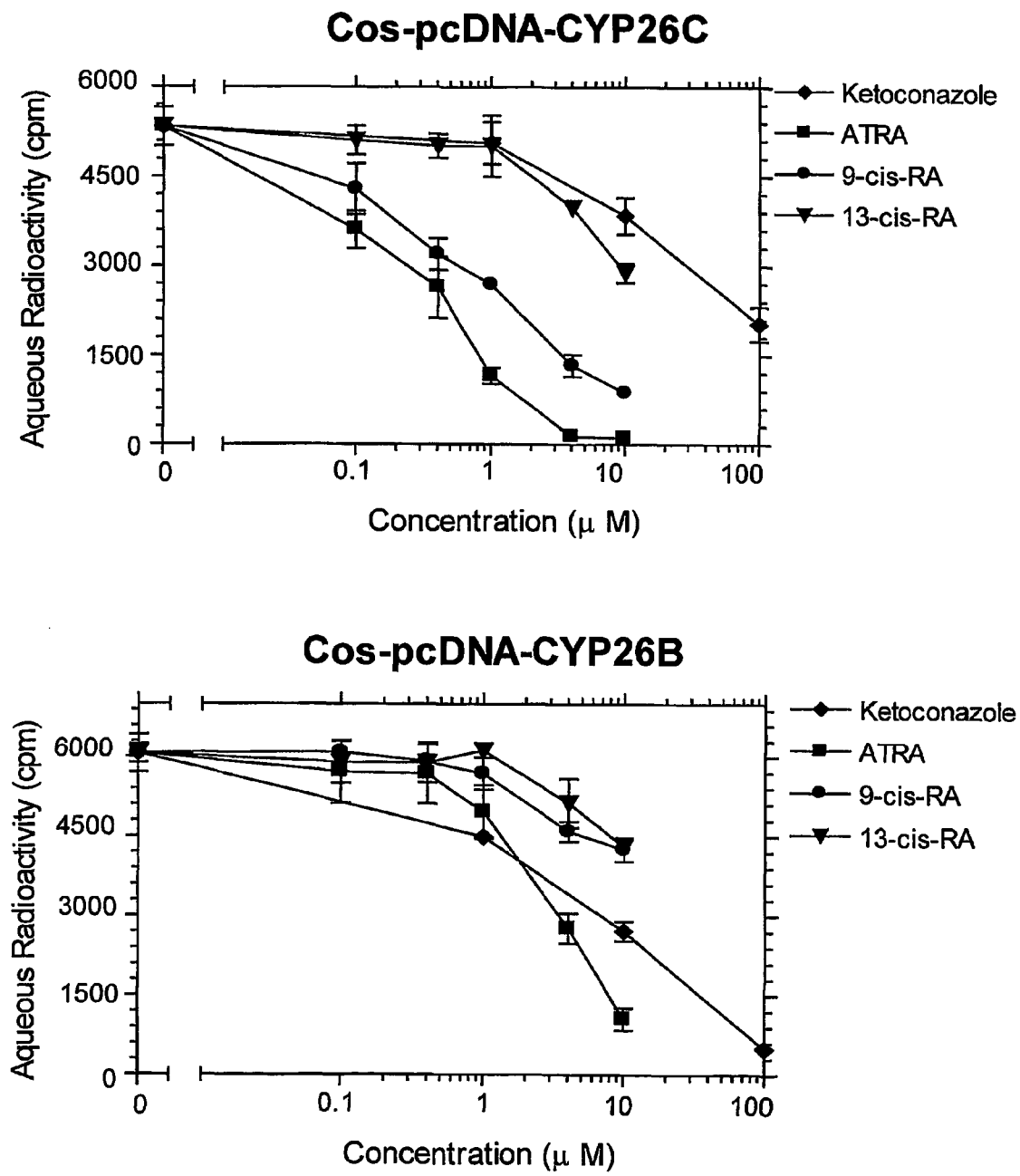
FIGS. 13A and B are linear graphs illustrating the comparison of [$^3$H]-RA-metabolism inhibition with increased concentration of unlabeled ATRA, 9-cis-RA, 13-cis-RA and Ketoconazole in transient Cos-P450RAI-3 (A) vs. Cos-CYP26-B (B) cell-based assay.

Since 9-cis-RA was found to compete for P450RAI-3, we compared the [$^3$H]-RA-metabolism inhibition was compared with increased concentrations of unlabeled ATRA, 9-cis-RA, 13-cis-RA and Ketoconazole in transient Cos-P450RAI-3 vs. Cos-CYP26-B-2 cell-based assay Results are presented in FIG. 13 and table 1

At lower concentrations, unlabeled ATRA competed for both P450RAI-3 and B, However 9-cis-RA isomer competed only for P450RAI-3. 13-cis-RA isomer was not a substrate for both. Ketoconazole inhibited CYP26-B but was only a weak inhibitor for P450RAI-3 (CYP26C).

TABLE 1

Summary of ID50 values in cell assay:
P450RAI-3/B
Transient Cos cell assay/ID$_{50}$ (µM)

| Substrate | P450RAI-3 1$^{st}$ Assay | P450RAI-3 2$^{nd}$ Assay | CYP26-B |
|---|---|---|---|
| ATRA | 0.2 | 0.35 | 3.5 |
| 9cis-RA | 1 | 1.2 | >10 |
| 13cis-RA | >10 | >10 | >10 |
| Retinol | >100 | | |
| Retinal | >100 | | |
| Ketoconazole | 70 | 50 | 7 |
| 4-OH-RA | 0.2 | | |
| 4-OXO-RA | 0.4 | | |
| 18-OH-RA | 1 | | |

Example 5

P450RAI-3 Expression in Insect Cells and Microsomes Preparation

Recombinant baculovirus expressing either P450RAI-3 or CYP26B (Bac-P450RAI-3 or Bac-CYP26B or CYP26B) was prepared and titrated by end-point dilution and infection of Sf9 cells in 96-well format. Baculovirus expressing vector was co-transfected into Sf9-insect cells. Infected cells were assessed for RA-metabolism after 72 hours post transfection using RA-metabolism cell based assay as follows: the RA-metabolism reaction was started by adding 50 µl of [$^3$H]-RA solution (20000 cpm, 2 nM final concentration) using an automatic repeating-pipette.

Cells were incubated for 3 hours. The reaction was stopped by adding 5 µl of 10% acetic acid. Organic and aqueous soluble radio-labelled metabolites were extracted using the Bligh-Dyer procedure.

P450RAI-3 as well as CYP26-B-infected Sf9-cells metabolized ATRA and converted it to water-soluble metabolites, FIG. 14.

Microsomes from P450RAI-3 and CYP26B infected Sf-9 cells were made as follows: exponentially growing cells were harvested, washed with ice-cold PBS, counted then homogenized and sonicated in lysis buffer containing protease inhibitors cocktail ($10^8$ cells par 5 ml lyses buffer). Since P450RAI-3 is a microsomal cytochrome, it preferably uses NADPH cytochromic P450 reductase and a flavoprotein for activity. The microsomes were isolated by differential centrifugations (10 min at 800×g, than 10 min at 10,000×g and finally the postmitichondirial supernatant was centrifuged at 100,000×g for 60 min using ultracentrifuge (Beckman). The microsomal pellet was isolated and homogenized gently in the storage buffer containing protease inhibitors cocktail. Protein concentration in the microsomal preparation was determined using a Bradford reaction assay kit with BSA as standards (Pierce). The absorbance at 562 nm of standards (BSA at 1, 0.5, 0.25, 0.125, and 0.0625 mg/ml) and 3 dilutions of microsomes samples (⅕, 1/10 and ½0) was determined using an automatic microplate reader (µQuant, BioTek instruments Inc.). The protein concentration directly calculated by the software (KCJunior). The microsomes were aliquoted at 1 mg/ml in storage buffer, checked for enzymatic activity, and than stored in liquid nitrogen until further use. All procedures carried out at 4° C. Microsomes were assessed for P450 content by carbon monoxide assay and total P450 content was determined at 3 nmol/ml.

RA-metabolism activity was assessed using RA-metabolism microsomes-based assay and Bligh Dyer extraction as follows: Using an automatic repeating-pipette, gently thawed and homogenized microsomes were plated in a 48-well plate in final volume of 150 µl of storage buffer containing 0.5 mg/ml BSA. At indicated concentration 2 µl of compound solution was added to the assay and 2 µl of DMSO was added to MS control (quadruplet) and No-MS control. 50 µl of [$^3$H]-RA solution (30,000 cpm, 2 nM final concentration) was added. The microsomes assay with the compounds and the [$^3$H]-ATRA were incubated first for 10 min at 37° C., and then the reaction started by adding 20 µl of NADPH solution (or 1 mM final). After 1-hour incubation the reaction was stopped by adding 5 µl of 10% acetic acid. Organic and aqueous soluble radio-labelled metabolites were extracted using the Bligh-Dyer procedure. Saturated activity obtained in presence of NADPH at 5 µg of microsomes, FIG. 14.

Example 6

Substrate Competition in Microsomes Assay: Comparison of P450RAI-3 vs. CYP26-B Sf9-Insect microsomes assay using ATRA, 9-cis-RA and 13-cis-RA competition assay using Sf9-Bac-P450RAI-3 insect microsomes: P450RAI-3 vs. CYP26-B.

Since 9-cis-RA competed for P450-RAI-3-RA metabolism the [$^3$H]-RA-metabolism inhibition with increase concentration of either unlabeled ATRA, 9-cis-RA, 13-cis-RA or Ketoconazole in Sf9-Bac-P450RAI-3 and in Sf9-Bac-CYP26-B insect microsomes was compared.

Figure 15:
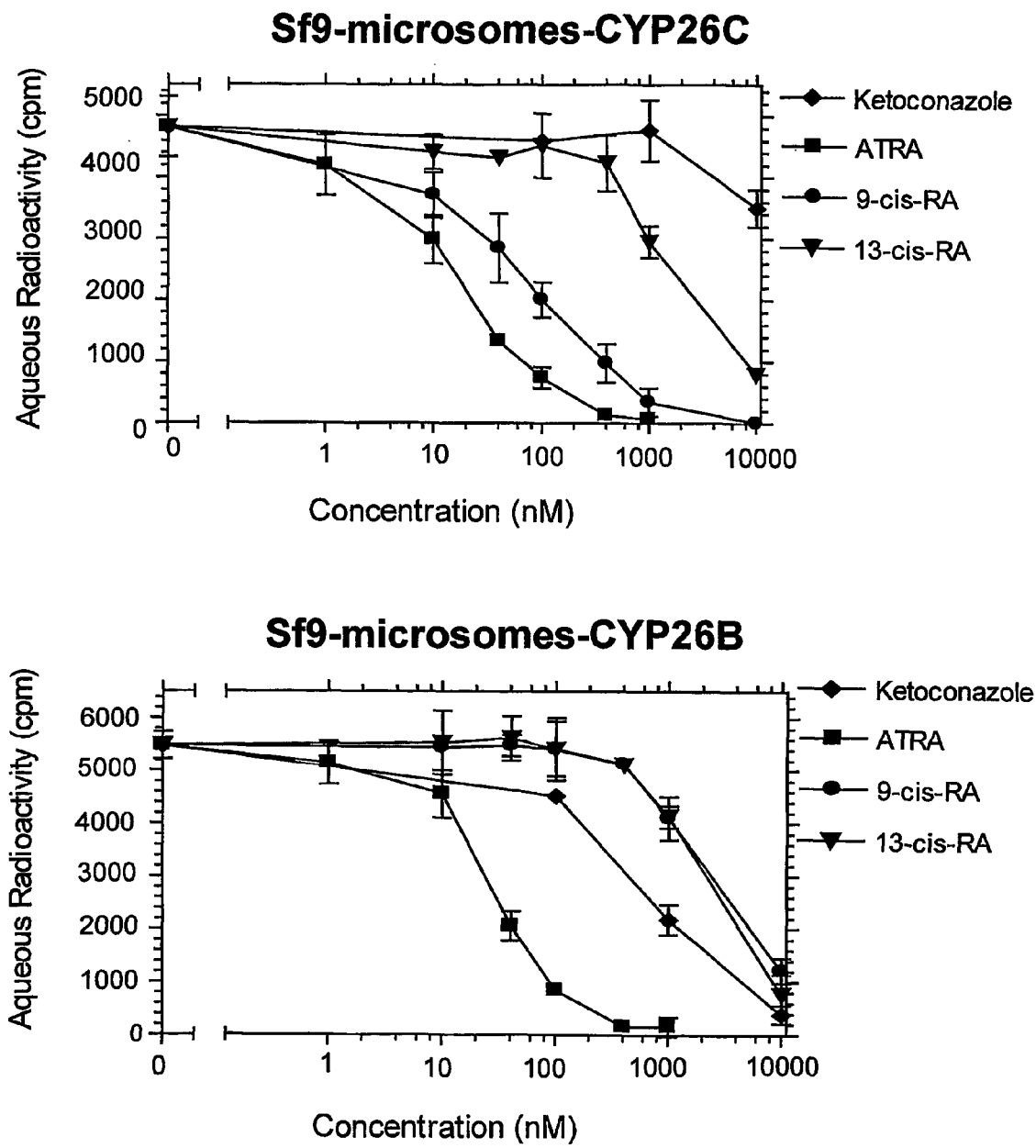
FIGS. 15A and B are linear graphs illustrating the comparison of [$^3$H]-RA-metabolism inhibition with increased concentration of either unlabeled ATRA, 9-cis-RA, 13-cis-RA or Ketoconazole in Sf9-Bac-P450RAI-3 (A) and in Sf9-Bac-CYP26-B (B) insect microsomes.

Results Presented in FIG. 15 and $ID_{50}$ values in table 2:

Unlabeled ATRA competed for both P450RAI-3 and CYP26-B with $ID_{50}$ values of 20 and 30 nM respectively. However, 9-cis-RA competed only for P450RAI-3 ($ID_{50}$ 80 nM), a very weak 9-cis-RA competition can be observed for CYP26-B at much higher concentrations isomer are a high affinity substrates for P450RAI-3.

TABLE 2

Summary of $ID_{50}$ values

| Insect microsomes | $ID_{50}$ (nM) Sf9-P450RAI-3 | $ID_{50}$ (nM) Sf9-CYP26-B |
|---|---|---|
| ATRA | 20 | 32 |
| 9cisRA | 86 | 5000 |
| 13cis-RA | 3000 | 4500 |
| Ketoconazole | >10000 | 750 |

Substrate Competition in Mammalian Microsomes: P450RAI-3 vs. CYP26-B

Microsomes prepared from either stable Hela-CYP26-B or transient P450RAI-3-transfected Cos cells were used. [$^3$H]-RA-metabolism inhibition assay was carried out with increased concentration of unlabeled ATRA, 13-ci-sRA and 9-cis-RA isomers as described in example 5.

Figure 16:
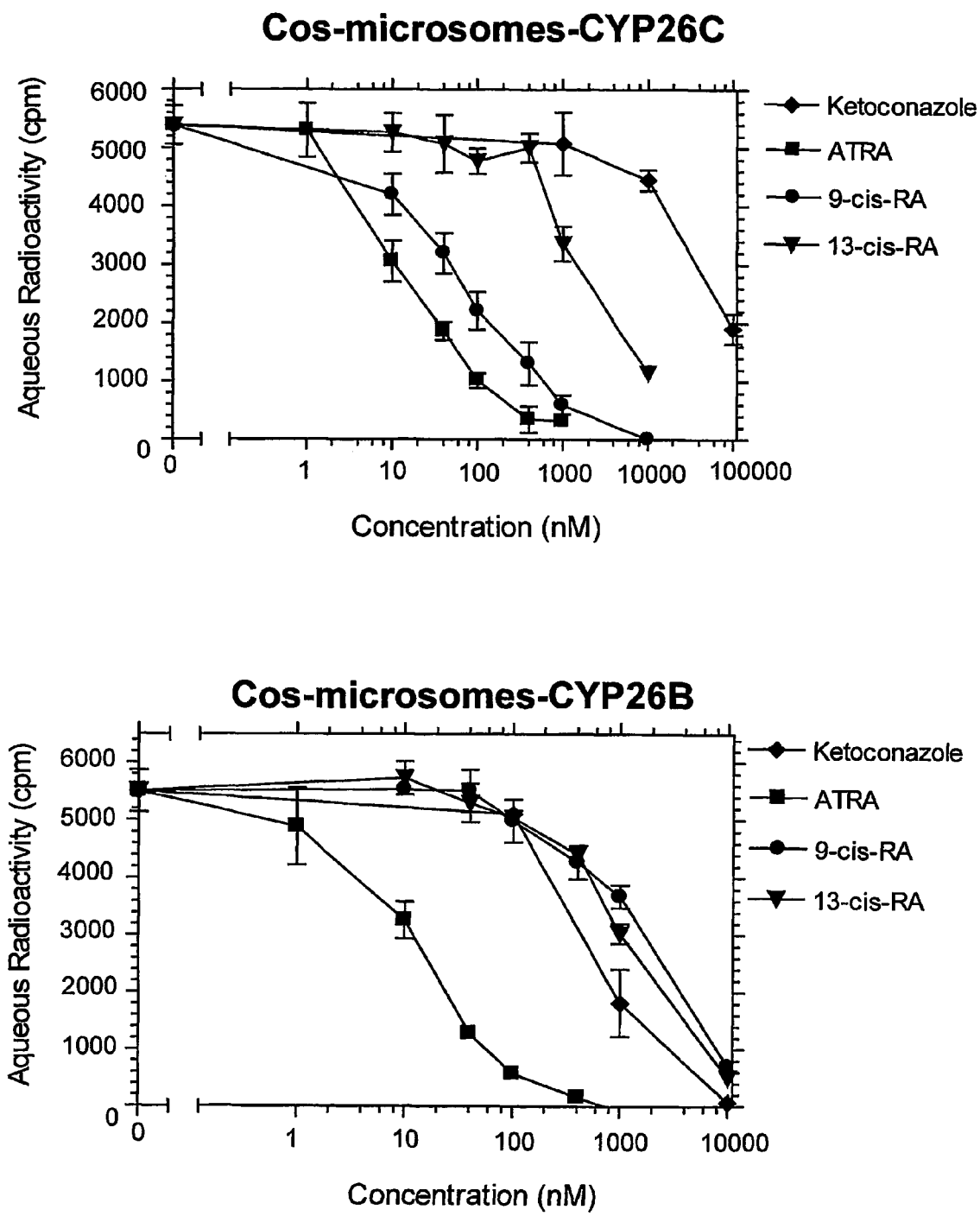
FIGS. 16A and 16B are linear graphs illustrating the results of the [$^3$H]-RA-metabolism inhibition assay carried out with increased concentration of unlabeled ATRA, 13-cisRA and 9-cis-RA isomers in P450RAI-3 (A) and CYP26-B (B) mammalian microsomes.

Results are presented in table 3 and FIG. 16.

Mammalian microsomes gave similar results previously obtained with microsomes prepared from Baculovirus Sf9 infected insect cells. Briefly, ATRA was the highest affinity substrate for CYP26-B and P450RAI-3 ($ID_{50}$ 20 nM). However 9cis-RA competed for P450RAI-3 ($ID_{50}$ 80 nM) but not CYP26B. As expected, 13-cis-RA did not compete at lower concentrations for either CYP26A or CYP 26B. Ketoconazole a weak inhibitor of P450RAI-3 ($ID_{50}$ 70 µM, instead of $ID_{50}$ 0.7 µM for CYP26B).

TABLE 3

Summary of $ID_{50}$ values in mammalian microsomes

| Mammalian | ID50 (nM) P450RAI-3 | CYP26-B |
|---|---|---|
| ATRA | 20 | 20 |
| 9cisRA | 85 | 4000 |
| 13cis-RA | 4000 | 2000 |
| Ketoconazole | 72000 | 740 |

Example 7

ATRA and 9-cis-RA Binding Assay

Binding experiments of ATRA to P450RAI-3 were done twice-using Sf9-Bac-P450RAI-3 insect microsomes. Result presented in FIG. 17, and ID50 values in table 4.

Experiment was carried out along with CYP26-B and Kd values of 48 nM and 114 nM were obtained for P450RAI-3 and CYP26-B, respectively. The second time P450RAI-3 was assayed alone and Kd value of 42 nM was obtained. Competition of ATRA binding to P450RAI-3 by ketoconazole was also done twice. The first time ketoconazole concentration of up to 10 µM was used but only 15% inhibition was obtained at the highest concentration. The second time the assay was done along with CYP26-B and ketoconazole concentration of up to 100 µM was used. Kd values of 1.5 µM and 70.5 µM were obtained for P450RAI-2 and P450RAI-3, respectively.

Binding of 9-cis-RA to CYP26-A, B, and C was also carried out at substrate concentrations of 0.05 nM to 1000 nM, FIG. 18.

Very good binding was only observed with P450RAI-3 microsomes. However, weak binding of 9-cis-RA to CYP26-A and CYP26-B was also observed. While Kd value of 69 nM was obtained for P450RAI-3, it was not possible to determine the Kd values for CYP26-A and CYP26-B because binding of 9-cis-RA to both proteins was linear for substrate concentration up to 1000 nM. Kd values were summarized in table 4

As was found with the enzymatic competition assay, the binding assay confirmed the high affinity of ATRA as well as 9-cis-RA for P450RAI-3

TABLE 4

Summary of Kd values

|  | P450RAI-3 | CYP2-6B | CYP26-A |
|---|---|---|---|
| ATRA | 45 | 100 | ND |
| 9cisRA | 69 | ND | ND |
| Ketoconazole | 75 | 1.5 | ND |

Example 8

P450RAI-3 Metabolism of 9-cis-RA

Figure 19:
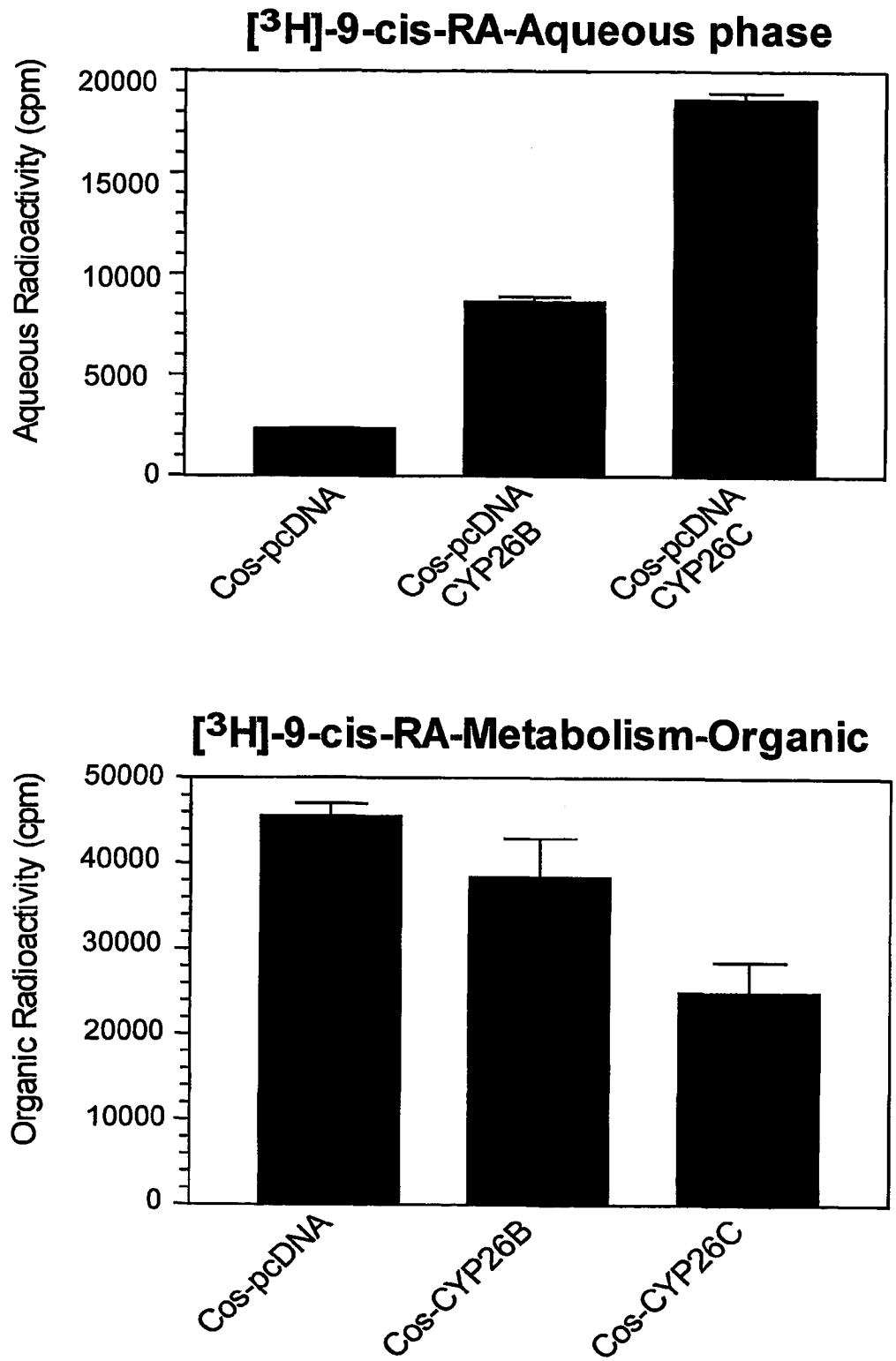
FIGS. 19A and B are bar graphs illustrating the analysis of water soluble (A) and organic (B) metabolites from 9-cis-RA-metabolism in P450RAI-3 transient transfected Cos cells as per Example 8.

Since 9-cis-RA was found to compete and bind to P450RAI-3, we conducted studies of 9-cis-RA-metabolism in P450RAI-3 transient transfected Cos cells. Mammalian Cos-1 cells were transfected with either pcDNA-P450RAI-3 or pcDNA-control vector according to the manufacturers directions using Fugene (Roche). After 48 hours post-tranfection, cells were washed with PBS and assessed for 9-cis-RA-metabolism activity as described using Bligh-Dyer procedure. Briefly, transfected cells were incubated with radio-labeled $^3$[H]-9-cis-RA (38000 cpm, 2 nM) for 3 hours. Organic and Water-soluble metabolites were extracted using Bligh-Dyer procedure and radioactivity counted, FIG. 19.

Figure 20:
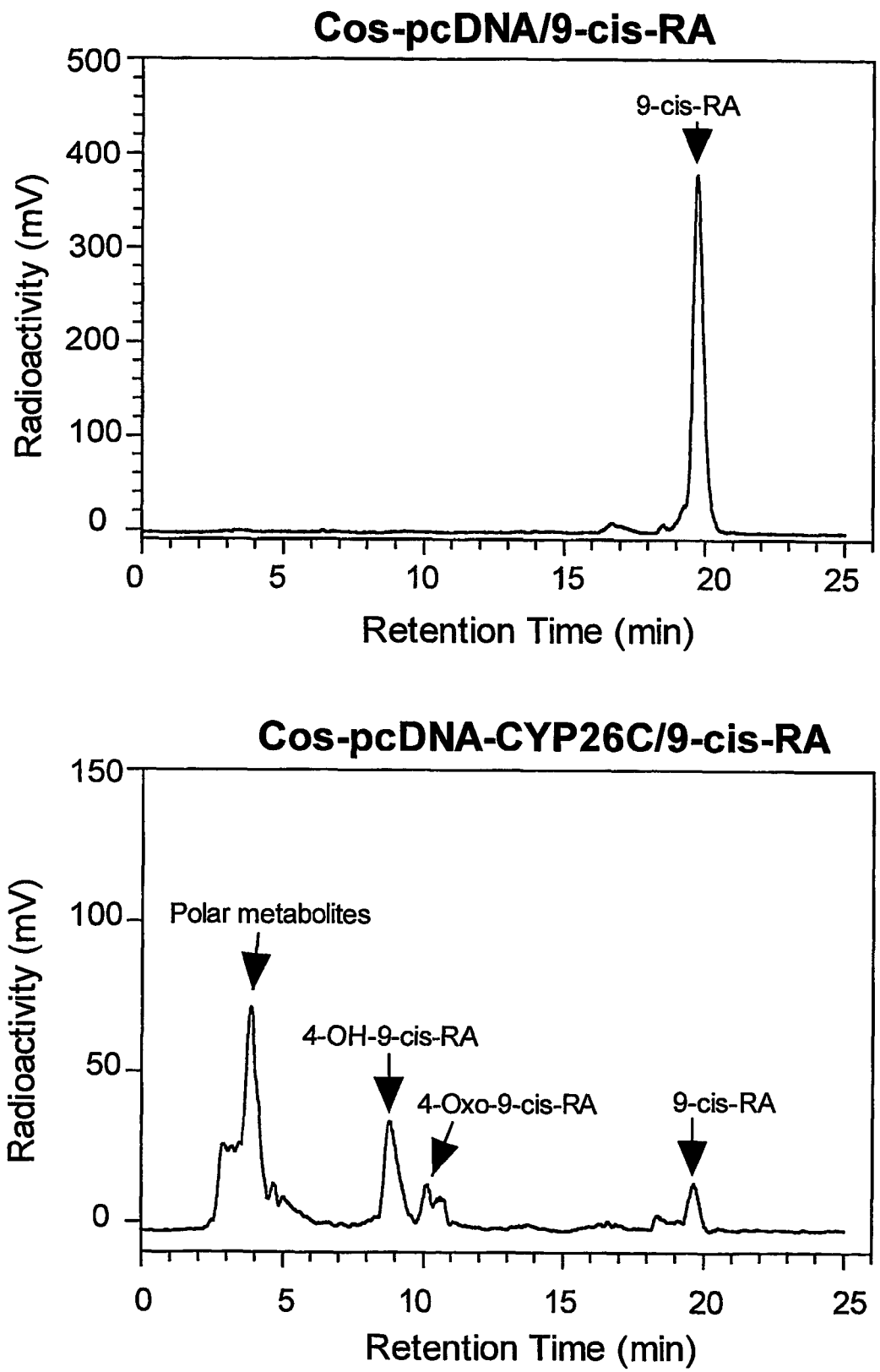
FIGS. 20A and B illustrate the HPLC analysis of 9-cis-RA metabolism in control (A) and P450RAI-3 (B) transient transfected Cos cells.

HPLC analysis of 9-cis-RA metabolism: the button Organic layer was dried out and residues were suspended in HPLC solvent and then analyzed by HPLC as described [White et al, PNAS, vol 97, pg. 6403], FIG. 20.

Results: P450RAI-3-tranfected Cos cells converted 9-cis-RA to the hydoxy and oxo-metabolites and to more polar water-soluble metabolites.

Example 9

P450RAI-3: LC/MS Analysis of ATRA and 9-cis-RA Metabolism Pathway

Hela-P450RAI-3 stable cells were used to determine the ATRA and 9-cis-RA metabolism pathway. Hela-P450RAI-3 cells were incubated with either 1_M ATRA or 9-cis-RA in 10 ml MEM media containing 10% FBS. After 5 hours incubation at 37° C., cells were acidified with acetic acid and total retinoids were extracted using Ethyl acetate method. The organic upper layer was pooled and evaporated in speed-vacuum, and dried residues were dissolved in HPLC mobile solvent and analyzed in LC/MS.

The HPLC system consisted of a waters alliance 2690 separations module. Chromatography was obtained on an Eclipse X DB-C18 reverse phase column (5 um, 2.1×150 mm from HP). A gradient elution program was used using acetonitrile, water and 10% acetic acid. The flow was held at 0.2 ml/min. The UV absorbance was set at 351 and used to monitor retinoid standards (ATRA, 9-cis-RA, 13-cis-RA, 4-OH-RA, 18-OH-RA, 4-Oxo-RA-RA).

Figure 21:
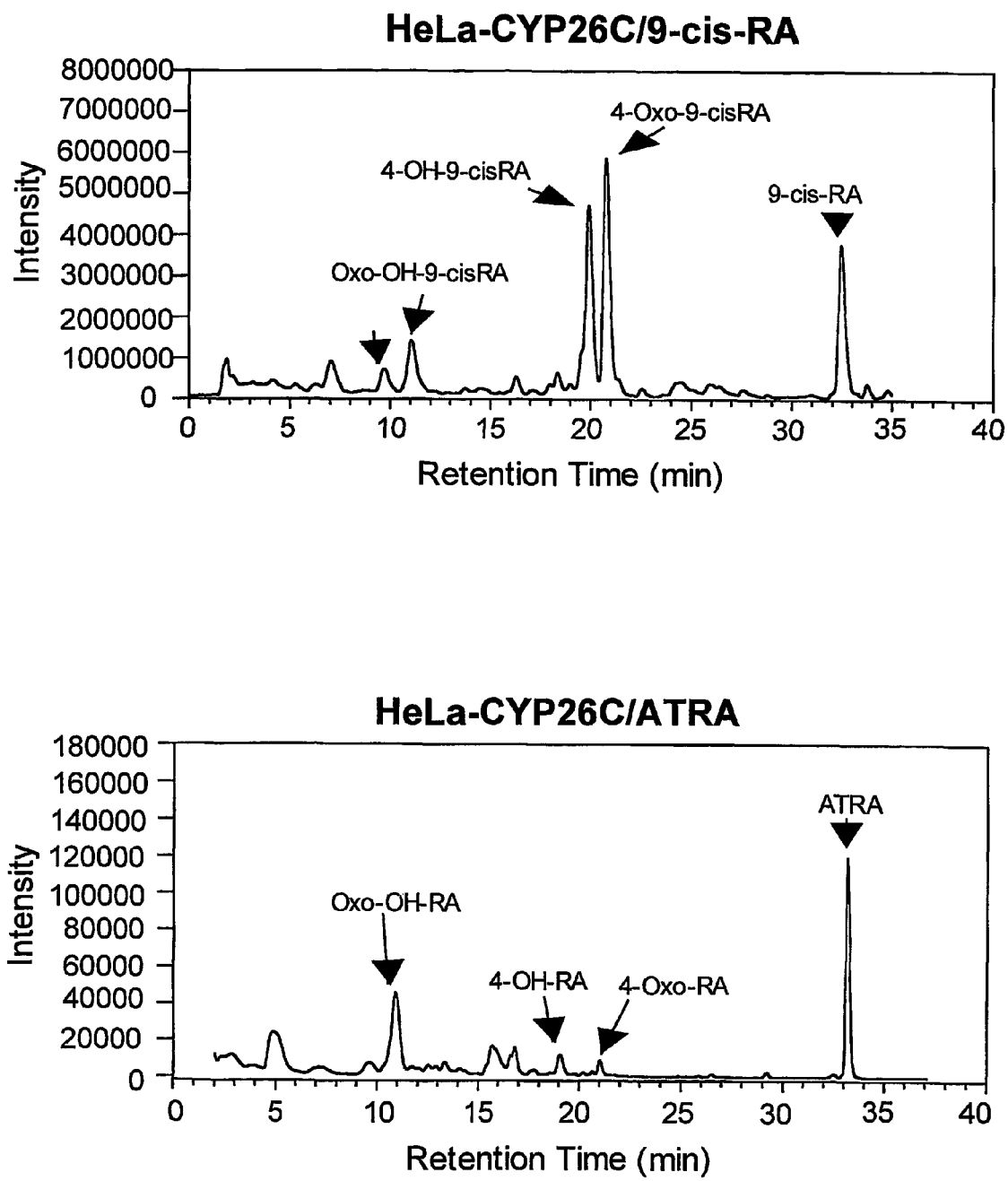
FIGS. 21A and B illustrate the mass spectrometry analysis of ATRA (B) and 9-cis-RA (A) metabolism by Hela-P450RAI-3 stable cells as per Example 9.

Mass Spectrometry condition used for this work consisted of a Micro-mass Quatro Ultima Tandem triple quadruple mass spectrometer equipped with electrospray interface (ESI) and operated in a negative mode. Two method for MS mode MS and MS/MS, 1) A Full scan mode from m/z 200-500 was used and 2) And MS/MS mode using a precursors ion scan mode was used to screen and identify the Hydroxy, and Oxo-metabolite peaks of RA, Results presented in FIG. 21

P450RAI-3 metabolized ATRA as well as 9-cis-RA to hydroxy and oxo-metabolites.

Example 10

Stable Mammalian Cell Expressing P450RAI-3

Cell Transfection and Cloning

Hela cells were transfected with either pcDNA or pcEBV-vector containing P450RAI-3 and hygromycin resistance gene. Then the transfected cells were selected in MEM media containing 10% FBS and Hygromycin 200_g/ml. Surviving selected cells were tested for RA-activity and cloned. Two high activity clones (pcEBVclone #1, pcDNA-clone#22) were selected, expanded assessed for ATRA and 9-cis-RA metabolism (FIG. 22).

Figure 23:
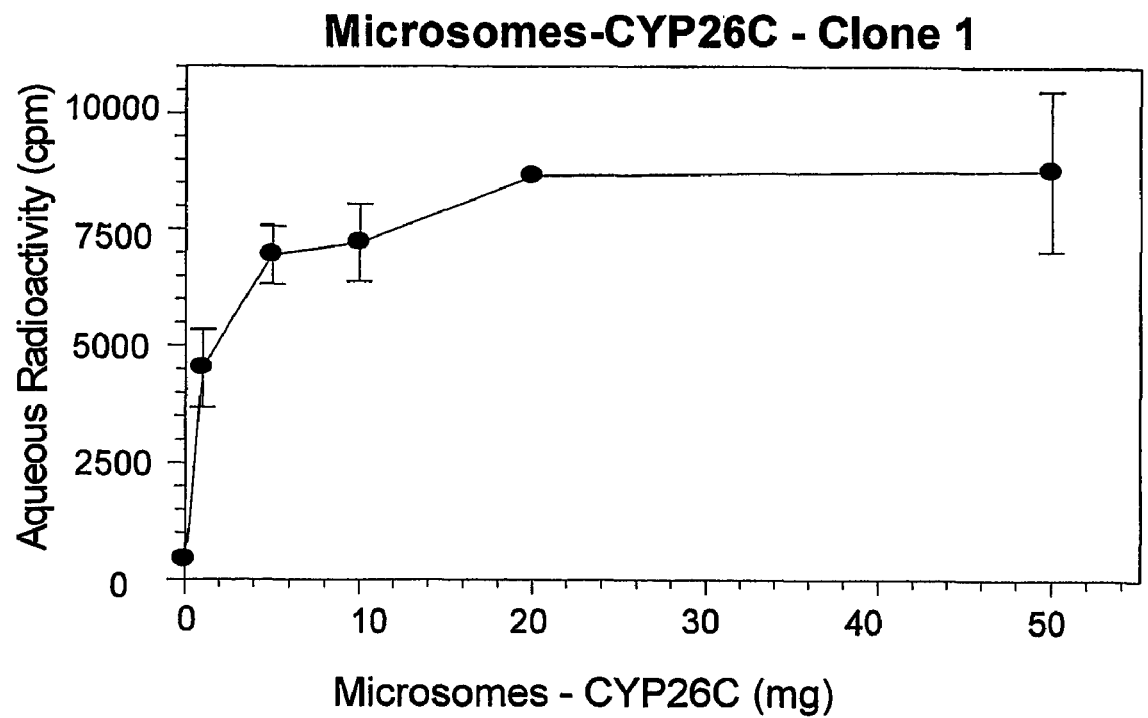
FIG. 23 is a graph illustrating RA metabolic activity in microsomes made from Hela-P450RAI-3 clone 1 as per Example 10.

Microsomes were made from Hela-P450RAI-3 clone 1 and assessed for RA-metabolism activity and then stored in liquid nitrogen (FIG. 23).

Mammalian cells which stably express CYP26C have been generated and shown to possess ATRA and 9-cis RA metabolic activity.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents, and patent applications are herein incorporated by reference in their entirety to the same

REFERENCES

Particulars of references cited above are given below. All of the listed references are incorporated herein by refer11ence.

Abu-Abed, S. S., Beckett, B. R., Chiba, H., Chithalen, J. V., Jones, G., Metzger, D., Chambon, P., and Petkovich, M. (1998). Mouse P450RAI (CYP26) expression and retinoic acid-inducible retinoic acid metabolism in F9 cells are regulated by retinoic acid receptor gamma and retinoid X receptor alpha. Journal of Biological Chemistry 273, 2409-15.

Achkar, C. C., Derguini, F., Blumberg, B., Langston, A., Arthur, A. L., Speck, J., Evans, R. M., Bolado, Jr., J. Nakanishi, K. and Buck, J. (1996) 4-Oxoreinol, a new natural ligand and transactivator of the retinoic acid receptors. Proc. Natl. Acad. Sci. USA 93, 4879-84.

Adamson, P. C., Boylan, J. F., Balis, F. M., Murphy, R. F., Godwin, K. A., Gudas, L. J. and Poplack, D. G. (1993). Time course of induction of metabolism of all-trans retinoic acid and the up-regulation of cellular retinoic acid-binding protein. Cancer Research 53, 472476.

Akimenko, M. A. and Ekker, M. (1995a). Anterior duplication of the Sonic hedgehog expression pattern in the pectoral fin buds of zebrafish treated with retinoic acid. Developmental Biology 170, 243-7.

Akimenko, M. A., Johnson, S. L., Westerfield, M. and Ekker, M. (1995b). Differential induction of four msx homeobox genes during fin development and regeneration in zebrafish. Development 121, 347-57.

Bartel, D. and Szostak, J. W. (1993). Science 261, 1411-1418.

Blaner, W. (1994). Retinol and retinoic acid metabolism. In: The Retinoids. (M. Sporn, Roberts, A. and Goodman, D. S., Editors) Raven Press, Inc.: New York.

Bligh, E. G. and Dyer, W. J. (1957). A rapid method of total lipid extraction and purification. Canadian Journal of Biochemistry 37, 911-917.

Blumberg, B., Bolado, Jr., J., Derguini, F., Craig, A. G., Moreno, T. A., Chakravarti, D., Heyman, R. A., Buck, J. and Evans, R. M. (1996) Novel retinoic acid receptor ligands in *Xenopus* embryos. Proc. Natl. Acad. Sci. USA 93, 4873-78.

Boss et al., U.S. Pat. No. 4,816,397.

Boylan, J. & Gudas, L. (1992) J. Biol. Chem. 267, 21486-21491

Boylan, J. F., Lufkin, T., Achkar, C. C., Taneha, R., Chambon, P. and Gudas, L. J. (1995). Targeted Disruption of Retinoic Acid Receptor a (RARa) and RARg Results in Receptor-Specific Alterations in Retinoic Acid-Mediated Differentiation and Retinoic Acid Metabolism. Mol. Cell Biol. 15, 843-851.

Butler, W. B., and Fontana, J. A. (1992). Responses to retinoic acid of tamoxifen-sensitive and -resistant sublines of human breast cancer cell line MCF-7. Cancer Research 52, 6164-7.

Cabilly et al. U.S. Pat. No. 4,816,567.

Cech et al., (a) U.S. Pat. No. 4,987,071.

Cech et al., (b) U.S. Pat. No. 5,116,742.

Chambon, P. (1995). The molecular and genetic dissection of the retinoid signaling pathway. [Review]. Recent Progress in Hormone Research 50, 317-32.

Chambon, P. (1996) Faseb J. 10, 940-954

Chiang, M. Y., Misner, D., Kempermann, G., Schikorski, T., Giguere, V., Sucov, H. M., Gage, F. H., Stevens, C. F. & Evans, R. M. (1998) Neuron 21, 1353-1361.

Chomienne, C., Fenaux and Degos, L. (1996). Retinoid differentiation therapy in promyelocytic leukemia. FASEB J. 1025-1030.

Chytil, F. (1984). Retinoic acid: Biochemistry, toxicology, pharmacology, and therapeutic use. Pharmacol. Rev. 36, 93-99.

Cole et al (1985). Monoclonal Antibodies in Cancer Therapy. Allen R. Bliss, Inc.

Creech Kraft, J., Schuh, T., Juchau, M. R. and Kimelman, D. (1994). Temporal distribution, localization and metabolism of all-trans retinol, didehydroretinol and all-trans retinal during *Xenopus* development. Biochem. J. 301, 111-119.

De Coster, R., Wouters, W. and Bruynseels, J. (1996). P450-dependent enzymes as targets for prostate cancer therapy. J. Ster. Biochem. Mol. Biol. 56, 133-43.

Duell, E. A., Astrom, A., Griffiths, C. E., Chambon, P. and Voorhees, J. J. (1992). Human skin levels of retinoic acid and cytochrome p-450-derived 4-hydroxyretinoic acid after topical application of retinoic acid in vivo compared to concentrations required to stimulate retinoic acid receptor-mediated transcription in vitro. Journal of Clinical Investigation 90, 1269-74.

Fiorella, P. D., Giguere, V. and Napoli, J. L. (1993). Expression of Cellular Retinoic Acid-binding Protein (Type II) in *Escherichia coli*. The Journal of Biological Chemistry 268, 21545-21552.

Formelli, F., Barua, A. and Olson, J. (1996). Bioactivities of N-(4-hydroxyphenyl) retinimide and retinoyl B-glucuronide. FASEB J. 10, 1014-1024.

Frolik, C. A., Roberts, A. B., Tavela, T. E., Roller, P. P., Newton, D. L. and Sporn, M. B. (1979). Isolation and identification of 4-hydroxy- and 4-oxoretinoic acid. In vitro metabolites of all-trans retinoic acid in hamster trachea and liver. Biochemistry 18, 2092-7.

Fujii, H., Sato, T., Kaneko, S., Gotoh, O., Fujii-Kuriyama, Y., Osawa, K., Kato, S., and Hamada, H. (1997). Metabolic inactivation of retinoic acid by a novel P450 differentially expressed in developing mouse embryos. EMBO Journal 16, 4163-73.

Gudas, L., Sporn, M. and Roberts, A. (1994). Cellular biology and biochemistry of the retinoids. In: The Retinoids. (M. Sporn, Roberts, A. and Goodman, D. S., Editors) Raven Press, Inc.: New York.

Guengerich, (1991) *J. Biol. Chem.* 266:10019-10022

Higgins, D. G. and Sharp, P. M. (1989). Fast and sensitive multiple sequence alignments on a microcomputer. CABIOS 5, 151-153.

Higgins, D. G., Bleasby, A. J., and Fuchs, R. (1991). CLUSTAL V: improved software for multiple sequence alignment. CABIOS 8, 189-191.

Hogan, B. et al., (1986). A Laboratory Manual, Cold Spring Harbor, N.Y., Cold Spring Harbor Laboratory.

Hollermann, T., Chen, Y., Grunz, H., and Pieler, T. (1998). Regionalized metabolic activity establishes boundaries of retinoic acid signaling. European Molecular Biology Organization 17, 7361-7372.

Hong, W. (1994). Retinoids and human cancer. In: The Retinoids. (M. Sporn, Roberts, A. and Goodman, D. S., Editors) Raven Press, Inc.: New York.

Houbenwcyl, (1987). Methods of Organic Chemistry, ed. E. Wansch. Vol. 15 I and II. Thieme, Stuttgart.

Hozumi, N and Sandhu, J. S. (1993). Recombinant antibody technology, its advent and advances. Cancer Invest. 11, 714-723.

Huse et al., (1989). Science 246, 1275-1281.

Iulianella, A., Beckett, B., Petkovich, M., and Lohnes, D. (1999). A molecular basis for retinoic acid-induced axial truncation. Developmental Biology 205, 33-48.

Jones, G., Ramshaw, H., Zhang, A., Cook, R., Byford, V., White, J. & Petkovich, M (1999) Endocrinology 140, 3303-3310.

Kennett, R. (1979). Cell fusion. Methods Enzymol. 58, 345-359.

Kohler and Milstein. (1975): Nature 256, 495-497.

Kozbor et al. (1983). Immunol. Today 4, 72.

Lammer, E. j., Chen, D. T., Hoar, R. M., Agnish, N. D., Benke, P. J., Braun, J. T., curry, C. J., Fernhoff, P. M., Grix, A. J., Lott, I. T. & et, a. I. (1985) N. Engl. J. Med. 313, 837-841.

Lammer, E. & Armstrong, D. (1992) in Retinoids in normal development and teratogenesis, ed. Morris-Kay, G. (Oxford University Press, Oxford), pp. 281-295.

Lane, M., Chen, A., Roman, S., Derguini, F. & Gudas, L. (1999) Proc. Natl. Acad. Sci. USA 96, 13524-13529.

Lemoine, N. R. and Cooper, D. N. (1996). Gene Therapy, Human Molecular Genetics Series, BIOS Scientific Publishers, Oxford, U.K.

Leo et al. (1989). Metabolism of retinol and retinoic acid by human liver cytochrome P450IIC8. Arch. Biochem. Biophys. 269, 305-312.

Lippman, S. M., Heyman, R. A., Kurie, J. M., Benner, S. E. and Hong, W. K. (1995). Retinoids and chemoprevention: clinical and basic studies. J. Cellular Biochem. Supplement 22, 1-10.

Lotan, R. M. (1995). Squamous differentiation and retinoids. Cancer Treat. Res. 74, 43-72.

Lotan, R. (1996). Retinoids in Cancer Chemoprevention. Faseb J. 10, 1031-1039.

Maden, M. and Holder, N. (1992). Retinoic acid and development of the central nervous system. [Review]. Bioessays 14, 431-8.

Mangelsdorf, D. J. and Evans, R. M. (1995). The RXR Heterodimers and Orphan Receptors. Cell 83, 841-850.

Merrifield, (1964]. J. Am. Chem. Assoc. 85, 2149-2154.

McCafferty et al., (1990). Nature 348, 552-554.

Mirski, S. and Cole, S. P. C. (1989). Antigens associated with multidrug resistance in H69AR, a small cell lung cancer cell line. Cancer Res. 49, 5719-5724.

Monia, B. P., Johnston, J. F., Geiger, T., Muller, M. and Fabbro, D. (1996). Antitumor activity of a phosphorothioate antisense oligodeoxynucleotide targeted against C-raf kinase. Nature Medicine 2, 668-75.

Moon, R. C., Mehta, R. G. and Rao, K. V. N. (1994). Retinoids and cancer in experimental animals. In: The Retinoids. (M. Sporn, Roberts, A. and Goodman, D. S., Editors) Raven Press, Inc.: New York.

Morriss-Kay, G. M. (1996). Embryonic development and pattern formation. FASEB J. 10, 961-968.

Morrison et al., (1985). Proc. Natl. Acad. Sci. USA 81, 6851.

Muindi, J. R. F., Frankel, S. R., Huselton, C., DeGrazia, F., Garland, W., Young, C. W. and Warrell, R. P., Jr. (1992). Clinical pharmacology of oral all-trans retinoic acid in patients with acute promyelocytic leukemia. Cancer Research 52, 2138-2142.

Muindi, J. R., Young, C. W. and Warrell, R. J. (1994a). Clinical pharmacology of all-trans retinoic acid. Leukemia 8, 1807-1812.

Muindi, J. R., Young, C. W. and Warrell, R. J. (1994b). Clinical pharmacology of all-trans retinoic acid. Leukemia 8, s16-s21.

Napoli, J. L., Boerman, M. H., Chai, X., Zhai, Y. and Fiorella, P. D. (1995). Enzymes and binding proteins affecting retinoic acid concentrations. J. Ster. Biochem. Mol. Biol. 53, 497-502.

Napoli, J. (1996). Retinoic acid biosynthesis and metabolism. FASEB J. 10, 993-1001.

Nebert et al. (1989), DNA 8:1-13

Nelson, D. et al (1996), *Pharmacogenetics* 6:142

Nelson, D. (1999a) *Arch. Biochem. Biophys.* 369:1-10

Nelson, D. (1999b) Arch. Biochem. Biophys. 371, 345-347.

Niederreither, K., Subbarayan, V., Dolle, P. & Chambon, P. (1999) Nature Genetics 21, 444-448.

Old, R. W. and Primrose, S. B., In: Principles of Gene Manipulation. An Introduction to Genetic Engineering, 4th ed. Oxford University Press. 63-66.

Ohno, C. K. and Petkovich, M. (1993). FTZ-F1 beta, a novel member of the *Drosophila* nuclear receptor family. Mechanisms of Development 40, 13-24.

Pijnappel, W. W., Hendriks, H. F., Folkers, G. E., van den Brink, C., Dekker, E. J., Edelenbosch, C., van der Saag, P. and Durston, A. J. (1993). The retinoid ligand 4-oxo-retinoic acid is a highly active modulator of positional specification. Nature 366, 340-4.

Ray, W. J., Bain, G., Yao, M., and Gottlieb, D. I. (1997). CYP26, a novel mammalian cytochrome P450, is induced by retinoic acid and defines a new family. Journal of Biological Chemistry 272, 18702-8.

Reddy, A. P., Chen, J., Zacharewski, T., Gronemeyer, H., Voorhees, J. J. and Fisher, G. J. (1992). Characterization and purification of human retinoic acid receptor-g1 overexpressed in the baculovirus-insect cell system. Biochem. J. 287, 833-840.

Rigas, J., Miller, V., Zhang, Z. F., Klimstra, D., Tong, W., Kris, M. and Warrell, R. (1996). Metabolic phenotypes of retinoic acid and the risk of lung cancer. Cancer Res. 56, 2692-2696.

Roberts, A. B., Nichols, M. D., Newton, D. L. and Sporn, M. B. (1979a). In vitro metabolism of retinoic acid in hamster intestine and liver. Journal of Biological Chemistry 254, 6296-302.

Roberts, A. B., Frolik, C. A., Nichols, M. D. and Sporn, M. B. (1979b). Retinoid-dependent induction of the in vivo and in vitro metabolism of retinoic acid in tissues of the vitamin A-deficient hamster. Journal of Biological Chemistry 254, 6303-9.

Sambrook, J., Fritsch E. F. and Maniatis, T. (1989). Molecular Cloning: A Laboratory Manual. Cold Spring Harbor Lab Press, Cold Spring Harbor, N.Y.

Staerz & Bevan (1986a). Proc. Natl. Acad. Sci. (USA) 83, 1453.

Staerz & Bevan (1986b). Immunology Today 7, 241.

Stewart, A. J., Canitrot, Y., Baracchini, E., Dean, N. M., Deeley, R. G., and Cole, S.P.C. (1996). Reduction of Expression of the multidrug resistance protein (MRP) in human tumor cells by antisense phophorothioate oligonucleotides. Biochem. Pharamcol. 51, 461469.

Swindell, E., Thaller, C., Sockanathan, S., Petkovich, M., Jessell, T. & Eichele, G. (1999) Dev. Biol. 216, 282-296.

Takatsuka, J., Takahashi, N. and De Luca, L. M. (1996). Retinoic Acid Metabolism and Inhibition of Cell Proliferation: An Unexpected Liaison. Cancer Research 56, 675-678.

Takeda et al., (1985). Nature 314, 452.

Tanaguchi et al., European Patent Publication EP171496.

Teng, et al. (1982) Meth. Enzymol. 92. 3-16.

Thompson, J. D., Higgins, D. G., and Gibson, T. J. (1994). CLUSTAL W: improving the sensitivity of progressive multiple sequence alignment through sequence weighting, positions-specific gap penalties and weight matrix choice. Nucleic Acids Research 22, 4673-4680.

Van Wauwe, J. P., Coene, M.-C., Goossens, J., Van Nijen, G., Cools, W. and Lauwers, W. (1988). Ketoconazole inhibits the in vitro and in vivo metabolism of all-trans retinoic acid. The Journal of Pharmacology and Experimental Therapeutics 245, 718-722.

Van Wauwe, J. P., Coene, M.-C., Goossens, J., Cools, W. and Monbaliu, J. (1990). Effects of cytochrome P450 inhibitors on the in vivo metabolism of all-trans-retinoic acid in rats. The Journal of Pharmacology and Experimental Therapeutics 252, 365-369.

Van Wauwe, J., Van Nyen, G., Coene, M., Stoppie, P., Cools, W., Goossens, J., Borghgraef, P. and Janssen, P. A. J. (1992). Liarazole, an Inhibitor of Retinoic Acid Metabolism, Exerts Retinoid-Mimetic Effects in Vivo. The Journal of Pharmacology and Experimental Therapeutics 261, 773-779.

Ward et al., (1989). Nature 341. 544-546.

Warrell, R. J. (1994). Applications for retinoids in cancer therapy. Seminars in Hematol. 31, 1-13.

Warrell, R. J., Maslak, P., Eardley, A., Heller, G., Miller, W. J. and Frankel, S. R. (1994). Treatment of acute promyelocytic leukemia with all-trans retinoic acid: an update of the New York experience. Leukemia 8, 929-933.

White, J. A., Boffa, M. B., Jones, B. and Petkovich, M. (1994). A zebrafish retinoic acid receptor expressed in the regenerating caudal fin. Development 120, 1861-72.

White, J. A., Guo, Y., Baetz, K., Beckett-Jones, B., Bonasoro, J., Hsu, K., Dilworth, J., Jones, G., and Petkovich, M. (1996a). Identification of the retinoic acid-inducible all trans retinoic acid 4-hydroxylase. Journal of Biological Chemistry 271, 29922-29927.

White, J. & Petkovich, M. (1996b) Met. Mol. Biol. 89, 389-404.

White, J. A., Beckett-Jones, B., Guo, Y. D., Dilworth, F. J., Bonasoro, J., Jones, G., and Petkovich, M. (1997). cDNA cloning of human retinoic acid-metabolizing enzyme (hP450RAI) identifies a novel family of cytochromes P450. Journal of Biological Chemistry 272, 18538-41.

White, J., Beckett, B., Scherer, S., Hebrick, J. and Petkovick, M. (1998) Genomics 48, 270-272.

Williams, J. B. and Napoli, J. L. (1987). Inhibition of retinoic acid metabolism by imidazole antimycotics in F9 embryonal carcinoma cells. Biochemical Pharmacology 36, 1386-1388.

Wouters, W., van, D. J., Dillen, A., Coene, M. C., Cools, W. and De, C. R. (1992). Effects of liarazole, a new antitumoral compound, on retinoic acid-induced inhibition of cell growth and on retinoic acid metabolism in MCF-7 human breast cancer cells. Cancer Research 52, 2841-6.NCES Yamamoto, M., Drager, U., Ong, D. & McCaffery, P. (1998) Eur. J. Biochem. 257, 344-350.

The invention claimed is:

1. An isolated cDNA molecule comprising a sequence selected from the group consisting of: (a) SEQ. ID. NO. 10 or encoding the amino acid sequence of SEQ. ID. NO. 11; (b) a polynucleotide of (a) wherein T can also be U: (c) a polynucleotide having a nucleic acid sequence which differs from any of the nucleic acid molecules of (a) to (c) in codon due to the degeneracy of the genetic code; (d) a polynucleotide that is a variant, of any one of the polynucleotides of (a) to (c); wherein said variant is at least 95% identical to SEQ ID NO:10 and encodes a polypeptide that retains the substrate specificity of the polypeptide comprising the amino acid sequence of SEQ ID NO:11 and (e) a polynucleotide that is a fragment of any one of the polynucleotides of (a) to (d), wherein said fragment encodes a polypeptide that retains the substrate specificity of the polypeptide comprising the amino acid sequence of SEQ ID NO:11.

2. The isolated cDNA molecule of claim 1, wherein the polynucleotide fragment comprises a nucleotide sequence selected from SEQ. ID NOS. 12, 14, 16, 18, 20 and 22 or encoding the amino acid sequence selected from SEQ. ID. NOS. 13, 15, 17, 19,21 and 23.

3. An isolated DNA molecule that is the complement of the cDNA molecule of claim 1.

4. The isolated cDNA molecule of claim 1 encoding a cytochrome P450 retinoic acid metabolizing protein, comprising SEQ. ID. NO. 10 or a cDNA molecule encoding the amino acid sequence of SEQ. ID. NO. 11 or a fragment thereof, wherein said fragment retains the substrate specificity of the polypeptide comprising the amino acid sequence of SEQ ID NO:11.

5. The isolated cDNA molecule of claim 4, wherein the retinoic acid is all trans retinoic acid(ATRA) or 9-cis-retinoic acid.

6. The isolated cDNA molecule of claim 1, wherein the nucleotide sequence of said cDNA molecule has sequential nucleotide deletions from either the C-terminus or the N-terminus of SEQ ID NO:10.

7. A recombinant vector comprising an isolated cDNA molecule of claim 1.

8. An isolated recombinant host cell comprising an isolated cDNA molecule of claim 1.

9. The recombinant host cell of claim 8 wherein the isolated cDNA molecule is operatively linked to a regulatory sequence to allow expression of a peptide encoded by said cDNA molecule.

10. A diagnostic kit for identification of polymorphisms in the P450RAI-3 gene, comprising the DNA molecule that is the complement thereof, and optionally directions for the method comprising screening the P450RAI-3 gene from a human for polymorphisms, wherein detection of said polymorphisms is indicative of the occurrence of a P450RAI-3-related condition or a predisposition thereto.

* * * * *

UNITED STATES PATENT AND TRADEMARK OFFICE
CERTIFICATE OF CORRECTION

PATENT NO. : 7,335,756 B2 Page 1 of 1
APPLICATION NO. : 10/477526
DATED : February 26, 2008
INVENTOR(S) : Jan Wisniewski et al.

It is certified that error appears in the above-identified patent and that said Letters Patent is hereby corrected as shown below:

In the Claims:

At Column 125, line 57, "variant; of" should be -- variant of --.

Signed and Sealed this

Twelfth Day of August, 2008

JON W. DUDAS
*Director of the United States Patent and Trademark Office*